(12) United States Patent
Delhomel et al.

(10) Patent No.: US 9,902,725 B2
(45) Date of Patent: Feb. 27, 2018

(54) HETEROCYCLIC DERIVATIVES AS RORGAMMA MODULATORS

(71) Applicant: GENFIT, Loos (FR)

(72) Inventors: Jean-Francois Delhomel, Arras (FR); Robert Walczak, Lille (FR); Zouher Majd, Ennetieres en Weppes (FR); Emilie Pihan, Toulouse (FR); Pascal Bonnet, Olivet (FR); Enrico Perspicace, Phalempin (FR)

(73) Assignee: Genfit, Loos (FR)

( * ) Notice: Subject to any disclaimer, the term of this patent is extended or adjusted under 35 U.S.C. 154(b) by 0 days.

(21) Appl. No.: 15/539,519

(22) PCT Filed: Dec. 22, 2015

(86) PCT No.: PCT/EP2015/081095
§ 371 (c)(1),
(2) Date: Jun. 23, 2017

(87) PCT Pub. No.: WO2016/102633
PCT Pub. Date: Jun. 30, 2016

(65) Prior Publication Data
US 2017/0349582 A1 Dec. 7, 2017

(30) Foreign Application Priority Data

Dec. 23, 2014 (EP) .................................... 14307168

(51) Int. Cl.
| | | |
|---|---|---|
| *C07D 471/04* | (2006.01) |
| *C07D 401/12* | (2006.01) |
| *C07D 403/12* | (2006.01) |
| *C07D 209/20* | (2006.01) |
| *C07D 401/14* | (2006.01) |

(52) U.S. Cl.
CPC ......... *C07D 471/04* (2013.01); *C07D 209/20* (2013.01); *C07D 401/12* (2013.01); *C07D 401/14* (2013.01); *C07D 403/12* (2013.01)

(58) Field of Classification Search
None
See application file for complete search history.

(56) References Cited

U.S. PATENT DOCUMENTS

| | | | | |
|---|---|---|---|---|
| 8,106,069 B2 * | 1/2012 | Salom | .................. | C07D 471/04 514/231.5 |
| 8,198,298 B2 * | 6/2012 | Salom | .................. | C07D 471/04 514/300 |

FOREIGN PATENT DOCUMENTS

| | | |
|---|---|---|
| WO | WO 2013/019626 | 2/2013 |
| WO | WO 2013/019682 | 2/2013 |

* cited by examiner

*Primary Examiner* — Michael Barker
(74) *Attorney, Agent, or Firm* — Cesari and McKenna, LLP

(57) ABSTRACT

The present invention provides novel compounds of formula (I) that are modulators of RORgamma. These compounds, and pharmaceutical compositions comprising the same, are suitable means for treating any disease wherein the modulation of RORgamma has therapeutic effects, for instance in autoimmune diseases, autoimmune-related diseases, inflammatory diseases, fibrotic diseases, or cholestatic diseases.

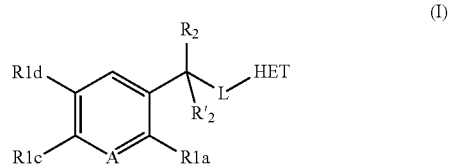

19 Claims, 10 Drawing Sheets

Ex.9-11, 13, 16-18, 23,
26-29, 33-34, 36-37, 39-44,
49-57, 60, 62, 64-66, 70-71,
74, 76-81, 88, 95, 97-99,
110-112, 122, 142

Protocol A

Protocol B

Protocol C

Protocol D

Protocol E

Protocol F

Protocol G

HETEROCYCLIC DERIVATIVES AS RORGAMMA MODULATORS

CROSS REFERENCE TO RELATED APPLICATIONS

This application is the National Stage of International Application No. PCT/EP2015/081095, filed on Dec. 22, 2015, which claims the benefit of European Application No. 14307168.6, filed on Dec. 23, 2014. The contents of both applications are hereby incorporated by reference in their entirety.

TECHNICAL FIELD

The present invention relates to novel compounds that are modulators of RORgamma and the pharmaceutical use of such compounds.

BACKGROUND

The retinoic acid-related orphan receptor γ (RORγ) is a member of the ROR subfamily of nuclear receptors which includes three genes; RORA, RORB and RORC (also known as RORγ). Rorγ encodes two isoforms RORγ1 and RORγ2 (also termed RORγt). RORγ1 is preferentially expressed in skeletal muscle and several other tissues, including pancreas, thymus, prostate, liver and testis (Hirose et al, 1994; Ortiz et al, 1995). RORγt is restricted to several distinct immune cell types (He et al, 1998). This immune system-specific isoform (RORγt) is the key lineage-defining transcription factor for the differentiation program of T helper type 17 (Th17) cells, a subset of CD4+ T-helper and the most prominent cells in producing a number of inflammatory cytokines, such as IL-17A, IL-17F, IL-22, and IL-23 considered as important pathogenic factors for many immune and inflammatory diseases. During the disease process Th17 cells are activated and are responsible for recruiting other inflammatory cell types, such as neutrophils, to mediate pathology in the target tissues (Korn et al, 2009). RORγt is also able to induce IL-17A and IL-17F in naïve CD4+ T-helper, NKT and iNKT cells (Rachitskaya et al, 2008), γδT cells (Murdoch & Lloyd, 2010), CD8+ Tcells (Liu et al, 2007) and CD4−CD8+ TCRab+T cells (Crispin et al, 2008). RORγt is also expressed in and is required for the generation of LTi cells (Eberl et al, 2004), which are central to the development of lymphoid organs such as lymph node and Peyer's patch (Lipp & Muller, 2004).

Overexpression of RORγt in naïve CD4+ T cells was demonstrated to drive the induction and development of Th17 cells. In contrast, RORγt deficiency in mice completely impairs Th17 cell differentiation and induces resistance to the development of autoimmune diseases, such as experimental autoimmune encephalomyelitis (EAE) a model of multiple sclerosis (Dang et al, 2011; Yang et al, 2008) or experimental autoimmune myocarditis (EAM) (Yamashita et al, 2011). In the same manner, mice lacking IL-17 are resistant to development of EAE, and collagen-induced arthritis (CIA), a model of rheumatoid arthritis. IL-17 neutralization with a targeted antibody suppresses autoimmune inflammation, joint damage, and bone destruction (Furuzawa-Carballeda et al, 2007; Lubberts et al, 2004; Stockinger et al, 2007). Moreover, blocking Th17 pathway demonstrated good efficacy in patients with some chronic inflammatory diseases. For example, the anti-p40 monoclonal antibody Ustekinumab (Stelara) that targets Th17 and Th1 through IL-23 and IL-12 respectively, has been approved for the treatment of moderate to severe plaque psoriasis in adult patients and showed a clinical (phase IIb) efficacy in refractory Crohn diseased patients (Tuskey & Behm, 2014).

Small molecule RORγt modulators have therapeutic effects in preclinical disease models. In particular, compounds TMP778 and SR1001 were efficacious in psoriasis and multiple sclerosis models, respectively, when administered by injection (Skepner et al, 2014; Solt et al, 2011).

To summarise, RORγt activity modulation results in the modulation of IL-17 dependent immune and inflammatory responses.

Currently, there is considerable evidence suggesting that RORγt/IL-17 component is closely associated with a range of chronic inflammatory diseases such as multiple sclerosis (MS), psoriasis, inflammatory bowel diseases (IBD), rheumatoid arthritis (RA), uveitis and lung diseases. Compounds able to modulate RORγt activity are also expected to provide a therapeutic benefit in the treatment of numerous medical disorders, including autoimmune, inflammatory, fibrotic and cholestatic disorders, such as asthma, ankylosing spondylitis, autoimmune cardiomyopathy, autoimmune hepatitis, Crohn's disease, chronic obstructive proliferative disease (COPD), diabetes mellitus type 1, lupus erythematosus, lupus nephritis, multiple sclerosis, psoriasis, psoriatic arthritis, rheumatoid arthritis, ulcerative colitis, myocarditis, pulmonary fibrosis (idiopathic pulmonary, interstitial lung, cystic and progressive massive fibrosis), NonAlcoholic SteatoHepatitis (NASH) and Alcoholic SteatoHepatitis (ASH), cardiac fibrosis and heart myocardial and endomyocardial fibrosis, arterial fibrosis, atherosclerosis/restenosis, intestinal fibrosis (occurs for example in Crohn's disease and collagenous colitis), kidney fibrosis, scleroderma and systemic sclerosis Primary Biliary Cirrhosis (PBC), Hepatitis (hepatitis A, hepatitis B, hepatitis C).

The present invention describes novel RORγt modulators, their preparation and their use in therapy, in particular in the treatment of immune, inflammatory, fibrotic and cholestatic diseases.

SUMMARY OF INVENTION

RORγ inverse agonists were proposed in Skepner et al., 2014 who allegedly showed that compound T was efficacious in psoriasis model when administered by injection. However, it is herein shown that such compound present a very poor drug likeness in the sense that it presents a poor eADME profile, a poor metabolic stability and has effects on P450 cytochrome mediated xenobiotic metabolism. In addition, compound T of Skepner et al., 2014 is ineffective in delaying the onset of experimental autoimmune encephalomyelitis, when administered orally. On the contrary, the compounds of the present invention are potent, orally available RORγ modulators that have a very good drug likeliness profile, as shown in the below experimental part.

The present invention thus provides novel compounds that are modulators of RORγ and have the following formula (I):

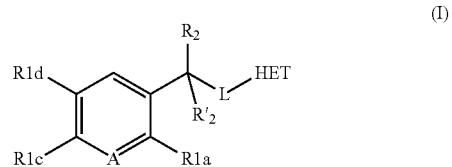

The present invention also provides pharmaceutical compositions comprising the compounds of formula (I) since they modulate RORγ in vitro and in cellular models, indicating that these compounds can have properties of pharmaceutical interest. Accordingly, further objects of the invention include methods of treatment comprising the administration of said pharmaceutical composition for the treatment of RORγ-related diseases such as autoimmune, inflammatory diseases, fibrotic and cholestatic diseases.

The present invention also provides a compound of formula (I), for use as a medicament.

The present invention also provides a compound of formula (I), for use in a method for the treatment of RORγ-related diseases.

Further objects of the present invention, including preferred compounds of formula (I), methods of preparing compounds of formula (I) and preferred medical uses or methods, in combination or not with other compounds, are provided in the Detailed Description.

DESCRIPTION OF THE FIGURES

Abbreviations Used in the Figures and in the Text

AcOH Acetic acid
atm p. atmospheric pressure
ca circa
CD Cluster of Differentiation
CFA Complete Freund's Adjuvant
CH2Cl2 Dichloromethane
CIA Collagen-Induced Arthritis
CMC CarboxyMethyl Cellulose
CNS Conserved non coding sequence
Cpd: Compound
DIPE DiIsoPropylEther
DCC N,N'-DiCyclohexylCarbodiimide
DMAP 4-(DiMethylAmino)Pyridine
DMEM: Dulbecco's modified Eagle's medium
DMF DiMethylFormamide
DMSO DiMethyl SulfOxide
dr diastereoisomeric excess
eADME Early Absorption, Distribution, Metabolism, and Excretion
EAE Experimental Autoimmune Encephalomyelitis
$EC_{50}$: Half maximal effective concentration
EDCl N-Ethyl-N'-(3-Dimethylaminopropyl)CarbodiImide HydroChloride
EAM Experimental Autoimmune Myocarditis
equiv equivalent
Et2O Diethyl ether
Et3N Triethylamine
EtOAc Ethyl acetate
EtOH Ethanol
H2 Hydrogen
H2SO4 Sulfuric acid
HCl Hydrochloric acid
HPLC High Performance Liquid Chromatography
HOBt 1-Hydroxybenzotriazole
HOPd Palladium Hydroxide
IBD Inflammatory Bowel Diseases
$IC_{50}$: Half maximal inhibitory concentration
IL-17 interleukin 17
K2CO3 Potassium carbonate
KCN Potassium cyanide
LiOH Lithium hydroxide
Na2CO3 Sodium carbonate
NaBH4 Sodium borohydride
NaHCO3 Sodium bicarbonate
NaOH Sodium hydroxide
N2 Nitrogen
NH4Cl Ammonium chloride
MeOH Methanol
MgSO4 Magnesium sulfate
MOG Myelin Oligodendrocyte Glycoprotein
mp melting point
NR Nuclear Receptor
PCR Polymerase Chain Reaction
Pd/C Palladium on activated charcoal
PMA Phorbol 12-Myristate 13-Acetate
POCl3 Phosphorus oxychloride
RA Rheumatoid Arthritis
ROR Retinoic Acid-Related Orphan Receptor
RPMI Roswell Park Memorial Institute medium
rt room temperature
SPF Specific Pathogen Free
TFA TriFluoroacetic Acid
Th17 T helper 17
THF TetraHydroFuran
TLC Thin-Layer Chromatography FIGS. 1 and 2—Intermediate Compounds for the Synthesis of the Compounds of Formula (I)

Figure 1A:
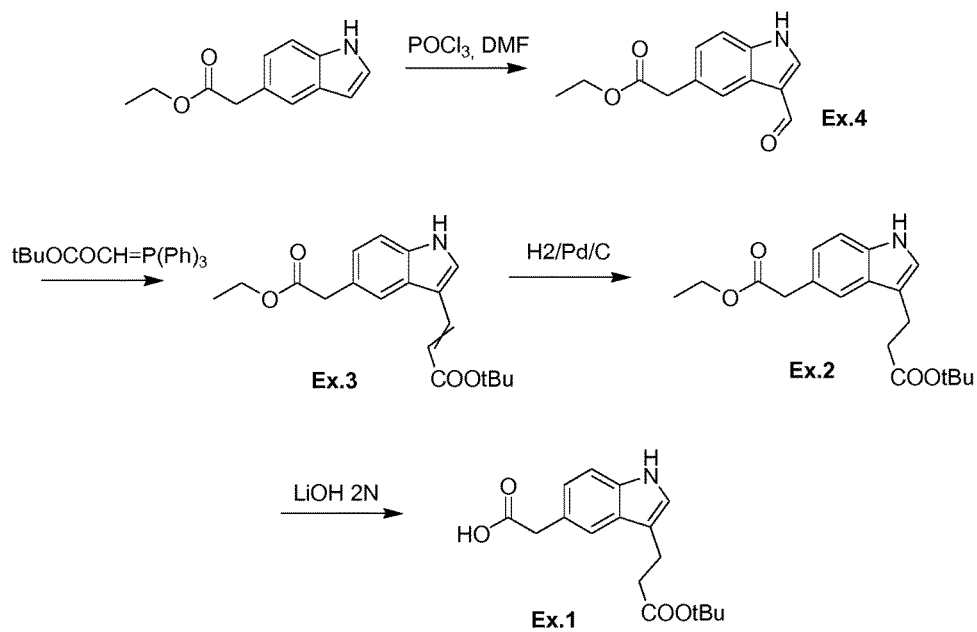
Figure 1B:
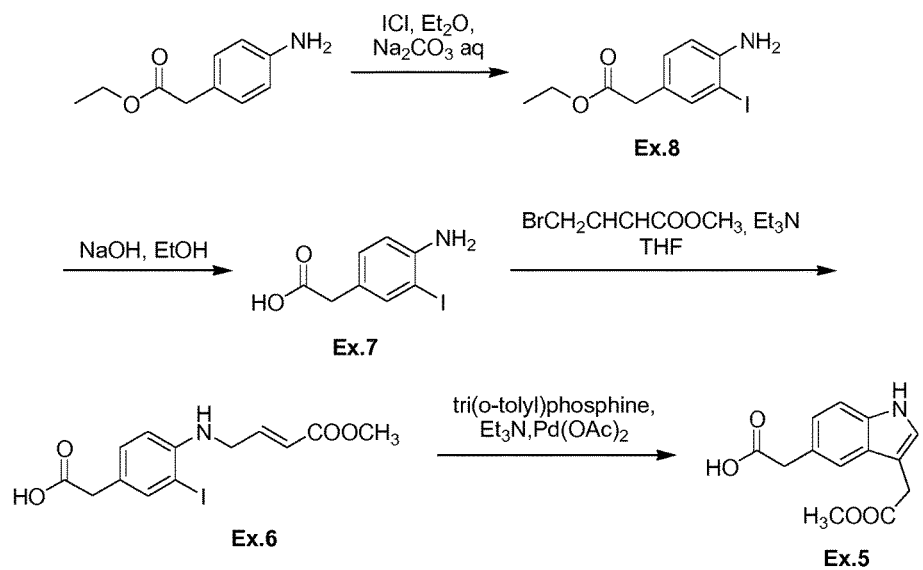
Figure 1C:
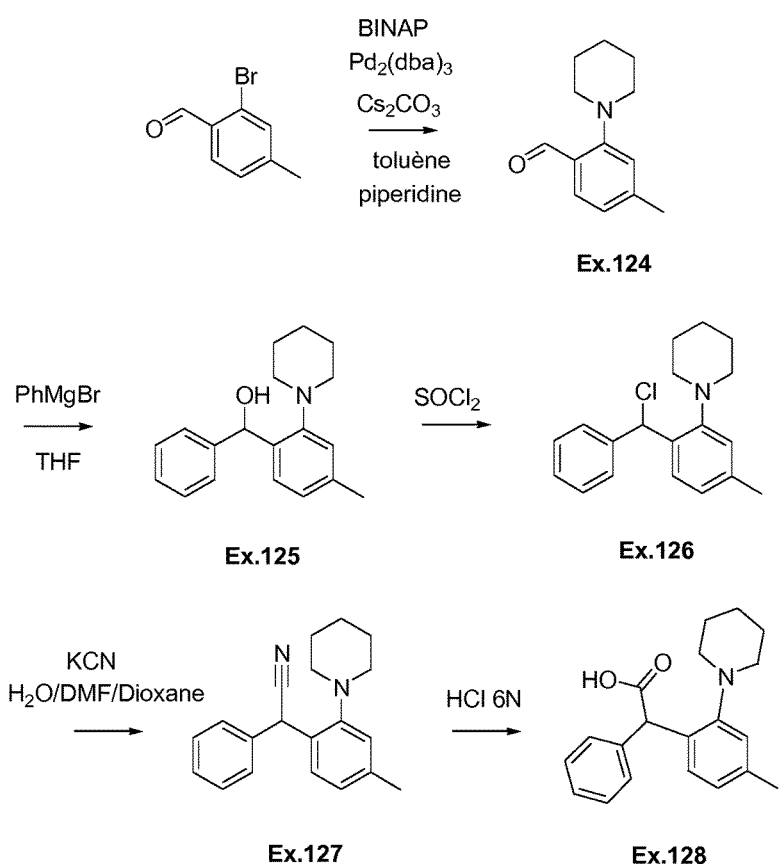

Intermediates are independently generated for the synthesis of compounds of formula (I): for example 2-{3-[3-(tert-butoxy)-3-oxopropyl]-1H-indol-5-yl}acetic acid Ex.1 (FIG. 1A), 2-[3-(2-methoxy-2-oxoethyl)-1H-indol-5-yl]acetic acid Ex.5 (FIG. 1B), and 2-[4-methyl-2-(piperidin-1-yl) phenyl]-2-phenylacetic acid Ex.128 (FIG. 1C)

Figure 2A:
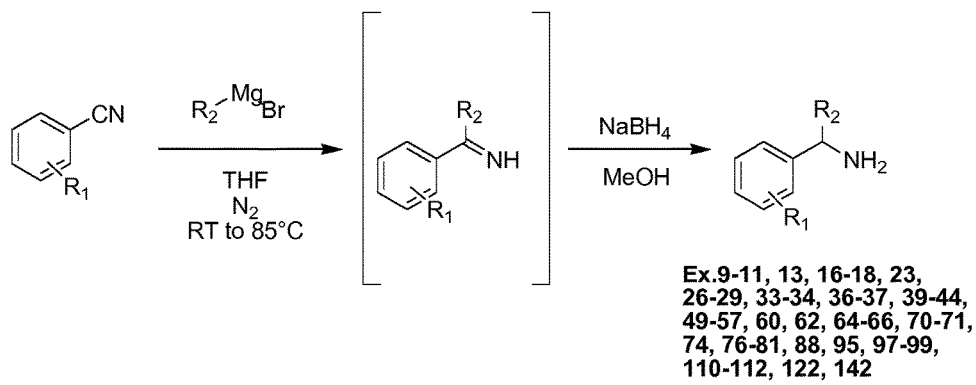
Figure 2B:
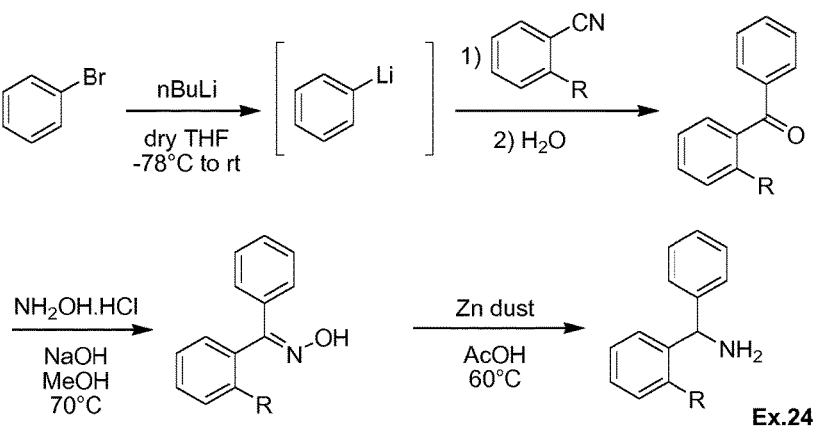
Figure 2C:
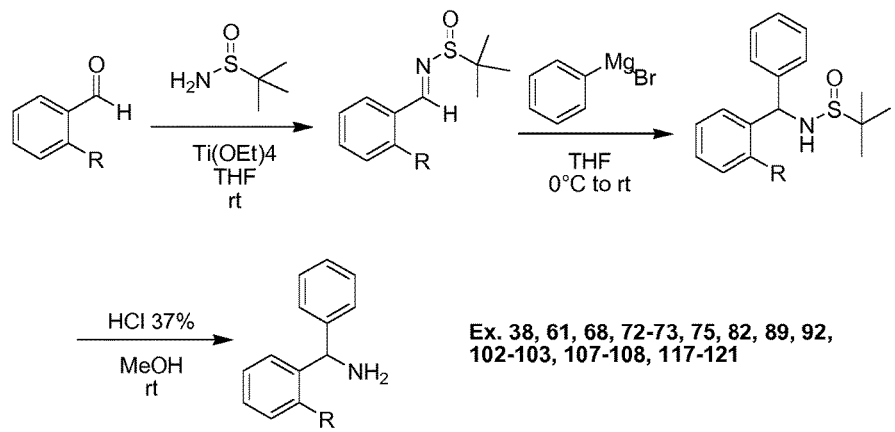
Figure 2D:
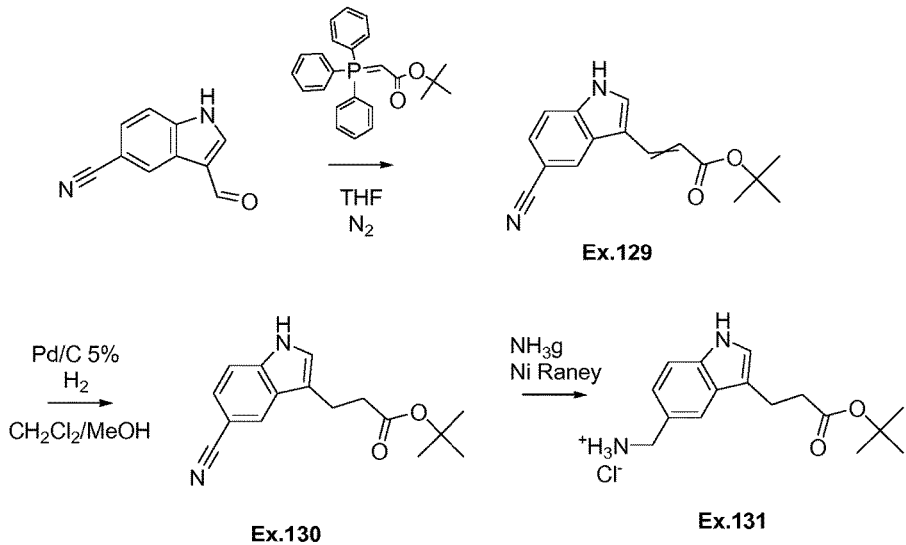
Figure 2E:
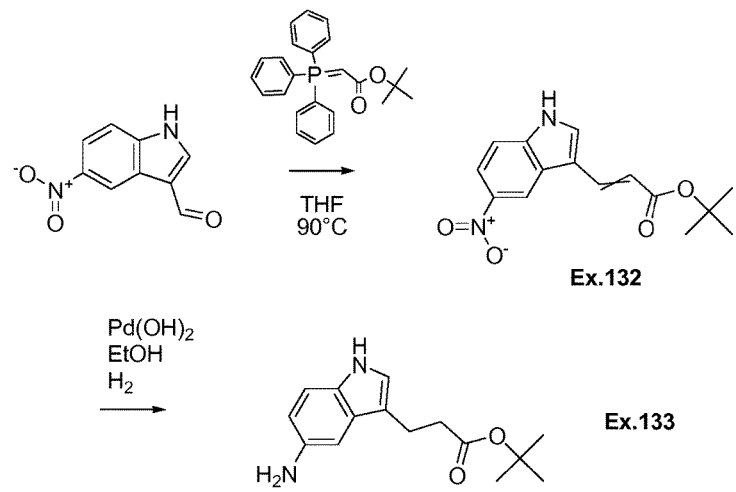
Figure 2F:
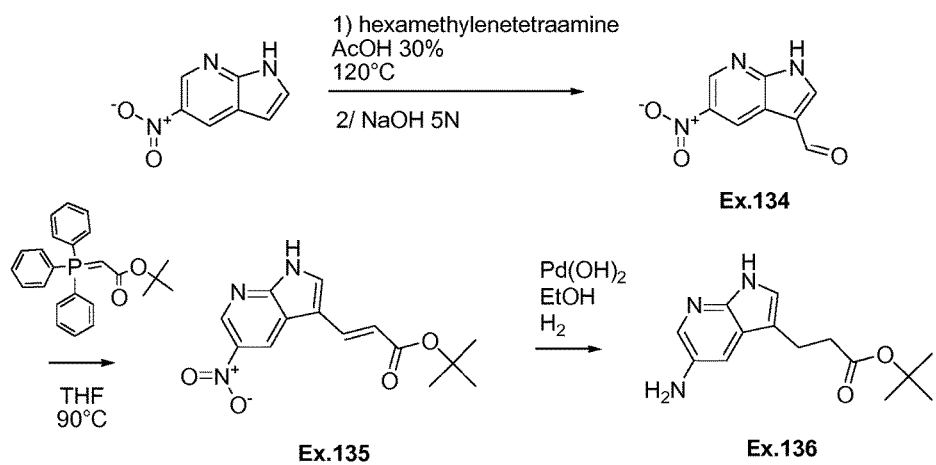

In a same manner were synthetised different substituted benzyl amines (FIG. 2A (Protocol A), FIG. 2B (Protocol B), and FIG. 2C (Protocol C)), {3-[3-(tert-butoxy)-3-oxopropyl]-1H-indol-5-yl}methanaminium chloride Ex.131 (FIG. 2D), and tert-butyl 3-(5-amino-1H-indol-3-yl)propanoate Ex.133 (FIG. 2E), and tert-butyl 3-(5-amino-1H-pyrrolo[2,3-b]pyridin-3-yl)propanoate Ex. 136 (FIG. 2F). Intermediate tert-butyl 3-((methoxycarbonyl)methyl)-5-amino-1H-indole-1-carboxylate Ex.140 was synthetised following protocol described in FIG. 2G.

FIG. 3—General Synthesis Scheme of Compounds of Formula (I)

Figure 3A:
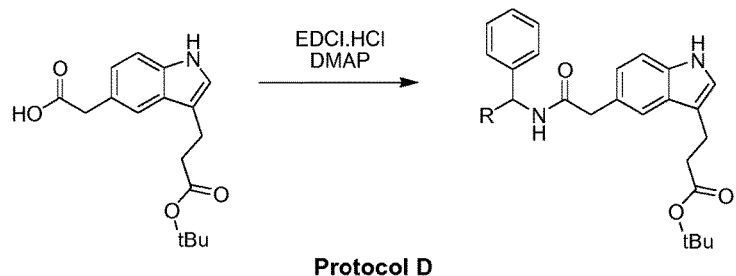
Figure 3B:
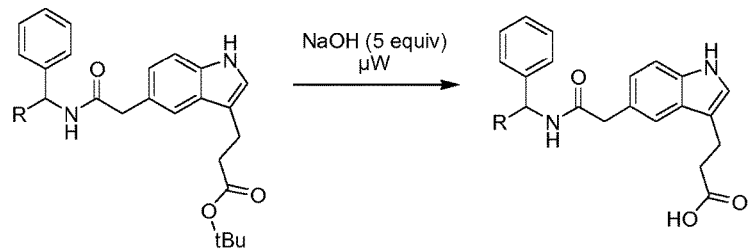
Figure 3C:
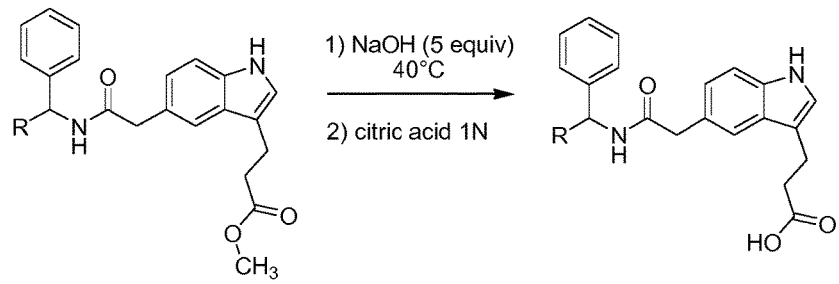
Figure 3D:
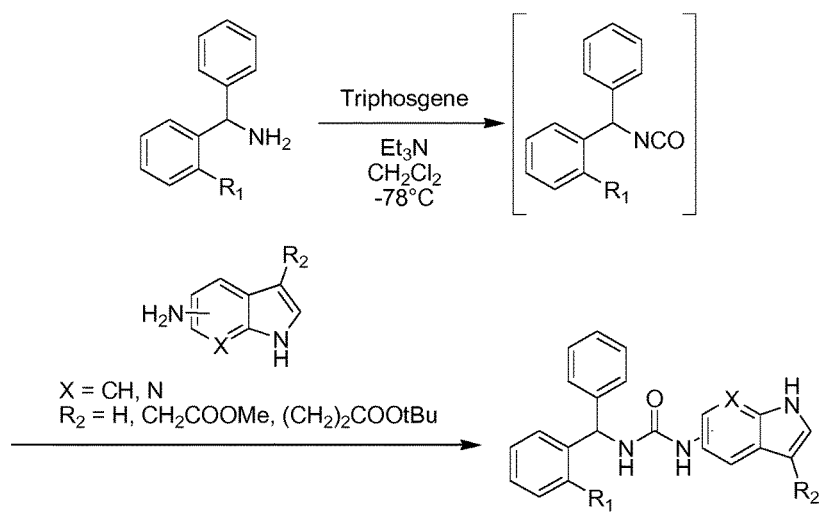

Compounds of formula (I) are generated using the Protocol D summarized in FIG. 3A. The tert-butyl esters used as precursors are synthesized following Protocol E (FIG. 3B). The methyl esters used as precursors are synthesized following Protocol F (FIG. 3C). Urea derivatives are synthetised following Protocol G (FIG. 3D).

FIG. 4—Inhibition of IL-17 Secretion Ex Vivo.

IL-17A (FIG. 4A) and IL-17F (FIG. 4B) secretion from murine splenocytes ex vivo. ($p<0.01$ vs. Vehicle, *$p<0.001$ vs. Vehicle, unpaired t test)

Figure 5A:
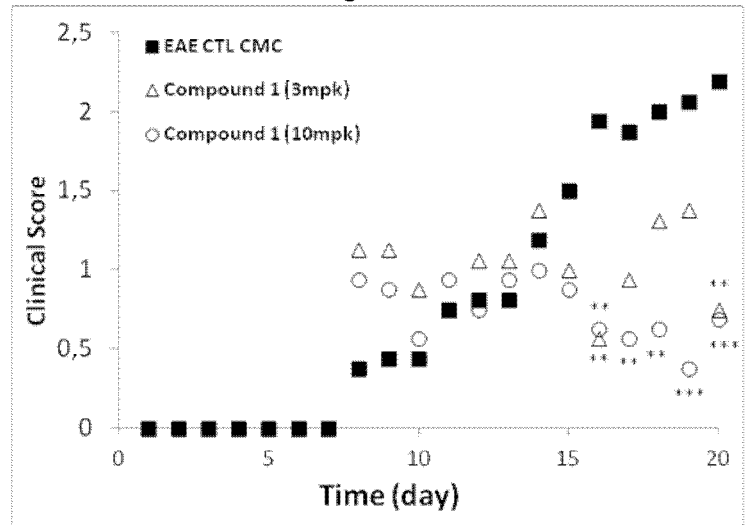
Figure 5B:
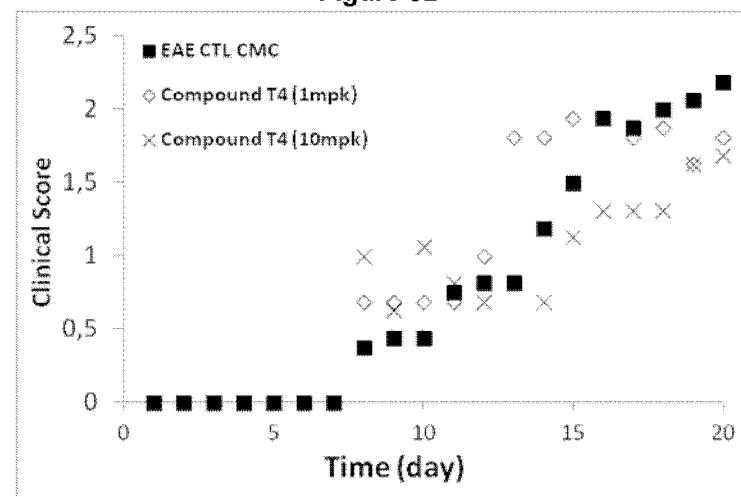

FIG. 5—Effect of Compounds According to the Invention on Clinical Score.

Figure 5C:
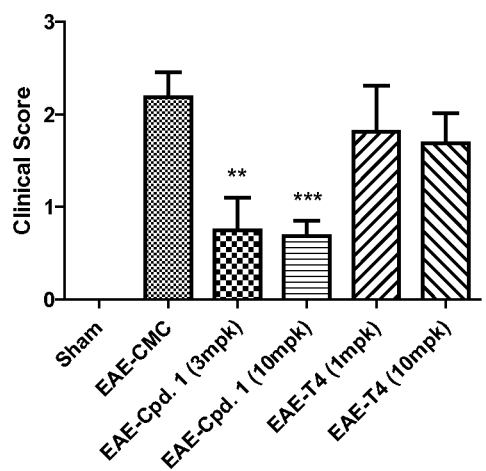

Clinical score from MOG-induced EAE mice treated with Cpd.1 (FIG. 5A) and comparative compound T-4 (FIG. 5B) scored by a visual inspection of behavior daily. FIG. 5C shows the EAE disease score for all animal groups at the day of sacrifice. ($p<0.01$ vs. Vehicle, *$p<0.001$ vs. Vehicle, unpaired t test).

DETAILED DESCRIPTION OF THE INVENTION

The present invention provides novel compounds that are modulators of RORgamma. These compounds, and pharmaceutical compositions comprising the same, are suitable for treating any disease wherein the activation of RORgamma has pathogenic effects, for instance in multiple autoimmune, inflammatory, fibrotic and cholestatic disorders.

The compounds according to the invention have the following formula (I):

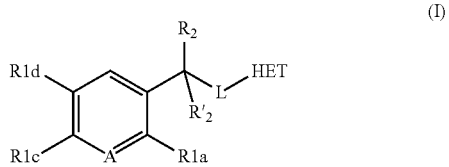

in which,

A is a C—R1b group or a nitrogen atom;

R1a is a hydrogen atom, a halogen atom, a nitrile group, a nitro group (NO2), an alkyl group, an alkyloxy group, an alkylthio group, an amino group, an alkylamino group, a dialkylamino group, or a heterocyclic group;

R1b is a hydrogen atom, an alkyloxy group, an alkyl group or a heterocyclic group;

or R1a and R1b can form, together with the carbon atoms to which they are attached, an aryl group or a heterocyclic group;

R1c is a hydrogen atom, a halogen atom, an alkyl group, an alkyloxy group, an alkylthio group, a heterocyclic group, a cyano group, an amido group or a hydroxyl group;

R1d is a hydrogen atom, a halogen atom, an alkyloxy group or an alkyl group;

R2 and R'2 are independently a hydrogen atom, an alkyl group, an alkynyl group, a cycloalkyl group, an aryl group or a heterocyclic group, with the proviso that R2 and R'2 are not simultaneously a hydrogen atom, or R2 and R2' can form, together with the carbon atom to which they are attached, a cycloalkyl group or a heterocycloalkyl group;

L is a NR7-CO—CH2, NR7-CO—NH, NR7-CO—C (CH3)2, NR7-CS—CH2, NR7-CS—NH, NR7-CS—C (CH3)2, NR7-SO2-CH2, NR7-SO2-C(CH3)2, CO—NH—CH2 or CO—NH—C(CH3)2 group;

HET is a heterocyclic group selected from:

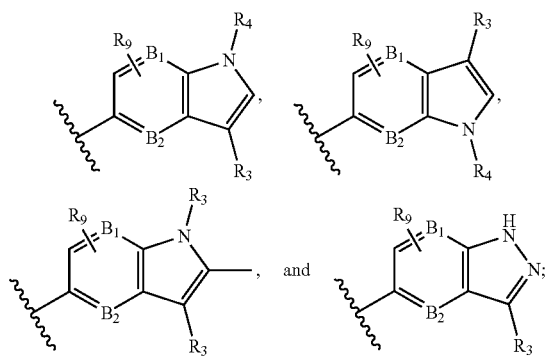

B1 and B2 are independently a nitrogen atom or a carbon atom;

R3 is a COR5 group, a CO-Alkyl-COR5 group or an alkyl group substituted by a COR5 group;

R4 is a hydrogen atom, an alkyl group or a hydroxyl group;

R5 is a hydroxyl group, an alkyloxy group, an alkyl group, a NR8R8' group or a —O—CH—(CH2-O—CO—R6)2 group;

R6 is a long chain alkyl group;

R7 is a hydrogen atom or an alkyl group;

R8 is a hydrogen atom or an alkyl group;

R8' is a hydrogen atom, an alkyl group, a C(=NH)NH2 group, a C(=NH)NHCOOtBu group or an alkoxy group; and R9 is a hydrogen atom, an alkyl group or a halogen atom.

As indicated below, in a particular embodiment, in the compound of formula (I) of the present invention:

an alkyl group may be substituted or unsubstituted, in particular a substituted or unsubstituted (C1-C7)alkyl or a (C1-C4)alkyl group;

an alkynyl group may be a substituted or unsubstituted alkynyl group, in particular a substituted or unsubstituted (C2-C6)alkynyl group;

a cycloalkyl group may be a substituted or unsubstituted cycloalkyl, such as a substituted or unsubstituted (C3-C14) cycloalkyl group an alkyloxy group may be either substituted or unsubstituted, such as a substituted or unsubstituted (C1-C7)alkyloxy or (C1-C4)alkyloxy group;

an alkylthio group may be either substituted or unsubstituted, such as a substituted or unsubstituted (C1-C7)alkylthio or (C1-C4)alkylthio group;

an alkylamino group may be a (C1-C7)alkylamino or (C1-C4)alkylamino group;

a dialkylamino group may be a (C1-C7)dialkylamino or (C1-C4)dialkylamino group;

an aryl group may be a substituted or unsubstituted (C6-C14)aryl group;

a heterocyclic group may be a substituted or unsubstituted heterocycloalkyl or heteroaryl group.

In a particular embodiment, the compound of the invention is of formula (I), wherein:

A is a C—R1b group or a nitrogen atom;

R1a is a hydrogen atom, a halogen atom, an alkyl group, an alkyloxy group, an amino group, an alkylamino group, a dialkylamino group or a heterocyclic group;

R1b is hydrogen, an alkyl group or a heterocyclic group;

R1a and R1b can form, together with the carbon atoms to which they are attached, an aryl group or a heterocyclic group;

R1c is a hydrogen atom, a halogen atom, an alkyl group, an alkyloxy group, a cyano group, an amido group or a hydroxyl group;

R1d is a hydrogen atom, a halogen atom, an alkyloxy group or an alkyl group;

R2 and R'2 are independently a hydrogen atom, an alkyl group, an alkynyl group, a cycloalkyl group, an aryl group or a heterocyclic group, with the proviso that R2 and R'2 are not simultaneously a hydrogen atom, or R2 and R2' can form, together with the carbon atom to which they are attached, a cycloalkyl group;

L is a NR7-CO—CH2, NR7-CO—NH, or CO—NH—CH2 group;

HET is a heterocyclic group selected from:

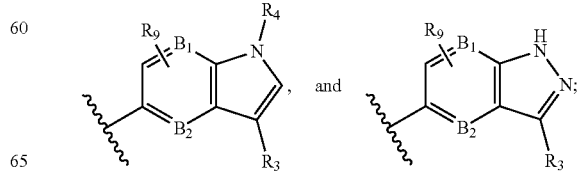

B1 and B2 are independently a nitrogen atom or a carbon atom;

R3 is a COR5 group, or a CO-Alkyl-COR5 group or an alkyl group substituted by a COR5 group;

R4 is a hydrogen atom or an alkyl group;

R5 is a hydroxyl group, an alkyloxy group, an alkyl group, a NR8R8' group or a —O—CH—(CH2-O—CO—R6)2 group;

R6 is a long chain alkyl group;

R7 is a hydrogen atom;

R8 is a hydrogen atom or an alkyl group;

R8' is a hydrogen atom, an alkyl group, a C(=NH)NH2 group or a C(=NH)NHCOOtBu group; and R9 is a hydrogen atom.

In another particular embodiment, the compound of the invention is of formula (I), wherein:

A is a C—R1b group or a nitrogen atom;

R1a is a halogen atom, a nitrile group, a nitro group (NO2), an alkyl group, an alkyloxy group, an alkylthio group, an amino group, an alkylamino group, a dialkylamino group or a heterocyclic group;

R1b is a hydrogen atom or a heterocyclic group;

wherein R1a and R1b can optionally form, together with the carbon atoms to which they are attached, an aryl group or a heterocyclic group;

R1c is a hydrogen atom, a halogen atom, an alkyl group, an alkyloxy group, an alkylthio or a heterocyclic group;

R1d is a hydrogen atom, a halogen atom or an alkyl group;

R2 and R'2 are independently a hydrogen atom, an alkyl group, a cycloalkyl group, an aryl group, or a heterocyclic group, with the proviso that R2 and R'2 are not simultaneously a hydrogen atom, or R2 and R2' can form, together with the carbon atom to which they are attached, a cycloalkyl group or a heterocycloalkyl group;

L is a NR7-CO—CH2, NR7-CO—NH, NR7-CO—C(CH3)2, NR7-CS—CH2, NR7-CS—NH, NR7-CS—C(CH3)2, NR7-SO2-CH2, NR7-SO2-C(CH3)2, CO—NH—CH2 or CO—NH—C(CH3)2 group;

HET is a heterocyclic group selected from:

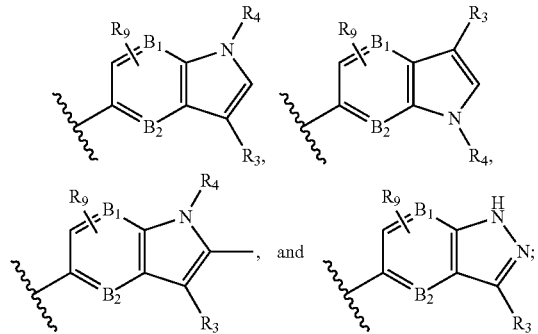

B1 and B2 are independently a nitrogen atom or a carbon atom;

R3 is a COR5 group or an alkyl group substituted by a COR5 group;

R4 is a hydrogen atom or a hydroxyl group;

R5 is a hydroxyl group, an alkyloxy group, a NR8R8' group or a —O—CH—(CH2-O—CO—R6)2 group;

R6 is a long chain alkyl group;

R7 is a hydrogen atom or an alkyl group;

R8 and R8' are independently a hydrogen atom or an alkyl group; and

R9 is a hydrogen atom, an alkyl group or a halogen atom.

The present invention also includes stereoisomers (diastereoisomers, enantiomers), pure or mixed, as well as racemic mixtures and geometric isomers, or tautomers of compounds of formula (I). The invention further includes salts, solvates (in particular hydrates) and polymorphs or crystalline forms of the compounds of formula (I).

According to a particular embodiment, the invention relates to a compound of formula (I) wherein:

A is a C—R1b group;

R1a is a halogen atom, a nitrile group, a nitro group (NO2), an alkyl group, an alkyloxy group, an alkylthio group, an alkylamino group, a dialkylamino group, a 1-pyrrolidinyl group, a 1-azepanyl group, a 4-morpholinyl group, a 1-piperidinyl group, a 1-piperazinyl group, wherein said piperidinyl or piperazinyl group can be optionally substituted by one or more alkyl groups;

R1b is a hydrogen atom, a 1-pyrrolidinyl group, a 1-azepanyl group, a 4-morpholinyl group, a 1-piperidinyl group or a 1-piperazinyl group;

R1c is a hydrogen atom, a halogen atom, an alkyl group or an alkyloxy group;

R2 is an alkyl group, a cycloalkyl group, an aryl group, or a heteroaryl group, and R'2 is a hydrogen atom.

In a particular embodiment, R1a is a hydrogen atom, a halogen atom (in particular a Br, Cl or F atom), a substituted or unsubstituted alkyl group (such as a C1-C4 alkyl group, in particular a methyl or ethyl group, more particularly a methyl group or a N(CH3)2-methyl group), an alkyloxy group (such as a OCH3, OCH2CH3 or O-isopropyl group), an amino group, an alkylamino group (such as a NH—CH3, NH—CH2CH3 or NH-isopropyl group), a dialkylamino group (such as a N(CH3)2 or N(CH2CH3)2 group) or a heterocyclic group. Illustrative substituted or unsubstituted heterocyclic group that may be in the R1a position include the heterocyclic groups selected from a pyridin group (such as a pyridin-1-yl group), a 1,2,3,6-tetrahydropyridin-1-yl group, a pyrrol group (such as a pyrrol-1-yl or a 2,5-dihydropyrrol-1-yl group), a piperidin group (such as a piperidin-1-yl group, for example a substituted piperidin-1-yl group such as a 2-CF3-piperidin-1-yl, a 3,3-difluoro-piperidin-1-yl, a 3,5-dimethyl-piperidin-1-yl, a 3-hydroxy-piperidin-1-yl or a 4,4-difluoro-piperidin-1-yl), a piperazin group (such as a piperazin-1-yl group, for example a 4-methyl-piperazin-1-yl or a 4-N-benzylpiperazin-1-yl group), a pyrrolidinyl group (such as a pyrrolidin-1-yl group), an azepanyl group (such as a azepan-1-yl group) and a morpholinyl group (such as a morpholin-1-yl group).

In a particular embodiment, R1a is a 1-piperidinyl group or a pyrrolidinyl group which is unsubstituted or substituted with one or more substituents such as one or more (such as two) halogen atoms, one or more (e.g two) alkyl groups (for example one or more, in particular two, methyl groups) or one or more —CF3 groups.

In a particular embodiment, A is a C—R1b group, wherein R1b is a hydrogen atom; an alkyl group, such as a C1-C4 alkyl group, in particular a methyl or ethyl group, more particularly a methyl group; or a heterocyclic group such as a piperidinyl group, for example a piperidin-1-yl group.

In a particular embodiment, R1a and R1b form, together with the carbon atoms to which they are attached, an aryl group or a heterocyclic group. In a particular embodiment, the group formed by R1a and R1b, and the part of the compound of formula (I) to which they are attached, is a substituted or unsubstituted indol group, such as a 1H-indol-7-yl group or a N-methyl-1H-indol-7yl group that is substituted or not, the resulting compound of formula (I) having the following structures, respectively:

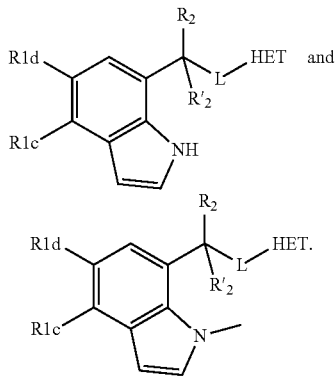

Other illustrative indol groups include the 1H-indol-5-yl and N-methyl-1H-indol-5-yl groups.

In a particular embodiment, the group formed by R1a and R1b, and the part of the compound of formula (I) to which they are attached, is a substituted or unsubstituted naphtyl group, i.e. the resulting compound of formula (I) has the following structure:

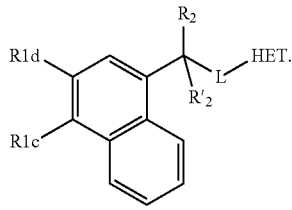

In a particular embodiment, the group formed by R1a and R1b, and the part of the compound of formula (I) to which they are attached, is a substituted or unsubstituted quinolin group, such as a substituted or unsubstituted quinolin-8-yl group, i.e. the resulting compound of formula (I) may have the following structure:

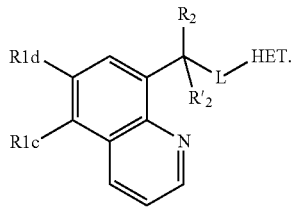

In another embodiment, R1c is a hydrogen atom, a halogen atom (for example a Br, Cl or F atom), a substituted or unsubstituted alkyl group (such as a C1-C4 alkyl group, in particular a methyl or ethyl group, more particularly a methyl group or a CF3 group), an alkyloxy group (such as a OCH3, OCH2CH3 or O-isopropyl group), a cyano group, an amido group or a hydroxyl group.

In a particular embodiment, R1d is a hydrogen atom, a halogen atom (such as a Br, Cl or F atom, more particularly a Br or Cl atom), a substituted or unsubstituted alkyl group (such as a C1-C4 alkyl group, in particular a methyl or ethyl group, more particularly a methyl group) or an alkyloxy group (such as a OCH3, OCH2CH3 or O-isopropyl group, more particularly a OCH3 group).

In a particular embodiment, R2 is a substituted or unsubstituted alkyl group (such as a C1-C6 alkyl group, in particular a methyl, ethyl, propyl, butyl group (e.g. an isobutyl group) or a pentyl group (e.g. an isopentyl group), a (tetrahydropyran-4-yl)methyl group, a 3-methyl-phenyl-methyl group, a cyclohexyl-methyl group); a substituted or unsubstituted alkynyl group (such as a propyn-2-yl group); a substituted or unsubstituted aryl group (such as a substituted or unsubstituted phenyl group, for example a phenyl, 3-fluoro-phenyl, 3-methyl-phenyl or 4-methyl-phenyl group; a substituted or unsubstituted thiazol group, such as a thiazol-2-yl or thiazol-5-yl group, a 2-methyl-thiazol-5-yl group or a 5-methyl-thiazol-2-yl group; a substituted or unsubstituted furan group, such as a 5-methyl-furan-2-yl group or a 4,5-dimethyl-furan-2-yl group; a substituted or unsubstituted thiophene group, such as a thiophen-2-yl group or a 5-methyl-thiophen-2-yl group; a substituted or unsubstituted pyridin group, such as a pyridin-2-yl group or a pyridin-3-yl group; a substituted or unsubstituted pyrimidin group, such as a pyrimidin-2-yl group); or a cycloalkyl group (such as a cyclopropyl group).

In a particular embodiment, R'2 is a hydrogen atom.

In a further particular embodiment, R2 and R'2 form, together with the carbon to which they are attached, a cycloalkyl group such as a cyclohexyl or cyclopentyl group.

In a particular embodiment, B1 and B2 are both nitrogen atoms. In another embodiment, B1 is a nitrogen atom and B2 is a carbon atom or B2 is a nitrogen atom and B1 is a carbon atom. In a preferred embodiment, B1 and B2 are carbon atoms.

Preferably L is NH—CO—CH2, NH—CO—NH, NH—SO2-CH2, CO—NH—CH2, N(CH3)-CO—CH2 or NH—CO—C(CH3)2. In a further preferable embodiment, L is selected in the group consisting of CO—NH—CH2, NH—CO—CH2 and NH—CO—NH.

In a particular embodiment, HET is selected from

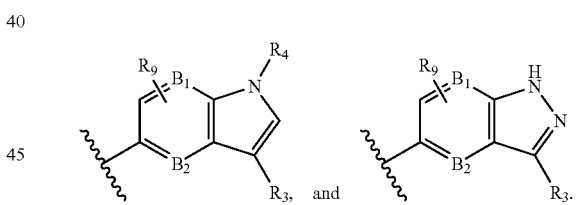

In a further particular embodiment, HET is one of the groups mentioned in the preceding sentence, B1 is CH or a nitrogen atom, and B2 is CH.

In a particular embodiment, R4 is a hydrogen atom or a substituted or unsubstituted alkyl group (such as a C1-C4 alkyl group, in particular such as a methyl or ethyl group, more particularly a methyl group).

In another particular embodiment, R3 is a COR5 group, a CO-alkyl-COR5 group or an alkyl group substituted by a COR5 group. In a more particular embodiment of the invention, the alkyl group in the CO-alkyl-COR5 group or the alkyl group substituted by a COR5 group is a (C1-C6) alkyl group, such as a methyl, ethyl, propyl (e.g. a n-propyl or isopropyl), a butyl (e.g. a n-butyl, isobutyl or tert-butyl), a pentyl or a hexyl group. Illustrative R3 groups include the groups selected from (CH2)2-CO—CH3, (CH2)2CONH (C=NH)NH2, (CH2)2CONH(C=NH)NHCOOtBu, (CH2)2-CO—NH(CH3), (CH2)2-CO—NH(IsoPr), (CH2)2-COOCH(CH2COOC15H31)2, (CH2)2COOEt, (CH2)2-

COOEt, (CH2)2COOH, (CH2)2-COOH, (CH2)2-COOtBu, (CH2)3-COOEt, (CH2)3-COOH, (CH2)4-COOEt, (CH2)4-COOH, CH2-COCH3, CH2-CON(CH3)(OCH3), CH2-CO—N(CH3)2, CH2-COOCH3, CH2-COOH, CHO, CO—(CH2)2-COOEt, CO—(CH2)2-COOH, CO—(CH2)3-COOEt, CO—(CH2)3-COOH and COOH.

In a particular embodiment, R9 is a hydrogen atom.

In a further particular embodiment, the invention relates to a compound of formula (I), in which R1a is a heterocyclic group, a halogen atom (such as a Br, Cl or F atom), a substituted or unsubstituted alkyl group, a dialkylamino group, a dialkylaminoalkyl group or an alkyloxy group;

A is a nitrogen atom or a C—R1b group;

R1b is an alkyl group or a hydrogen atom;

or R1a and R1b can form, together with the carbon atoms to which they are attached, an aryl group or a heterocyclic group;

R1c is a hydrogen atom, a halogen atom, a substituted or unsubstituted alkyl group, a cyano group, or an alkyloxy group;

R1d is a hydrogen atom, a halogen atom, a substituted or unsubstituted alkyl group or an alkyloxy group;

R2 is a substituted or unsubstituted alkyl group; a substituted or unsubstituted aryl group; or a cycloalkyl group;

R'2 is a hydrogen atom;

or R2 and R'2 can form together with the carbon atom to which they are attached a cycloalkyl group;

L is a CO—NH—CH2, NH—CO—CH2 or NH—CO—NH group;

HET is selected from

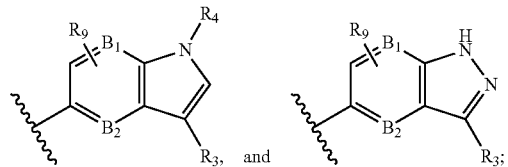

and

B1 and B2 are CH;

R4 is a hydrogen atom or a substituted or unsubstituted alkyl group;

R3 is a CO-alkyl-COR5 group or an alkyl group substituted by a COR5 group; and

R9 is a hydrogen atom.

In a particular embodiment, the invention relates to a compound of formula (I), in which A is a CH group, R1a is a heterocycloalkyl group, R1c is a hydrogen atom or an alkyl group, R2 is a phenyl group or an alkyl group, L represents a NH—CO—CH2 group or a NH—CO—NH group, HET has the following structure

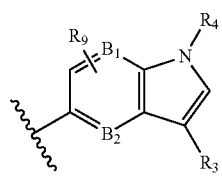

in which B1 and B2 are carbon atoms, R9 is a hydrogen atom, R4 is a hydrogen atom and R3 represents a CH2-CH2-COR5 group, wherein R5 is a hydroxyl group or an alkyloxy group.

In a particular embodiment, the R3 group is a —CH2-CH2-COR5 group.

In a particular embodiment, the R2 is a hydrogen atom and R2' is a phenyl group optionally substituted with one or more halogen atoms, in particular with a fluorine atom.

In a particular embodiment, R2 is a hydrogen atom and R2' is a pyridine group.

In a further particular embodiment, the invention relates to a compound of formula (I), in which A is a CH group, R1a is a piperidinyl group, R1c is a hydrogen atom or an alkyl group, R2 is a heterocyclic group, preferably a furan-2-yl group substituted or not by an alkyl group, L represents a NH—CO—CH2 group, HET has the following structure

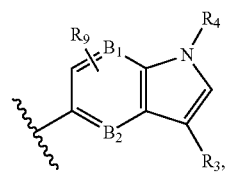

in which B1 and B2 are carbon atoms, R9 is a hydrogen atom, R4 is a hydrogen atom and R3 represents a CH2-CH2-COR5 group, wherein R5 is a hydroxyl group or an alkyloxy group.

The term "alkyl" refers to a saturated hydrocarbon radical that is linear or branched, substituted or not, having preferably from one to seven, and even more preferably from one to four carbon atoms, such as methyl, ethyl, n-propyl, isopropyl, n-butyl, isobutyl, tert-butyl, or sec-butyl. The alkyl group can be optionally substituted by one or more halogen atoms, by an aryl group or by a cycloalkyl group. Further possible substituents of an alkyl group also include one or more substituents selected from an amino group, an alkylamino group, a dialkylamino group, and an alkynyl group.

The term alkynyl denotes linear or branched hydrocarbon groups containing from 2 to 6 carbon atoms and containing at least one triple bond. Examples of alkynyl containing from 3 to 6 carbon atoms are 1-propynyl, 2-propynyl, 1-butynyl, 2-butynyl, 3-butynyl, 1-pentynyl, 2-pentynyl, 3-pentynyl, 4-pentynyl, 1-hexynyl, 2-hexynyl, 3-hexynyl, 4-hexynyl, 5-hexynyl and the isomeric forms thereof.

The term "long chain alkyl group" refers to a saturated hydrocarbon radical that is linear or branched, substituted or not, having preferably from ten to twenty carbon atoms. In a particular embodiment, the long chain alkyl group has preferably 12 to 18 carbon atoms, in particular 12, 13, 14, 15, 16, 17 or 18 carbon atoms, more particularly 15 carbon atoms. The long chain alkyl group may be substituted by the substituents provided above for an alkyl. However, in a particular embodiment, the long chain alkyl group is an unsubstituted alkyl group.

The terms "alkyloxy" and "alkylthio" refer to an alkyl group as defined above that is linked to the remainder of the compound by an oxygen or sulfur atom, respectively.

The term "alkylamino" refers to monoalkylamino (—NHR) or dialkylamino (—NRR') group where R and R' independently represent an alkyl group as defined above. In a particular embodiment, the alkyl group(s) of the alkylamino group may be substituted or not with a cycloalkyl group, an aryl group, a heterocyclic group, or an alkyloxycarbonyl group.

The term "cycloalkylamino" refers to a —NH-cycloalkyl group or a —N(alkyl)cycloalkyl group.

The term "amino group" designates a —NH₂ group.

The term "hydroxyl group" refers to a —OH group.

The term "cycloalkyl" designates a substituted or unsubstituted alkyl group that forms one cycle having preferably from three to fourteen carbon atoms, and more preferably five to six carbon atoms, such as cyclopropyl, cyclopentyl and cyclohexyl. The cycloalkyl group of the present invention may be unsubstituted, or substituted, for example with an alkyl group, in particular with a alkyl group substituted with one or more halogen atoms, such as the CF3 group.

The term "carbonyl" designates a CO group.

The term "amido" designates a CO—NH2 group.

The term "aryl" designates an aromatic group, substituted or not, having preferably from six to fourteen carbon atoms such as phenyl, a-naphtyl, b-naphtyl, or biphenyl.

The term "heterocyclic" refers to a heterocycloalkyl group or a heteroaryl group. The term "heterocycloalkyl" group refers to a cycloalkyl as indicated above that further comprises one or several heteroatoms selected among nitrogen, oxygen or sulfur. They generally comprise from four to fourteen carbon atoms, such as morpholinyl, piperazinyl, piperidinyl, pyrrolidinyl, tetrahydropyranyl, dithiolanyl and azepanyl groups. In a particular embodiment, the heterocycloalkyl group is a 5-, 6- or 7-membered cycle. The term "heteroaryl" refers to an aryl group as indicated above, substituted or not, that further comprises one or several heteroatoms selected among nitrogen, oxygen or sulfur. They generally comprise from four to fourteen carbon atoms. In a particular embodiment, the heteroaryl group is a 5-, 6- or 10-membered cycle. Representative heteroaryl groups include a pyridinyl, pyrimidinyl, furanyl, thiophenyl, quinolinyl, and isoquinolinyl group.

The aryl group or the heterocyclic group can be optionally substituted by one or more halogen atom(s), alkyl group(s), or alkyloxy group(s).

By halogen atom, an atom of bromine, chlorine, fluorine or iodine is understood, in particular an atom of bromine, chlorine or fluorine.

Specific compounds according to the invention include:

Cpd.1: 3-{5-[({phenyl[2-(piperidin-1-yl)phenyl]methyl}carbamoyl)methyl]-1H-indol-3-yl}propanoic acid;

Cpd.2: tert-butyl 3-{5-[({phenyl[2-(piperidin-1-yl)phenyl]methyl}carbamoyl)methyl]-1H-indol-3-yl}propanoate;

Cpd.3: 3-[5-({[(3-fluorophenyl)[2-(piperidin-1-yl)phenyl]methyl]carbamoyl}methyl)-1H-indol-3-yl]propanoic acid;

Cpd.4: tert-butyl 3-[5-({[(3-fluorophenyl)[2-(piperidin-1-yl)phenyl]methyl]carbamoyl}methyl)-1H-indol-3-yl]propanoate;

Cpd.5: 3-{5-[({[4-methyl-2-(pyrrolidin-1-yl)phenyl](phenyl)methyl}carbamoyl)methyl]-1H-indol-3-yl}propanoic acid;

Cpd.6: tert-butyl 3-{5-[({[4-methyl-2-(pyrrolidin-1-yl)phenyl](phenyl)methyl}carbamoyl)methyl]-1H-indol-3-yl}propanoate;

Cpd.7: 3-[5-({[(2-chloro-4-methylphenyl)(phenyl)methyl]carbamoyl}methyl)-1H-indol-3-yl]propanoic acid;

Cpd.8: tert-butyl 3-[5-({[(2-chloro-4-methylphenyl)(phenyl)methyl]carbamoyl}methyl)-1H-indol-3-yl]propanoate;

Cpd.9: 3-[5-({[(2-bromo-4-methylphenyl)(phenyl)methyl]carbamoyl}methyl)-1H-indol-3-yl]propanoic acid;

Cpd.10: tert-butyl 3-[5-({[(2-bromo-4-methylphenyl)(phenyl)methyl]carbamoyl}methyl)-1H-indol-3-yl]propanoate;

Cpd.11: 3-[5-({[(2,4-dimethylphenyl)(phenyl)methyl]carbamoyl}methyl)-1H-indol-3-yl]propanoic acid;

Cpd.12: tert-butyl 3-[5-({[(2,4-dimethylphenyl)(phenyl)methyl]carbamoyl}methyl)-1H-indol-3-yl]propanoate;

Cpd.13: 3-[5-({[(2,5-dimethylphenyl)(phenyl)methyl]carbamoyl}methyl)-1H-indol-3-yl]propanoic acid;

Cpd.14: tert-butyl 3-[5-({[(2,5-dimethylphenyl)(phenyl)methyl]carbamoyl}methyl)-1H-indol-3-yl]propanoate;

Cpd.15: 3-{5-[({[6-methyl-2-(pyrrolidin-1-yl)pyridin-3-yl](phenyl)methyl}carbamoyl)methyl]-1H-indol-3-yl}propanoic acid;

Cpd.16: tert-butyl 3-{5-[({[6-methyl-2-(pyrrolidin-1-yl)pyridin-3-yl](phenyl)methyl}carbamoyl)methyl]-1H-indol-3-yl}propanoate;

Cpd.17: 3-[5-({[(2-fluoro-4-methylphenyl)(phenyl)methyl]carbamoyl}methyl)-1H-indol-3-yl]propanoic acid;

Cpd.18: tert-butyl 3-[5-({[(2-fluoro-4-methylphenyl)(phenyl)methyl]carbamoyl}methyl)-1H-indol-3-yl]propanoate;

Cpd.19: 3-[5-({[(2-fluoro-5-methylphenyl)(phenyl)methyl]carbamoyl}methyl)-1H-indol-3-yl]propanoic acid;

Cpd.20: tert-butyl 3-[5-({[(2-fluoro-5-methylphenyl)(phenyl)methyl]carbamoyl}methyl)-1H-indol-3-yl]propanoate;

Cpd.21: 3-[5-({[(2,4-dimethylphenyl)(pyridin-2-yl)methyl]carbamoyl}methyl)-1H-indol-3-yl]propanoic acid;

Cpd.22: tert-butyl 3-[5-({[(2,4-dimethylphenyl)(pyridin-2-yl)methyl]carbamoyl}methyl)-1H-indol-3-yl]propanoate;

Cpd.23: 3-[5-({[phenyl({2-[2-(trifluoromethyl)piperidin-1-yl]phenyl})methyl]carbamoyl}-methyl)-1H-indol-3-yl]propanoic acid;

Cpd.24: tert-butyl 3-[5-({[phenyl({2-[2-(trifluoromethyl)piperidin-1-yl]phenyl})methyl]carbamoyl}methyl)-1H-indol-3-yl]propanoate;

Cpd.25: 3-{5-[({[2-(3,5-dimethylpiperidin-1-yl)phenyl](phenyl)methyl}carbamoyl)methyl]-1H-indol-3-yl}propanoic acid;

Cpd.26: tert-butyl 3-{5-[({[2-(3,5-dimethylpiperidin-1-yl)phenyl](phenyl)methyl}carbamoyl)methyl]-1H-indol-3-yl}propanoate;

Cpd.27: 3-[5-({[(2,4-dimethylphenyl)(pyridin-3-yl)methyl]carbamoyl}methyl)-1H-indol-3-yl]propanoic acid;

Cpd.28: tert-butyl 3-[5-({[(2,4-dimethylphenyl)(pyridin-3-yl)methyl]carbamoyl}methyl)-1H-indol-3-yl]propanoate;

Cpd.29: 3-{5-[({3-methyl-1-[2-(piperidin-1-yl)phenyl]butyl}carbamoyl)methyl]-1H-indol-3-yl}propanoic acid;

Cpd.30: tert-butyl 3-{5-[({3-methyl-1-[2-(piperidin-1-yl)phenyl]butyl}carbamoyl)methyl]-1H-indol-3-yl}propanoate;

Cpd.31: 3-[5-({[(5-methylquinolin-8-yl)(phenyl)methyl]carbamoyl}methyl)-1H-indol-3-yl]propanoic acid;

Cpd.32: tert-butyl 3-[5-({[(5-methylquinolin-8-yl)(phenyl)methyl]carbamoyl}methyl)-1H-indol-3-yl]propanoate;

Cpd.33: 3-[5-({[(4-chloro-2-methylphenyl)(phenyl)methyl]carbamoyl}methyl)-1H-indol-3-yl]propanoic acid;

Cpd.34: tert-butyl 3-[5-({[(4-chloro-2-methylphenyl)(phenyl)methyl]carbamoyl}methyl)-1H-indol-3-yl]propanoate;

Cpd.35: 3-{5-[({[2-(azepan-1-yl)phenyl](phenyl)methyl}carbamoyl)methyl]-1H-indol-3-yl}propanoic acid;

Cpd.36: tert-butyl 3-{5-[({[2-(azepan-1-yl)phenyl](phenyl)methyl}carbamoyl)methyl]-1H-indol-3-yl}propanoate;

Cpd.37: 3-[5-({[(4-methylnaphthalen-1-yl)(phenyl)methyl]carbamoyl}methyl)-1H-indol-3-yl]propanoic acid;

Cpd.38: tert-butyl 3-[5-({[(4-methylnaphthalen-1-yl)(phenyl)methyl]carbamoyl}methyl)-1H-indol-3-yl]propanoate;
Cpd.39: 2-{5-[({phenyl[2-(piperidin-1-yl)phenyl]methyl}carbamoyl)methyl]-1H-indol-3-yl}acetic acid; and
Cpd.40: methyl 2-{5-[({phenyl[2-(piperidin-1-yl)phenyl]methyl}carbamoyl)methyl]-1H-indol-3-yl}acetate;
Cpd.41 tert-butyl 3-[5-({[(2-chloro-5-methylphenyl)(phenyl)methyl]carbamoyl}methyl)-1H-indol-3-yl]propanoate;
Cpd.42 3-[5-({[(2-chloro-5-methylphenyl)(phenyl)methyl]carbamoyl}methyl)-1H-indol-3-yl]propanoic acid;
Cpd.43 tert-butyl 3-[5-({[(4-bromo-2-methylphenyl)(phenyl)methyl]carbamoyl}methyl)-1H-indol-3-yl]propanoate;
Cpd.44 3-[5-({[(4-bromo-2-methylphenyl)(phenyl)methyl]carbamoyl}methyl)-1H-indol-3-yl]propanoic acid;
Cpd.45 tert-butyl 3-[5-({[(4-fluoro-2-methylphenyl)(phenyl)methyl]carbamoyl}methyl)-1H-indol-3-yl]propanoate;
Cpd.46 3-[5-({[(4-fluoro-2-methylphenyl)(phenyl)methyl]carbamoyl}methyl)-1H-indol-3-yl]propanoic acid;
Cpd.47 tert-butyl 3-{5-[({phenyl[2-(pyrrolidin-1-yl)-4-(trifluoromethyl)phenyl]methyl}carbamoyl)methyl]-1H-indol-3-yl}propanoate;
Cpd.48 3-{5-[({phenyl[2-(pyrrolidin-1-yl)-4-(trifluoromethyl)phenyl]methyl}carbamoyl)methyl]-1H-indol-3-yl}propanoic acid;
Cpd.49 tert-butyl 3-{5-[({[4-bromo-2-(pyrrolidin-1-yl)phenyl](phenyl)methyl}carbamoyl)methyl]-1H-indol-3-yl}propanoate;
Cpd.50 3-{5-[({[4-bromo-2-(pyrrolidin-1-yl)phenyl](phenyl)methyl}carbamoyl)methyl]-1H-indol-3-yl}propanoic acid;
Cpd.51 tert-butyl 3-[5-({[(2-aminophenyl)(phenyl)methyl]carbamoyl}methyl)-1H-indol-3-yl]propanoate;
Cpd.52 3-[5-({[(2-aminophenyl)(phenyl)methyl]carbamoyl}methyl)-1H-indol-3-yl]propanoic acid;
Cpd.53 tert-butyl 3-{5-[({[2-(dimethylamino)phenyl](phenyl)methyl}carbamoyl)methyl]-1H-indol-3-yl}propanoate;
Cpd.54 3-{5-[({[2-(dimethylamino)phenyl](phenyl)methyl}carbamoyl)methyl]-1H-indol-3-yl}propanoic acid;
Cpd.55 tert-butyl 3-{5-[({phenyl[2-(piperidin-1-yl)phenyl]methyl}carbamoyl)amino]-1H-indol-3-yl}propanoate;
Cpd.56 3-{5-[({phenyl[2-(piperidin-1-yl)phenyl]methyl}carbamoyl)amino]-1H-indol-3-yl}propanoic acid;
Cpd.57 tert-butyl 3-{5-[({3-methyl-1-[2-(morpholin-4-yl)phenyl]butyl}carbamoyl)methyl]-1H-indol-3-yl}propanoate;
Cpd.58 3-{5-[({3-methyl-1-[2-(morpholin-4-yl)phenyl]butyl}carbamoyl)methyl]-1H-indol-3-yl}propanoic acid;
Cpd.59 tert-butyl 3-{5-[({[4-cyano-2-(pyrrolidin-1-yl)phenyl](phenyl)methyl}carbamoyl)methyl]-1H-indol-3-yl}propanoate;
Cpd.60 3-{5-[({[4-cyano-2-(pyrrolidin-1-yl)phenyl](phenyl)methyl}carbamoyl)methyl]-1H-indol-3-yl}propanoic acid;
Cpd.61 tert-butyl 3-{5-[({[5-chloro-2-(piperidin-1-yl)phenyl](phenyl)methyl}carbamoyl)methyl]-1H-indol-3-yl}propanoate;
Cpd.62 3-{5-[({[5-chloro-2-(piperidin-1-yl)phenyl](phenyl)methyl}carbamoyl)methyl]-1H-indol-3-yl}propanoic acid;
Cpd.63 3-{5-[({[4-carbamoyl-2-(pyrrolidin-1-yl)phenyl](phenyl)methyl}carbamoyl)methyl]-1H-indol-3-yl}propanoic acid;
Cpd.64 methyl 2-{5-[({[4-methyl-2-(pyrrolidin-1-yl)phenyl](phenyl)methyl}carbamoyl)methyl]-1H-indol-3-yl}acetate;
Cpd.65 2-{5-[({[4-methyl-2-(pyrrolidin-1-yl)phenyl](phenyl)methyl}carbamoyl)methyl]-1H-indol-3-yl}acetic acid;
Cpd.66 methyl 2-{5-[({[4-bromo-2-(pyrrolidin-1-yl)phenyl](phenyl)methyl}carbamoyl)methyl]-1H-indol-3-yl}acetate;
Cpd.67 2-{5-[({[4-bromo-2-(pyrrolidin-1-yl)phenyl](phenyl)methyl}carbamoyl)methyl]-1H-indol-3-yl}acetic acid;
Cpd.68 methyl 2-{5-[({phenyl[2-(piperidin-1-yl)phenyl]methyl}carbamoyl)amino]-1H-indol-3-yl}acetate;
Cpd.69 2-{5-[({phenyl[2-(piperidin-1-yl)phenyl]methyl}carbamoyl)amino]-1H-indol-3-yl}acetic acid;
Cpd.70 methyl 2-{5-[({[2-(dimethylamino)phenyl](phenyl)methyl}carbamoyl)methyl]-1H-indol-3-yl}acetate;
Cpd.71 2-{5-[({[2-(dimethylamino)phenyl](phenyl)methyl}carbamoyl)methyl]-1H-indol-3-yl}acetic acid;
Cpd.72 methyl 2-{5-[({phenyl[2-(pyrrolidin-1-yl)phenyl]methyl}carbamoyl)methyl]-1H-indol-3-yl}acetate;
Cpd.73 2-{5-[({phenyl[2-(pyrrolidin-1-yl)phenyl]methyl}carbamoyl)methyl]-1H-indol-3-yl}acetic acid;
Cpd.74 methyl 2-{5-[({[2-(azepan-1-yl)phenyl](phenyl)methyl}carbamoyl)methyl]-1H-indol-3-yl}acetate;
Cpd.75 2-{5-[({[2-(azepan-1-yl)phenyl](phenyl)methyl}carbamoyl)methyl]-1H-indol-3-yl}acetic acid;
Cpd.76 tert-butyl 3-{5-[({[4-methyl-2-(piperidin-1-yl)phenyl](phenyl)methyl}carbamoyl)methyl]-1H-indol-3-yl}propanoate;
Cpd.77 3-{5-[({[4-methyl-2-(piperidin-1-yl)phenyl](phenyl)methyl}carbamoyl)methyl]-1H-indol-3-yl}propanoic acid;
Cpd.78 tert-butyl 3-{5-[({phenyl[2-(pyrrolidin-1-yl)phenyl]methyl}carbamoyl)methyl]-1H-indol-3-yl}propanoate;
Cpd.79 3-{5-[({phenyl[2-(pyrrolidin-1-yl)phenyl]methyl}carbamoyl)methyl]-1H-indol-3-yl}propanoic acid;
Cpd.80 tert-butyl 3-{5-[({[4-methyl-2-(morpholin-4-yl)phenyl](phenyl)methyl}carbamoyl)methyl]-1H-indol-3-yl}propanoate;
Cpd.81 3-{5-[({[4-methyl-2-(morpholin-4-yl)phenyl](phenyl)methyl}carbamoyl)methyl]-1H-indol-3-yl}propanoic acid;
Cpd.82 tert-butyl 3-[5-({[(4-methoxy-2-methylphenyl)(phenyl)methyl]carbamoyl}methyl)-1H-indol-3-yl]propanoate;
Cpd.83 3-[5-({[(4-methoxy-2-methylphenyl)(phenyl)methyl]carbamoyl}methyl)-1H-indol-3-yl]propanoic acid;
Cpd.84 methyl 2-{5-[({[4-chloro-2-(pyrrolidin-1-yl)phenyl](phenyl)methyl}carbamoyl)methyl]-1H-indol-3-yl}acetate;
Cpd.85 2-{5-[({[4-chloro-2-(pyrrolidin-1-yl)phenyl](phenyl)methyl}carbamoyl)methyl]-1H-indol-3-yl}acetic acid;
Cpd.86 methyl 2-{5-[({[4-methyl-2-(piperidin-1-yl)phenyl](phenyl)methyl}carbamoyl)methyl]-1H-indol-3-yl}acetate;
Cpd.87 2-{5-[({[4-methyl-2-(piperidin-1-yl)phenyl](phenyl)methyl}carbamoyl)methyl]-1H-indol-3-yl}acetic acid;

Cpd.88 methyl 2-{5-[({phenyl[2-(pyrrolidin-1-yl)-4-(trifluoromethyl)phenyl]methyl}carbamoyl)methyl]-1H-indol-3-yl}acetate;

Cpd.89 2-{5-[({phenyl[2-(pyrrolidin-1-yl)-4-(trifluoromethyl)phenyl]methyl}carbamoyl)methyl]-1H-indol-3-yl}acetic acid;

Cpd.90 tert-butyl 3-{5-[({[4-chloro-2-(pyrrolidin-1-yl)phenyl](phenyl)methyl}carbamoyl)methyl]-1H-indol-3-yl}propanoate;

Cpd.91 3-{5-[({[4-chloro-2-(pyrrolidin-1-yl)phenyl](phenyl)methyl}carbamoyl)methyl]-1H-indol-3-yl}propanoic acid;

Cpd.92 tert-butyl 3-{5-[({[4-fluoro-2-(pyrrolidin-1-yl)phenyl](phenyl)methyl}carbamoyl)methyl]-1H-indol-3-yl}propanoate;

Cpd.93 3-{5-[({[4-fluoro-2-(pyrrolidin-1-yl)phenyl](phenyl)methyl}carbamoyl)methyl]-1H-indol-3-yl}propanoic acid;

Cpd.94 tert-butyl 3-{5-[({phenyl[2-(piperidin-1-yl)phenyl]methyl}carbamoyl)amino]-1H-pyrrolo[2,3-b]pyridin-3-yl}propanoate;

Cpd.95 3-{5-[({phenyl[2-(piperidin-1-yl)phenyl]methyl}carbamoyl)amino]-1H-pyrrolo[2,3-b]pyridin-3-yl}propanoic acid;

Cpd.96 methyl 2-{5-[({[4-methyl-2-(morpholin-4-yl)phenyl](phenyl)methyl}carbamoyl)methyl]-1H-indol-3-yl}acetate;

Cpd.97 2-{5-[({[4-methyl-2-(morpholin-4-yl)phenyl](phenyl)methyl}carbamoyl)methyl]-1H-indol-3-yl}acetic acid;

Cpd.98 tert-butyl 3-[5-({[(2-methoxy-4-methylphenyl)(phenyl)methyl]carbamoyl}methyl)-1H-indol-3-yl]propanoate;

Cpd.99 3-[5-({[(2-methoxy-4-methyl phenyl)(phenyl)methyl]carbamoyl}methyl)-1H-indol-3-yl]propanoic acid;

Cpd.100 tert-butyl 3-[5-({[(2,4-dimethylphenyl)(5-methylthiophen-2-yl)methyl]carbamoyl}methyl)-1H-indol-3-yl]propanoate;

Cpd.101 3-[5-({[(2,4-dimethyl phenyl)(5-methylthiophen-2-yl)methyl]carbamoyl}methyl)-1H-indol-3-yl]propanoic acid;

Cpd.102 tert-butyl 3-{5-[({[4-methyl-2-(4-methylpiperazin-1-yl)phenyl](phenyl)methyl}carbamoyl)methyl]-1H-indol-3-yl}propanoate;

Cpd.103 3-{5-[({[4-methyl-2-(4-methylpiperazin-1-yl)phenyl](phenyl)methyl}carbamoyl)methyl]-1H-indol-3-yl}propanoic acid;

Cpd.104 tert-butyl 3-[5-({[3-methyl-1-(naphthalen-1-yl)butyl]carbamoyl}methyl)-1H-indol-3-yl]propanoate;

Cpd.105 3-[5-({[3-methyl-1-(naphthalen-1-yl)butyl]carbamoyl}methyl)-1H-indol-3-yl]propanoic acid;

Cpd.106 tert-butyl 3-{5-[({phenyl[2-(1H-pyrrol-1-yl)phenyl]methyl}carbamoyl)methyl]-1H-indol-3-yl}propanoate;

Cpd.107 3-{5-[({phenyl[2-(1H-pyrrol-1-yl)phenyl]methyl}carbamoyl)methyl]-1H-indol-3-yl}propanoic acid;

Cpd.108 tert-butyl 3-{5-[({[4-methoxy-2-(pyrrolidin-1-yl)phenyl](phenyl)methyl}carbamoyl)methyl]-1H-indol-3-yl}propanoate;

Cpd.109 3-{5-[({[4-methoxy-2-(pyrrolidin-1-yl)phenyl](phenyl)methyl}carbamoyl)methyl]-1H-indol-3-yl}propanoic acid;

Cpd.110 tert-butyl 3-{5-[({[4-methoxy-2-(piperidin-1-yl)phenyl](phenyl)methyl}carbamoyl)methyl]-1H-indol-3-yl}propanoate;

Cpd.111 3-{5-[({[4-methoxy-2-(piperidin-1-yl)phenyl](phenyl)methyl}carbamoyl)methyl]-1H-indol-3-yl}propanoic acid;

Cpd.112 N,N-dimethyl-2-{5-[({[4-methyl-2-(morpholin-4-yl)phenyl](phenyl)methyl}carbamoyl)methyl]-1H-indol-3-yl}acetamide;

Cpd.113 tert-butyl 3-{5-[({[5-methyl-2-(piperidin-1-yl)phenyl](phenyl)methyl}carbamoyl)methyl]-1H-indol-3-yl}propanoate;

Cpd.114 3-{5-[({[5-methyl-2-(piperidin-1-yl)phenyl](phenyl)methyl}carbamoyl)methyl]-1H-indol-3-yl}propanoic acid;

Cpd.115 N-methyl-3-{5-[({phenyl[2-(piperidin-1-yl)phenyl]methyl}carbamoyl)methyl]-1H-indol-3-yl}propanamide;

Cpd.116 tert-butyl 3-{5-[({[5-bromo-2-(pyrrolidin-1-yl)phenyl](phenyl)methyl}carbamoyl)methyl]-1H-indol-3-yl}propanoate;

Cpd.117 3-{5-[({[5-bromo-2-(pyrrolidin-1-yl)phenyl](phenyl)methyl}carbamoyl)methyl]-1H-indol-3-yl}propanoic acid;

Cpd.118 3-{5-[({phenyl[2-(piperidin-1-yl)phenyl]methyl}carbamoyl)methyl]-1H-indol-3-yl}-N-(propan-2-yl)propanamide;

Cpd.119 tert-butyl 3-{5-[({[2-(ethylamino)-4-methylphenyl](phenyl)methyl}carbamoyl)methyl]-1H-indol-3-yl}propanoate;

Cpd.120 3-{5-[({[2-(ethylamino)-4-methylphenyl](phenyl)methyl}carbamoyl)methyl]-1H-indol-3-yl}propanoic acid;

Cpd.121 tert-butyl 3-(5-{[({2-[(dimethylamino)methyl]phenyl}(phenyl)methyl)carbamoyl]methyl}-1H-indol-3-yl)propanoate;

Cpd.122 3-(5-{[({2-[(dimethylamino)methyl]phenyl}(phenyl)methyl)carbamoyl]methyl}-1H-indol-3-yl)propanoic acid;

Cpd.123 tert-butyl 3-{5-[({[2-(3-hydroxypiperidin-1-yl)phenyl](phenyl)methyl}carbamoyl)methyl]-1H-indol-3-yl}propanoate;

Cpd.124 3-{5-[({[2-(3-hydroxypiperidin-1-yl)phenyl](phenyl)methyl}carbamoyl)methyl]-1H-indol-3-yl}propanoic acid;

Cpd.125 tert-butyl 3-(5-{[({4-methyl-2-[(propan-2-yl)amino]phenyl}(phenyl)methyl)carbamoyl]methyl}-1H-indol-3-yl)propanoate;

Cpd.126 3-(5-{[({4-methyl-2-[(propan-2-yl)amino]phenyl}(phenyl)methyl)carbamoyl]methyl}-1H-indol-3-yl)propanoic acid;

Cpd.127 tert-butyl 3-{5-[({phenyl[2-(1,2,3,6-tetrahydropyridin-1-yl)phenyl]methyl}carbamoyl)methyl]-1H-indol-3-yl}propanoate;

Cpd.128 3-{5-[({phenyl[2-(1,2,3,6-tetrahydropyridin-1-yl)phenyl]methyl}carbamoyl)methyl]-1H-indol-3-yl}propanoic acid;

Cpd.129 tert-butyl 3-{5-[({1-[2-(pyrrolidin-1-yl)phenyl]cyclopentyl}carbamoyl)methyl]-1H-indol-3-yl}propanoate;

Cpd.130 3-{5-[({1-[2-(pyrrolidin-1-yl)phenyl]cyclopentyl}carbamoyl)methyl]-1H-indol-3-yl}propanoic acid;

Cpd.131 tert-butyl 3-{5-[({[4-methyl-2-(piperidin-1-yl)phenyl](pyrimidin-2-yl)methyl}carbamoyl)methyl]-1H-indol-3-yl}propanoate;

Cpd.132 3-{5-[({[4-methyl-2-(piperidin-1-yl)phenyl](pyrimidin-2-yl)methyl}carbamoyl)methyl]-1H-indol-3-yl}propanoic acid;

Cpd.133 tert-butyl 3-{5-[({1-[2-(dimethylamino)-4-methylphenyl]-3-methylbutyl}carbamoyl)methyl]-1H-indol-3-yl}propanoate;

Cpd.134 3-{5-[({1-[2-(dimethylamino)-4-methylphenyl]-3-methylbutyl}carbamoyl)methyl]-1H-indol-3-yl}propanoic acid;

Cpd.135 tert-butyl 3-{5-[({[5-methoxy-2-(piperidin-1-yl)phenyl](phenyl)methyl}carbamoyl)methyl]-1H-indol-3-yl}propanoate;

Cpd.136 3-{5-[({[5-methoxy-2-(piperidin-1-yl)phenyl](phenyl)methyl}carbamoyl)methyl]-1H-indol-3-yl}propanoic acid;

Cpd.137 tert-butyl 3-{5-[({[4-methyl-2-(piperidin-1-yl)phenyl](5-methylthiophen-2-yl)methyl}carbamoyl)methyl]-1H-indol-3-yl}propanoate;

Cpd.138 3-{5-[({[4-methyl-2-(piperidin-1-yl)phenyl](5-methylthiophen-2-yl)methyl}carbamoyl)methyl]-1H-indol-3-yl}propanoic acid;

Cpd.139 tert-butyl 3-{5-[({[4-methyl-2-(piperidin-1-yl)phenyl](1,3-thiazol-2-yl)methyl}carbamoyl)methyl]-1H-indol-3-yl}propanoate;

Cpd.140 3-{5-[({[4-methyl-2-(piperidin-1-yl)phenyl](1,3-thiazol-2-yl)methyl}carbamoyl)methyl]-1H-indol-3-yl}propanoic acid;

Cpd.141 tert-butyl 3-{5-[({[2-(azepan-1-yl)-4-methoxyphenyl](phenyl)methyl}carbamoyl)methyl]-1H-indol-3-yl}propanoate;

Cpd.142 3-{5-[({[2-(azepan-1-yl)-4-methoxyphenyl](phenyl)methyl}carbamoyl)methyl]-1H-indol-3-yl}propanoic acid;

Cpd.143 tert-butyl 3-{5-[({1-[2-(piperidin-1-yl)phenyl]cyclohexyl}carbamoyl)methyl]-1H-indol-3-yl}propanoate;

Cpd.144 3-{5-[({1-[2-(piperidin-1-yl)phenyl]cyclohexyl}carbamoyl)methyl]-1H-indol-3-yl}propanoic acid;

Cpd.145 tert-butyl 3-{5-[({[4-methyl-2-(propan-2-yloxy)phenyl](phenyl)methyl}carbamoyl)methyl]-1H-indol-3-yl}propanoate;

Cpd.146 3-{5-[({[4-methyl-2-(propan-2-yloxy)phenyl](phenyl)methyl}carbamoyl)methyl]-1H-indol-3-yl}propanoic acid;

Cpd.147 tert-butyl 3-[5-({[(5-methylfuran-2-yl)[2-(piperidin-1-yl)phenyl]methyl]carbamoyl}methyl)-1H-indol-3-yl]propanoate;

Cpd.148 3-[5-({[(5-methylfuran-2-yl)[2-(piperidin-1-yl)phenyl]methyl]carbamoyl}methyl)-1H-indol-3-yl]propanoic acid;

Cpd.149 tert-butyl 3-{5-[({[4-ethoxy-2-(piperidin-1-yl)phenyl](phenyl)methyl}carbamoyl)methyl]-1H-indol-3-yl}propanoate;

Cpd.150 3-{5-[({[4-ethoxy-2-(piperidin-1-yl)phenyl](phenyl)methyl}carbamoyl)methyl]-1H-indol-3-yl}propanoic acid;

Cpd.151 tert-butyl 3-{5-[({phenyl[2-(piperidin-1-yl)-4-(propan-2-yloxy)phenyl]methyl}carbamoyl)methyl]-1H-indol-3-yl}propanoate;

Cpd.152 3-{5-[({phenyl[2-(piperidin-1-yl)-4-(propan-2-yloxy)phenyl]methyl}carbamoyl)methyl]-1H-indol-3-yl}propanoic acid;

Cpd.153 tert-butyl 3-[5-({[(5-methyl-1,3-thiazol-2-yl)[2-(piperidin-1-yl)phenyl]methyl]carbamoyl}methyl)-1H-indol-3-yl]propanoate;

Cpd.154 3-[5-({[(5-methyl-1,3-thiazol-2-yl)[2-(piperidin-1-yl)phenyl]methyl]carbamoyl}methyl)-1H-indol-3-yl]propanoic acid;

Cpd.155 tert-butyl 3-[5-({[(2-methyl-1,3-thiazol-5-yl)[2-(piperidin-1-yl)phenyl]methyl]carbamoyl}methyl)-1H-indol-3-yl]propanoate;

Cpd.156 3-[5-({[(2-methyl-1,3-thiazol-5-yl)[2-(piperidin-1-yl)phenyl]methyl]carbamoyl}methyl)-1H-indol-3-yl]propanoic acid;

Cpd.157 tert-butyl 3-[5-({[(3-methylphenyl)[2-(piperidin-1-yl)phenyl]methyl]carbamoyl}methyl)-1H-indol-3-yl]propanoate;

Cpd.158 3-[5-({[(3-methylphenyl)[2-(piperidin-1-yl)phenyl]methyl]carbamoyl}methyl)-1H-indol-3-yl]propanoic acid;

Cpd.159 ethyl 3-{5-[({[4-methyl-2-(propan-2-yloxy)phenyl](phenyl)methyl}carbamoyl)methyl]-1H-indazol-3-yl}propanoate;

Cpd.160 3-{5-[({[4-methyl-2-(propan-2-yloxy)phenyl](phenyl)methyl}carbamoyl)methyl]-1H-indazol-3-yl}propanoic acid;

Cpd.161 tert-butyl 3-{5[({2-cyclohexyl-1-[2-(piperidin-1-yl)phenyl]ethyl}carbamoyl)methyl]-1H-indol-3-yl}propanoate;

Cpd.162 3-{5-[({2-cyclohexyl-1-[2-(piperidin-1-yl)phenyl]ethyl}carbamoyl)methyl]-1H-indol-3-yl}propanoic acid;

Cpd.163 tert-butyl 3-[5-({[cyclopropyl(4-methylnaphthalen-1-yl)methyl]carbamoyl}methyl)-1H-indol-3-yl]propanoate;

Cpd.164 3-[5-({[cyclopropyl(4-methylnaphthalen-1-yl)methyl]carbamoyl}methyl)-1H-indol-3-yl]propanoic acid;

Cpd.165 methyl 2-{5-[({[5-chloro-2-(piperidin-1-yl)phenyl](phenyl)methyl}carbamoyl)methyl]-1H-indol-3-yl}acetate;

Cpd.166 2-{5-[({[5-chloro-2-(piperidin-1-yl)phenyl](phenyl)methyl}carbamoyl)methyl]-1H-indol-3-yl}acetic acid;

Cpd.167 tert-butyl 3-[5-({[1H-indol-7-yl(phenyl)methyl]carbamoyl}methyl)-1H-indol-3-yl]propanoate;

Cpd.168 3-[5-({[1H-indol-7-yl(phenyl)methyl]carbamoyl}methyl)-1H-indol-3-yl]propanoic acid;

Cpd.169 tert-butyl 3-[5-({[(1-methyl-1H-indol-7-yl)(phenyl)methyl]carbamoyl}methyl)-1H-indol-3-yl]propanoate;

Cpd.170 3-[5-({[(1-methyl-1H-indol-7-yl)(phenyl)methyl]carbamoyl}methyl)-1H-indol-3-yl]propanoic acid;

Cpd.171 tert-butyl 3-{5[({1-[2-(piperidin-1-yl)phenyl]pentyl}carbamoyl)methyl]-1H-indol-3-yl}propanoate;

Cpd.172 3-{5-[({1-[2-(piperidin-1-yl)phenyl]pentyl}carbamoyl)methyl]-1H-indol-3-yl}propanoic acid;

Cpd.173 tert-butyl 3-{5[({1-[2-(diethylamino)phenyl]-3-methylbutyl}carbamoyl)methyl]-1H-indol-3-yl}propanoate;

Cpd.174 3-{5-[({1-[2-(diethylamino)phenyl]-3-methylbutyl}carbamoyl)methyl]-1H-indol-3-yl}propanoic acid;

Cpd.175 tert-butyl 3-[5-({[2-(3-methylphenyl)-1-[2-(piperidin-1-yl)phenyl]ethyl]carbamoyl}methyl)-1H-indol-3-yl]propanoate;

Cpd.176 3-[5-({[2-(3-methylphenyl)-1-[2-(piperidin-1-yl)phenyl]ethyl]carbamoyl}methyl)-1H-indol-3-yl]propanoic acid;

Cpd.177 tert-butyl 3-{5-[({3-methyl-1-[2-(piperidin-1-yl)phenyl]butyl}carbamoyl)amino]-1H-pyrrolo[2,3-b]pyridin-3-yl}propanoate;

Cpd.178 3-{5-[({3-methyl-1-[2-(piperidin-1-yl)phenyl]butyl}carbamoyl)amino]-1H-pyrrolo[2,3-b]pyridin-3-yl}propanoic acid;

Cpd.179 tert-butyl 3-{5-[({[2-(4,4-difluoropiperidin-1-yl)phenyl](phenyl)methyl}carbamoyl)methyl]-1H-indol-3-yl}propanoate;
Cpd.180 3-{5-[({[2-(4,4-difluoropiperidin-1-yl)phenyl](phenyl)methyl}carbamoyl)methyl]-1H-indol-3-yl}propanoic acid;
Cpd.181 tert-butyl 3-{5-[({1-[4-bromo-2-(pyrrolidin-1-yl)phenyl]-3-methylbutyl}carbamoyl)methyl]-1H-indol-3-yl}propanoate;
Cpd.182 3-{5-[({1-[4-bromo-2-(pyrrolidin-1-yl)phenyl]-3-methylbutyl}carbamoyl)methyl]-1H-indol-3-yl}propanoic acid;
Cpd.183 tert-butyl 3-[5-({[(2-amino-4-methylphenyl)(phenyl)methyl]carbamoyl}methyl)-1H-indol-3-yl]propanoate;
Cpd.184 3-[5-({[(2-amino-4-methylphenyl)(phenyl)methyl]carbamoyl}methyl)-1H-indol-3-yl]propanoic acid;
Cpd.185 tert-butyl 3-{5-[({3,3-dimethyl-1-[2-(piperidin-1-yl)phenyl]butyl}carbamoyl)methyl]-1H-indol-3-yl}propanoate;
Cpd.186 3-{5-[({3,3-dimethyl-1-[2-(piperidin-1-yl)phenyl]butyl}carbamoyl)methyl]-1H-indol-3-yl}propanoic acid;
Cpd.187 tert-butyl 3-[5-({[(4-methylphenyl)[2-(piperidin-1-yl)phenyl]methyl]carbamoyl}methyl)-1H-indol-3-yl]propanoate;
Cpd.188 3-[5-({[(4-methylphenyl)[2-(piperidin-1-yl)phenyl]methyl]carbamoyl}methyl)-1H-indol-3-yl]propanoic acid;
Cpd.189 tert-butyl 3-[5-({[2-(oxan-4-yl)-1-[2-(piperidin-1-yl)phenyl]ethyl]carbamoyl}methyl)-1H-indol-3-yl]propanoate;
Cpd.190 3-[5-({[2-(oxan-4-yl)-1-[2-(piperidin-1-yl)phenyl]ethyl]carbamoyl}methyl)-1H-indol-3-yl]propanoic acid;
Cpd.191 tert-butyl 3-{5-[({[2-(dimethylamino)-4-methylphenyl](phenyl)methyl}carbamoyl)methyl]-1H-indol-3-yl}propanoate;
Cpd.192 3-{5-[({[2-(dimethylamino)-4-methylphenyl](phenyl)methyl}carbamoyl)methyl]-1H-indol-3-yl}propanoic acid;
Cpd.193 methyl 2-{5-[({3-methyl-1-[2-(piperidin-1-yl)phenyl]butyl}carbamoyl)methyl]-1H-indol-3-yl}acetate;
Cpd.194 2-{5-[({3-methyl-1-[2-(piperidin-1-yl)phenyl]butyl}carbamoyl)methyl]-1H-indol-3-yl}acetic acid;
Cpd.195 tert-butyl 3-{5-[({[2-(morpholin-4-yl)phenyl](phenyl)methyl}carbamoyl)methyl]-1H-indol-3-yl}propanoate;
Cpd.196 3-{5-[({[2-(morpholin-4-yl)phenyl](phenyl)methyl}carbamoyl)methyl]-1H-indol-3-yl}propanoic acid;
Cpd.197 tert-butyl 3-{5-[({1-[2-(azepan-1-yl)phenyl]-3-methylbutyl}carbamoyl)methyl]-1H-indol-3-yl}propanoate;
Cpd.198 3-{5-[({1-[2-(azepan-1-yl)phenyl]-3-methylbutyl}carbamoyl)methyl]-1H-indol-3-yl}propanoic acid;
Cpd.199 tert-butyl 3-{5-[({[2-(2,5-dihydro-1H-pyrrol-1-yl)-4-methylphenyl](phenyl)methyl}carbamoyl)methyl]-1H-indol-3-yl}propanoate;
Cpd.200 3-{5-[({[2-(2,5-dihydro-1H-pyrrol-1-yl)-4-methylphenyl](phenyl)methyl}carbamoyl)methyl]-1H-indol-3-yl}propanoic acid;
Cpd.201 tert-butyl 3-{5-[({[3-methyl-2-(piperidin-1-yl)phenyl](phenyl)methyl}carbamoyl)methyl]-1H-indol-3-yl}propanoate;
Cpd.202 3-{5-[({[3-methyl-2-(piperidin-1-yl)phenyl](phenyl)methyl}carbamoyl)methyl]-1H-indol-3-yl}propanoic acid;
Cpd.203 tert-butyl 3-{5-[({[4-methyl-2-(methylamino)phenyl](phenyl)methyl}carbamoyl)methyl]-1H-indol-3-yl}propanoate;
Cpd.204 3-{5-[({[4-methyl-2-(methylamino)phenyl](phenyl)methyl}carbamoyl)methyl]-1H-indol-3-yl}propanoic acid;
Cpd.205 methyl 5-[({phenyl[2-(piperidin-1-yl)phenyl]methyl}carbamoyl)methyl]-1H-indole-3-carboxylate;
Cpd.206 1-(2-{[2-(3-carboxy-1H-indol-5-yl)acetamido](phenyl)methyl}phenyl)piperidin-1-ium chloride;
Cpd.207 5-({[(2-bromo-4-methylphenyl)(phenyl)methyl]carbamoyl}methyl)-1H-indole-3-carboxylic acid;
Cpd.208 tert-butyl 3-[5-({2-[4-methyl-2-(piperidin-1-yl)phenyl]-2-phenylacetamido}methyl)-1H-indol-3-yl]propanoate;
Cpd.209 3-[5-({2-[4-methyl-2-(piperidin-1-yl)phenyl]-2-phenylacetamido}methyl)-1H-indol-3-yl]propanoic acid;
Cpd.210 ethyl 4-oxo-4-{5-[({phenyl[2-(piperidin-1-yl)phenyl]methyl}carbamoyl)methyl]-1H-indol-3-yl}butanoate;
Cpd.211 ethyl 4-{5-[({phenyl[2-(piperidin-1-yl)phenyl]methyl}carbamoyl)methyl]-1H-indol-3-yl}butanoate;
Cpd.212 4-{5-[({phenyl[2-(piperidin-1-yl)phenyl]methyl}carbamoyl)methyl]-1H-indol-3-yl}butanoic acid;
Cpd.213 4-oxo-4-{5-[({phenyl[2-(piperidin-1-yl)phenyl]methyl}carbamoyl)methyl]-1H-indol-3-yl}butanoic acid;
Cpd.214 ethyl 5-oxo-5-{5-[({phenyl[2-(piperidin-1-yl)phenyl]methyl}carbamoyl)methyl]-1H-indol-3-yl}pentanoate;
Cpd.215 5-oxo-5-{5-[({phenyl[2-(piperidin-1-yl)phenyl]methyl}carbamoyl)methyl]-1H-indol-3-yl}pentanoic acid;
Cpd.216 ethyl 5-{5-[({phenyl[2-(piperidin-1-yl)phenyl]methyl}carbamoyl)methyl]-1H-indol-3-yl}pentanoate;
Cpd.217 5-{5-[({phenyl[2-(piperidin-1-yl)phenyl]methyl}carbamoyl)methyl]-1H-indol-3-yl}pentanoic acid;
Cpd.218 tert-butyl 3-{5-[({1-[2-(diethylamino)phenyl]pentyl}carbamoyl)methyl]-1H-indol-3-yl}propanoate;
Cpd.219 3-{5-[({1-[2-(diethylamino)phenyl]pentyl}carbamoyl)methyl]-1H-indol-3-yl}propanoic acid;
Cpd.220 methyl 2-[5-({[(2-bromo-4-methylphenyl)(phenyl)methyl]carbamoyl}methyl)-1H-indol-3-yl]acetate;
Cpd.221 2-[5-({[(2-bromo-4-methylphenyl)(phenyl)methyl]carbamoyl}methyl)-1H-indol-3-yl]acetic acid;
Cpd.222 methyl 2-[5-({[(2,4-dimethylphenyl)(5-methylthiophen-2-yl)methyl]carbamoyl}methyl)-1H-indol-3-yl]acetate;
Cpd.223 2-[5-({[(2,4-dimethyl phenyl)(5-methylthiophen-2-yl)methyl]carbamoyl}methyl)-1H-indol-3-yl]acetic acid;
Cpd.224 methyl 2-{5-[({[2-(morpholin-4-yl)phenyl](phenyl)methyl}carbamoyl)methyl]-1H-indol-3-yl}acetate;
Cpd.225 2-{5-[({[2-(morpholin-4-yl)phenyl](phenyl)methyl}carbamoyl)methyl]-1H-indol-3-yl}acetic acid;
Cpd.226 tert-butyl 3-[5-({[(2-bromo-4-methylphenyl)(pyrimidin-2-yl)methyl]carbamoyl}methyl)-1H-indol-3-yl]propanoate;
Cpd.227 3-[5-({[(2-bromo-4-methylphenyl)(pyrimidin-2-yl)methyl]carbamoyl}methyl)-1H-indol-3-yl]propanoic acid;
Cpd.228 tert-butyl 3-[5-({[(4-methyl-1H-indol-7-yl)(phenyl)methyl]carbamoyl}methyl)-1H-indol-3-yl]propanoate;
Cpd.229 3-[5-({[(4-methyl-1H-indol-7-yl)(phenyl)methyl]carbamoyl}methyl)-1H-indol-3-yl]propanoic acid;

Cpd.230 tert-butyl 3-{5-[({1-[4-methyl-2-(piperidin-1-yl)phenyl]pentyl}carbamoyl)methyl]-1H-indol-3-yl}propanoate;
Cpd.231 3-{5-[({1-[4-methyl-2-(piperidin-1-yl)phenyl]pentyl}carbamoyl)methyl]-1H-indol-3-yl}propanoic acid;
Cpd.232 tert-butyl 3-{5-[({[2-(3,3-difluoropiperidin-1-yl)phenyl](phenyl)methyl}carbamoyl)methyl]-1H-indol-3-yl}propanoate;
Cpd.233 3-{5-[({[2-(3,3-difluoropiperidin-1-yl)phenyl](phenyl)methyl}carbamoyl)methyl]-1H-indol-3-yl}propanoic acid;
Cpd.234 tert-butyl N-[(3-{5-[({phenyl[2-(piperidin-1-yl)phenyl]methyl}carbamoyl)methyl]-1H-indol-3-yl}propanamido)methanimidoyl]carbamate;
Cpd.235 1-{2-[(2-{3-[2-(carbamimidoylcarbamoyl)ethyl]-1H-indol-5-yl}acetamido)(phenyl)methyl]phenyl}piperidin-1-ium chloride;
Cpd.236 ethyl 3-{5-[({phenyl[2-(piperidin-1-yl)phenyl]methyl}carbamoyl)methyl]-1H-indazol-3-yl}propanoate;
Cpd.237 3-{5-[({phenyl[2-(piperidin-1-yl)phenyl]methyl}carbamoyl)methyl]-1H-indazol-3-yl}propanoic acid;
Cpd.238 methyl 2-{5-[({phenyl[3-(piperidin-1-yl)phenyl]methyl}carbamoyl)methyl]-1H-indol-3-yl}acetate
Cpd.239 2-{5-[({phenyl[3-(piperidin-1-yl)phenyl]methyl}carbamoyl)methyl]-1H-indol-3-yl}acetic acid
Cpd.240 tert-butyl 3-{5-[({3-methyl-1-[2-(propan-2-yloxy)phenyl]butyl}carbamoyl)methyl]-1H-indol-3-yl}propanoate;
Cpd.241 3-{5-[({3-methyl-1-[2-(propan-2-yloxy)phenyl]butyl}carbamoyl)methyl]-1H-indol-3-yl}propanoic acid;
Cpd.242 tert-butyl 3-[5-({[1-(2-ethoxyphenyl)-3-methylbutyl]carbamoyl}methyl)-1H-indol-3-yl]propanoate;
Cpd.243 3-[5-({[1-(2-ethoxyphenyl)-3-methylbutyl]carbamoyl}methyl)-1H-indol-3-yl]propanoic acid;
Cpd.244 tert-butyl 3-{5[({4-methyl-1-[2-(piperidin-1-yl)phenyl]pentyl}carbamoyl)methyl]-1H-indol-3-yl}propanoate;
Cpd.245 3-{5-[({4-methyl-1-[2-(piperidin-1-yl)phenyl]pentyl}carbamoyl)methyl]-1H-indol-3-yl}propanoic acid;
Cpd.246 tert-butyl 3-[5-({[(2,4-diethoxyphenyl)(phenyl)methyl]carbamoyl}methyl)-1H-indol-3-yl]propanoate;
Cpd.247 3-[5-({[(2,4-diethoxyphenyl)(phenyl)methyl]carbamoyl}methyl)-1H-indol-3-yl]propanoic acid;
Cpd.248 tert-butyl 3-{5-[({3-methyl-1-[4-methyl-2-(propan-2-yloxy)phenyl]butyl}carbamoyl)methyl]-1H-indol-3-yl}propanoate;
Cpd.249 3-{5-[({3-methyl-1-[4-methyl-2-(propan-2-yloxy)phenyl]butyl}carbamoyl)methyl]-1H-indol-3-yl}propanoic acid;
Cpd.250 tert-butyl 3-{5-[({[2-(azepan-1-yl)-4-methylphenyl](phenyl)methyl}carbamoyl)methyl]-1H-indol-3-yl}propanoate;
Cpd.251 3-{5-[({[2-(azepan-1-yl)-4-methylphenyl](phenyl)methyl}carbamoyl)methyl]-1H-indol-3-yl}propanoic acid;
Cpd.252 tert-butyl 3-[5-({[(4,5-dimethylfuran-2-yl)[2-(piperidin-1-yl)phenyl]methyl]carbamoyl}methyl)-1H-indol-3-yl]propanoate;
Cpd.253 3-[5-({[(4,5-dimethylfuran-2-yl)[2-(piperidin-1-yl)phenyl]methyl]carbamoyl}methyl)-1H-indol-3-yl]propanoic acid;
Cpd.254 tert-butyl 3-[5-({[(5-methylfuran-2-yl)[2-(propan-2-yloxy)phenyl]methyl]carbamoyl}methyl)-1H-indol-3-yl]propanoate;
Cpd.255 3-[5-({[(5-methylfuran-2-yl)[2-(propan-2-yloxy)phenyl]methyl]carbamoyl}methyl)-1H-indol-3-yl]propanoic acid;
Cpd.256 methyl 2-[5-({[(2-bromo-4-methylphenyl)(pyrimidin-2-yl)methyl]carbamoyl}methyl)-1H-indol-3-yl]acetate;
Cpd.257 2-[5-({[(2-bromo-4-methylphenyl)(pyrimidin-2-yl)methyl]carbamoyl}methyl)-1H-indol-3-yl]acetic acid;
Cpd.258 N-methoxy-N-methyl-2-{5-[({phenyl[2-(piperidin-1-yl)phenyl]methyl}carbamoyl)methyl]-1H-indol-3-yl}acetamide;
Cpd.259 tert-butyl 3-{5-[({[4-hydroxy-2-(piperidin-1-yl)phenyl](phenyl)methyl}carbamoyl)methyl]-1H-indol-3-yl}propanoate;
Cpd.260 tert-butyl 3-{5-[({1-[2-(piperidin-1-yl)phenyl]but-3-yn-1-yl}carbamoyl)methyl]-1H-indol-3-yl}propanoate;
Cpd.261 3-{5-[({1-[2-(piperidin-1-yl)phenyl]but-3-yn-1-yl}carbamoyl)methyl]-1H-indol-3-yl}propanoic acid;
Cpd.262 tert-butyl 3-{5-[({3-methyl-1-[2-(piperidin-1-yl)phenyl]butyl}carbamoyl)amino]-1H-indol-3-yl}propanoate;
Cpd.263 tert-butyl 3-{5-[({[2-(4-benzylpiperazin-1-yl)-4-methylphenyl](phenyl)methyl}carbamoyl)methyl]-1H-indol-3-yl}propanoate;
Cpd.264 tert-butyl 3-{5-[({[4-hydroxy-2-(piperidin-1-yl)phenyl](phenyl)methyl}carbamoyl)methyl]-1H-indol-3-yl}propanoate;
Cpd.265 3-{5-[({[4-hydroxy-2-(piperidin-1-yl)phenyl](phenyl)methyl}carbamoyl)methyl]-1H-indol-3-yl}propanoic acid;
Cpd.266 3-(hexadecanoyloxy)-2-[(3-{5-[({phenyl[2-(piperidin-1-yl)phenyl]methyl}carbamoyl)methyl]-1H-indol-3-yl}propanoyl)oxy]propyl hexadecanoate;
Cpd.267 tert-butyl 3-{5-[({[4-methyl-2-(piperidin-1-yl)phenyl](5-methylfuran-2-yl)methyl}carbamoyl)methyl]-1H-indol-3-yl}propanoate; and
Cpd.2683-{5-[({[4-methyl-2-(piperidin-1-yl)phenyl](5-methylfuran-2-yl)methyl}carbamoyl)methyl]-1H-indol-3-yl}propanoic acid.

In the present invention, the terms "RORgamma", "RORγ" and "RORg" are used interchangeably.

"RORγ modulator" refers to a chemical compound that modulates, either directly or indirectly, the activity of RORγ. In particular, the RORγ modulator inhibits, either directly or indirectly, the activity of RORγ. RORγ modulators include antagonists and inverse agonists of RORγ.

RORgamma modulators can be used as medicinal products. Consequently, the present invention provides a compound of formula (I) for use as a medicament. The present invention further provides pharmaceutical compositions comprising a compound of formula (I) and a pharmaceutically acceptable carrier. Such pharmaceutical compositions, optionally in combination with one or more other therapeutically active substances, can be used in methods for treating diseases for which the modulation of RORgamma has positive effects in a subject.

The compounds of the invention may in particular be used in the treatment of autoimmune or autoimmune-related diseases, inflammation-related diseases and/or fibrotic diseases, cholestatic and cholestasis-related diseases.

The term "autoimmune diseases" is used to designate a condition that arises from an abnormal immune response of the body against substances and tissues normally present in the body. The disease may be restricted to certain organs (e.g in type I diabetes or autoimmune thyroiditis) or involve a particular tissue in different places (e.g. in Goodpasture's disease, affection of the basement membrane in the lung and the kidney).

The term "inflammation" is used to designate a condition that arise from a protective response involving host cells, blood vessels, and proteins and other mediators which may serve to eliminate the cause of cell/tissue injury, as well as the necrotic cells/tissues resulting from the original insult, and to initiate the process of repair. The inflammatory reaction may be manifested by pain, heat, redness, swelling, blood vessels dilatation, blood flow increase and loss of function.

Fibrosis is a pathologic process, which includes scar formation and over production of extracellular matrix, by the connective tissue, as a response to tissue damage. Damage to tissue can result from a variety of stimuli including autoimmune reactions and mechanical injury. This can be a reactive, benign, or pathological state that occurs in an organ or tissue. In response to injury this is called scarring and if fibrosis arises from a single cell line this is called a fibroma. Physiologically the deposit of connective tissue can obliterate the architecture and function of the underlying organ or tissue.

Cholestasis is defined as a decrease in bile flow due to impaired secretion by hepatocytes (hepato-cellular cholestasis) or to obstruction of bile flow through intra- or extra-hepatic bile ducts (obstructive cholestasis). In clinical practice, cholestasis is any condition in which the flow of bile from the liver is slowed or blocked.

Examples of autoimmune diseases, autoimmune-related diseases, inflammatory diseases, fibrotic diseases, and cholestatic diseases include arthritis, asthma, severe, glucocorticoid-nonresponsive asthma, asthma exacerbations due to ongoing and/or past pulmonary infection, Addison's disease, allergy, agammaglobulinemia, alopecia areata, ankylosing spondylitis, atherosclerosis, atopic allergy, atopic dermatitis, autoimmune cardiomyopathy, autoimmune enteropathy, autoimmune hemolytic anemia, autoimmune hepatitis, autoimmune lymphoproliferative syndrome, autoimmune pancreatitis, autoimmune peripheral neuropathy, Crohn's disease, Celiac disease, colitis, chronic inflammatory demyelinating polyneuropathy, chronic obstructive pulmonary disease (COPD), dermatomyositis, diabetes mellitus type 1, diffuse cutaneous systemic sclerosis, eczema, gastrointestinal disorder, Goodpasture's syndrome, Graves' disease, Guillain-Barre syndrome, Hashimoto's encephalopathy, Hashimoto's thyroiditis, idiopathic thrombocytopenic purpura, inflammatory bowel disease (IBD), irritable bowel syndrome, lupus, lupus erythematosus, lupus nephritis, mixed connective tissue disease, Kawasaki disease, multiple sclerosis, neuromyelitis optica, myasthenia gravis, narcolepsy, optic neuritis, osteorathritis, pemphigus vulgaris, pernicious anaemia, polymyositis, psoriasis, psoriatic arthritis, reactive arthritis, relapsing polychondritis, respiratory disorder, rheumatoid arthritis, rheumatic fever, Sjorgen's syndrome, systemic lupus erythematosus, transverse myelitis, undifferentiated connective tissue disease, ulcerative colitis, uveitis, vasculitis, Wegener's granulomatosis, systemic inflammatory response syndrome (SIRS), sepsis, Behcets disease, allergic contact dermatitis, cutaneous lupus erythematosus, dry eye and glomerulonephritis, myocarditis, acute liver failure (ALF), including acute-on-chronic liver failure (ACLF), pulmonary fibrosis (idiopathic pulmonary, interstitial lung, cystic and progressive massive fibrosis), liver fibrosis and cirrhosis of diverse etiologies (congenital, of autoimmune origin, induced by cardiometabolic diseases, alcohol consumption, cholestasis, drugs, infectious agents, trauma, radiation), metabolic syndrome, NonAlcoholic SteatoHepatitis (NASH) and Alcoholic SteatoHepatitis (ASH), cardiac fibrosis and heart myocardial and endomyocardial fibrosis, arterial fibrosis, atherosclerosis/restenosis, mediastinal fibrosis (soft tissue of the mediastinum), macular degeneration, retinal and vitreal retinopathy, ocular scarring, cataract, Alzheimer's disease, cancer, local, disseminated or metastatic cancer, scleroderma, glioblastoma, myelofibrosis (bone marrow), retroperitoneal fibrosis (soft tissue of the retroperitoneum), nephrogenic systemic fibrosis (skin, joints, eyes, and internal organs), keloid (skin), intestinal fibrosis (occurs for example in Crohn's disease and collagenous colitis), kidney fibrosis, scleroderma and systemic sclerosis (skin, lungs, kidneys, heart, and gastrointestinal tract), arthrofibrosis (knee, shoulder, other joints), Peyronie's disease (penis), Dupuytren's contracture (hands and fingers), some forms of adhesive capsulitis (shoulder), obesity, Primary Biliary Cirrhosis (PBC), Primary Sclerosing Cholangitis (PSC), Intarhepatic Cholestasis of Pregnancy (ICP), Progressive Familial Intrahepatic Cholestasis (PFIC), Biliary atresia, Cholelithiasis, Infectious cholangitis, Cholangitis associated with Langerhans cell histiocytosis, Alagille syndrome, Nonsyndromic ductal paucity, Hepatitis (hepatitis A, hepatitis B, hepatitis C), Alpha1-antitrypsin deficiency, Inborn errors of bile acid synthesis, Drug-induced cholestasis, Total parenteral nutrition (TPN)-associated cholestasis.

The term "treatment" or "treating" refers to therapy, prevention, or prophylaxis of a disorder, in particular of autoimmune and multiple inflammatory disorders in a subject in need thereof. The treatment involves the administration of a pharmaceutical composition to subjects (e.g. patients) having a declared disorder to prevent, cure, delay, reverse, or slow down the progression of the disorder, improving thereby the condition of patients. A treatment may be also administered to subjects that are either healthy or at risk of developing a disorder such as an autoimmune, inflammatory, fibrotic or cholestatic disorder.

The term "subject" refers to a mammal and more particularly a human. The subjects to be treated according to the invention can be appropriately selected on the basis of several criteria associated with autoimmune, inflammatory, fibrotic and cholestatic pathological processes such as previous and/or present drug treatments, associated pathologies, genotype, exposure to risk factors, as well as any other relevant biomarker that can be evaluated by means of any suitable immunological, biochemical, or enzymatic method.

The Examples show how Compounds of formula (I) can be produced and tested.

The details of the general methods of synthesis and purification of intermediate products for Compounds of formula (I) are provided in Example 1.

Specific reaction intermediates can be synthesized and purified from compounds that may be already available commercially or that can readily be synthesized.

The details of the general methods of synthesis and purification of Compounds of formula (I) are provided in Example 2.

General schemes of synthesis of the compounds of formula (I) are presented in FIG. 3A to FIG. 3D.

The functional groups optionally present in the reaction intermediates that are generated for obtaining the desired compounds of formula (I) can be protected, either permanently, or temporarily, by protective groups, which ensure unequivocal synthesis of the desired compounds. The reactions of protection and deprotection are carried out according to techniques well known by a person skilled in the art or such as those described in the literature, as in the book "Greene's Protective Groups in Organic Synthesis" (Wuts & Greene, 2007).

The compounds according to the invention may contain one or more asymmetric centers. The present invention includes stereoisomers (diastereoisomers, enantiomers), pure or mixed, as well as racemic mixtures and geometric isomers, or tautomers of compounds of formula (I). When an enantiomerically pure (or enriched) mixture is desired, it can be obtained either by purification of the final product or of chiral intermediates, or by asymmetric synthesis according to methods known by a person skilled in the art (using for example chiral reactants and catalysts). Certain compounds according to the invention can have various stable tautomeric forms and all these forms and mixtures thereof are included in the invention. The techniques for obtaining and characterizing the stereoisomers, pure or mixed, as well as racemic mixtures and geometric isomers, or tautomers are described in the literature, such as in the book "Chirality in Drug Design and Development" (Reddy & Mehvar, 2004).

The compounds of formula (I) can be purified by precipitation or solid/liquid extraction after evaporation of the reaction medium. Further or other purification step can be performed by chromatography over silica gel or by crystallization, when the compound is stable as a solid form, by applying techniques well known in the literature or, more in general, for chemicals (Armarego & Chai, 2009).

Moreover, the required purification and/or (re-)crystallization steps that are appropriate for isolating compounds of formula (I) from the reaction mixture, can be used for obtaining amorphous, polymorphous, mono- or poly-crystalline forms. Such polymorphisms may present distinct pharmacological and/or chemical properties, for example in terms of solubility, intrinsic dissolution rate, melting temperature, bioavailability, and/or possible transition from a polymorphic state to another one in pharmaceutical compositions and/or biological fluids.

The (re-)crystallisation assays can be performed in panels of different solvents (such as isopropanol, acetone, methanol, diisopropyl ether or water) or mixture thereof, and by applying different conditions, such as reaction volumes or temperatures. The resulting samples can be analyzed by different techniques such as microscopy, calorimetry, and/or spectroscopy that allow establishing the features of a particular crystalline form, such as structure, solubility, stability or conversion to other forms (Bauer, 2004; Erdemir et al, 2007; Morissette et al, 2004; Yin & Grosso, 2008).

Such a polymorphism study allows characterizing the crystalline form of a compound that is pharmaceutically acceptable for both pharmacological and manufacturing points of view.

Certain compounds of formula (I) can be isolated in the form of zwitterions and each of these forms is included in the invention, as well as mixtures thereof.

Compounds of formula (I) and their salts can be stable in liquid or solid forms. The present invention includes all solid and liquid forms of formula (I), which includes the amorphous, polymorphic, mono- and poly-crystalline forms. In particular, the compounds of formula (I) can exist in the free form or in the solvated form, i.e. in the form of associations or combinations with one or more molecules of a solvent, for example with pharmaceutically acceptable solvents such as water (hydrates) or ethanol. The present invention also includes the prodrugs of the compounds according to the invention which, after administration to a subject, are converted to the compounds as described in the invention or to their metabolites having therapeutic activities comparable to the compounds according to the invention.

Specific compounds of formula (I) can comprise at least one atom of the structure that is replaced by an isotope (radioactive or not). Examples of isotopes that can be included in the structure of the compounds according to the invention can be selected from hydrogen, carbon, nitrogen, oxygen, sulphur such as $^{2}H$, $^{3}H$, $^{13}C$, $^{14}C$, $^{15}N$, $^{18}O$, $^{17}O$, $^{35}S$ respectively. When non-radioactive, the stable isotope can be selectively incorporated in the structure in place of hydrogen (in the case of deuterium) or carbon (in the case of $^{13}C$) not only as means of performing absorption, distribution, metabolism, and excretion (ADME) studies but also as means for obtaining compounds that may retain the desired biochemical potency and selectivity of the original compound while the metabolic fate is substantially altered. In some favourable cases, this modification has the potential to have a positive impact effect on safety, efficacy and/or tolerability of the original compound (Mutlib, 2008). Otherwise radioactive isotopes $^{3}H$ and $^{14}C$ are particularly preferred as they are easy to prepare and detect in studies of the bioavailability in vivo of the substances. The heavy isotopes (such as $^{2}H$) are particularly preferred as they are used as internal standards in analytical studies and as possible variants of pharmaceutical interest.

Compounds of formula (I) can be obtained as specific salts, hydrates, and polymorphs that can be obtained during the final purification step of the compound or, in the case of salts, by incorporating the salt into the previously purified compound. The selection of a compound of formula (I) that is produced according to the methods of the Invention as an optimal candidate for drug development can be automated for a comprehensive biopharmaceutical characterization at the scale-up stage and for the solid or liquid formulation that is appropriate for the desired route of administration and therapeutic indication (Kumar et al, 2007; Mahato & Narang, 2011; Stahl & Wermuth, 2002).

In view of their use as medicinal products, the compounds of formula (I) can be formulated as pharmaceutically acceptable salts obtained from organic or inorganic bases or acids of such compounds. Alternatively, the compounds of formula (I) can be formulated as pharmaceutically acceptable hydrates or polymorphs of such compounds. These salts, hydrates, and polymorphs can be obtained during the final purification step of the compound or, in the case of salts, by incorporating the salt into the previously purified compound (Stahl & Wermuth, 2002).

These salts can be prepared with pharmaceutically acceptable acids but the salts of other acids useful for purifying or isolating the compounds of formula (I) also form part of the invention. In particular, when the compounds according to the invention are in the form of a salt, it is a salt of an alkali metal, in particular a salt of sodium or of potassium, or a salt of an alkaline-earth metal, in particular magnesium or calcium, or a salt with an organic amine, more particularly with an amino acid such as arginine or lysine.

The present invention further provides pharmaceutical compositions comprising a compound of formula (I), or its pharmaceutically acceptable salt, and optionally at least one pharmaceutically acceptable carrier or diluent. The pharmaceutical compositions comprising a compound of formula (I) may comprise one or several excipients or vehicles acceptable within a pharmaceutical context (e.g., for liquid formulations, saline solutions, physiological solutions, isotonic solutions).

A further object of the invention are methods of preparing such pharmaceutical compositions, comprising admixing a compound of formula (I), with at least one pharmaceutically acceptable carrier, vehicle, or diluent. These methods involve, for example, conventional mixing, dissolving, granulation, dragee-making, levigating, emulsifying, encapsulating, entrapping, lyophilizing processes or spray drying (Gennaro, 2000; Rowe et al, 2003).

The phrase "pharmaceutically acceptable" refers to those properties and/or substances that are acceptable to the patient from a pharmacological/toxicological point of view and to the manufacturing pharmaceutical chemist from a physical/chemical point of view regarding composition, formulation, stability, patient acceptance and bioavailability.

The term "carrier", "vehicle", or "excipient" refers to any substance, not itself a therapeutic agent, that is added to a pharmaceutical composition to be used as a carrier, vehicle, and/or diluent for the delivery of a therapeutic agent to a subject in order to improve its handling or storage properties or to permit or facilitate formation of a dosage unit of the composition into a discrete article. The pharmaceutical compositions of the invention, either individually or in combination, can comprise one or several agents or vehicles chosen among dispersants, solubilisers, stabilisers, preservatives, etc. Agents or vehicles useful for these formulations (liquid and/or injectable and/or solid) are particularly methylcellulose, hydroxymethylcellulose, polysorbate 80, mannitol, gelatin, lactose, vegetable oils, liposomes, etc. Acceptable excipients can be chosen among disintegrants, binding agents, adhesives, wetting agents, lubricants, glidants, flavors, dyes, fragrances, stearic acid, magnesium oxide, sodium and calcium salts of phosphoric and sulfuric acids, magnesium carbonate, talc, gelatin, lactose, sucrose, starches, polymers, such as polyvinyl alcohol and polyethylene glycols, and other pharmaceutically acceptable materials added to improve taste, odor or appearance of the composition.

The compounds can be made up in solid or liquid form, such as tablets, capsules, powders, syrups, elixirs and the like, aerosols, sterile solutions, suspensions or emulsions, and the like. The composition may be presented in a solid preformulation composition wherein the active ingredients are dispersed evenly throughout the composition so that the composition may be readily subdivided into equally effective dosage forms such as tablets, pills and capsules. Additionally, the combined compositions may be delivered using sustained-release formulations.

The compositions can be formulated as injectable suspensions, gels, oils, pills, suppositories, powders, gel caps, capsules, aerosols, etc., eventually by means of galenic forms or devices assuring a prolonged and/or slow release. For this kind of formulation, agents such as cellulose, carbonates or starches can advantageously be used. The compositions of the present invention can also be formulated in the form of liposome delivery systems, such as small unilamellar vesicles, large unilamellar vesicles, and multilamellar vesicles. Liposomes can be formed from a variety of lipids, including but not limited to amphipathic lipids such as phosphatidylcholines, sphingomyelins, phophatidylcholines, cardiolipins, phosphatidylethanolamines, phosphatidylserines, phosphatidylglycerols, phosphatidic acids, phosphatidylinositols, diacyl trimethylammonium propanes, diacyl dimethylammonium propanes, and stearylamine, neutral lipids such as triglycerides, and combinations thereof.

The pharmaceutical combination of the invention can be administered in a systematic or parenteral way, by using oral, topical, perlingual, nasal, rectal, transmucosal, transdermal, intestinal, intramuscular, intravenously, subcutaneous, intraarterial, intraperitoneal, intrapulmonary or intraocular route, by using methods known in the art.

Formulations for oral administration may be in the form of aqueous solutions and suspensions, in addition to solid tablets and capsule formulations. The aqueous solutions and suspensions may be prepared from sterile powders or granules. The compounds may be dissolved in water, polyethylene glycol, propylene glycol, ethanol, corn oil, cottonseed oil, peanut oil, sesame oil, benzyl alcohol, sodium chloride, and/or various buffers.

For administration by inhalation, the pharmaceutical compositions comprising a compound of formula (I) are conveniently delivered in the form of an aerosol spray presentation from pressurized packs or a nebulizer, with the use of a suitable propellant, e.g., dichlorodifluoromethane, trichlorofluoromethane, dichlorotetrafluoroethane, 1,1,1,2-tetrafluoroethane, 1,1,1,2,3,3,3-heptafluoropropane, carbon dioxide or other suitable gas, alone or in combination. Pressurized aerosols may be formulated as suspensions or solutions, and include an appropriate propellant formulation, and various excipients, such as surfactants, co-solvents, etc. In the case of a pressurized aerosol the dosage unit may be determined by providing a valve to deliver a metered amount. Capsules and cartridges of e.g. gelatin for use in an inhaler or insufflators may be formulated containing a powder mix of the compound and a suitable powder base such as lactose or starch.

The tablets or pills of the composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of material can be used for such enteric layers or coatings, such materials including a number of polymeric acids with such as shellac and cellulose acetate.

The liquid forms in which the pharmaceutical compositions can be incorporated for oral administration or by injection include, aqueous solutions, suitably flavoured syrups, aqueous or oil suspensions, and flavoured emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. The liquid forms in suitably flavored suspending or dispersing agents may also include the synthetic and natural gums, for example, tragacanth, acacia, methylcellulose and the like. For parenteral administration, sterile suspensions and solutions are desired. A person skilled in the art will take care to select the possible compound or compounds to be added to these compositions in such a way that the advantageous properties intrinsically attaching to the present invention are not or substantially not altered by the addition envisaged, as is also explained in the literature, for example in the book "Pharmaceutical Dosage Forms and Drug Delivery" (2007; edited by Mahato R; published by CRC Press).

A pharmaceutical composition as disclosed herein is understood to be useful for treating a RORγ related-disease, that is, the active ingredients are contained in an amount to achieve their intended purpose. At this scope, a compound of formula (I) should be administered in an effective amount by using a pharmaceutical composition as above-defined. Administration can be performed daily or even several times per day, if necessary, and in an amount that can be optimal or suboptimal, if they are compared with dosages that are normally used for such compounds.

The term "an effective amount" refers to an amount of the compound sufficient to produce the desired therapeutic result; in particular the compounds of formula (I) are administered in amounts that are sufficient to display desired effect.

Optimal dosages of compounds of formula (I) to be administered may be readily determined by those skilled in the art, and will vary with the particular compound used, the strength of the preparation, the mode of administration, and the severity of the condition to be treated. In addition, factors associated with the particular patient being treated, including patient age, weight, diet and time of administration, will result in the need to adjust dosages and interval. The frequency and/or dose relative to the simultaneous or separate administrations can be adapted by one of ordinary skill in the art, in function of the patient, the pathology, the form of administration, etc. For instance, a compound of formula (I) should be provided in a dosage that allows its administration in the amount 0.01 mg/day to 1000 mg/day, preferably from 0.1 mg/day to 10 mg/day.

The compounds of formula (I) can advantageously be formulated and/or administered in combination with one or more other therapeutically active substances, marketed or under development, that are selected according to a specific autoimmune, inflammatory, fibrotic or cholestatic disorder or any other disorders that may be found associated to said disorder in medical settings and that should be also treated. Such a combined administration includes two possibilities: the two agents are administered to a subject at substantially similar times; or the two agents are administered to a subject at different times, at independent intervals that may or may not overlap or coincide. As such, the invention also relates to a kit-of-parts, comprising a compound of the invention, in association with another therapeutically active substance, for their simultaneous, separate or sequential use in the therapy, in particular in the treatment of an autoimmune, inflammatory, fibrotic or cholestatic disorder.

The invention also relates to a pharmaceutical composition comprising a compound of formula (I) and another therapeutically active substance.

A non-exhaustive list of therapeutically active substances that may be advantageously formulated and/or administered with compounds of formula (I) includes:
  Anti-inflammatory, and anti-oxidant agents;
  Immunosuppressor agents;
  Hepatoprotective agents;
  Agents used in the treatment of heart failure or coronary insufficiency Anti-hypertensive and hypotensive agents;
  Anti-coagulant, vasodilators, and anti-ischemic agents;
  Agents used in the treatment of metabolic diseases, such as anti-diabetic, anti-NASH, hypolipidemic, hypocholesterolemic, anti-atherosclerotic and anti-obesity agents.
  Anti-viral agents;
  Anti-cancer agents and cancer prevention agents;
  Anti-cholestatic agents.

A further embodiment of the invention is a method of treating a RORγ related-disease comprising the administration of a compound of formula (I) to a patient in need thereof.

Several other advantages of the invention will rise in the reading of the following examples; they should be considered as illustrative data and not as limitative ones.

EXAMPLES

Chemical names follow IUPAC nomenclature. Starting materials and solvents were purchased from commercial suppliers (Acros Organic, Sigma Aldrich, Combi-Blocks, Fluorochem, Fluka, Alfa Aesar or Lancaster) and were used as received without further purification. Some starting materials can be readily synthesized by a person skilled in the art. Air and moisture sensitive reactions were carried out under an inert atmosphere of nitrogen, and glassware was oven-dried. No attempts were made to optimize reaction yields. Thin-layer chromatography (TLC) was done on Merck silica gel 60 UV254 (250 µm) plates. Visualization was accomplished with UV light. Column chromatography was performed on Geduran silica gel 60 (40-63 µm) from Merck. Melting points (mp) were recorded with a Büchi Melting Point B-545 and are uncorrected. All microwave irradiation experiments were carried out in a Biotage Initiator microwave apparatus. $^1$H spectra were recorded on Bruker Advance I spectrometer at 300 MHz. Chemical shifts (δ) are reported in ppm (parts per million), by reference to the hydrogenated residues of deuterated solvent as internal standard: 2.50 ppm for DMSO-d6, 7.26 ppm for CDCl3, and 3.31, and 4.78 for Methanol-d4. The spectral splitting patterns are designated as follows: s, singlet; d, doublet; dd, doublet of doublets; ddd, doublet of doublet of doublets; t, triplet; dt, doublet of triplets; q, quartet; m, multiplet; br s, broad singlet. Coupling constants (J) are quoted to the nearest 0.1 Hz. All tested compounds exhibited ≥95% chemical purity assessed by HPLC on a Merck HITACHI Lachrom L-7000 series and Merck HITACHI diode array detector L-7455 with a Waters column Symmetry C18 (3.5 µm, 4.6*75 mm) and using a gradient of MeOH/Millipore water containing 0.1% of formic acid. Mass spectrometry measurements were performed on qTOF Waters Micromass Ultima API and AutoPurification System 2767 with an Acquity QDa detector from Waters. All solvents are HPLC grade.

The compounds of the invention are prepared according to the general methods and general protocols of synthesis given below. Representative procedures suitable for the preparation of compounds of formula (I) are outlined in the Reaction Schemes for intermediate (FIG. 1) and final (FIG. 2) compounds. Reagents and conditions may be adapted and additional steps employed to produce further compounds encompassed in the present invention having alternative substituent groups, or for achieving such compounds at higher yield and/or of higher purity.

Example 1: Synthesis of Intermediates for the Synthesis of Compounds According to the Invention In the following, compounds termed "Ex. X" are intermediate compounds used for the synthesis of compounds of the present invention.

The general treatments and purification steps are carried out according to techniques well known by a person skilled in the art or such as those described in the literature: the reaction was quenched either with water, brine or sat. NH4Cl. Excess or solvent used for the reaction was removed under reduced pressure. The aqueous layer was extracted three times with a non-water miscible solvent (e.g. Et2O, EtOAc, CH2Cl2). The organic layer was dried over MgSO4, filtered and the solution was concentrated under reduced pressure. Purification of the crude material was realized either by double extraction using conc. HCl and NaOH 2N, by hydrochloride formation or by purification on silica gel column chromatography using standard mixture systems (cyclohexane/EtOAc, CH2Cl2/MeOH and CH2Cl2/EtOAc).

Intermediate Ex.1: 2-{3-[3-(tert-butoxy)-3-oxopropyl]-1H-indol-5-yl}acetic acid (FIG. 1A)

TABLE 1.1

| Cpd. | Starting compounds, Reaction conditions and purification, Yield, Appearance, $^1$H NMR (solvent) data |
|---|---|
| Ex. 1 | 2-{3-[3-(tert-butoxy)-3-oxopropyl]-1H-indol-5-yl}acetic acid<br>A solution of tert-butyl 3-(5-((ethoxycarbonyl)methyl)-1H-indol-3-yl)propanoate Ex. 2 (6.30 g, 19 mmol) and LiOH 2N (19 mL) in THF/MeOH (4:1, 30 mL) was stirred at rt for 2 h. The solution was concentrated under reduced pressure with a temperature of bath of 20° C. The reaction mixture was acidified with citric acid 1N to pH = 4-5. The aqueous layer was extracted with EtOAc. The organic layer was washed with water, dried over MgSO4, filtered and concentrated under reduced pressure<br>Yield: quantitative; appearance: yellowish solid; 1H NMR, d (ppm) (DMSO-d6): 1.37 (s, 9H); 2.55 (t, 2H, J = 7.8 Hz); 2.88 (t, 2H, J = 7.8 Hz); 3.57 (s, 2H); 6.95 (dd, 1H, J = 8.7 Hz, J = 2.0 Hz); 7.08 (d, 1H, J = 2.2 Hz); 7.25 (d, 1H, J = 8.3 Hz); 7.36 (br s, 1H); 10.73 (br s, 1H); 12.06 (br s, 1H) |
| Ex. 2 | tert-butyl 3-[5-(2-ethoxy-2-oxoethyl)-1H-indol-3-yl]propanoate<br>A solution of tert-butyl-3-[5-(2-ethoxy-2-oxoethyl)-1H-indol-3-yl]prop-2-enoate Ex. 3 and Pd/C 5% (1 spatula) in MeOH (100 mL) was stirred at rt under H2 overnight at atm p.. The suspension was filtered on Celite and the solution was concentrated under reduced pressure. The crude material was purified by column chromatography on silica gel (CH2Cl2/MeOH, 98:2)<br>Yield: 61%; Appearance: colorless oil; 1H NMR, d (ppm) (DMSO-d6): 1.38 (s, 9H); 2.55 (t, 2H, J = 7.3 Hz); 2.89 (t, 2H, J = 7.3 Hz); 3.60 (s, 3H); 3.70 (s, 2H); 4.07 (q, 2H, J = 7.1 Hz); 6.96 (dd, 1H, J = 8.3 Hz J = 1.4 Hz); 7.10 (d, 1H, J = 1.4 Hz); 7.27 (d, 1H); 7.38 (s, 1H); 10.77 (br s, 1H) |
| Ex. 3 | tert-butyl (2E)-3-[5-(2-ethoxy-2-oxoethyl)-1H-indol-3-yl]prop-2-enoate<br>A solution of ethyl 2-(3-formyl-1H-indol-5-yl)acetate Ex. 4 (6.7 g, 29.2 mmol) and (tert-butoxycarbonylmethylene)-triphenylphosphorane (24.2 g, 64.3 mmol) in dry THF (30 mL) was heated at 90° C. overnight under N2 atmosphere. The solvent was removed under reduced pressure and water was added to the residue. The aqueous layer was extracted with EtOAc. The organic layer was dried over MgSO4, filtered and the solution was concentrated under reduced pressure<br>Yield: quantitative; Appearance: yellowish oil; 1H NMR, d (ppm) (DMSO-d6): 1.50 (s, 9H); 3.61 (s, 3H); 3.81 (s, 2H); 4.02 (q, 2H, J = 7.1 Hz); 6.27 (d, 1H, J = 1.6 Hz); 7.10 (dd, 1H, J = 8.3 Hz J = 1.4 Hz); 7.40 (d, 1H, J = 8.3 Hz); 7.70-7.80 (m, 2H); 7.91 (s, 1H); 11.72 (br s, 1H) |
| Ex. 4 | ethyl 2-(3-formyl-1H-indol-5-yl)acetate<br>To a solution of DMF (100 mL) was added dropwise POCl3 (18 mL, 197 mmol) at 0° C. The reaction mixture was kept at 0° C. for 30 min. A solution of ethyl 2-(1H-indol-5-yl)acetate (20 g, 98.4 mmol) dissolved in DMF (20 mL) was added dropwise and the reaction was warmed to rt. The reaction was poured into water. The aqueous layer was washed with EtOAc. The aqueous layer was basified with NaHCO3 powder and extracted once with Et2O. A precipitate was formed in the filtrate upon standing for 18 h. The solid was collected by filtration and washed twice with water<br>Yield: 69%; Appearance: pale brown needles; 1H NMR, d (ppm) (DMSO-d6): 1.17 (t, 3H, J = 7.2 Hz); 3.73 (s, 2H); 4.07 (q, 2H, J = 7.2 Hz); 7.15 (dd, 1H, J = 2.0 Hz, J = 8.5 Hz); 7.44 (dd, 1H, J = 0.8 Hz, J = 8.4 Hz); 7.99 (dd, 1H, J = 0.6 Hz, J = 1.9 Hz); 8.27 (s, 1H); 9.91 (s, 1H); 12.10 (br s, 1H) |

Intermediate Ex.5: 2-[3-(2-methoxy-2-oxoethyl)-1H-indol-5-yl]acetic acid (FIG. 1B)

TABLE 1.2

| Cpd. | Starting compounds, Reaction conditions and purification, Yield, appearance, $^1$H NMR (solvent) data |
|---|---|
| Ex. 5 | 2-[3-(2-methoxy-2-oxoethyl)-1H-indol-5-yl]acetic acid<br>To a solution of 2-(3-iodo-4-{[4-methoxy-4-oxobut-2-en-1-yl]amino}phenyl)acetic acid Ex. 6 (275 mg, 0.73 mmol) in dry and degassed acetonitrile was introduced tri(o-tolyl)phosphine (67 mg, 0.22 mmol) followed by Et3N (611 µL, 4.40 mmol) and palladium (II) acetate (25 mg, 0.11 mmol). The reaction was refluxed for 3-4 h under N2 atmosphere. The completion of the reaction was monitored by HPLC. Water was added to the reaction mixture. The aqueous layer was extracted with EtOAc. The combined organic layer was washed with brine, dried over MgSO4, filtered and the solution was concentrated under reduced pressure. The residue was triturated with Et2O and impurities were removed by filtration. The filtrate was concentrated to dryness<br>Yield: 55%; Appearance: colorless oil; 1H NMR, d (ppm) (DMSO-d6): 3.58 (s, 2H); 3.61 (s, 3H); 3.73 (s, 2H); 6.99 (dd, 1H, J = 8.3 Hz J = 1.5 Hz); 7.24 (d, 1H, J = 1.5 Hz); 7.29 (d, 1H, J = 8.3 Hz); 7.35 (s, 1H); 10.92 (br s, 1H); 12.20 (br s, 1H) |

TABLE 1.2-continued

| Cpd. | Starting compounds, Reaction conditions and purification, Yield, appearance, $^1$H NMR (solvent) data |
|---|---|
| Ex. 6 | 2-(3-iodo-4-{[(2E)-4-methoxy-4-oxobut-2-en-1-yl]amino}phenyl)acetic acid<br>To a solution of 2-(4-amino-3-iodophenyl)acetic acid Ex. 7 (610 mg, 2.20 mmol) in dry THF (5 mL) was added Et3N (297 μL, 2.20 mmol) and methyl 4-bromobut-2-enoate (263 μL, 2.20 mmol). The reaction mixture was heated at 35° C. for 2 h30. The mixture was concentrated under reduced pressure to dryness. The residue was purified by column chromatography on silica gel (CH2Cl2/MeOH, 9:1)<br>Yield: 33%; Appearance: colorless oil; 1H NMR, d (ppm) (DMSO-d6): 3.38 (s, 2H); 3.66 (s, 3H); 3.99-4.02 (m, 2H); 5.29 (t, 1H, J = 6.0 Hz); 5.86 (d, 1H, J = 15.7 Hz); 6.43 (d, 1H, J = 8.5 Hz); 6.88-6.96 (m, 1H); 7.04 (dd, 1H, J = 8.3 Hz, J = 1.9 Hz); 7.55 (d, 1H, J = 1.9 Hz); 12.29 (s, 1H) |
| Ex. 7 | 2-(4-amino-3-iodophenyl)acetic acid<br>A solution of ethyl 2-(4-amino-3-iodophenyl)acetate Ex. 8 (1.11 g, 3.64 mmol) in EtOH (5 mL) and NaOH 2N (3.64 mL) was stirred at rt for 1 h. The reaction mixture was poured into cold water and acidified with citric acid 1N to pH = 4-5. The organic layer was extracted with EtOAc. The combined organic layer was washed with brine, dried over MgSO4, filtered and the solution was concentrated to dryness. The title compound was used for the next step without further purification.<br>Yield: quantitative; Appearance: brown solid; 1H NMR, d (ppm) (DMSO-d6): 3.35 (s, 2H); 5.11 (br s, 2H); 6.69 (d, 1H, J = 8.2 Hz); 6.96 (dd, 1H, J = 8.2 Hz, J = 1.9 Hz); 7.44 (d, 1H, J = 1.9 Hz); 12.21 (s, 1H) |
| Ex. 8 | ethyl 2-(4-amino-3-iodophenyl)acetate<br>In a reactor protected from light, at rt, were added Et2O (93 mL), sat. Na2CO3 (15 mL) and ethyl 2-(4-aminophenyl)acetate (2.50 g, 13.9 mmol). After few minutes of stirring, iodine monochloride (1.14 mL, 22.7 mmol) was added to the solution. The reaction mixture was stirred at rt for 4 h. The mixture was poured into water and the aqueous layer was extracted with EtOAc. The combined organic phase was dried over MgSO4, filtered and the solution was concentrated under reduced pressure. The crude material was purified by column chromatography on silica gel (cyclohexane/EtOAc, 8:2)<br>Yield: 26%; Appearance: yellowish oil; 1H NMR, d (ppm) (DMSO-d6): 1.17 (t, 3H, J = 7.1 Hz); 3.44 (s, 2H); 4.05 (q, 2H, J = 7.1 Hz); 5.18 (s, 2H); 6.70 (d, 1H, J = 8.2 Hz); 6.97 (dd, 1H, J = 8.3 Hz, J = 1.9 Hz); 7.45 (d, 1H, J = 1.9 Hz) |

Intermediate Ex.128: 2-[4-methyl-2-(piperidin-1-yl)phenyl]-2-phenylacetic acid (FIG. 10)

TABLE 1.3

| Cpd. | Starting compounds, Reaction conditions and purification, Yield, Appearance, $^1$H NMR (solvent) data |
|---|---|
| Ex. 124 | 4-methyl-2-(piperidin-1-yl)benzaldehyde<br>A solution of 2-bromo-4-methylbenzaldehyde (4.0 g, 20 mmol), piperidine (1.711 g, 20 mmol), BINAP (501 mg, 0.8 mmol), Pd2(dba)3 (368 mg, 0.4 mmol) and Cs2CO3 (9.821 g, 30 mmol) in toluene and under inert atmosphere was heated at 80° C. for 16 h. The solution was concentrated to dryness. The crude material was purified on silica gel column chromatography using hexanes/EtOAc (10:1)<br>Yield: 87% |
| Ex. 125 | (4-methyl-2-(piperidin-1-yl)phenyl)(phenyl)methanol<br>To a solution of 4-methyl-2-(piperidin-1-yl)benzaldehyde Ex. 124 (959 mg, 4.72 mmol) in dry THF was added at rt phenylmagnesiumbromide 1M (5.66 mL, 5.66 mmol). The solution was stirred at rt for 14 h. The solution was concentrated to dryness. The crude material was purified on silica gel column chromatography using hexanes/EtOAc (15:1) as eluent<br>Yield: 58% |
| Ex. 126 | 1-(2-(chloro(phenyl)methyl)-5-methylphenyl)piperidine<br>A solution of (4-methyl-2-(piperidin-1-yl)phenyl)(phenyl)methanol Ex. 125 (768 mg, 2.73 mg) and SOCl2 (974 mg, 8.19 mmol) in dry toluene was stirred at rt for 14 h. The solution was concentrated to dryness. The product was used in the next without further purification. |
| Ex. 127 | 2-(4-methyl-2-(piperidin-1-yl)phenyl)-2-phenylacetonitrile<br>A solution of 1-(2-(chloro(phenyl)methyl)-5-methylphenyl)piperidine Ex. 126 (915 mg, 3.05 mmol), potassium cyanide (178 mg, 3.05 mmol), 18-Crown-6 (1.082 g, 4.58 mmol) in H2O/DMF/Dioxane (2:2.5:1) was heated at 40° C. for 72 h. The solution was concentrated to dryness. The crude material was purified on flash chromatography using hexanes/EtOAc (1:0 to 20:1) as eluent<br>Yield: 29% |
| Ex. 128 | 2-(4-methyl-2-(piperidin-1-yl)phenyl)-2-phenylacetic acid<br>A solution of 2-(4-methyl-2-(piperidin-1-yl)phenyl)-2-phenylacetonitrile Ex. 127 (228 mg, 0.79 mmol) and HCl 6N (3.3 mL) in dioxane was heated at 90° C. for 16 h. The excess of solvent was removed under reduced pressure. Water was |

TABLE 1.3-continued

| Cpd. | Starting compounds, Reaction conditions and purification, Yield, Appearance, ¹H NMR (solvent) data |
|---|---|
| | added. The aqueous layer was extracted with a non-water miscible solvent. The combined organic layers were dried over MgSO4, filtered and the solution was concentrated under reduced pressure. The crude material was then purified on silica gel column chromatography using CH2Cl2/MeOH (100:0 to 94:6) followed by trituration on a mixture of Et2O/EtOAc<br>Yield: 55%; appearance: white solid; 1H NMR (300 MHz, DMSO-d6, d in ppm): 1.50 (br s, 2H); 1.66-1.60 (m, 4H); 2.25 (s, 3H); 2.71-2.65 (m, 4H); 5.36 (br s, 1H); 6.93-6.85 (m, 2H); 7.02 (br s, 1H); 7.35-7.22 (m, 5H); 12.41 (br s, 1H). |

Intermediates Benzylamino (FIG. 2)

Protocol A: to a solution of 2-substituted benzonitrile (1 eq.) in THF (50 mL for 50 mmol of starting material) was added phenyl magnesium bromide 1M (2 eq.) at rt under N2 atmosphere. After completion of the imine formation, MeOH was added to quench the excess of Grignard reagent at 0° C. Then, reducing agent (either NaBH4/MeOH, Zn/AcOH, Zn/ammonium acetate/ammonia/EtOH or ammonium formate/Pd(OH)2/EtOH) (1.5 eq.-2 eq.) was added either directly to the reaction mixture or imine intermediate was isolated before. The reaction was stirred at rt or gently heated at 40-60° C. The completion of the reaction was monitored by TLC.

Protocol B: step 1: to a solution of bromobenzene (1 eq.) in dry THF (50 mL for 50 mmol of starting material) was added n-BuLi (1.5 eq.) at −78° C. under N2 atmosphere. After 40 min of stirring at −78° C., the 2-substituted benzonitrile (1 eq.) dissolved/diluted in dry THF (small amount) was introduced dropwise. After 30 min of stirring, the ice bath was removed and the reaction mixture was warmed to rt. Step 2: a solution of substituted benzophenone (1 eq.) isolated at the step before, hydroxyl amine hydrochloride (1.1 eq.) and NaOH (1.1 eq.) in MeOH (50 mL for 50 mmol of starting material) was heated at 70° C. Step 3: the corresponding isolated oxime (1 eq.) was heated with zinc dust (1 eq.) in AcOH at 60° C. The reaction was monitored by TLC at all steps.

Protocol C: step 1: a solution of 2-substituted benzaldehyde (1 eq.) was dissolved in THF (20 mL for 2 g). To the solution was added titanium ethoxide (3 eq.) followed by rac-2-methyl-2-propane-sulfinamide (1 eq.). The reaction mixture was stirred at rt for 20 h. Step 2: to the previous synthesised imine in dry toluene (6 mL for 1 g), a solution of phenyl magnesium bromide (1.5 eq.) was added at 0° C. and the reaction mixture was stirred at rt for 24 h. Step 3: the previous synthesised intermediates was dissolved in MeOH (5 mL for 500 mg). Conc. HCl (2.5 mL for 500 mg) was added to cleave the protecting group and the solution was stirred at rt overnight. The reaction mixture was poured into CH2Cl2 (20 mL) and a solution of sodium hydroxide 2 M was added dropwise. The reaction was monitored by TLC at all steps.

TABLE 1.4

| Cpd. | Starting compounds, Reaction conditions and purification, Yield, Appearance, ¹H NMR (solvent) data |
|---|---|
| Ex. 9 | phenyl[2-(piperidin-1-yl)phenyl]methanaminium chloride<br>The titled compound was obtained following the procedure described in WO2006035157 (Protocol A)<br>Yield: 80%; appearance: yellow oil; 1H NMR, d (ppm) (DMSO-d6):<br>1.5-1.65 (m, 6H); 2.40 (s large, 2H); 2.62 (m, 2H); 2.80 (m, 2H); 5.56 (s, 1H); 7.05 (m, 1H); 7.1-7.2 (m, 4H); 7.27 (t, 2H, J = 7.3 Hz); 7.35 (d, 2H, J = 7.3 Hz); 7.45 (dd, 1H, J = 7.3 Hz, J = 1.5 Hz |
| Ex. 10 | (3-fluorophenyl)[2-(piperidin-1-yl)phenyl]methanaminium chloride<br>The titled compound was obtained following the modified procedure described in WO2006035157 (protocol A)<br>Yield: 15%; appearance: brown solid; 1H NMR, d (ppm) (DMSO-d6):<br>1.51-.61 (m, 6H); 2.48-2.50 (m, 2H); 2.71-2.73 (s, 2H); 5.97 (s, 1H); 7.11-7.53 (m, 7H); 7.75 (dd, 1H, J = 7.7 Hz, J = 1.4 Hz); 9.17 (br s, 3H) |
| Ex. 11 | [4-methyl-2-(pyrrolidin-1-yl)phenyl](phenyl)methanamine<br>The titled compound was obtained following the modified procedure described in WO2006035157 (Protocol A)<br>Yield: 27%; appearance: yellow oil; 1H NMR, d (ppm) (DMSO-d6): 1.81 (t, 4H, J = 6.5 Hz); 2.14-2.20 (m, 2H); 2.21 (s, 3H); 2.92 (m, 2H); 3.02 (m, 2H); 5.44 (s, 1H); 6.75 (dd, 1H, J = 6.8 Hz, J = 1.1 Hz); 6.87 (s, 1H); 7.20 (m, 4H); 7.29 (m, 2H) |
| Ex. 12 | (2-chloro-4-methylphenyl)(phenyl)methanamine<br>The titled compound was obtained following the procedure described in WO2013019653<br>Yield: 72%; appearance: brown oil; 1H NMR, d (ppm) (DMSO-d6): 2.25 (s, 3H); 5.37 (s, 1H); 7.13-7.19 (m, 4H); 7.22-7.32 (m, 5H); 7.59 (d, 1H, J = 7.9 Hz) |
| Ex. 13 | (2-bromo-4-methylphenyl)(phenyl)methanamine<br>The titled compound was obtained following the modified procedure described in WO2006035157 (Protocol A)<br>Yield: 50%; appearance: beige solid; 1H NMR, d (ppm) (DMSO-d6): 2.31 (s, 3H); 5.73 (br s, 1H); 7.33-7.46 (m, 6H); 7.54 (br s, 1H); 7.76 (d, 1H, J = 8.0 Hz); 9.22 (br s, 3H) |
| Ex. 14 | (2,4-dimethylphenyl)(phenyl)methanaminium chloride<br>The titled compound was obtained following the procedure described in WO2013019653 |

TABLE 1.4-continued

| Cpd. | Starting compounds, Reaction conditions and purification, Yield, Appearance, $^1$H NMR (solvent) data |
|---|---|
| | Yield: 66%; appearance: beige solid; 1H NMR, d (ppm) (DMSO-d6): 2.20 (s, 3H); 2.26 (s, 3H); 5.62 (s, 1H); 7.03 (br s, 1H); 7.12 (d, 1H, J = 7.9 Hz); 7.28-7.42 (m, 5H); 7.46 (d, 1H, J = 7.9 Hz); 8.58 (br s, 3H) |
| Ex. 16 | [6-methyl-2-(pyrrolidin-1-yl)pyridin-3-yl](phenyl)methanamine<br>The titled compound was obtained following the modified procedure described in WO2006035157 (Protocol A). The imine intermediate was isolated and reduced with ammonium formate in EtOH with the presence of Pd(OH)2<br>Yield: 13%; appearance: brown oil; 1H NMR, d (ppm) (DMSO-d6): 1.77-1.86 (m, 4H); 2.28 (s, 3H); 3.42-3.46 (m, 4H); 5.38 (s, 1H); 6.57 (d, 1H, J = 7.6 Hz); 7.14-7.20 (m, 1H); 7.25-7.33 (m, 4H); 7.41 (d, 1H, J = 7.6 Hz) |
| Ex. 17 | (2-fluoro-4-methylphenyl)(phenyl)methanaminium chloride<br>The titled compound was obtained following the modified procedure described in WO2006035157 (Protocol A)<br>Yield: 20%; appearance: white solid; 1H NMR, d (ppm) (DMSO-d6): 2.32 (s, 3H); 5.74 (s, 1H); 7.09-7.15 (m, 2H); 7.36-7.50 (m, 5H); 7.63 (t, 1H, J = 8.3 Hz); 9.17 (s, 3H) |
| Ex. 18 | (2-fluoro-5-methylphenyl)(phenyl)methanaminium chloride<br>The titled compound was obtained following the modified procedure described in WO2006035157 (Protocol A)<br>Yield: 61%; appearance: brown solid; 1H NMR, d (ppm) (DMSO-d6): 2.32 (s, 3H); 5.74 (s, 1H); 7.11-7.28 (m, 2H); 7.33-7.50 (m, 5H); 7.60 (dd, 1H, J = 7.4 Hz, J = 1.9 Hz); 9.20 (s, 3H) |
| Ex. 19 | (2,4-dimethylphenyl)(pyridin-2-yl)methanamine<br>The titled compound was obtained following the procedure described in WO2013019621<br>To a solution of N-[(2,4-dimethylphenyl)(pyridin-2-yl)methylidene]hydroxylamine (320 mg, 1.40 mmol) in AcOH was added Zinc (370 mg, 5.6 mmol). The mixture was kept at 60° C. for 64 h. Water was added and the reaction mixture was filtered on Celite and washed with Et2O. The filtrate was basified with NaOH 1N to pH = 9 and extracted with EtOAc. The combined organic layer was dried over MgSO4, filtered and the solution was concentrated under reduced pressure.<br>Yield: 96%; appearance: white solid; 1H NMR, d (ppm) (DMSO-d6): 2.26 (s, 3H); 2.37 (s, 3H); 4.53 (br s, 2H); 5.51 (s, 1H); 6.95 (s, 2H); 7.09 (s, 1H); 7.13 (d, 1H, J = 8.0 Hz); 7.54 (t, 1H, J = 5.7 Hz); 7.93 (dt, 1H, J = 7.9 Hz, J = 1.6 Hz); 8.66 (d, 1H, J = 4.8 Hz) |
| Ex. 20 | phenyl({2-[2-(trifluoromethyl)piperidin-1-yl]phenyl})methanaminium chloride<br>To a solution of 2-[2-(trifluoromethyl)piperidin-1-yl]benzonitrile (1 g, 3.9 mmol) in THF was added phenyl magnesium bromide 1M in THF (7.9 mL, 7.9 mmol) at rt under N2 atmosphere. The reaction mixture was heated at 85° C. for 18 h. The reaction mixture was cooled to 0° C. and a solution of concentrated ammonia and sat. NH4Cl (1/1) was added. The solution was extracted with Et2O, the organic layer was dried over MgSO4, filtered and the solvent was evaporated under reduced pressure. The residue was purified by column chromatography on silica gel (cyclohexane/EtOAc, 8:2), taken up in MeOH and NaBH4 (1.1 equiv) was added. The reaction mixture was stirred for 18 h at rt, the solvent was removed by evaporation under reduced pressure, the residue was taken up in water, extracted with Et2O and HCl 1M in EtOH was added. The precipitate formed was filtered.<br>Yield: 37%; appearance: white solid; 1H NMR, d (ppm): 1.33-1.38 (m, 1H); 1.57-163 (m, 2H); 1.93-1.97 (m, 1H); 2.29-2.32 (m, 1H); 2.56 (m, 1H); 2.74-2.77 (m, 2H); 3.10-3.12 (m, 1H); 5.97-6.01 (m, 1H); 7.32-7.51 (m, 8H); 7.75 (d, 1H, J = 7.6 Hz); 9.01 (s, 3H) |
| Ex. 21 | [2-(3,5-dimethylpiperidin-1-yl)phenyl](phenyl)methanamine<br>To a solution of 2-(3,5-dimethylpiperidin-1-yl)benzonitrile (0.5 g, 2.3 mmol) in THF was added phenyl magnesium bromide 1M in THF (4.7 mL, 4.7 mmol) at rt under N2 atmosphere. The reaction mixture was heated at 55° C. for 18 h. The reaction mixture was cooled to rt, MeOH was added and then NaBH4 (194 mg, 5.1 mmol). The reaction mixture was stirred for 10 h at rt. Water was added to quench the reaction. The solution was concentrated by evaporation under reduced pressure. The residue was taken up in HCl 6N, washed with Et2O and the aqueous layer was basified with NaOH 2N. The aqueous layer was extracted with EtOAc. The organic layer was dried over MgSO4, filtered and the solvent was evaporated under reduced pressure.<br>Yield: 37%; appearance: yellow oil; 1H NMR, d (ppm): 0.59 (q, 1H, J = 11.4 Hz); 0.72 (d, 3H, J = 6.4 Hz); 0.83 (d, 3H, J = 6.4 Hz); 1.62-1.84 (m, 3H); 2.03-2.15 (m, 2H); 2.25 (br s, 2H); 2.5-2.53 (m, 1H); 2.95 (dd, 1H, J = 11.2 Hz, J = 1.7 Hz); 5.51 (s, 1H); 7.05-7.19 (m, 4H); 7.23 (t, 2H, J = 7.6 Hz); 7.35 (d, 2H, J = 7.1 Hz); 7.51 (d, 1H, J = 7.7 Hz) |
| Ex. 23 | 3-methyl-1-[2-(piperidin-1-yl)phenyl]butan-1-aminium chloride<br>The titled compound was obtained following the procedure described in WO2006035157 (Protocol A)<br>Yield: 41%; appearance: red oil; 1H NMR, d (ppm) (DMSO-d6): 0.84 (d, 3H, J = 6.4 Hz); 0.92 (d, 3H, J = 6.4 Hz); 1.33-1.88 (m, 9H); 2.63 (m, 2H); 2.94 (m, 2H); 4.78 (t, 1H, J = 7.6 Hz); 7.18-7.33 (m, 3H); 7.67 (d, 1H, J = 7.6 Hz); 8.65 (br s, 3H) |

TABLE 1.4-continued

| Cpd. | Starting compounds, Reaction conditions and purification, Yield, Appearance, $^1$H NMR (solvent) data |
|---|---|
| Ex. 24 | (5-methylquinolin-8-yl)(phenyl)methanamine<br>The titled compound was obtained following the modified procedure described in WO2006035157 (Protocol B) using AcOH/Zn as reducing agent<br>Yield: 50%; appearance: beige solid; 1H NMR, d (ppm) (DMSO-d6): 2.63 (s, 3H); 3.32 (br s, 2H); 6.30 (s, 1H); 7.09-7.15 (m, 1H); 7.20-7.25 (m, 2H, J = 7.1 Hz); 7.41-7.46 (m, 3H); 7.55 (dd, 1H, J = 8.6 Hz, J = 4.2 Hz); 7.69 (d, 1H, J = 7.2 Hz); 8.44 (dd, 1H, J = 8.5 Hz, J = 1.7 Hz); 8.93 (dd, 1H, J = 4.2 Hz, J = 1.7 Hz) |
| Ex. 25 | (4-chloro-2-methylphenyl)(phenyl)methanaminium chloride<br>The titled compound was obtained following the procedure described in WO2013019682<br>Yield: 29%; appearance: white solid; 1H NMR, d (ppm) (DMSO-d6): 2.27 (s, 3H); 5.72 (s, 1H); 7.36-7.43 (m, 7H); 7.64 (d, 1H, J = 8.5 Hz); 9.11 (br s, 3H) |
| Ex. 26 | [2-(azepan-1-yl)phenyl](phenyl)methanamine<br>The titled compound was obtained following the modified procedure described in WO2006035157 (Protocol A)<br>Yield: 41%; appearance: red oil; 1H NMR, d (ppm) (DMSO-d6): 1.52-1.68 (m, 8H); 2.20 (br s, 2H); 2.86-3.05 (m, 4H); 5.65 (s, 1H); 7.01-7.06 (m, 1H); 7.12-7.17 (m, 3H); 7.23-7.37 (m, 5H) |
| Ex. 27 | (4-methylnaphthalen-1-yl)(phenyl)methanaminium chloride<br>The titled compound was obtained following the modified procedure described in WO2006035157 (Protocol A)<br>Yield: 57%; appearance: white solid; 1H NMR, d (ppm) (DMSO-d6): 2.68 (s, 3H); 6.40 (br s, 1H); 7.30-7.40 (m, 3H); 7.51-61 (m, 5H); 7.83 (d, 1H, J = 7.3 Hz); 8.07-8.11 (m, 2H); 9.27 (br s, 3H) |
| Ex. 28 | (2-chloro-5-methylphenyl)(phenyl)methanaminium chloride<br>The titled compound was obtained following the modified procedure described in WO2006035157 (Protocol A)<br>Yield: 72%; appearance: white solid; 1H NMR, d (ppm) (DMSO-d6): 2.18 (s, 3H); 2.46 (s, 3H); 3.52-3.66 (m, 2H); 6.33 (d, 1H, J = 8.1 Hz); 7.04-7.35 (m, 11H); 8.95 (d, 1H, J = 8.0 Hz); 12.09 (s, 1H) |
| Ex. 29 | (4-fluoro-2-methylphenyl)(phenyl)methanaminium chloride<br>The titled compound was obtained following the modified procedure described in WO2006035157 (Protocol A)<br>Yield: 22%; appearance: white solid; 1H NMR, d (ppm) (DMSO-d6): 2.29 (s, 3H); 5.71 (s, 1H); 7.11-7.45 (m, 7H); 7.64-7.69 (m, 1H); 9.09 (s, 2H) |
| Ex. 31 | (4-bromo-2-methylphenyl)(phenyl)methanaminium chloride<br>The titled compound was obtained following the procedure described in WO2013019682<br>Yield: 38%; appearance: white solid; 1H NMR, d (ppm) (DMSO-d6): 2.24 (s, 3H); 5.71 (s, 1H); 7.37-7.43 (m, 5H); 7.50-7.57 (m, 3H); 9.11 (s, 2H) |
| Ex. 32 | 3-methyl-1-(naphthalen-1-yl)butan-1-aminium chloride<br>The titled compound was obtained following the procedure described in (Asada et al, 2010)<br>Yield: 19%; appearance: pale brown solid; 1H NMR, d (ppm) (DMSO-d6): 0.86 (d, 3H, J = 6.5 Hz); 0.90 (d, 3H, J = 6.6 Hz); 1.42-1.55 (m, 1H); 1.83-2.03 (m, 2H); 5.19 (t, 1H, J = 7.3 Hz); 7.57-7.69 (m, 3H); 7.84 (d, 1H, J = 6.6 Hz); 7.97-8.04 (m, 2H); 8.23 (d, 1H, J = 8.5 Hz); 8.60 (br s, 3H) |
| Ex. 33 | {[1,1'-biphenyl]-2-yl}(phenyl)methanaminium chloride<br>The titled compound was obtained following the modified procedure described in WO2006035157 (Protocol A)<br>Yield: 44%; appearance: white solid; 1H NMR, d (ppm) (DMSO-d6): 5.44 (s, 1H); 7.12-7.15 (m, 2H); 7.22-7.39 (m, 6H); 7.45-7.52 (m, 4H); 7.54-7.60 (m, 1H, J = 7.6 Hz, J = 1.4 Hz); 8.83 (d, 1H, J = 7.7 Hz); 9.06 (br s, 3H) |
| Ex. 34 | cyclopropyl(4-methylnaphthalen-1-yl)methanaminium chloride<br>The titled compound was obtained following the modified procedure described in WO2006035157 (Protocol A)<br>Yield: 15%; appearance: white solid; 1H NMR, d (ppm) (DMSO-d6): 0.30-0.51 (m, 2H); 0.55-0.71 (m, 2H); 1.45-1.55 (m, 1H); 2.68 (s, 3H); 4.61 (d, 1H, J = 9.2 Hz); 7.47 (d, 1H, J = 7.7 Hz); 7.61-7.66 (m, 2H); 7.79 (d, 1H, J = 7.4 Hz); 8.09-8.13 (m, 1H); 8.19-8.22 (m, 1H); 8.55 (br s, 3H) |
| Ex. 35 | [2-(dimethylamino)phenyl](phenyl)methanaminium chloride<br>The titled compound was obtained following the procedure described in (Dubrovskiy & Larock, 2012)<br>Yield: 53%; appearance: yellow oil; 1H NMR, d (ppm) (DMSO-d6): 2.06 (s, 6H); 5.62 (s, 1H); 7-7.06 (m, 1H); 7.12-7.18 (m, 3H); 7.23-7.28 (m, 2H); 7.33-7.37 (m, 3H) |
| Ex. 36 | [5-chloro-2-(piperidin-1-yl)phenyl](phenyl)methanamine<br>The titled compound was obtained following the modified procedure described in WO2006035157 (Protocol A)<br>Yield: 95%; appearance: green oil; 1H NMR, d (ppm) (DMSO-d6): 0.84 (d, 3H, J = 6.4 Hz); 0.92 (d, 3H, J = 6.4 Hz); 1.33-188 (m, 9H); 2.63 (m, 2H); 2.94 (m, 2H); 4.78 (t, 1H, J = 7.6 Hz); 7.18-7.33 (m, 3H); 7.67 (d, 1H, J = 7.6 Hz); 8.65 (br s, 3H) |
| Ex. 37 | phenyl[2-(pyrrolidin-1-yl)-4-(trifluoromethyl)phenyl]methanamine<br>The titled compound was obtained following the modified procedure described in WO2006035157 (Protocol A) using Zn/ammonium acetate/ammonia/EtOH as reducing agent. The starting material 4-(trifluoromethyl)-2-(pyrrolidin-1- |

TABLE 1.4-continued

| Cpd. | Starting compounds, Reaction conditions and purification, Yield, Appearance, $^1$H NMR (solvent) data |
|---|---|
| | yl)benzonitrile was obtained as described in WO 2011120604<br>Yield: 93%; appearance: white solid; 1H NMR, d (ppm) (DMSO-d6):<br>1.78-1.87 (m, 4H); 2.39 (br s, 2H); 2.95-3.02 (m, 2H); 3.06-3.13 (m, 2H); 5.43 (s, 1H); 7.07 (dd, 1H, J = 8.2 Hz, J = 2.0 Hz); 7.11 (d, 1H, J = 2.0 Hz); 7.12-7.18 (m, 1H); 7.22-7.31 (m, 5H) |
| Ex. 38 | [4-bromo-2-(pyrrolidin-1-yl)phenyl](phenyl)methanamine<br>The titled compound was obtained following the procedure described in (Robak et al, 2010) (Protocol C)<br>Yield: 47%; appearance: white solid; 1H NMR, d (ppm) (DMSO-d6):<br>1.78-1.87 (m, 4H); 2.39 (br s, 2H); 2.95-3.02 (m, 2H); 3.06-3.13 (m, 2H); 5.43 (s, 1H); 7.07 (dd, 1H, J = 8.2 Hz, J = 2.0 Hz); 7.11 (d, 1H, J = 2.0 Hz); 7.12-7.18 (m, 1H); 7.22-7.31 (m, 5H) |
| Ex. 39 | 3-methyl-1-[2-(morpholin-4-yl)phenyl]butan-1-amine<br>The titled compound was obtained following the procedure described in WO2006035157 (Protocol A)<br>Yield: 45%; appearance: orange solid; 1H NMR, d (ppm) (DMSO-d6):<br>0.94 (m, 6H); 1.48-1.63 (m, 3H); 1.95 (m, 2H); 2.84 (m, 2H); 2.98 (m, 2H); 3.85 (m, 4H); 4.57 (m, 1H); 7.16 (m, 2H); 7.24 (m, 1H); 7.40 (m, 1H) |
| Ex. 40 | 1-[2-(azepan-1-yl)phenyl]-3-methylbutan-1-amine<br>The titled compound was obtained following the procedure described in WO2006035157 (Protocol A)<br>Yield: 24%; appearance: brown oil; 1H NMR, d (ppm) (DMSO-d6): 0.94 (m, 6H); 1.52-1.67 (m, 3H); 1.74 (m, 8H); 3.03 (m, 4H); 4.56 (m, 1H); 7.07-7.23 (m, 3H); 7.31-7.34 (m, 1H) |
| Ex. 41 | 2-cyclohexyl-1-[2-(piperidin-1-yl)phenyl]ethan-1-amine<br>The titled compound was obtained following the procedure described in WO2006035157 (Protocol A)<br>Yield: 22%; appearance: yellow oil; 1H NMR, d (ppm) (CDCl3): 0.86-1.88 (m, 21H); 2.80 (m, 4H); 4.53 (m, 1H); 7.09-7.24 (m, 3H); 7.35 (m, 1H) |
| Ex. 42 | 2-(1-aminopentyl)-N,N-diethylaniline<br>The titled compound was obtained following the modified procedure described in WO2006035157 (Protocol A)<br>Yield: 71%; appearance: colorless oil; 1H NMR, d (ppm) (DMSO-d6): 0.90 (t, 3H, J = 7.3 Hz); 1.00 (t, 6H, J = 7.0 Hz); 1.21-1.45 (m, 4H); 1.63-1.71 (m, 4H); 2.96 (q, 4H, J = 7.0 Hz); 4.55 (m, 1H); 7.11-7.24 (m, 3H); 7.37 (d, 1H, J = 7.6 Hz) |
| Ex. 43 | 2-(1-amino-3-methylbutyl)-N,N-diethylaniline<br>The titled compound was obtained following the procedure described in WO2006035157 (Protocol A)<br>Yield: 67%; appearance: brown oil; 1H NMR, d (ppm) (DMSO-d6): 0.93 (d, 3H, J = 2.9 Hz); 0.96 (d, 3H, J = 2.9 Hz); 1.01 (t, 6H, J = 7.3 Hz); 1.41-1.71 (m, 5H); 2.96 (q, 4H, J = 7.3 Hz); 4.64 (m, 1H); 7.10-7.23 (m, 3H); 7.37 (d, 1H, J = 7.8 Hz) |
| Ex. 44 | 2-(3-methylphenyl)-1-[2-(piperidin-1-yl)phenyl]ethan-1-amine<br>The titled compound was obtained following the procedure described in WO2006035157 (Protocol A)<br>Yield: 72%; appearance: brown oil; 1H NMR, d (ppm) (DMSO-d6): 1.65 (m, 4H); 1.76 (m, 4H); 2.36 (s, 3H); 2.72-2.87 (m, 4H); 3.04 (dd, 1H, J = 13.1 Hz, J = 4.4 Hz); 4.7 (m, 1H); 7.04-7.25 (m, 6H); 7.51 (d, 1H, J = 7.3 Hz) |
| Ex. 46 | 2-[amino(phenyl)methyl]-N,N,5-trimethylaniline<br>The titled compound was obtained following the procedure described in WO2013019682<br>Yield: 85%; appearance: yellow oil; 1H NMR, d (ppm) (DMSO-d6): 2.22 (s, 3H); 2.38 (br s, 2H); 2.57 (s, 6H); 6.82 (dd, 1H, J = 7.9 Hz, J = 0.7 Hz); 6.82 (d, 1H, J = 0.7 Hz); 7.10-7.25 (m, 6H) |
| Ex. 47 | 4-[amino(phenyl)methyl]-3-(pyrrolidin-1-yl)benzonitrile<br>A solution of previously synthesized (4-bromo-2-(pyrrolidin-1-yl)phenyl)(phenyl)methanamine (250 mg, 0.76 mmol), Pd(PPh3)4 (174 mg, 0.15 mmol) and Zn(CN)2 (106 mg, 0.91 mmol) in anhydrous DMF was heated at 80° C. under N2 atmosphere overnight. After cooling, water was added to quench the reaction. The aqueous solution was extracted with Et2O. The organic layer was washed with HCl 1N. The aqueous layer was basified with NaOH 2N up to pH = 9 and extracted with Et2O. The organic layer was dried over MgSO4, filtered and the solution was concentrated under reduced pressure. The compound was pure enough and used in the next step without further purification<br>Yield: 76%; appearance: yellow oil; 1H NMR, d (ppm) (DMSO-d6):<br>1.79-1.88 (m, 4H); 2.43 (br s, 2H); 3.02-3.07 (m, 2H); 3.11-3.19 (m, 2H); 5.50 (s, 1H); 7.13-7.19 (m, 1H); 7.23-7.28 (m, 4H); 7.31 (dd, 1H, J = 8.0 Hz, J = 1.6 Hz); 7.35 (d, 1H, J = 1.6 Hz); 7.50 (d, 1H, J = 7.9 Hz) |
| Ex. 49 | phenyl[3-(piperidin-1-yl)phenyl]methanaminium chloride<br>The titled compound was obtained following the modified procedure described in WO2006035157 (Protocol A)<br>Yield: 92%; appearance: white solid; 1H NMR, d (ppm) (Methanol d4):<br>1.65 (br s, 2H); 1.77 (br s, 4H); 3.26 (br s, 4H); 5.61 (s, 1H); 6.96-7.14 (m, 3H); 7.34-7.50 (m, 6H) |
| Ex. 50 | phenyl[4-(piperidin-1-yl)phenyl]methanaminium chloride<br>The titled compound was obtained following the modified procedure described in WO2006035157 (Protocol A) |

TABLE 1.4-continued

| Cpd. | Starting compounds, Reaction conditions and purification, Yield, Appearance, $^1$H NMR (solvent) data |
|---|---|
| | Yield: 46%; appearance: pale yellow solid; 1H NMR, d (ppm) (Methanol d4): 1.82 (brs, 2H); 2.04-2.12 (m, 4H); 3.63-3.67 (m, 4H); 5.79 (s, 1H); 7.41-7.51 (m, 5H); 7.68 (d, 2H, J = 8.6 Hz); 7.84 (d, 2H, J = 8.8 Hz) |
| Ex. 51 | phenyl[2-(pyrrolidin-1-yl)phenyl]methanaminium chloride<br>The titled compound was obtained following the modified procedure described in WO2006035157 (Protocol A)<br>Yield: 57%; appearance: white solid; 1H NMR, d (ppm) (DMSO-d6): 1.89 (br s, 4H); 2.99 (br s, 4H); 6.01 (br s, 1H); 7.25 (br s, 1H); 7.32-7.49 (m, 7H); 7.62 (d, 1H, J = 7.8 Hz); 9.02 (br s, 3H) |
| Ex. 52 | [2-(morpholin-4-yl)phenyl](phenyl)methanaminium chloride<br>The titled compound was obtained following the modified procedure described in WO2006035157 (Protocol A)<br>Yield: 47%; appearance: white solid; 1H NMR, d (ppm) (DMSO-d6): 2.51-2.57 (m, 2H); 2.78-2.84 (m, 2H); 3.69 (t, 4H, J = 4.4 Hz); 6.03 (d, 1H, J = 5.5 Hz); 7.28-7.51 (m, 8H); 7.76 (d, 1H, J = 7.3 Hz); 9.04 (s, 2H) |
| Ex. 53 | [4-methyl-2-(piperidin-1-yl)phenyl](phenyl)methanamine<br>The titled compound was obtained following the modified procedure described in WO2006035157 (Protocol A). The starting material 4-methyl-2-(piperidin-1-yl)benzonitrile was obtained as described in WO2011120604<br>Yield: 76%; appearance: yellow oil; 1H NMR, d (ppm) (Methanol d4): 1.49-1.61 (m, 6H); 2.22 (s, 3H); 2.54-2.61 (m, 2H); 2.77-2.81 (m, 2H); 5.49 (s, 1H); 6.86 (dd, 1H, J = 1.0 Hz, J = 7.9 Hz); 6.91 (s, 1H); 7.11 (t, 1H, J = 7.3 Hz); 7.22 (t, 2H, J = 7.2 Hz); 7.30 (d, 1H, J = 7.8 Hz); 7.35 (d, 2H, J = 7.2 Hz) |
| Ex. 54 | phenyl[2-(1H-pyrrol-1-yl)phenyl]methanaminium chloride<br>The titled compound was obtained following the modified procedure described in WO2006035157 (Protocol A). The starting material 2-(1H-pyrrol-1-yl)benzonitrile was prepared from 2-bromobenzonitrile using a Ullmann reaction: to a solution of 2-bromobenzonitrile (1 eq.), pyrrole (1. eq.) and K3PO4 (2 eq.) in dry toluene under N2 atmosphere was added 1,10-phenanthroline (0.2 eq.) followed by CuI (0.1 eq.). The reaction mixture was heated at 110° C. (pre-heated oil bath) for 72 h<br>Yield: 22%; appearance: white solid; 1H NMR, d (ppm) (Methanol d4): 5.37 (s, 1H); 6.28 (t, 2H); 6.65 (t, 2H); 7.17 (m, 2H); 7.36-7.43 (m, 4H); 7.57 (dt, 1H, J = 7.8 Hz, J = 1.7 Hz); 7.65 (dt, 1H, J = 7.5 Hz, J = 1.5 Hz); 7.73 (dd, 1H, J = 7.5 Hz, J = 1.7 Hz) |
| Ex. 55 | (4-methoxy-2-methylphenyl)(phenyl)methanamine<br>The titled compound was obtained following the modified procedure described in WO2006035157 (Protocol A).<br>Yield: 88%; appearance: brown oil; 1H NMR, d (ppm) (Methanol d4): 2.19 (s, 3H); 3.77 (s, 3H); 5.26 (s, 1H); 6.71 (d, 1H, J = 2.7 Hz); 6.79 (dd, 1H, J = 2.8 Hz, J = 8.6 Hz); 7.17-7.31 (m, 5H); 7.37 (d, 1H, J = 8.6 Hz) |
| Ex. 56 | (2-methoxy-4-methyl phenyl)(phenyl)methanaminium chloride<br>The titled compound was obtained following the modified procedure described in WO2006035157 (Protocol A).<br>Yield: 62%; appearance: white solid; 1H NMR, d (ppm) (Methanol d4): 2.37 (s, 3H); 3.87 (s, 3H); 5.73 (s, 1H); 6.85 (d, 1H, J = 7.7 Hz); 6.95 (s, 1H); 7.06 (d, 1H, J = 7.8 Hz); 7.36-7.47 (m, 5H) |
| Ex. 57 | [4-methyl-2-(morpholin-4-yl)phenyl](phenyl)methanaminium chloride<br>The titled compound was obtained following the modified procedure described in WO2006035157 (Protocol A).<br>Yield: 37%; appearance: white solid; 1H NMR, d (ppm) (Methanol d4): 2.38 (s, 3H); 2.67-2.79 (m, 4H); 3.74 (t, 4H, J = 4.6 Hz); 6.11 (s, 1H); 7.19 (d, 1H, J = 7.9 Hz); 7.26 (s, 1H); 7.36-7.45 (m, 6H) |
| Ex. 60 | [4-chloro-2-(pyrrolidin-1-yl)phenyl](phenyl)methanamine<br>The titled compound was obtained following the modified procedure described in WO2006035157 (Protocol A). The starting material 4-(chloro)-2-(pyrrolidin-1-yl)benzonitrile was synthesized according to procedure described in WO2011120604 and using Zn/ammonium acetate in EtOH as reducing agent.<br>Yield: quantitative; appearance: orange oil; 1H NMR, d (ppm) (DMSO-d6): 1.78-1.87 (m, 4H); 2.39 (br s, 2H); 2.95-3.02 (m, 2H); 3.06-3.13 (m, 2H); 5.43 (s, 1H); 7.07 (dd, 1H, J = 8.2 Hz, J = 2.0 Hz); 7.11 (d, 1H, J = 2.0 Hz); 7.12-7.18 (m, 1H); 7.22-7.31 (m, 5H) |
| Ex. 61 | [2-(2,5-dihydro-1H-pyrrol-1-yl)-4-methylphenyl](phenyl)methanaminium chloride<br>The titled compound was obtained following the procedure described in (Robak et al, 2010) (Protocol C). The starting material 4-methyl-2-(2H-pyrrol-1(5H)-yl)benzaldehyde was prepared from 2-bromo-4-methylbenzaldehyde using a Buchwald-Hartwig reaction (2-bromo-4-methylbenzaldehyde (1 eq.), 2,5-dihydro-1H-pyrrole (1 eq.), BINAP (0.04 eq.), Pd2(dba)3 (0.02 eq.), Cs2CO3 (1.5 eq.) in toluene at 80° C. for 7 h)<br>Yield: 47%; appearance: white solid; 1H NMR, d (ppm) (Methanol d4): 2.41 (s, 3H); 4.17-4.33 (m, 4H); 5.96 (s, 2H); 6.34 (s, 1H); 7.30-7.51 (m, 8H) |
| Ex. 62 | [4-methyl-2-(4-methylpiperazin-1-yl)phenyl](phenyl)methanaminium chloride<br>The titled compound was obtained following the modified procedure described in WO2006035157 (Protocol A). The starting material 4-methyl-2-(4-methylpiperazin-1-yl)benzonitrile was prepared from 2-bromo-4- |

TABLE 1.4-continued

| Cpd. | Starting compounds, Reaction conditions and purification, Yield, Appearance, $^1$H NMR (solvent) data |
|---|---|
| | methylbenzonitrile using a Buchwald-Hartwig reaction (2-bromo-4-methylbenzonitrile (1 eq.), N-methylpiperazine (1.5 eq.), BINAP (0.05 eq.), Pd2(dba)3 (0.03 eq.), Cs2CO3 (2 eq.) in toluene at 90° C. for 16 h) Yield: 50%; appearance: white solid; 1H NMR, d (ppm) (DMSO-d6): 2.30 (s, 3H); 2.71 (s, 3H); 3.05-3.16 (m, 6H); 5.93 (s, 1H); 7.14 (d, 2H, J = 8.2 Hz); 7.29-7.42 (m, 3H); 7.49 (d, 2H, J = 6.9 Hz); 7.60 (d, 1H, J = 7.8 Hz); 9.12 (br s, 2H) |
| Ex. 63 | (2,4-dimethylphenyl)(5-methylthiophen-2-yl)methanaminium chloride Magnesium turnings (0.118 g, 4.87 mmol) and crystal of iodine were suspended in dry THF (2 mL) and 1-bromo-2,4-dimethylbenzene (0.60 mL, 4.47 mmol) in dry THF (4 mL) was added dropwise at rt. Reaction was stirred for 80 min (the mixture discolored) and then 5-methylthiophene-2-carbonitrile (0.43 mL, 4.06 mmol) in dry THF (3 mL) was added dropwise. Reaction was carried out at reflux for 18 h. In other flask, in anhydrous conditions more magnesium organic compound was done by suspending magnesium turnings (3.5 eq.) and crystal of iodine in dry THF (4 mL) and addition of 1-bromo-2,4-dimethylbenzene (3 eq.). After 2 h of stirring at 40° C., the mixture was transferred to proper flask which was firstly cooled down. Reaction was continued at reflux for 17 h. The reaction was cooled down and quenched with sat. NH4Cl. THF was evaporated and extraction with EtOAc was done. The combined organic layers were dried over MgSO4, filtered and the the solution was concentrated to dryness. The residue was dissolved in methanol (10 mL and reaction mixture was cooled down to 0° C. Next sodium borohydride (0.307 g, 8.12 mmol) was added and reaction was carried out at rt for 17 h. The treatment was as described in general protocol. The crude material was purified on silica gel column chromatography using hexanes/EtOAc (10:1) as eluent followed by hydrochloride formation Yield: 54%; appearance: white solid; 1H NMR, d (ppm) (Methanol d4): 2.26 (s, 3H); 2.34 (s, 3H); 2.43 (d, 3H, J = 0.8 Hz); 5.89 (s, 1H); 6.71-6.72 (m, 1H); 6.88 (d, 1H); 7.11 (m, 1H); 7.18 (m, 1H); 7.37 (d, 1H, J = 8.3 Hz) |
| Ex. 64 | (1H-indol-7-yl)(phenyl)methanamine The titled compound was obtained following the modified procedure described in WO2006035157 (Protocol A) Yield: 85%; appearance: pale yellow solid; 1H NMR, d (ppm) (Methanol d4): 5.56 (s, 1H); 6.44 (d, 1H, J = 3.2 Hz); 7.02 (t, 1H, J = 7.6 Hz); 7.13 (d, 1H, J = 7.3 Hz); 7.18-7.23 (m, 2H); 7.26-7.32 (m, 2H); 7.41-7.48 (m, 3H) |
| Ex. 65 | (1-methyl-1H-indol-7-yl)(phenyl)methanaminium chloride The titled compound was obtained following the modified procedure described in WO2006035157 (Protocol A) Yield: 52%; appearance: white solid; 1H NMR, d (ppm) (Methanol d4): 3.90 (s, 3H); 6.49 (d, 1H, J = 3.2 Hz); 6.59 (s, 1H); 7.01 (d, 1H); 7.16-7.23 (m, 2H); 7.35-7.46 (m, 5H); 7.66 (dd, 1H, J = 2.2 Hz, J = 6.7 Hz) |
| Ex. 66 | [4-fluoro-2-(pyrrolidin-1-yl)phenyl](phenyl)methanaminium chloride The titled compound was obtained following the modified procedure described in WO2006035157 (Protocol A) using Zn/ammonium acetate/ammonia/EtOH as reducing agent. The starting material 4-fluoro-2-(pyrrolidin-1-yl)benzonitrile was obtained as described in WO2011120604 Yield: 68%; appearance: white solid; 1H NMR, d (ppm) (DMSO-d6): 1.78-1.87 (m, 4H); 2.39 (br s, 2H); 2.95-3.02 (m, 2H); 3.06-3.13 (m, 2H); 5.43 (s, 1H); 7.07 (dd, 1H, J = 8.2 Hz, J = 2.0 Hz); 7.11 (d, 1H, J = 2.0 Hz); 7.12-7.18 (m, 1H); 7.22-7.31 (m, 5H) |
| Ex. 67 | [2-(1H-imidazol-1-yl)phenyl](phenyl)methanamine To a solution of (2-bromophenyl)(phenyl)methanamine (500 mg, 2 mmol) in acetonitrile (10 mL) was added imidazole (190 mg, 2.80 mmol), Cu2O (14 mg, 0.1 mmol), Cs2CO3 (1.24 g, 3.8 mmol) and 8-hydroxyquinoline (55 mg, 0.38 mmol). The reaction was carried out for 70 h at 90° C. The mixture was filtered through Celite and concentrated to dryness, then partitioned between water and CH2Cl2. The aqueous layer was extracted twice. The combined organic layers were dried over MgSO4, filtered and the solution was concentrated under reduced pressure. The crude material was purified on silica gel column chromatography using i) CH2Cl2/MeOH (20:1) ii) EtOAc:hexanes to EtOAc:MeOH (1:1 to 7:3) as eluents followed by hydrochloride formation slurred with diethyl ether. The free base was realized and slurred with pentane:Et2O (1:1) Yield: 46%; appearance: green solid; 1H NMR, d (ppm) (Methanol d4): 4.98 (s, 1H); 7.03-7.06 (m, 2H); 7.11 (s, 1H); 7.15 (s, 1H); 7.18-7.29 (m, 4H); 7.43 (dt, 1H, J = 1.5 Hz, J = 7.7 Hz); 7.51 (s, 1H); 7.58 (dt, 1H, J = 1.2 Hz, J = 7.6 Hz); 7.81 (dd, 1H, J = 1.4 Hz, J = 7.9 Hz) |
| Ex. 68 | [4-methoxy-2-(pyrrolidin-1-yl)phenyl](phenyl)methanaminium chloride The titled compound was obtained following the procedure described in (Robak et al, 2010) (Protocol C). The starting material 4-methoxy-2-(pyrrolidin-1-yl)benzaldehyde was prepared from 2-bromo-4-methoxybenzaldehyde using a Buchwald-Hartwig reaction (2-bromo-4-methoxybenzaldehyde (1 eq.), pyrrolidine (1 eq.), BINAP (0.04 eq.), Pd2(dba)3 (0.02 eq.), Cs2CO3 (1.5 eq.) in toluene at 100° C. for 17 h) Yield: 92%; appearance: pale yellow solid; 1H NMR, d (ppm) (Methanol d4): 2.26 (m, 4H); 3.71 (m, 2H); 3.90 (s, 3H); 6.60 (s, 1H); 7.15 (m, 1H); 7.23 (m, 1H); 7.4-7.52 (m, 6H) |

TABLE 1.4-continued

| Cpd. | Starting compounds, Reaction conditions and purification, Yield, Appearance, $^1$H NMR (solvent) data |
|---|---|
| Ex. 69 | (2-bromo-4-methylphenyl)(pyrimidin-2-yl)methanaminium chloride<br>2-bromo-1-iodo-4-methylbenzene (3.38 g, 11.38 mmol) was dissolved in THF and cooled down to −40° C. Isopropylomagnesium chloride 2M in THF (2.85 mL, 34.15 mmol) was added dropwise at −40° C. on a period of 30 min. The reaction was carried out 3 h at −40° C. and then 2-cyanopyrimidine (0.4 g, 3.81 mmol) (dissolved in small amount of THF) was added dropwise. The mixture was slowly warmed to rt and then stirred for additional 2 h. MeOH was added followed by NaBH4 (220 mg, 5.82 mmol) and the reaction mixture was stirred at rt for 16 h. Sat. NH4Cl was added to quench the reaction. The excess of MeOH was removed under reduced pressure. The aqueous layer was extracted with EtOAc. The combined organic layers were dried over MgSO4, filtered and the solution was concentrated to dryness. The crude material was purified on silica gel column chromatography using hexanes/EtOAc/MeOH (8:1:0 to 0:7:3) followed by hydrochloride formation<br>Yield: 42%; appearance: pale red solid; 1H NMR, d (ppm) (Methanol d4): 2.35 (s, 3H); 6.17 (s, 1H); 7.15 (d, 1H, J = 8.0 Hz); 7.22 (dd, 1H, J = 0.9 Hz, J = 8.0 Hz); 7.51 (dt, 1H, J = 0.5 Hz, J = 4.9 Hz); 7.62 (dd, 1H, J = 0.7 Hz); 8.87 (d, 2H, J = 5.0 Hz) |
| Ex. 70 | [2-(4-benzylpiperazin-1-yl)-4-methylphenyl](phenyl)methanaminium chloride<br>The titled compound was obtained following the modified procedure described in WO2006035157 (Protocol A). The starting material 2-(4-benzylpiperazin-1-yl)-4-methylbenzonitrile was prepared from 2-bromo-4-methylbenzonitrile using a Buchwald-Hartwig reaction (2-bromo-4-methylbenzonitrile (1 eq.), piperazine (3 eq.), BINAP (0.04 eq.), Pd2(dba)3 (0.02 eq.), Cs2CO3 (2 eq.) in toluene at 90° C. for 78 h) followed by an insertion of protecting group (4-methyl-2-(piperazin-1-yl)benzonitrile (1 eq.), benzyl chloride (3.5 eq.), K2CO3 (6 eq.) in THF rt (20 h) to 40° C. (20 h))<br>Yield: 54%; appearance: pale yellow solid; 1H NMR, d (ppm) (Methanol d4): 2.38 (s, 3H); 2.85-3.22 (m, 5H); 3.38-3.59 (m, 3H); 4.42 (s, 2H); 6.11 (s, 1H); 7.25-7.58 (m, 13H) |
| Ex. 71 | {2-[(dimethylamino)methyl]phenyl}(phenyl)methanamine<br>The titled compound was obtained following the modified procedure described in WO2006035157 (Protocol A)<br>Yield: 41%; appearance: pale brown solid; 1H NMR, d (ppm) (Methanol d4): 2.39 (s, 6H); 3.38 (d, 1H, J = 12.9 Hz); 4.02 (d, 1H, J = 12.9 Hz); 5.73 (s, 1H); 7.10-7.13 (m, 1H); 7.33-7.48 (m, 8H) |
| Ex. 72 | 1-[2-(piperidin-1-yl)phenyl]but-3-yn-1-aminium chloride<br>The titled compound was obtained following the procedure described in (Robak et al, 2010) (Protocol C).<br>Yield: 50%; appearance: pale brown solid; 1H NMR, d (ppm) (Methanol d4): 1.77-2.06 (m, 6H); 2.61 (t, 1H, J = 2.7 Hz); 3.04 (dd, 2H, J = 2.2 Hz, J = 7.0 Hz); 3.34-3.56 (m, 4H); 5.29 (br s, 1H); 7.56-7.73 (m, 4H) |
| Ex. 73 | [4-methoxy-2-(piperidin-1-yl)phenyl](phenyl)methanamine<br>The titled compound was obtained following the procedure described in (Robak et al, 2010) (Protocol C). The starting material 4-methoxy-2-(piperidin-1-yl)benzaldehyde was prepared from 2-bromo-4-methoxybenzaldehyde using a Buchwald-Hartwig reaction (2-bromo-4-methoxybenzaldehyde (1 eq.), piperidine (1 eq.), BINAP (0.04 eq.), Pd2(dba)3 (0.02 eq.), Cs2CO3 (1.5 eq.) in toluene at 90° C. for 17 h)<br>Yield: 97%; appearance: pale brown solid; 1H NMR, d (ppm) (DMSO-d6): 1.66-1.83 (m, 6H); 2.97 (brs, 4H); 3.86 (s, 3H); 6.26 (br s, 1H); 7.00-7.09 (m, 2H); 7.39-7.50 (m, 6H) |
| Ex. 74 | [5-bromo-2-(pyrrolidin-1-yl)phenyl](phenyl)methanaminium chloride<br>The titled compound was obtained following the modified procedure described in WO2006035157 (Protocol A)<br>Yield: 39%; appearance: orange solid; 1H NMR, d (ppm) (Methanol d4): 1.97-1.99 (m, 4H); 2.99-3.10 (m, 4H); 6.10 (br s, 1H); 7.34-7.54 (m, 8H) |
| Ex. 75 | phenyl[2-(1,2,3,6-tetrahydropyridin-1-yl)phenyl]methanaminium chloride<br>The titled compound was obtained following the procedure described in (Robak et al, 2010) (Protocol C). The starting material 2-(5,6-dihydropyridin-1(2H)-yl)benzaldehyde was prepared from 2-fluorobenzaldehyde using a SNAr reaction (2-fluorobenzaldehyde (1 eq.), 1,2,3,6-tetrahydropyridine (1.1 eq.), K2CO3 (2 eq.) in DMF at 100° C. for 72 h)<br>Yield: 20%; appearance: white solid; 1H NMR, d (ppm) (Methanol d4): 2.28 (br s, 2H); 2.95-3.09 (m, 2H); 3.40-3.48 (m, 2H); 5.75-5.80 (m, 1H); 5.88-5.92 (m, 1H); 6.24 (s, 1H); 7.41-7.54 (m, 9H) |
| Ex. 76 | [2-(ethylamino)-4-methylphenyl](phenyl)methanaminium chloride<br>The titled compound was obtained following the modified procedure described in WO2006035157 (Protocol A). The starting material 2-(ethylamino)-4-methylbenzonitrile was prepared from 2-bromo-4-methylbenzonitrile using a Buchwald-Hartwig reaction (2-bromo-4-methylbenzonitrile (1 eq.), ethylamine in THF 2M (1.5 eq.), BINAP (0.05 eq.), Pd2(dba)3 (0.03 eq.), Cs2CO3 (2 eq.) in toluene at 90° C. for 6 h)<br>Yield: 71%; appearance: pale yellow solid; 1H NMR, d (ppm) (Methanol d4): 1.20 (t, 3H, J = 7.2 Hz); 2.34 (s, 3H); 3.04-3.18 (m, 2H); 5.87 (s, 1H); 6.80-6.86 (m, 2H); 7.15 (d, 1H, J = 7.9 Hz); 7.39-7.50 (m, 5H) |

TABLE 1.4-continued

| Cpd. | Starting compounds, Reaction conditions and purification, Yield, Appearance, $^1$H NMR (solvent) data |
|---|---|
| Ex. 77 | {4-methyl-2-[(propan-2-yl)amino]phenyl}(phenyl)methanaminium chloride<br>The titled compound was obtained following the modified procedure described in WO2006035157 (Protocol A). The starting material 2-(isopropylamino)-4-methylbenzonitrile was prepared from 2-bromo-4-methylbenzonitrile using a Buchwald-Hartwig reaction (2-bromo-4-methylbenzonitrile (1 eq.), isopropylamine (1.5 eq.), BINAP (0.05 eq.), Pd2(dba)3 (0.03 eq.), Cs2CO3 (2 eq.) in toluene at 90° C. for 6 h)<br>Yield: 43%; appearance: pale yellow solid; 1H NMR, d (ppm) (Methanol d4):<br>1.06 (d, 3H, J = 6.2 Hz); 1.15 (d, 3H, J = 6.2 Hz); 2.25 (s, 3H); 3.51-3.58 (m, 1H); 5.88 (s, 1H); 6.61 (s, 2H); 7.25-7.47 (m, 6H); 8.94 (br s, 3H) |
| Ex. 78 | [2-(4,4-difluoropiperidin-1-yl)phenyl](phenyl)methanaminium chloride<br>The titled compound was obtained following the modified procedure described in WO2006035157 (Protocol A). The starting material 2-(4,4-difluoropiperidin-1-yl)benzonitrile was prepared from 2-bromobenzonitrile using a Buchwald-Hartwig reaction (2-bromobenzonitrile (1 eq.), 4,4-difluoropiperidine (1 eq.), BINAP (0.04 eq.), Pd2(dba)3 (0.02 eq.), Cs2CO3 (1.5 eq.) in toluene at 85° C. for 48 h)<br>Yield: 44%; appearance: white solid; 1H NMR, d (ppm) (DMSO-d6):<br>2.00-2.17 (m, 4H); 2.58-2.67 (m, 2H); 2.86-2.77 (m, 2H); 6.02 (br s, 1H); 7.32-7.51 (m, 8H); 7.74 (d, 1H, J = 7.4 Hz); 8.97 (br s, 3H) |
| Ex. 79 | [2-(3,3-difluoropiperidin-1-yl)phenyl](phenyl)methanaminium chloride<br>The titled compound was obtained following the modified procedure described in WO2006035157 (Protocol A). The starting material 2-(3,3-difluoropiperidin-1-yl)benzonitrile was prepared from 2-bromobenzonitrile using a Buchwald-Hartwig reaction (2-bromobenzonitrile (1 eq.), 3,3-difluoropiperidine hydrochloride (1 eq.), BINAP (0.04 eq.), Pd2(dba)3 (0.02 eq.), Cs2CO3 (2.5 eq.) in toluene at 85° C. for 48 h)<br>Yield: 13%; appearance: white solid; 1H NMR, d (ppm) (DMSO-d6):<br>1.71-1.83 (m, 2H); 1.92-2.13 (m, 2H); 2.82-3.02 (m, 2H); 3.18-3.33 (m, 2H); 5.98 (s, 1H); 7.31-7.49 (m, 8H); 7.76 (d, 1H, J = 7.3 Hz); 9.01 (br s, 3H) |
| Ex. 80 | [4-methyl-2-(methylamino)phenyl](phenyl)methanaminium chloride<br>The titled compound was obtained following the modified procedure described in WO2006035157 (Protocol A). The starting material 4-methyl-2-(methylamino)benzonitrile was prepared from 2-bromo-4-methylbenzonitrile using a Ullmann reaction (2-bromo-4-methylbenzonitrile (1 eq.), methylamine in H2O 40% (5 eq.), Cu2O (0.1 eq.) at 100° C. for 16 h)<br>Yield: 47%; appearance: white solid; 1H NMR, d (ppm) (Methanol d4):<br>2.32 (s, 3H); 2.78 (s, 3H); 5.70 (s, 1H); 6.62-6.66 (m, 2H); 7.00 (d, 1H, J = 7.8 Hz); 7.37-7.48 (m, 5H) |
| EX. 81 | 1-{2-[amino(phenyl)methyl]phenyl}piperidin-3-ol<br>The titled compound was obtained following the modified procedure described in WO2006035157 (Protocol A). The starting material 2-(3-hydroxypiperidin-1-yl)benzonitrile was prepared from 2-bromobenzonitrile using a Buchwald-Hartwig reaction (2-bromobenzonitrile (1 eq.), piperidin-3-ol (1.1 eq.), BINAP (0.04 eq.), Pd2(dba)3 (0.02 eq.), Cs2CO3 (1.5 eq.) in toluene at 85° C. for 67 h)<br>Yield: 72%; appearance: yellow solid; 1H NMR, d (ppm) (Methanol d4):<br>1.41-1.89 (m, 4H); 2.44-3.03 (m, 4H); 3.61-3.88 (m, 1H); 6.64 (d, 1H, J = 17.9 Hz); 7.12-7.39 (m, 9H) |
| Ex. 82 | 1-[2-(dimethylamino)-4-methylphenyl]-3-methylbutan-1-aminium chloride<br>The titled compound was obtained following the procedure described in (Robak et al, 2010) (Protocol C). The starting material 2-(dimethylamino)-4-methylbenzaldehyde was prepared from 2-bromo-4-methylbenzaldehyde using a Buchwald-Hartwig reaction (2-bromo-4-methylbenzaldehyde (1.1 eq.), N,N-dimethylamine in THF 2M (1 eq.), BINAP (0.04 eq.), Pd2(dba)3 (0.02 eq.), Cs2CO3 (1.5 eq.) in toluene at 60° C. to 80° C. for 46 h)<br>Yield: 14%; appearance: white solid; 1H NMR, d (ppm) (Methanol d4):<br>0.98 (d, 3H, J = 6.6 Hz); 1.04 (d, 3H, J = 6.6 Hz); 1.49-1.58 (m, 1H); 1.82-2.03 (m, 2H); 2.45 (s, 3H); 3.16 (br s, 6H); 5.20 (br s, 1H); 7.43-7.64 (m, 3H) |
| Ex. 87 | 4-[amino(phenyl)methyl]-3-(piperidin-1-yl)phenol<br>To a solution of (4-methoxy-2-(piperidin-1-yl)phenyl)(phenyl)methanamine (1 eq.) in CH2Cl2 was added a solution of BBr3 1M in CH2Cl2 (3 eq.) at −40° C. Atfer addition, the reaction was warmed to rt. Water was added to quench the reaction. The two phases were separated and the aqueous layer was extracted with CH2Cl2. The combined organic layer was dried over MgSO4, filtered and the solution was concentrated under reduced pressure. The crude material was purified on silica gel column chromatography using CHCl3/MeOH (10:1 to 9:1) as eluent affording the titled compound.<br>Yield: 68%; appearance: pale brown solid; 1H NMR, d (ppm) (Methanol d4):<br>1.55-1.72 (m, 6H); 2.18-2.32 (m, 4H); 5.97 (s, 1H); 6.70 (dd, 1H, J = 2.5 Hz, J = 8.5 Hz); 6.81 (d, 1H, J = 2.5 Hz); 7.19 (d, 1H, J = 8.5 Hz); 7.42-7.48 (m, 5H) |
| Ex. 88 | [4-methyl-2-(piperidin-1-yl)phenyl](pyrimidin-2-yl)methanamine<br>4-methyl-2-(piperidin-1-yl)benzenamine (synthesized following the procedure described in WO2004002481) (1 g, 5.26 mmol) was dissolved in conc. H2SO4 (2.8 mL, 10 eq.). The solution was coolded at −5° C. and NaNO2 (362 mg, 5.25 mmol) dissolved in small amount of water was added dropwise at 0° C. under good stirring. After diazonium salt formation (ca 2 h), KI (1.31 g, 7.89 mmol) followed by urea (63 mg, 1.05 mmol) were added. The reaction was warmed to |

| Cpd. | Starting compounds, Reaction conditions and purification, Yield, Appearance, ¹H NMR (solvent) data |
|---|---|
| | rt and stirred at this temperature for 25 h. The reaction mixture was diluted with water and the aqueous solution was extracted with a non-water miscible organic solvent. The combined organic layers were dried over MgSO4, filtered and the solution was concentrated to dryness. The crude material was purified on silica gel column chromatography using hexanes/EtOAc (10:1) as eluent. The previously synthesized 1-(2-iodo-5-methylphenyl)piperidine (1.25 g, 4.15 mmol) was diluted in THF and cooled down to −40° C. To the solution was added dropwise isopropylmagnesium chloride 2M in THF (2.08 mL, 4.16 mmol). The reaction mixture was stirred at −40° C. for 3 h. 2-Cyanopyrimidine (250 mg, 2.38 mmol) dissolved in small amount of dry THF was introduced dropwise into the reactor and the resulting reaction mixture was stirred for additional 1 h. MeOH was added followed by NaBH4 (134 mg, 3.54 mmol) and the reaction mixture was stirred at rt for 2 h. Sat. NH4Cl was added to quench the reaction. The excess of MeOH was removed under reduced pressure. The aqueous layer was extracted with EtOAc. The combined organic layers were dried over MgSO4, filtered and the solution was concentrated to dryness. The crude material was purified two times in order to get the titled compound pure enough: i) silica gel column chromatography using CH2Cl2/EtOAc/MeOH (6:1:0 to 1:1:0 to 0:4:1) as eluent, ii) purification on preparative TLC using CH2Cl2/MeOH (12:1) as eluent<br>Yield: 24%; appearance: colorless oil; 1H NMR, d (ppm) (DMSO-d6): 1.52-1.67 (m, 6H); 2.30 (s, 3H); 2.67-2.74 (m, 2H); 2.90-2.98 (m, 2H); 5.68 (s, 1H); 6.92 (dd, 1H, J = 1.0 Hz, J = 7.9 Hz); 7.07 (d, 1H, J = 1.0 Hz); 7.10 (d, 1H, J = 7.9 Hz); 7.36 (t, 1H, J = 4.9 Hz); 8.77 (d, 2H, J = 4.9 Hz) |
| Ex. 89 | [5-methoxy-2-(piperidin-1-yl)phenyl](phenyl)methanaminium chloride<br>The titled compound was obtained following the procedure described in (Robak et al, 2010) (Protocol C). The starting material 5-methoxy-2-(piperidin-1-yl)benzaldehyde was prepared from 2-bromo-5-methoxybenzaldehyde using a Buchwald-Hartwig reaction (2-bromo-5-methoxybenzaldehyde (1 eq.), piperidine (1 eq.), BINAP (0.04 eq.), Pd2(dba)3 (0.02 eq.), Cs2CO3 (1.5 eq.) in toluene at 90° C. for 48 h)<br>Yield: 56%; appearance: white solid; 1H NMR, d (ppm) (DMSO-d6): 1.32-1.69 (m, 6H); 2.27-2.47 (m, 2H); 2.56-2.80 (m, 2H); 3.78 (s, 3H); 5.97 (br s, 1H); 6.92-6.99 (m, 1H); 7.24-7.30 (m, 1H); 7.33-7.43 (m, 4H); 7.50-7.52 (m, 2H); 8.99 (br s, 2H). |
| Ex. 90 | [4-methyl-2-(piperidin-1-yl)phenyl](5-methylthiophen-2-yl)methanaminium chloride<br>4-methyl-2-(piperidin-1-yl)benzenamine (synthesized following the procedure described in WO2004002481 A1)(5.3 g, 27.85 mmol) was dissolved in conc. H2SO4 (14.8 mL, 10 eq.). The solution was cooled at −5° C. and NaNO2 (1.92 g, 27.85 mmol) dissolved in small amount of water was added dropwise at 0° C. under good stirring. After diazonium salt formation (ca 30 min), KI (6.9 g, 41.78 mmol) followed by urea (0.3 g, 5.57 mmol) were added. The reaction was warmed to rt and stirred at this temperature for 20 h. The reaction mixture was diluted with water and the aqueous solution was extracted with a non-water miscible organic solvent. The combined organic layers were dried over MgSO4, filtered and the solution was concentrated to dryness. The crude material was purified on silica gel column chromatography using hexanes/EtOAc (12:1) as eluent. The previously synthesized 1-(2-iodo-5-methylphenyl)piperidine (2.13 g, 7.07 mmol) was diluted in THF and cooled down to −40° C. To the solution was added dropwise isopropylmagnesium chloride 2M in THF (6.19 mL, 12.37 mmol). The reaction mixture was stirred at −40° C. for 3 h. 5-Methylthiophene-2-carbonitrile (0.5 g, 4.06 mmol) dissolved in small amount of dry THF was introduced dropwise into the reactor and the resulting reaction mixture was stirred for additional 2 h. MeOH was added followed by NaBH4 (230 mg, 6.08 mmol) and the reaction mixture was stirred at 30° C. for 3 h. Sat. NH4Cl was added to quench the reaction. The excess of MeOH was removed under reduced pressure. The aqueous layer was extracted with EtOAc. The combined organic layers were dried over MgSO4, filtered and the solution was concentrated to dryness. The crude material was purified several times in order to get the titled compound pure enough: i) silica gel column chromatography using CH2Cl2/MeOH (20:1), ii) silica gel column chromatography using CDCl3/MeOH (100:1), iii) hydrochloride formation, iv) trituration of hydrochloride in Et2O/EtOH (20:1) and filtration, v) free base formation and purification on preparative TLC using CHCl3/MeOH (10:1) as eluent and vi) hydrochloride formation<br>Yield: 6%; appearance: pale brown solid; 1H NMR, d (ppm) (Methanol d4): 1.62-1.93 (m, 6H); 2.42 (s, 3H); 2.45 (d, 3H, J = 1.1 Hz); 2.80-3.21 (m, 4H); 6.46-6.62 (m, 1H); 6.75-6.76 (m, 1H); 7.01 (d, 1H, J = 3.6 Hz); 7.28-7.40 (m, 2H); 7.50-7.56 (m, 1H) |
| Ex. 91 | [4-methyl-2-(piperidin-1-yl)phenyl](1,3-thiazol-2-yl)methanaminium chloride<br>The previously synthesized 1-(2-iodo-5-methylphenyl)piperidine (1.90 g, 6.31 mmol) was diluted in THF. To the solution was added magnesium turnings (160 mg, 6.58 mmol). the reaction mixture was stirred at 20° C. and then heated at 60° C. for 3 h. The reaction mixture was cooled down to 0° C. and thiazole-2-carbonitrile (0.4 g, 3.63 mmol) dissolved in small amount of dry THF was introduced dropwise into the reactor and the resulting reaction mixture was |

TABLE 1.4-continued

| Cpd. | Starting compounds, Reaction conditions and purification, Yield, Appearance, $^1$H NMR (solvent) data |
|---|---|
| | stirred for additional 2 h at rt. MeOH was added followed by NaBH4 (200 mg, 5.29 mmol) and the reaction mixture was stirred at rt for 24 h. Sat. NH4Cl was added to quench the reaction. The excess of MeOH was removed under reduced pressure. The aqueous layer was extracted with EtOAc. The combined organic layers were dried over MgSO4, filtered and the solution was concentrated to dryness. The crude material was purified several times in order to get the titled compound pure enough: i) silica gel column chromatography using CH2Cl2/EtOAc/MeOH (10:1:0 to 0:9:1), ii) purification on preparative TLC using Et2O/MeOH (12:1) as eluent and iii) hydrochloride formation<br>Yield: 5%; appearance: pale brown solid; 1H NMR, d (ppm) (Methanol d4): 1.57-1.85 (m, 6H); 2.39 (s, 3H); 2.91-3.05 (m, 4H); 6.43 (s, 1H); 7.19 (d, 1H, J = 7.9 Hz); 7.37 (s, 1H); 7.42 (d, 1H, J = 8.0 Hz); 7.67 (d, 1H, J = 3.3 Hz); 7.88 (d, 1H, J = 3.3 Hz) |
| Ex. 92 | [2-(azepan-1-yl)-4-methoxyphenyl](phenyl)methanaminium chloride<br>The titled compound was obtained following the procedure described in (Robak et al, 2010) (Protocol C). The starting material 2-(azepan-1-yl)-4-methoxybenzaldehyde was prepared from 2-bromo-4-methoxybenzaldehyde using a Buchwald-Hartwig reaction (2-bromo-4-methoxybenzaldehyde (1 eq.), hexamethyleneimine (1 eq.), BINAP (0.04 eq.), Pd2(dba)3 (0.02 eq.), Cs2CO3 (1.5 eq.) in toluene at 90° C. for 17 h)<br>Yield: 40%; appearance: pale brown solid; 1H NMR, d (ppm) (Methanol d4): 1.80 (br s, 8H); 3.32 (br s, 2H); 3.89 (s, 3H); 4.89 (br s, 2H); 6.40 (br s, 1H); 7.04-7.12 (m, 2H); 7.42-7.50 (m, 6H) |
| Ex. 95 | [4-methyl-2-(propan-2-yloxy)phenyl](phenyl)methanamine<br>The titled compound was obtained following the modified procedure described in WO2006035157 (Protocol A). The starting material 2-isopropoxy-4-methylbenzonitrile was prepared from 2-hydroxy-4-methylbenzonitrile (synthesized according to WO2011120604)<br>Yield: 36%; appearance: colorless oil; 1H NMR, d (ppm) (Methanol d4): 1.14 (d, 3H, J = 6.0 Hz); 1.19 (d, 3H, J = 6.0 Hz); 2.30 (s, 3H); 4.54-4.62 (m, 1H); 5.28 (s, 1H); 6.71-6.75 (m, 2H); 7.13-7.20 (m, 2H); 7.24-7.32 (m, 4H) |
| Ex. 97 | (4-methyl-1H-indol-7-yl)(phenyl)methanamine<br>To a solution of 1-bromo-4-methyl-2-nitrobenzene (2.0 g, 9.26 mmol) in THF was added vinyl magnesium bromide 1M in THF (27.8 mL, 27.77 mmol) at −50° C. The reaction was finished after 1 h 30. The reaction was quenched with sat. NH4Cl. The aqueous layer was extracted with a non-water miscible organic solvent. The combined organic layers were dried over MgSO4, filtered and the solution was concentrated to dryness. The crude material was purified on silica gel column chromatography usinf hexanes/EtOAc (9:1) as eluent. A solution of the freshly synthesized 7-bromo-4-methyl-1H-indole (1.1 g, 5.24 mmol), zinc cyanide (860 mg, 7.32 mmol) and Pd(PPh3)4 (0.03 eq.) in DMF was heated under microwave irradiation at 170° C. for 1 h. After cooling, water was added to quench the reaction. The aqueous layer was extracted with a non-water miscible organic solvent. The combined organic layers were dried over MgSO4, filtered and the solution was concentrated under reduced pressure. The crude material was purified on silica gel column chromatography using hexanes/EtOAc (12:1 to 4:1) as eluent. The titled compound was then obtained following the modified procedure described in WO2006035157 (Protocol A)<br>Yield: 2%; appearance: pale brown solid; 1H NMR, d (ppm) (Methanol d4): 2.49 (s, 3H); 5.51 (s, 1H); 6.47 (d, 1H, J = 3.2 Hz); 6.81 (dd, 1H, J = 0.6 Hz, J = 7.3 Hz); 7.01 (d, 1H, J = 7.3 Hz); 7.17-7.22 (m, 2H); 7.25-7.31 (m, 2H); 7.39-7.43 (m, 2H) |
| Ex. 98 | [4-ethoxy-2-(piperidin-1-yl)phenyl](phenyl)methanamine<br>To a solution of 2-bromo-4-hydroxybenzonitrile (400 mg, 2.02 mmol) and Cs2CO3 (1.31 g, 4.02 mmol) in DMF was added bromoethane (0.24 mL, 3.23 mmol) at rt. The reaction was heated at 50° C. for 1 h. Water was added to quench the reaction. The aqueous layer was extracted with a non-water miscible organic solvent. The combined organic layers were dried over MgSO4, filtered and the solution was concentrated to dryness. The crude material was purified on silica gel column chromatography using hexanes/EtOAc (20:1) as eluent. 4-Ethoxy-2-(piperidin-1-yl)benzonitrile was prepared from the previous intermediate using a Buchwald-Hartwig reaction (2-bromo-4-ethoxybenzonitrile (1 eq.), piperidine (1 eq.), BINAP (0.04 eq.), Pd2(dba)3 (0.03 eq.), Cs2CO3 (1.5 eq.) in toluene at 80° C. for 77 h). The titled compound was then obtained following the modified procedure described in WO2006035157 (Protocol A)<br>Yield: 9%; appearance: colorless oil; 1H NMR, d (ppm) (DMSO-d6): 1.29 (t, 3H, J = 7.0 Hz); 1.45-1.65 (m, 6H); 2.20 (s, 2H); 2.53-2.62 (m, 2H) 2.76-2.87 (m, 2H); 3.97 (q, 2H, J = 7.0 Hz); 5.46 (s, 1H); 6.59-6.65 (m, 2H); 7.10-7.16 (m, 1H); 7.20-7.27 (m, 2H); 7.28-7.33 (m, 1H); 7.33-7.38 (m, 2H) |
| Ex. 99 | phenyl[2-(piperidin-1-yl)-4-(propan-2-yloxy)phenyl]methanamine<br>To a solution of 2-bromo-4-hydroxybenzonitrile (400 mg, 2.02 mmol) and Cs2CO3 (1.31 g, 4.02 mmol) in DMF was added 2-bromopropane (0.60 mL, 6.46 mmol) at rt. The reaction was heated at 50° C. for 44 h. Water was added to quench the reaction. The aqueous layer was extracted with a non-water |

TABLE 1.4-continued

| Cpd. | Starting compounds, Reaction conditions and purification, Yield, Appearance, $^1$H NMR (solvent) data |
|---|---|
| | miscible organic solvent. The combined organic layers were dried over MgSO4, filtered and the solution was concentrated to dryness. The crude material was purified on silica gel column chromatography using hexanes/EtOAc (15:1) as eluent. 4-Isopropoxy-2-(piperidin-1-yl)benzonitrile was prepared from the previous intermediate using a Buchwald-Hartwig reaction (2-bromo-4-isopropoxybenzonitrile (1 eq.), piperidine (1 eq.), BINAP (0.04 eq.), Pd2(dba)3 (0.03 eq.), Cs2CO3 (1.5 eq.) in toluene at 80° C. for 48 h). The titled compound was then obtained following the modified procedure described in WO2006035157 (Protocol A)<br>Yield: 12%; appearance: red visqueous solid; 1H NMR, d (ppm) (DMSO-d6): 1.29 (t, 3H, J = 7.0 Hz); 1.45-1.65 (m, 6H); 2.20 (s, 2H); 2.53-2.62 (m, 2H); 2.76-2.87 (m, 2H); 3.97 (q, 2H, J = 7.0 Hz); 5.46 (s, 1H); 6.59-6.65 (m, 2H); 7.10-7.16 (m, 1H); 7.20-7.27 (m, 2H); 7.28-7.33 (m, 1H); 7.33-7.38 (m, 2H) |
| Ex. 100 | (5-methylfuran-2-yl)[2-(piperidin-1-yl)phenyl]methanamine<br>Step 1: to a solution of 2-iodoaniline (2.0 g, 9.13 mmol) in acetonitrile (30 mL) was added K2CO3 (2.52 g, 18.3 mmol). The solution was stirred at rt for 15 min and then 1,5-diiodopentane (3.55 g, 11.0 mmol) was added to the solution under stirring. The reaction mixture was stirred under reflux for 48 h. The reaction was quenched with brine and the aqueous layer was extracted with EtOAc. The combined organic layers were dried over MgSO4, filtered and the solution was concentrated to dryness. The crude material was purified on silica gel column chromatography using cyclohexane/EtOAc (98:2) as eluent. Hydrochloride was formed, triturated in dry Et2O and filtered-off. Free base was obtained using NaHCO3 10%. pH of aqueous solution was adjusted to pH = 7 with citric acid 10% and then extracted with CH2Cl2. The combined organic layer were dried over MgSO4, filtered and the solution was concentrated under reduced pressure affording 1.84 g of colorless oil (yield: 70%). 1H NMR (300 MHz, DMSO-d6, d in ppm): 1.40-1.75 (m, 6H); 2.84 (m, 4H); 6.80 (td, 1H, J = 7.9 Hz, J = 1.5 Hz); 7.09 (dd, 1H, J = 7.9 Hz, J = 1.5 Hz); 7.34 (td, 1H, J = 7.9 Hz, J = 1.5 Hz); 7.81 (dd, 1H, J = 7.9 Hz, J = 1.5 Hz)<br>Step 2: 5-methylfuran-2-carbaldehyde (1.0 g, 9.08 mmol) was dissolved in dry THF (5 mL). Titanium ethoxide (7.62 mL, 36.3 mmol) and rac-2-methyl-2-propane-sulfinamide (1.76 g, 14.5 mmol) were added to the reaction mixture. The solution was stirred at rt for 3 days. Additional rac-2-methyl-2-propane-sulfinamide (660 mg, 5.45 mmol) and titanium ethoxide (1 mL, 9.08 mmol) were introduced. The reaction mixture was stirred for additional 3 days. Brine was added to quench the reaction and the solution was stirred vigorously. EtOAc was added and the resulting mixture was filtered on Celite. The two layers were partitioned. The organic layer was dried over MgSO4, filtered and the solution was concentrated under reduced pressure to afford orange oil (yield: 88%). RMN 1H (300 MHz, DMSO-d6, d in ppm): 1.13 (s, 9H); 2.38 (s, 3H); 6.39 (m, 1H); 7.26 (d, 1H, J = 3.1 Hz); 8.20 (s, 1H)<br>Step 3: 1-(2-iodophenyl)piperidine (940 mg, 3.30 mmol) was dissolved in dry THF (4 mL) and the solution was cooled down to −50° C. under N2 atmosphere. iPrMgCl 2M in THF (1.6 mL, 3.3 mmol) was introduced dropwise to the previous solution at −40° C. The reaction mixture was slowly warmed to rt and kept at rt for 1 h. The completion of halogen exchange was monitored by TLC. 2-Methyl-N-[(1E)-(5-methylfuran-2-yl)methylidene]propane-2-sulfinamide (400 mg, 1.9 mmol) diluted in dry THF (0.5 mL) was added dropwise at rt. The solution was stirred at rt for 2 h. Sat. NH4Cl was used to quench the reaction. The aqueous layer was extracted with EtOAc. The combined organic layers were dried over MgSO4, filtered and the solution was concentrated under vacuo. The crude material was purified on silica gel column chromatography using cyclohexane/EtOAc (8:2) as eluent affording pale yellow oil (yield: 13%). RMN 1H (300 MHz, DMSO-d6, d in ppm): 1.06 (d, 18H); 1.4-1.7 (m, 12H); 2.16 (d, 6H); 2.71 (m, 8H); 5.81 (d, 1H); 5.85-6.1 (m, 7H); 7-7.3 (m, 6H); 7.4-7.55 (m, 2H) (2 diastereoisomers)<br>Step 4: to a solution of 2-methyl-N-[(5-methylfuran-2-yl)[2-(piperidin-1-yl)phenyl]methyl]propane-2-sulfinamide (95 mg, 0.25 mmol) in MeOH (2 mL) was added HCl 6M (0.85 mL, 5.70 mmol). After 5 h of stirring at rt, the reaction was quenched with water and CH2Cl2. The two layers were separated. The aqueous layer was basified with NaOH 2N to pH = 10 and extracted with EtOAc. The combined organic layers were dried over MgSO4, filtered and the solution was concentrated under reduced pressure affording the titled compound<br>Yield: quantitative; appearance: colorless oil; 1H NMR, d (ppm) (DMSO-d6): 1.4-1.7 (m, 6H); 2.15 (s, 3H); 2.15-2.2 (m, 2H); 2.75 (m, 4H); 5.40 (s, 1H); 5.91 (m, 1H); 5.96 (d, 1H, J = 3.0 Hz); 7.00-7.25 (m, 3H); 7.17 (d, 1H, J = 7.1 Hz) |
| Ex. 101 | 3,3-dimethyl-1-[2-(piperidin-1-yl)phenyl]butan-1-amine<br>Step 1: a solution of 3,3-dimethylbutanal (1.0 g, 10 mmol) was diluted in CH2Cl2 (10 mL). To the solution was added titanium ethoxide (3.42 g, 15 mmol) followed by rac-2-methyl-2-propane-sulfinamide (600 mg, 5 mmol). The reaction mixture was stirred at rt for 2 h. Water was added to quench the reaction. The two phases were separated. The aqueous layer was extracted with CH2Cl2. The combined organic layers were dried over MgSO4, filtered and the solution was concentrated to dryness. The crude material was purified on silica gel column chromatography using hexanes/EtOAc (4:1) as eluent.<br>Step 2: to a solution of 1-(2-bromophenyl)piperidine (700 mg, 2.91 mmol) in |

TABLE 1.4-continued

| Cpd. | Starting compounds, Reaction conditions and purification, Yield, Appearance, ¹H NMR (solvent) data |
|---|---|
| | THF was added dropwise n-BuLi 2M (1.5 mL, 2.91 mmol) at −60° C. The reaction was warmed to rt for 4 h. The resulting mixture was transfered and added dropwise at rt to the previoulsy synthesized imine (300 mg, 1.48 mmol) dissolved in THF. After completion, the reaction was quenched with water. The organic layer was extracted with a non-water miscible organic solvent. The combined organic layers were dried over MgSO4, filtered and the solution was concentrated to dryness. The crude material was purified on silica gel column chromatography using hexanes/EtOAc (4:1) as eluent. Step 3: the previous synthesized intermediate (290 mg, 0.8 mmol) was dissolved in MeOH. Conc. HCl (0.8 mL) was added at 0° C. to cleave the protecting group and the solution was stirred for 3 h. The reaction mixture was poured into CH2Cl2 and a solution of sodium hydroxide 2M was added dropwise to adjust the pH. The two phases were separated and the aqueous layer was extracted with CH2Cl2. The combined organic layers were dried over MgSO4, filtered and the solution was concentrated to dryness. The crude material was purified on silica gel column chromatography using CH2Cl2/MeOH (6:1) as eluent affording the titled compound Yield: 69%; appearance: off-white foam; 1H NMR, d (ppm) (DMSO-d6): 0.84 (s, 9H); 1.44-1.75 (m, 8H); 2.52-2.74 (m, 2H); 2.87-3.03 (m, 2H); 4.44 (t, 1H, J = 6.3 Hz); 7.00-7.07 (m, 2H); 7.08-7.16 (m, 1H); 7.38-7.43 (m, 1H) |
| Ex. 102 | 1-[4-methyl-2-(piperidin-1-yl)phenyl]pentan-1-aminium chloride The titled compound was obtained following the procedure described in (Robak et al, 2010) (Protocol C). The starting material 4-methyl-2-(piperidin-1-yl)benzaldehyde was prepared from 2-bromo-4-methylbenzaldehyde using a Buchwald-Hartwig reaction (2-bromo-4-methylbenzaldehyde (1 eq.), piperidine (1.5 eq.), BINAP (0.05 eq.), Pd2(dba)3 (0.02 eq.), Cs2CO3 (1.4 eq.) in toluene at 90° C. for 6 h). Yield: 40%; appearance: pale yellow solid; 1H NMR, d (ppm) (DMSO-d6): 0.82 (t, 3H, J = 7.2 Hz); 0.96-1.42 (m, 5H); 1.48-1.77 (m, 6H); 1.88-2.01 (m, 1H); 2.30 (s, 3H); 2.59-3.11 (m, 4H); 4.55-4.80 (br s, 1H); 6.88-7.29 (m, 2H); 7.39-7.58 (m, 1H); 8.42 (br s, 2H) |
| Ex. 103 | 1-[4-methyl-2-(piperidin-1-yl)phenyl]butan-1-aminium chloride The titled compound was obtained following the procedure described in (Robak et al, 2010) (Protocol C). The starting material 4-methyl-2-(piperidin-1-yl)benzaldehyde was prepared from 2-bromo-4-methylbenzaldehyde using a Buchwald-Hartwig reaction (2-bromo-4-methylbenzaldehyde (1 eq.), piperidine (1.5 eq.), BINAP (0.05 eq.), Pd2(dba)3 (0.02 eq.), Cs2CO3 (1.4 eq.) in toluene at 90° C. for 17 h). Yield: 22%; appearance: pale orange solid; 1H NMR, d (ppm) (DMSO-d6): 0.88 (t, 3H, J = 7.3 Hz); 1.11-1.24 (m, 2H); 1.47-1.72 (m, 8H); 2.30 (s, 3H); 2.54-2.66 (m, 2H); 2.82-2.94 (m, 2H); 4.65 (s, 1H); 7.00-7.11 (m, 2H); 7.38-7.45 (m, 1H); 8.30 (br s, 2H) |
| Ex. 105 | (2-methyl-1,3-thiazol-5-yl)[2-(piperidin-1-yl)phenyl]methanamine Step 1: to a solution of 2-iodoaniline (2.0 g, 9.13 mmol) in acetonitrile (30 mL) was added K2CO3 (2.52 g, 18.3 mmol). The solution was stirred at rt for 15 min and then 1,5-diiodopentane (3.55 g, 11.0 mmol) was added to the solution under stirring. The reaction mixture was stirred under reflux for 48 h. The reaction was quenched with brine and the aqueous layer was extracted with EtOAc. The combined organic layers were dried over MgSO4, filtered and the solution was concentrated to dryness. The crude material was purified on silica gel column chromatography using cyclohexane/EtOAc (98:2) as eluent. Hydrochloride was formed, triturated in dry Et2O and filtered-off. Free base was obtained using NaHCO3 10%. pH of aqueous solution was adjusted to pH = 7 with citric acid 10% and then extracted with CH2Cl2. The combined organic layer were dried over MgSO4, filtered and the solution was concentrated under reduced pressure affording 1.84 g of colorless oil (yield: 70%). 1H NMR (300 MHz, DMSO-d6, d in ppm): 1.40-1.75 (m, 6H); 2.84 (m, 4H); 6.80 (td, 1H, J = 7.9 Hz, J = 1.5 Hz); 7.09 (dd, 1H, J = 7.9 Hz, J = 1.5 Hz); 7.34 (td, 1H, J = 7.9 Hz, J = 1.5 Hz); 7.81 (dd, 1H, J = 7.9 Hz, J = 1.5 Hz) Step 2: 2-methylthiazole-5-carbaldehyde (900 mg, 7.08 mmol) was dissolved in dry THF (5 mL). Titanium ethoxide (4.45 mL, 21.2 mmol) and rac-2-methyl-2-propane-sulfinamide (1.20 g, 9.9 mmol) were added to the reaction mixture. The solution was stirred at rt overnight. Brine was added to quench the reaction and the solution was stirred vigorously. EtOAc was added and the resulting mixture was filtered on Celite. The two layers were partitionated. The organic layer was dried over MgSO4, filtered and the solution was concentrated under reduced pressure. The crude material was purified on silica gel column chromatography using cyclohexane/EtOAc (75:25) as eluent to afford orange solid (yield: 86%). 1H NMR (300 MHz, DMSO-d6, d in ppm): 1.14 (s, 9H); 2.72 (s, 3H); 8.35 (s, 1H); 8.70 (s, 1H) Step 3: 1-(2-iodophenyl)piperidine (990 mg, 3.50 mmol) was dissolved in dry THF (10 mL) and the solution was cooled down to −50° C. under N2 atmosphere. iPrMgCl 2M in THF (1.8 mL, 3.7 mmol) was introduced dropwise to the previous solution at −40° C. The reaction mixture was slowly warmed to rt and kept at rt for 1 h. The completion of halogen exchange was monitored by TLC. 2-Methyl-N-[(1E)-(2-methyl-1,3-thiazol-5-yl)methylidene]propane-2-sulfinamide (455 mg, 2.0 mmol) diluted in dry THF (0.5 mL) was added |

| Cpd. | Starting compounds, Reaction conditions and purification, Yield, Appearance, ¹H NMR (solvent) data |
|---|---|
|  | dropwise at rt. The solution was stirred at rt for 4 h. Sat. NH4Cl was used to quench the reaction. The aqueous layer was extracted with EtOAc. The combined organic layers were dried over MgSO4, filtered and the solution was concentrated under vacuo. The crude material was purified on silica gel column chromatography using cyclohexane/EtOAc (6:4) as eluent affording colorless oil (yield: 65%). 1H NMR (300 MHz, DMSO-d6, d in ppm): 1.13 (s, 9H); 1.4-1.7 (m, 6H); 2.55 (s, 3H); 2.6-2.8 (m, 4H); 6.18 (d, 1H, J = 7.0 Hz); 6.26 (d, 1H, J = 7.0 Hz); 7.1-7.35 (m, 4H); 7.50 (dd, 1H, J = 7.6 Hz, J = 1.5 Hz) Step 4: to a solution of 2-methyl-N-[(2-methyl-1,3-thiazol-5-yl)[2-(piperidin-1-yl)phenyl]nethyl]propane-2-sulfinamide (240 mg, 0.61 mmol) in MeOH (5 mL) was added HCl 6M (2.04 mL, 12.30 mmol). After 48 h of stirring at rt, the reaction was quenched with water and EtOAc. The two layers were separated. The aquous layer was basified with NaOH 2N to pH = 10 and extracted with EtOAc. The combined organic layers were dried over MgSO4, filtered and the solution was concentrated under reduced pressure affording the titled compound Yield: 67%; appearance: colorless oil; 1H NMR, d (ppm) (DMSO-d6): 1.4-1.7 (m, 6H); 2.42 (br s, 2H); 2.55 (d, 3H, J = 1.0 Hz); 2.60 (m, 2H); 2.80 (m, 2H); 5.69 (s, 1H); 7.0-7.25 (m, 3H); 7.28 (d, 1H, J = 1.0 Hz); 7.50 (dd, 1H, J = 7.6 Hz, J = 1.5 Hz) |
| Ex. 106 | (5-methyl-1,3-thiazol-2-yl)[2-(piperidin-1-yl)phenyl]methanamine Step 1: to a solution of 2-iodoaniline (2.0 g, 9.13 mmol) in acetonitrile (30 mL) was added K2CO3 (2.52 g, 18.3 mmol). The solution was stirred at rt for 15 min and then 1,5-diiodopentane (3.55 g, 11.0 mmol) was added to the solution under stirring. The reaction mixture was stirred under reflux for 48 h. The reaction was quenched with brine and the aqueous layer was extracted with EtOAc. The combined organic layers were dried over MgSO4, filtered and the solution was concentrated to dryness. The crude material was purified on silica gel column chromatography using cyclohexane/EtOAc (98:2) as eluent. Hydrochloride was formed, triturated in dry Et2O and filtered-off. Free base was obtained using NaHCO3 10%. pH of aqueous solution was adjusted to pH = 7 with citric acid 10% and then extracted with CH2Cl2. The combined organic layer were dried over MgSO4, filtered and the solution was concentrated under reduced pressure affording 1.84 g of colorless oil (yield: 70%). 1H NMR (300 MHz, DMSO-d6, d in ppm): 1.40-1.75 (m, 6H); 2.84 (m, 4H); 6.80 (td, 1H, J = 7.9 Hz, J = 1.5 Hz); 7.09 (dd, 1H, J = 7.9 Hz, J = 1.5 Hz); 7.34 (td, 1H, J = 7.9 Hz, J = 1.5 Hz); 7.81 (dd, 1H, J = 7.9 Hz, J = 1.5 Hz) Step 2: 5-methylthiazole-2-carbaldehyde (1 g, 7.86 mmol) was dissolved in dry THF (5 mL). Titanium ethoxide (4.95 mL, 23.59 mmol) and rac-2-methyl-2-propane-sulfinamide (1.33 g, 11.01 mmol) were added to the reaction mixture. The solution was stirred at rt 3 days. Additional rac-2-methyl-2-propane-sulfinamide (572 mg, 4.72 mmol) and titanium ethoxide (1 mL, 9.08 mmol) were introduced. The reaction mixture was stirred for additional 1 day. Brine was added to quench the reaction and the solution was stirred vigorously. EtOAc was added and the resulting mixture was filtered on Celite. The two layers were partitionated. The organic layer was dried over MgSO4, filtered and the solution was concentrated under reduced pressure. The crude material was purified on silica gel column chromatography using cyclohexane/EtOAc (75:25) as eluent to afford yellow solid (yield: 54%). 1H NMR (300 MHz, DMSO-d6, d in ppm): 1.17 (s, 9H); 2.54 (d, 3H, J = 1.1 Hz); 7.87 (d, 1H, J = 1.1 Hz); 8.45 (s, 1H) Step 3: 1-(2-iodophenyl)piperidine (990 mg, 3.50 mmol) was dissolved in dry THF (10 mL) and the solution was cooled down to −50° C. under N2 atmosphere. iPrMgCl 2M in THF (1.8 mL, 3.7 mmol) was introduced dropwise to the previous solution at −40° C. The reaction mixture was slowly warmed to rt and kept at rt for 1 h. The completion of halogen exchange was monitored by TLC. 2-methyl-N-[(1E)-(5-methyl-1,3-thiazol-2-yl)methylidene]propane-2-sulfinamide (455 mg, 2.0 mmol) diluted in dry THF (0.5 mL) was added dropwise at rt. The solution was stirred at rt for 4 h. Sat. NH4Cl was used to quench the reaction. The aqueous layer was extracted with EtOAc. The combined organic layers were dried over MgSO4, filtered and the solution was concentrated under vacuo. The crude material was purified on silica gel column chromatography using cyclohexane/EtOAc (7:3) as eluent affording colorless oil (yield: quantitative). 1H NMR (300 MHz, DMSO-d6, d in ppm): 1.16 (s, 9H); 1.4-1.7 (m, 6H); 2.38 (d, 3H, J = 0.7 Hz); 2.62 (m, 2H); 2.82 (m, 2H); 6.03 (d, 1H, J = 8.3 Hz); 6.32 (d, 1H, J = 8.3 Hz); 7.12 (td, 1H, J = 7.7 Hz, J = 1.5 Hz); 7.1-7.35 (m, 3H); 7.41 (dd, 1H, J = 7.7 Hz, J = 1.5 Hz) (2 diastereoisomers) Step 4: to a solution of 2-methyl-N-[(5-methyl-1,3-thiazol-2-yl)[2-(piperidin-1-yl)phenyl]methyl]propane-2-sulfinamide (820 mg, 2.09 mmol) in MeOH (8 mL) was added HCl 6M (6.98 mL, 41.90 mmol). After 5 h of stirring at rt, the reaction was quenched with water and CH2Cl2. The two layers were separated. The aqueous layer was basified with NaOH 2N to pH = 10 and extracted with EtOAc. The combined organic layers were dried over MgSO4, filtered and the solution was concentrated under reduced pressure to afford the titled compound Yield: 82%; appearance: orange oil; 1H NMR, d (ppm) (DMSO-d6): 1.4-1.7 (m, 6H); 2.35 (s, 3H); 2.65 (m, 2H); 2.85 (m, 2H); 5.65 (s, 1H); 7.25 (td, 1H, |

TABLE 1.4-continued

| Cpd. | Starting compounds, Reaction conditions and purification, Yield, Appearance, $^1$H NMR (solvent) data |
|---|---|
| | J = 7.6 Hz, J = 1.5 Hz); 7.1-7.2 (m, 2H); 7.26 (m, 1H); 7.32 (dd, 1H, J = 7.6 Hz, J = 1.5 Hz) |
| Ex. 107 | (4-methylphenyl)[2-(piperidin-1-yl)phenyl]methanaminium chloride<br>The titled compound was obtained following the procedure described in (Robak et al, 2010) (Protocol C).<br>Yield: 43%; appearance: orange solid; 1H NMR, d (ppm) (DMSO-d6): 1.42-1.71 (m, 6H); 2.29 (s, 3H); 2.54 (br s, 2H); 2.75 (br s, 2H); 5.93 (br s, 1H); 7.18-7.43 (m, 7H); 7.68-7.73 (m, 1H); 8.93 (s, 3H) |
| Ex. 108 | (3-methylphenyl)[2-(piperidin-1-yl)phenyl]methanaminium chloride<br>The titled compound was obtained following the procedure described in (Robak et al, 2010) (Protocol C).<br>Yield: 16%; appearance: brownish solid; 1H NMR, d (ppm) (DMSO-d6): 1.45-1.72 (m, 6H); 2.29 (s, 3H); 2.52-2.63 (m, 2H); 2.77 (br s, 2H); 5.94 (br s, 1H); 7.12-7.19 (m, 1H); 7.24-7.42 (m, 6H); 7.69-7.76 (m, 1H); 9.01 (s, 3H) |
| Ex. 109 | 2-(oxan-4-yl)-1-[2-(piperidin-1-yl)phenyl]ethan-1-aminium chloride<br>Step 1: a solution of 2-(tetrahydro-2H-pyran-4-yl)acetaldehyde (900 mg, 7.02 mmol) was diluted in CH2Cl2 (10 mL). To the solution was added titanium ethoxide (2.40 g, 10.53 mmol) followed by rac-2-methyl-2-propane-sulfinamide (426 mg, 3.51 mmol). The reaction mixture was stirred at rt for 8 h. Water was added to quench the reaction. The two phases were separated. The aqueous layer was extracted with CH2Cl2. The combined organic layers were dried over MgSO4, filtered and the solution was concentrated to dryness. The crude material was purified on silica gel column chromatography using hexanes/EtOAc (4:1) as eluent.<br>Step 2: to a solution of 1-(2-bromophenyl)piperidine (1.35 mg, 5.62 mmol) in THF was added dropwise n-BuLi 2M in THF (2.81 mL, 5.62 mmol) at −60° C. The reaction was warmed to rt for 3 h. The resulting mixture was transfered and added dropwise at rt to the previoulsy synthesized imine (650 mg, 2.81 mmol) dissolved in THF. After completion, the reaction was quenched with water. The organic layer was extracted with a non-water miscible organic solvent. The combined organic layers were dried over MgSO4, filtered and the solution was concentrated to dryness. The crude material was purified on silica gel column chromatography using EtOAc as eluent.<br>Step 3: the previous synthesized intermediate (285 mg, 0.73 mmol) was dissolved in MeOH. Conc. HCl (0.8 mL) was added at 0° C. to cleave the protecting group and the solution was stirred for 17 h. The reaction mixture was poured into CH2Cl2 and a solution of sodium hydroxide 2M was added dropwise to adjust the pH. The two phases were separated and the aqueous layer was extracted with CH2Cl2. The combined organic layers were dried over MgSO4, filtered and the solution was concentrated to dryness. The crude material was purified on silica gel column chromatography using CH2Cl2/MeOH (6:1) as eluent followed by hydrochloride formation affording the titled compound<br>Yield: 69%; appearance: off-white solid; 1H NMR, d (ppm) (DMSO-d6): 1.00-1.73 (m, 11H); 1.78-1.92 (m, 2H); 2.56-2.72 (m, 2H); 2.81-3.08 (s, 1H); 3.07-3.24 (m, 2H); 3.73-3.87 (m, 2H); 4.80 (br s, 1H); 7.16 (m, 1H); 7.38 (t, 1H, J = 7.1 Hz); 7.61 (d, 2H, J = 7.7 Hz); 8.33-8.52 (s, 1H) |
| Ex. 110 | 1-[2-(piperidin-1-yl)phenyl]pentan-1-aminium chloride<br>The titled compound was obtained following the procedure described in WO2006035157 (Protocol A)<br>Yield: 61%; appearance: white solid; 1H NMR, d (ppm) (DMSO-d6): 0.80 (t, 3H, J = 7.3 Hz); 1.04-1.35 (m, 4H); 1.62-1.74 (m, 7H); 1.94-2.02 (m, 1H); 2.53-2.70 (m, 2H); 2.80-3 (m, 2H); 4.68 (m, 1H); 7.16 (td, 1H, J = 7.2 Hz, J = 1.4 Hz); 7.21-7.35 (m, 2H); 7.64 (dd, 1H, J = 7.7 Hz, J = 1.4 Hz); 8.61 (br s, 3H) |
| Ex. 111 | [3-methyl-2-(piperidin-1-yl)phenyl](phenyl)methanaminium chloride<br>The titled compound was obtained following the modified procedure described in WO2006035157 (Protocol A) using Zn/ammonium acetate/ammonia/EtOH as reducing agent. The starting material 3-methyl-2-(piperidin-1-yl)benzonitrile was obtained from 2-bromo-3-methylbenzonitrile using the same protocol described in WO2006035157 (Protocol A)<br>Yield: 33%; appearance: white solid; 1H NMR, d (ppm) (DMSO-d6): 1.78-1.87 (m, 4H); 2.39 (br s, 2H); 2.95-3.02 (m, 2H); 3.06-3.13 (m, 2H); 5.43 (s, 1H); 7.07 (dd, 1H, J = 8.2 Hz, J = 2.0 Hz); 7.11 (d, 1H, J = 2.0 Hz); 7.12-7.18 (m, 1H); 7.22-7.31 (m, 5H) |
| Ex. 112 | [5-methyl-2-(piperidin-1-yl)phenyl](phenyl)methanaminium chloride<br>The titled compound was obtained following the modified procedure described in WO2006035157 (Protocol A) using Zn/ammonium acetate/ammonia/EtOH as reducing agent. The starting material 5-methyl-2-(piperidin-1-yl)benzonitrile was obtained from 2-bromo-5-methylbenzonitrile using the same protocol described in WO2006035157 (Protocol A)<br>Yield: 70%; appearance: white solid; 1H NMR, d (ppm) (DMSO-d6): 1.52-1.60 (m, 6H); 3.00 (s, 3H); 2.46-2.50 (m, 2H); 2.65-2.75 (m, 2H); 5.95 (s, 1H); 7.15-7.44 (m, 5H); 7.47-7.50 (m, 2H); 7.55 (s, 1H); 9.02 (br s, 3H) |
| Ex. 114 | 1-[2-(piperidin-1-yl)phenyl]cyclohexan-1-amine<br>Step 1: a mixture of 2-(2-aminophenyl)acetonitrile (8.00 g, 60.5 mmol), 1,5-dibromopentane (14.6 g, 63.6 mmol), K2CO3 (25.1 g, 182 mmol) and NaI (907 mg, 6.05 mmol) in MeCN (500 mL) was heated 3 days at 90° C. The mixture |

| Cpd. | Starting compounds, Reaction conditions and purification, Yield, Appearance, $^1$H NMR (solvent) data |
|---|---|
| | was cooled down to rt, diluted with EtOAc and filtered. The filtrate was washed with brine, dried over MgSO4, filtered and the solution was concentrated under reduced pressure. The crude brown oil was purified on silica gel column chromatography using cyclohexane/EtOAc (70:30) to afford pale brown oil (5.31 g of starting material was recovered as a brown solid). Hydrochloride was performed. The solid was diluted with water, adjusted to pH = 9-10 with NaOH 5N and extracted with EtOAc. The organic layer was dried over MgSO4, filtered and the solution was concentrated under reduced pressure to afford pale brown oil which was purified on silica gel column chromatography using cyclohexane/EtOAc (70:30) to provide 1.54 g of yellow oil (yield: 13%). 1H NMR (300 MHz, CDCl3, d in ppm): 1.59-1.63 (m, 2H); 1.70-1.78 (m, 4H); 2.80-2.83 (m, 4H); 3.85 (s, 2H); 7.11-7.19 (m, 2H); 7.30-7.36 (m, 1H); 7.44-7.48 (m, 1H).<br>Step 2: to a solution of NaOtBu (3.99 g, 41.5 mmol) in THF (4 mL) at 0° C. was slowly added NMP (2 mL). The mixture was stirred 15 min at 0° C. before addition of a solution of 1,5-dibromopentane (2.51 g, 10.9 mmol) and freshly synthesized 2-(2-(piperidin-1-yl)phenyl)acetonitrile (2.08 g, 10.4 mmol) in THF/NMP 50/50 (4 mL). The mixture was then stirred at rt overnight. The mixture was diluted with water/sat. NH4Cl and extracted with EtOAc. The organic layer was washed with brine, dried over MgSO4, filtered and the solution was concentrated under reduced pressure. The crude yellow oil was purified on silica gel column chromatography using cyclohexane/CH2Cl2 (70:30) to provide 1.40 g of yellow solid (yield: 50%). 1H NMR (300 MHz, CDCl3, d in ppm): 1.15-1.45 (m, 2H); 1.66-1.99 (m, 12H); 2.32-2.43 (m, 2H); 2.63-2.78 (m, 2H); 2.90-2.95 (m, 2H); 7.18-7.23 (m, 1H); 7.31-7.36 (m, 2H); 7.40-7.43 (m, 1H).<br>Step 3: a mixture of freshly prepared 1-(2-(piperidin-1-yl)phenyl)cyclohexanecarbonitrile (1.30 g, 4.84 mmol) and H2SO4 (1.08 mL, 19.4 mmol) in MeCN was heated under microwave for 1 h at 100° C. The mixture was poured onto water, adjusted to pH = 5-6 with NaOH 5N and extracted with EtOAc. The organic layer was washed with brine, dried over MgSO4, filtered and the solution concentrated to dryness to provide 600 mg of beige solid (yield: 43%) which was used in the next step without further purification. 1H NMR (300 MHz, CDCl3, d in ppm): 1.21-1.46 (m, 2H); 1.62-1.89 (m, 12H); 2.41-2.45 (m, 2H); 2.76-2.85 (m, 2H); 3.00-3.04 (m, 2H); 7.21-7.32 (m, 2H); 7.36 (dd, 1H, J = 7.8 Hz, J = 1.8 Hz); 7.48 (dd, 1H, J = 7.8 Hz, J = 1.8 Hz).<br>Step 4: to a mixture of freshly synthesized 1-(2-(piperidin-1-yl)phenyl)cyclohexanecarboxylic acid (500 mg, 1.74 mmol), DMAP (468 mg, 3.83 mmol), Et3N (0.46 mL, 3.48 mmol) and EDCl (367 mg, 1.91 mmol) in DMF in a sealed tube was rapidly added NH4Cl (140 mg, 2.61 mmol). The mixture was then stirred at rt overnight. The mixture was diluted with EtOAc, washed with sat. NH4Cl, with NaOH 0.5N and then with brine. The organic layer was dried over MgSO4, filtered and the solution was concentrated under reduced pressure. The crude beige solid was purified on silica gel column chromatography using CH2Cl2/MeOH (96:4) to provide 255 mg of off white solid (yield: 51%). 1H NMR (300 MHz, CDCl3, d in ppm): 1.25-1.81 (m, 12H); 2.13-2.29 (m, 4H); 2.63-2.67 (m, 2H); 2.80-2.90 (m, 2H); 5.20-5.50 (br s, 2H); 7.18-7.23 (m, 1H); 7.26-7.31 (m, 1H); 7.34-7.37 (m, 1H); 7.49-7.52 (m, 1H).<br>Step 5: to a mixture of 1-(2-(piperidin-1-yl)phenyl)cyclohexanecarboxamide (255 mg, 0.89 mmol) and KOH (100 mg, 1.78 mmol) in MeOH was added iodobenzenediacetate (516 mg, 1.60 mmol). The mixture was then stirred at rt for 3 h. The mixture was diluted with EtOAc, washed with water and then with brine. The organic layer was dried over MgSO4, filtered and the solution concentrated under reduced pressure. The crude oil was purified on silica gel column chromatography using cyclohexane/EtOAc (90:10) to provide 120 mg of colorless oil (yield: 43%). 1H NMR (300 MHz, CDCl3, d in ppm): 1.25-1.43 (m, 2H); 1.64-1.87 (m, 12H); 2.65-2.76 (m, 6H); 6.02 (br s, 1H); 7.15-7.18 (m, 1H); 7.23 (td, 1H, J = 7.8 Hz, J = 1.5 Hz); 7.32 (dd, 1H, J = 7.8 Hz, J = 1.5 Hz); 7.43 (dd, 1H, J = 7.8 Hz, J = 1.5 Hz).<br>Step 6: a mixture of methyl 1-(2-(piperidin-1-yl)phenyl)cyclohexylcarbamate (120 mg, 0.38 mmol) and NaOH 5N (0.23 mL, 1.14 mmol) in EtOH was heated under microwaves at 150° C. for 30 min. The mixture was diluted with EtOAc, washed with water and brine. The organic layer was dried over MgSO4, filtered and the solution was concentrated under reduced pressure to provide the titled compound<br>Yield: 92%; appearance: colorless oil; 1H NMR, d (ppm) (CDCl3): 1.26-1.39 (m, 2H); 1.56-1.93 (m, 14H); 2.22 (brs, 2H); 2.68-2.77 (m, 2H); 2.90-2.93 (m, 2H); 7.15 (td, 1H, J = 7.8 Hz, J = 1.8 Hz); 7.23 (td, 1H, J = 7.8 Hz, J = 1.8 Hz); 7.34 (dd, 1H, J = 7.8 Hz, J = 1.8 Hz); 7.41 (dd, 1H, J = 7.8 Hz, J = 1.8 Hz) |
| Ex. 115 | 1-[2-(pyrrolidin-1-yl)phenyl]cyclopentan-1-amine<br>Step 1: a mixture of 2-(2-aminophenyl)acetonitrile (5.52 g, 34.2 mmol), 1,4-dibromobutane (9.60 g, 44.5 mmol), K2CO3 (14.2 g, 103 mmol) and NaI (513 mg, 3.42 mmol) in MeCN (280 mL) was heated at 100° C. overnight. TLC showed still some starting material, 1,4-dibromobutane (738 mg, 3.42 mmol) was added and the mixture was heated at 90° C. overnight. The mixture was diluted with EtOAc and filtered over Celite. The filtrate was concentrated under |

TABLE 1.4-continued

| Cpd. | Starting compounds, Reaction conditions and purification, Yield, Appearance, $^1$H NMR (solvent) data |
|---|---|
| | reduced pressure. The crude beige oil was purified on silica gel column chromatography using cyclohexane/EtOAc (70:30 to 60:40) to afford a beige oil and 3.72 g of starting material recovered. Hydrochloride was performed. The solid was diluted with water, basified to pH = 8-9 with NaOH 1N and extracted twice with EtOAc. The organic layer was dried over MgSO4, filtered and the solution was concentrated to dryness to provide 1.20 g of pale brown oil (yield: 19%). 1H NMR (300 MHz, CDCl3, d in ppm): 1.94-1.99 (m, 4H); 3.11-3.16 (m, 4H); 3.78 (s, 2H); 6.99-7.08 (m, 2H); 7.24-7.30 (m, 1H); 7.40 (dd, 1H, J = 7.5 Hz, J = 1.2 Hz).<br>Step 2: to a solution NaH (1.13 g, 28.3 mmol) in DMF (15 mL) at 0° C. was slowly added 2-(2-bromophenyl)acetonitrile (2.20 g, 11.8 mmol) in DMF (2 mL). The mixture was stirred for 15 min at 0° C. before addition of 1,4-dibromobutane (2.68 g, 12.4 mmol) in DMF (3 mL) and NaI (177 mg, 1.18 mmol). The mixture was then heated at 100° C. for 4 h. The solution was cooled down to rt, quenched with sat. NH4Cl, diluted with water and extracted EtOAc. The organic layer was dried over MgSO4, filtered and the solution was concentrated under reduced pressure. The crude yellow oil was purified on silica gel column chromatography using cyclohexane/EtOAc (90:10) to provide 980 mg a strong yellow solid (yield: 34%). 1H NMR (300 MHz, CDCl3, d in ppm): 1.87-2.05 (m, 10H); 2.61-2.64 (m, 2H); 3.05-3.09 (m, 4H); 7.14-7.20 (m, 1H); 7.30-7.37 (m, 2H); 7.41-7.44 (m, 1H).<br>Step 3: a mixture of 1-(2-(pyrrolidin-1-yl)phenyl)cyclopentanecarbonitrile (775 mg, 3.22 mmol) and H2SO4 (0.36 mL, 6.45 mmol) in H2O was stirred at rt overnight. The reaction mixture was diluted with water, adjusted to pH = 6-7 with NaOH 2N and extracted with EtOAc. The organic layer was washed with brine, dried over MgSO4, filtered and the solution was concentrated under reduced pressure to afford 785 mg of light yellow solid (yield: 94%). 1H NMR (300 MHz, DMSO-d6, d in ppm): 1.65-1.84 (m, 10H); 2.26-2.30 (m, 2H); 2.80-2.90 (m, 4H); 7.11-7.34 (m, 4H); 11.52 (br s, 1H).<br>Step 4: to a mixture of 1-(2-(pyrrolidin-1-yl)phenyl)cyclopentanecarboxylic acid (555 mg, 2.14 mmol), DMAP (575 mg, 4.71 mmol), Et3N (0.57 mL, 4.28 mmol) and EDCI (451 mg, 2.35 mmol)in DMF in a sealed tube was rapidely added NH4Cl (137 mg, 2.57 mmol). The solution was then stirred at rt for 4 h. The reaction mixture was diluted with EtOAc, washed with sat. NH4Cl, brine and NaOH 1N. The organic layer was dried over MgSO4, filtered and the solution was concentrated under reduced pressure to provide 400 mg yellow solid (yield: 48%). The basic aqueous layer was acidified to pH = 4-5 with HCl 2N and extracted with EtOAc. The organic layer was dried over MgSO4, filtered and the solution was concentrated under reduced pressure to afford 90 mg of white solid (starting material recovered). 1H NMR (300 MHz, CDCl3, d in ppm): 1.71-1.98 (m, 10H); 2.54-2.56 (m, 2H); 2.96-3.00 (m, 4H); 5.25 (br s, 2H); 7.15-7.20 (m, 1H); 7.27-7.38 (m, 2H); 7.43 (dd, 1H, J = 7.8 Hz, J = 1.5 Hz).<br>Step 5: to a mixture of 1-(2-(pyrrolidin-1-yl)phenyl)cyclopentanecarboxamide (390 mg, 1.51 mmol) and KOH (169 mg, 3.02 mmol) in MeOH was added iodobenzenediacetate (875 mg, 2.72 mmol). The mixture was then stirred at rt for 1 h. The mixture was diluted with EtOAc, washed with water and brine. The organic layer was dried over MgSO4, filtered and the solution was concentrated under reduced pressure. The crude black oil was purified on silica gel column chromatography using cyclohexane/EtOAc (80:20) to afford 105 mg of beige solid (yield: 24%). 1H NMR (300 MHz, CDCl3, d in ppm): 1.77-1.86 (m, 4H); 1.93-2.03 (m, 6H); 2.60-2.65 (m, 2H); 2.95-3.00 (m, 4H); 3.51 (s, 3H); 5.86 (br s, 1H); 7.13 (td, 1H, J = 7.5 Hz, J = 1.5 Hz); 7.26 (td, 1H, J = 7.8 Hz, J = 1.5 Hz); 7.35 (dd, 1H, J = 7.8 Hz, J = 1.5 Hz); 7.46 (dd, 1H, J = 7.8 Hz, J = 1.5 Hz).<br>Step 6: a mixture of methyl 1-(2-(pyrrolidin-1-yl)phenyl)cyclopentylcarbamate (100 mg, 0.35 mmol) and NaOH 5N (0.21 mL, 1.04 mmol) in EtOH was heated under microwave at 150° C. for 30 min. The reaction mixture was diluted with EtOAc, washed with water and brine. The organic layer was dried over MgSO4, filtered and the solution was concentrated under reduced pressure to provide the title compound which was directly used in the next step without further purification<br>Yield: 99%; appearance: yellow oil; 1H NMR, d (ppm) (CDCl3): 1.74-2.05 (m, 10H); 2.40-2.60 (m, 4H); 2.98-3.05 (m, 4H); 7.10-7.15 (m, 1H); 7.22-7.28 (m, 1H); 7.34-7.40 (m, 2H) |
| Ex. 117 | 3-methyl-1-[2-(propan-2-yloxy)phenyl]butan-1-amine<br>The titled compound was obtained following the procedure described in (Robak et al, 2010) (Protocol C). The starting material 2-isopropoxybenzaldehyde was prepared from 2-hydroxybenzaldehyde (2-hydroxybenzaldehyde (1 eq.), 2-bromopropane (2 eq.), K2CO3 2 (eq.), in DMF at rt for 70 h).<br>Yield: 24%; appearance: colorless oil; 1H NMR, d (ppm) (DMSO-d6): 0.86-0.89 (m, 6H); 1.25-1.43 (m, 8H); 1.55-1.67 (m, 1H); 4.11-4.18 (m, 1H); 4.57-4.66 (m, 1H); 6.83-6.95 (m, 2H); 7.09-7.16 (m, 1H); 7.34-7.39 (m, 1H) |
| Ex. 118 | 3-methyl-1-[4-methyl-2-(propan-2-yloxy)phenyl]butan-1-amine<br>The titled compound was obtained following the procedure described in (Robak et al, 2010) (Protocol C). The starting material 2-isopropoxy-4-methylbenzaldehyde was prepared from 2-hydroxy-4-methylbenzaldehyde (2- |

TABLE 1.4-continued

| Cpd. | Starting compounds, Reaction conditions and purification, Yield, Appearance, $^1$H NMR (solvent) data |
|---|---|
| | hydroxy-4-methylbenzaldehyde (1 eq.), 2-bromopropane (2 eq.), K2CO3 2 (eq.), in DMF at rt for 68 h). Yield: 16%; appearance: colorless oil; 1H NMR, d (ppm) (DMSO-d6): 0.86 (dd, 6H, J = 6.6 Hz; J = 1.5 Hz); 1.25-1.28 (m, 6H); 1.29-1.41 (m, 2H); 1.55-1.61 (m, 1H); 1.71-2.12 (br s, 2H); 2.55 (s, 3H); 4.09 (dd, 1H, J = 7.9 Hz, J = 6.1 Hz); 4.59 (dt, 1H, J = 12.0 Hz, J = 6.0 Hz); 6.67 (d, 1H, J = 7.7 Hz); 6.73 (s, 1H); 7.22 (d, 1H, J = 7.7 Hz) |
| Ex. 119 | 1-(2-ethoxyphenyl)-3-methylbutan-1-aminium chloride The titled compound was obtained following the procedure described in (Robak et al, 2010) (Protocol C). The starting material 2-ethoxybenzaldehyde was prepared from 2-hydroxybenzaldehyde (2-hydroxybenzaldehyde (1 eq.), bromopropane (2.6 eq.), K2CO3 (2 eq.), in acetone at 50° C. for 24 h). Yield: 12%; appearance: white solid; 1H NMR, d (ppm) (DMSO-d6): 0.87 (m, 6H); 1.37 (t, 4H, J = 6.9 Hz); 1.74 (t, 2H, J = 7.2 Hz); 4.09 (q, 2H, J = 4.0 Hz); 4.58 (t, 1H, J = 7.6 Hz); 6.99-7.10 (m, 2H); 7.31-7.37 (m, 1H); 7.47-7.52 (m, 1H); 8.34 (s, 3H) |
| Ex. 120 | 4-methyl-1-[2-(piperidin-1-yl)phenyl]pentan-1-aminium chloride The titled compound was obtained following the procedure described in (Robak et al, 2010) (Protocol C). The starting material 2-(piperidin-1-yl)benzaldehyde is commercially available. Yield: 56%; appearance: white solid; 1H NMR, d (ppm) (DMSO-d6): 0.83 (dd, 6H, J = 6.6 Hz, J = 1.5 Hz); 0.94-0.96 (m, 1H); 1.15-1.25 (m, 1H); 1.52-1.71 (m, 8H); 1.9-2.1 (m, 1H); 2.68 (br s, 2H); 2.94 (br s, 2H); 7.19-7.41 (m, 3H); 7.7 (s, 1H); 8.53 (br s, 3H) |
| Ex. 121 | (2,4-diethoxyphenyl)(phenyl)methanaminium chloride The titled compound was obtained following the procedure described in (Robak et al, 2010) (Protocol C). The starting material 2,4-diethoxybenzaldehyde was prepared from 2,4-dihydroxybenzaldehyde (2,4-dihydroxybenzaldehyde (1 eq.), bromopropane (3 eq.), K2CO3 (3 eq.), in DMF at 50° C. for 20 h). Yield: 52%; appearance: light greenish solid; 1H NMR, d (ppm) (DMSO-d6): 1.30 (m, 6H); 3.96-4.08 (m, 4H); 5.62 (s, 1H); 6.56-6.62 (m, 2H); 7.30-7.47 (m, 6H); 8.83 (s, 3H) |
| Ex. 122 | 1-[4-bromo-2-(pyrrolidin-1-yl)phenyl]-3-methylbutan-1-amine The titled compound was obtained following the modified procedure described in WO2006035157 (Protocol A). The starting material 4-bromo-2-(pyrrolidin-1-yl)benzonitrile was obtained by reacting 4-bromo-2-fluorobenzonitrile with pyrrolidine at rt. Yield: 20%; appearance: brown solid; 1H NMR, d (ppm) (Methanol d4): 0.96 (d, 3H, J = 6.6 Hz); 1.00 (d, 3H, J = 6.5 Hz); 1.43-1.52 (m, 1H); 1.76-1.87 (m, 2H); 2.08-2.16 (m, 4H); 3.30 (m, 4H); 4.97 (br s, 1H); 7.37-7.43 (m, 2H); 7.56 (s, 1H) |
| Ex. 123 | 2-[amino(phenyl)methyl]-5-methylaniline Step 1: a solution of (2-amino-4-methylphenyl)(phenyl)methanone (2 g, 9.5 mmol), hydroxyl amine hydrochloride (3.1 g, 47 mmol) in MeOH (40 mL) was introduced in a sealed tube and heated at 150° C. for 5 days. The excess of solvent was removed under reduced pressure. The crude material was diluted with sat. NaHCO3. The aqueous layer was extracted with EtOAc. The combined organic layers were dried over MgSO4, filtered and the solution was concentrated to dryness. The crude material was used for the next step without further purification. Step 2: the freshly prepared oxime (2.1 g, 9.9 mmol) was suspended in ammonia (47.5 mL) and EtOH (9.5 mL). Ammonium acetate (0.38 g, 4.9 mmol) was then added followed by the portionwise addition of zinc dust (3.2 g, 49 mmol). Once the addition was completed the reaction mixture was slowly heated at 50° C. The reaction was monitored by TLC. After completion, inorganic materials were filtered-off on Celite. The solution was concentrated to dryness and the crude material was purified on silica gel column chromatography using cyclohexane/EtOAc (5:5) as eluent with few amount of Et3N. Yield: 25%; appearance: orange solid; 1H NMR, d (ppm): 2.09 (s, 3H); 2.31 (br s, 2H); 5.03 (s, 1H); 5.10 (br s, 2H); 6.27 (dd, 1H, J = 7.7 Hz, J = 1.1 Hz); 6.38-6.39 (m, 1H); 6.77 (d, 1H, J = 7.7 Hz); 7.17-7.19 (m, 1H); 7.24-7.27 (m, 2H); 7.35-7.38 (m, 2H) |
| Ex. 141 | (5-methylfuran-2-yl)[2-(propan-2-yloxy)phenyl]methanamine Step 1: 5-methylfuran-2-carbaldehyde (1.30 g, 11.81 mmol) was dissolved in dry THF. Titanium ethoxide (8.08 g, 35.43 mmol) and rac-2-methyl-2-propane-sulfinamide (1.43 g, 11.81 mmol) were added to the reaction mixture. The solution was stirred at rt for 2 days. Brine was added to quench the reaction and the solution was stirred vigorously. EtOAc was added and the resulting mixture was filtered on Celite. The two layers were partitionated. The organic layer was dried over MgSO4, filtered and the solution was concentrated under reduced pressure and used in the next step without further purification. Step 2: magnesium (350 mg, 14.42 mmol) was suspended in small amount of dry THF. Few crystals of iodine was added followed by 1-bromo-2-isopropoxybenzene (1 g, 4.65 mmol) dissolved in dry THF. The reaction mixture was stirred at rt. The completion of halogen exchange was monitored |

TABLE 1.4-continued

| Cpd. | Starting compounds, Reaction conditions and purification, Yield, Appearance, $^1$H NMR (solvent) data |
|---|---|
| | by TLC. 2-Methyl-N-[(1E)-(5-methylfuran-2-yl)methylidene]propane-2-sulfinamide (3.03 g, 13.95 mmol) diluted in dry THF was added dropwise at rt. The solution was stirred at rt for 2 h. Sat. NH4Cl was used to quench the reaction. The aqueous layer was extracted with EtOAc. The combined organic layers were dried over MgSO4, filtered and the solution was concentrated under vacuo. The crude material was purified on silica gel column chromatography using hexanes/EtOAc (4:1) as eluent. Step 3: to a solution of 2-methyl-N-[(5-methylfuran-2-yl)[2-(propan-2-yloxy)phenyl]methyl]propane-2-sulfinamide (1.63 g, 4.66 mmol) in MeOH was added HCl 36% (3.5 eq) at 0° C. After 20 min of stirring, the reaction was quenched with water and CH2Cl2. The two layers were separated. The aquous layer was basified with NaOH 2N to pH = 10 and extracted with EtOAc. The combined organic layers were dried over MgSO4, filtered and the solution was concentrated under reduced pressure.The crude material was purified on silica gel column chromatography two times: i) using CH2Cl2/MeOH (95:5) as eluent and ii) using CH2Cl2/EtOAc (9:1), then CH2Cl2/MeOH (8:2) as eluent. A third purification on neutral alumina using CH2Cl2/EtOAc (95:5) as eluent afforded the expected molecule. Yield: 16%, appearance: brown oil; 1H NMR, d (ppm): 1.22 (dd, 6H, J = 14.0 Hz, J = 6.0 Hz); 2.17 (s, 3H); 2.68 (s, 2H); 4.65-4.55 (m, 1H); 5.24 (s, 1H); 5.96-5.92 (m, 2H); 6.89 (td, 1H, J = 7.5 Hz, J = 0.8 Hz); 6.97 (d, 1H, J = 7.9 Hz); 7.22-7.16 (m, 1H); 7.30 (dd, 1H, J = 7.6 Hz, J = 1.7 Hz) |
| Ex. 142 | [2-(azepan-1-yl)-4-methylphenyl](phenyl)methanamine The titled compound was obtained following the modified procedure described in WO2006035157 (Protocol A) Yield: 21%; appearance: yellow oil; 1H NMR, d (ppm): 1.45-1.75 (m, 10H), 2.21 (s, 3H), 2.83-2.87 (m, 2H), 2.95-3.02 (m, 2H), 5.58 (s, 1H), 6.84 (d, 1H, J = 7.83 Hz), 6.93 (s, 1H), 7.07-7.16 (m, 1H), 7.17-7.26 (m, 3H), 7.27-7.34 (m, 2H) |
| Ex. 143 | (4,5-dimethylfuran-2-yl)[2-(piperidin-1-yl)phenyl]methanamine Step 1: to a solution of 2-iodoaniline (2.0 g, 9.13 mmol) in acetonitrile (30 mL) was added K2CO3 (2.52 g, 18.3 mmol). The solution was stirred at rt for 15 min and then 1,5-diiodopentane (3.55 g, 11.0 mmol) was added to the solution under stirring. The reaction mixture was stirred under reflux for 48 h. The reaction was quenched with brine and the aqueous layer was extracted with EtOAc. The combined organic layers were dried over MgSO4, filtered and the solution was concentrated to dryness. The crude material was purified on silica gel column chromatography using cyclohexane/EtOAc (98:2) as eluent. Hydrochloride was formed, triturated in dry Et2O and filtered-off. Free base was obtained using NaHCO3 10%. pH of aqueous solution was adjusted to pH = 7 with citric acid 10% and then extracted with CH2Cl2. The combined organic layer were dried over MgSO4, filtered and the solution was concentrated under reduced pressure affording 1.84 g of colorless oil (yield: 70%). 1H NMR (300 MHz, DMSO-d6, d in ppm): 1.40-1.75 (m, 6H); 2.84 (m, 4H); 6.80 (td, 1H, J = 7.9 Hz, J = 1.5 Hz); 7.09 (dd, 1H, J = 7.9 Hz, J = 1.5 Hz); 7.34 (td, 1H, J = 7.9 Hz, J = 1.5 Hz); 7.81 (dd, 1H, J = 7.9 Hz, J = 1.5 Hz) Step 2: 4,5-dimethylfuran-2-carbaldehyde (1.0 g, 8.06 mmol) was dissolved in dry THF (5 mL). Titanium ethoxide (6.76 mL, 32.2 mmol) and rac-2-methyl-2-propane-sulfinamide (1.27 g, 10.5 mmol) were added to the reaction mixture. The solution was stirred at rt for 12 h. Sat. NH4Cl was added to quench the reaction and the solution was stirred vigorously. EtOAc was added and the resulting mixture was filtered on Celite. The two layers were partitionated. The organic layer was dried over MgSO4, filtered and the solution was concentrated under reduced pressure to afford yellow oil (yield: quantitative). RMN 1H (300 MHz, DMSO-d6, d in ppm): 1.12 (s, 9H), 1.96 (s, 3H), 2.30 (s, 3H), 7.15 (s, 1H), 8.14 (s, 1H) Step 3: iPrMgCl 2M in THF (1.54 mL, 3.08 mmol) was diluted in dry THF (6 mL) and the solution was cooled down to −60° C. under N2 atmosphere. 1-(2-iodophenyl)piperidine (884 mg, 3.08 mmol) was introduced dropwise to the previous solution at −60° C. The reaction mixture was slowly warmed to rt and kept at rt for 1 h. The completion of halogen exchange was monitored by TLC. N-[(1E)-(4,5-dimethylfuran-2-yl)methylidene]-2-methylpropane-2-sulfinamide (400 mg, 1.76 mmol) diluted in dry THF (2 mL) was added dropwise at rt. The solution was stirred at rt for 2 h. Sat. NH4Cl was used to quench the reaction. The aqueous layer was extracted with EtOAc. The combined organic layers were dried over MgSO4, filtered and the solution was concentrated under vacuo. The crude material was purified on silica gel column chromatography using cyclohexane/EtOAc (8:2 to 7:3) as eluent affording pale yellow oil (yield: 90%). RMN 1H (300 MHz, DMSO-d6, d in ppm): 1.0-1.1 (m, 9H), 1.4-1.7 (m, 6H), 1.83 (s, 3H), 2.08 (m, 3H), 2.6-2.75 (m, 4H), 5.7-6.0 (m, 3H), 7.0-7.3 (m, 3H), 7.4-7.5 (m, 1H) (2 diastereoisomers) Step 4: to a solution of N-[(4,5-dimethylfuran-2-yl)[2-(piperidin-1-yl)phenyl]nethyl]-2-methylpropane-2-sulfinamide (620 mg, 1.60 mmol) in MeOH (2 mL) was added HCl 6M (2.66 mL, 15.96 mmol). After 8 h of stirring at rt, the reaction was quenched with water and CH2Cl2. The two layers were separated. The aqueous layer was basified with NaOH 2N to pH = 10 and extracted with EtOAc. The combined organic layers were dried over MgSO4, |

TABLE 1.4-continued

| Cpd. | Starting compounds, Reaction conditions and purification, Yield, Appearance, $^1$H NMR (solvent) data |
|---|---|
| | filtered and the solution was concentrated under reduced pressure to give the titled compound<br>Yield: 65%, appearance: yellow oil; 1H NMR, d (ppm) (DMSO-d6): 1.4-1.7 (m, 6H), 1.82 (d, 3H, J = 0.5 Hz), 2.07 (s, 3H), 2.70-2.80 (m, 4H), 5.35 (s, 1H), 5.87 (s, 1H), 6.95-7.12 (m, 2H), 7.16 (dd, 1H, J = 7.1 Hz, J = 1.7 Hz), 7.34 (dd, 1H, J = 7.7 Hz, J = 1.7 Hz) |
| Ex. 144a | [4-methyl-2-(piperidin-1-yl)phenyl](5-methylfuran-2-yl)methanamine |
| Ex. 144b | Step 1: 4-methyl-2-(piperidin-1-yl)benzenamine (synthesized following the procedure described in WO 2004002481A1 (7.62 g, 40.0 mmol) was dissolved in conc. H2SO4 (21.4 mL, 10 eq.). The solution was coolded at −5° C. and NaNO2 (2.76 g, 40.0 mmol) dissolved in small amount of water was added dropwise at 0° C. under good stirring. After diazonium salt formation (ca 2 h), KI (9.97 g, 60.0 mmol) followed by urea (480 mg, 8.0 mmol) were added. The reaction was warmed to rt and stirred at this temperature for 3 h. The reaction mixture was diluted with water and the aqueous solution was extracted with a non-water miscible organic solvent. The combined organic layers were dried over MgSO4, filtered and the solution was concentrated to dryness. The crude material was purified on silica gel column chromatography using hexanes/EtOAc/Et3N (100:0:0 to 95:5:0.1) as eluent.<br>Step 2: 5-methylfurfural (1.5 g, 13.62 mmol) was dissolved in dry THF. Titanium ethoxide (7.77 g, 34.05 mmol) and R-2-methyl-2-propane-sulfinamide (1.73 g, 14.30 mmol) were added to the reaction mixture. The solution was stirred at rt for 18 h. Sat. NH4Cl was added to quench the reaction and the solution was stirred vigorously. EtOAc was added and the resulting mixture was filtered on Celite. The two layers were partitionated. The organic layer was dried over MgSO4, filtered and the solution was concentrated under reduced pressure. The crude material was used in the next step without further purification.<br>Step 3: the previously synthesized 1-(2-iodo-5-methylphenyl)piperidine (268 mg, 0.89 mmol) was diluted in dry THF and the solution was cooled down to −78° C. under N2 atmosphere. nBuLi 1.6M in THF (650 µL, 1.03 mmol) was introduced dropwise to the previous solution at −78° C. The completion of halogen exchange was monitored by TLC. 2-methyl-N-[(1E)-(5-methylfuran-2-yl)methylidene]propane-2-sulfinamide (200 mg, 0.94 mmol) diluted in dry THF was added dropwise at −78° C. The solution was stirred for additional 2 h. Sat. NH4Cl was used to quench the reaction. The aqueous layer was extracted with EtOAc. The combined organic layers were dried over MgSO4, filtered and the solution was concentrated under vacuo. The crude material was purified on silica gel column chromatography using hexanes/EtOAc (10:1 to 8:1) as eluent. The two diastereoisomers were separated as chemicals have undergone racemisation.<br>Step 4: to a solution of (R)-2-methyl-N-[(R)-[4-methyl-2-(piperidin-1-yl)phenyl](5-methylfuran-2-yl)methyl]propane-2-sulfinamide Ex. 144a or (R)-2-methyl-N-[(S)-[4-methyl-2-(piperidin-1-yl)phenyl](5-methylfuran-2-yl)methyl]propane-2-sulfinamide Ex. 144b (213 mg, 1.60 mmol) in MeOH was added HCl 36% (1.1 mL) at 0° C. After 2 h of stirring at rt, the reaction was quenched with water and CH2Cl2. The two layers were separated. The aquous layer was basified with NaOH 2N to pH = 10 and extracted with EtOAc. The combined organic layers were dried over MgSO4, filtered and the solution was concentrated under reduced pressure.<br>Ex. 144a (R or S): Yield: 50%; appearance: yellow oil; 1H NMR, d (ppm) (DMSO-d6): 1.50 (m, 2H); 1.58-1.66 (m, 4H); 2.12 (s, 2H); 2.17 (s, 3H); 2.25 (s, 3H); 2.73-2.78 (m, 4H); 5.36 (s, 1H); 5.92 (d, J = 2.9 Hz, 1H); 5.97 (d, J = 3.0 Hz, 1H); 6.86 (d, J = 7.8 Hz, 1H); 6.92 (s, 1H); 7.22 (d, J = 7.8 Hz, 1H).<br>Ex. 144b (R or S): Yield: 41%; appearance: orange solid (hydrochloride); 1H NMR, d (ppm) (DMSO-d6): 1.54 (m, 2H); 1.62-1.66 (m, 4H); 2.25 (s, 3H); 2.31 (s, 3H); 2.73 (br s, 4H); 5.93 (s, 1H); 6.09 (d, J = 3.1 Hz, 1H); 6.26 (d, J = 2.9 Hz, 1H); 7.10-7.14 (m, 2H); 7.56 (d, J = 7.9 Hz, 1H); 8.94 (s, 3H). |

The following amines are commercially available

| Ex. 15 | (2,5-dimethylphenyl)(phenyl)methanaminium chloride |
| Ex. 45 | [2-(piperidin-1-yl)phenyl]methanamine |
| Ex. 48 | 2-[amino(phenyl)methyl]aniline |

Intermediate Ex.131: {3-[3-(tert-butoxy)-3-oxopropyl]-1H-indol-5-yl}methanaminium chloride (FIG. 2D)

TABLE 1.5

| Cpd. | Starting compounds, Reaction conditions and purification, | Yield, Appearance, $^1$H NMR (solvent) data |
|---|---|---|
| Ex. 129 | (Z/E) tert-butyl 3-(5-cyano-1H-indol-3-yl)acrylate A solution of 3-formyl-1H-indole-5-carbonitrile (500 mg, 2.94 mmol) and (tert-butoxycarbonylmethylene)triphenylphosphorane (2.21 g, 5.88 mmol) in dry THF was heated under N2 for 2 days. The solvent was removed to dryness. Water was added and the aqueous layer was extracted with EtOAc. The combined organic layers were dried over MgSO4, filtered and the solution was concentrated under reduced pressure. The crude material was purified on silica gel column chromatography using cyclohexane/EtOAc (6:4) as eluent to provide both Z and E enantiomers of tert-butyl 3-(5-cyano-1H-indol-3-yl)acrylate Yield: 100%; appearance: pale yellow solid; H NMR (DMSO-d6, d in ppm): 1.39 (s, 9H); 5.70 (d, 1H, J = 12.6 Hz); 7.33 (d, 1H, J = 12.6 Hz); 7.53 (dd, 1H, J = 8.3 Hz, J = 1.4 Hz); 7.61 (d, 1H, J = 8.3 Hz); 8.35 (s, 1H); 8.79 (d, 1H, J = 1.4 Hz); 12.15 (br s, 1H). | |
| Ex. 130 | tert-butyl 3-(5-cyano-1H-indol-3-yl)propanoate A solution of tert-butyl 3-(5-cyano-1H-indol-3-yl)acrylate Ex. 129 (815 mg, 3.04 mmol) and Pd/C 5% in CH2Cl2/MeOH (1:2) was stirred overnight at rt under H2 atmosphere. The solution was filtered on Celite and the filtrate was concentrated to dryness. The compound was pure enough and used in the next step without further purification. Yield: 85%; Appearance: colorless oil; 1H NMR (DMSO-d6, d in ppm): 1.34 (s, 9H); 2.56 (t, 2H, J = 7.3 Hz); 2.93 (t, 2H, J = 7.3 Hz); 7.32 (d, 1H, J = 2.0 Hz); 7.39 (dd, 1H, J = 8.5 Hz, J = 2.0 Hz); 7.48 (d, 1H, J = 8.5 Hz); 8.09 (m, 1H); 11.39 (br s, 1H). | |
| Ex. 131 | {3-[3-(tert-butoxy)-3-oxopropyl]-1H-indol-5-yl}methanaminium chloride The reaction was carried out in a high pressure reactor. To a solution of tert-butyl 3-(5-cyano-1H-indol-3-yl)propanoate Ex. 130 (600 mg, 2.22 mmol) in EtOH saturated with NH3(g) was added Ni Raney (39 mg, 0.67 mmol). The reaction mixture was stirred under H2 (1088 psi) at rt for 24 h. The solution was filtered on Celite and the solution was concentrated to dryness. Hydrochloride salt was performed Yield: 90%; appearance: white solid; 1H NMR (DMSO-d6, d in ppm): 1.37 (s, 9H); 2.54 (t, 2H, J = 7.3 Hz); 2.88 (t, 2H, J = 7.3 Hz); 3.76 (s, 2H); 7.1-7.2 (m, 2H); 7.22 (d, 1H, J = 7.9 Hz); 7.43 (s, 1H); 10.65 (br s, 1H). | |

Intermediate Ex.133: tert-butyl 3-(5-amino-1H-indol-3-yl)propanoate (FIG. 2E)

TABLE 1.6

| Cpd. | Starting compounds, Reaction conditions and purification, | Yield, Appearance, $^1$H NMR (solvent) data |
|---|---|---|
| Ex. 132 | tert-butyl 3-(5-nitro-1H-indol-3-yl)acrylate A mixture of 5-nitro-1H-indole-3-carbaldehyde (1.39 g, 7.31 mmol) and tert-butyl 2-(triphenylphosphoranylidene)acetate (5.5 g, 14.6 mmol) in THF was heated at 90° C. overnight. The solvent was removed under reduced pressure. Water was added to the residue. The aqueous layer was extracted with EtOAc. The combined organic layers were dried over MgSO4, filtered and the solution was concentrated to dryness. The crude oil was purified twice on silica gel column chromatography using CH2Cl2/MeOH (98:2) as eluent followed by a trituration in small amount of CH2Cl2 Yield: 64%; Appearance: yellow solid; 1H NMR (300 MHz, DMSO-d6, d in ppm): 1.50 (s, 9H); 6.37 (d, 1H, J = 16.0 Hz); 7.63 (d, 1H, J = 9.0 Hz); 7.82 (d, 1H, J = 16.0 Hz); 8.08 (dd, 1H, J = 9.0 Hz, J = 2.1 Hz); 8.19 (s, 1H); 8.71 (d, 1H, J = 2.1 Hz); 12.35 (br s, 1H). | |

TABLE 1.6-continued

| Cpd. | Starting compounds, Reaction conditions and purification, | Yield, Appearance, $^1$H NMR (solvent) data |
| --- | --- | --- |
| Ex. 133 | tert-butyl 3-(5-amino-1H-indol-3-yl)propanoate To a solution of tert-butyl 3-(5-nitro-1H-indol-3-yl)acrylate Ex. 132 (1.35 g, 4.68 mmol) in EtOH (35 mL) was added Pd(OH)2 (33 mg, 0.23 mmol). The mixture was then stirred under hydrogen at rt for 6 h. The mixture was diluted with EtOH and filtered on Celite. The filtrate was concentrated under reduced pressure. The crude material was diluted with small amount of CH2Cl2 and filtered Yield: 84%; Appearance: pale brown solid; 1H NMR (300 MHz, DMSO-d6, d in ppm): 1.38 (s, 9H); 2.49 (t, 2H, J = 7.2 Hz); 2.78 (t, 2H, J = 7.2 Hz); 4.43 (br s, 2H); 6.45 (dd, 1H, J = 8.4 Hz, J = 2.1 Hz); 6.62 (d, 1H, J = 1.8 Hz); 6.89 (d, 1H, J = 2.1 Hz); 7.00 (d, 1H, J = 8.4 Hz); 10.25 (br s, 1H). | |

Intermediate Ex.136: tert-butyl 3-(5-amino-1H-pyrrolo[2,3-b]pyridin-3-yl)propanoate (FIG. 2F)

TABLE 1.7

| Cpd. | Starting compounds, Reaction conditions and purification, | Yield, Appearance, $^1$H NMR (solvent) data |
| --- | --- | --- |
| Ex. 134 | 5-nitro-1H-pyrrolo[2,3-b]pyridine-3-carbaldehyde A solution of 5-nitro-1H-pyrrolo[2,3-b]pyridine (600 mg, 3.68 mmol) and hexamethylenetetraamine (773 mg, 5.52 mmol) in AcOH 30% was heated at 120° C. for 3 h. The reaction mixture was diluted with water and filtered to afford a yellow solid. The filtrate was basified to pH = 9-10 with NaOH 5N and extracted with EtOAc. The organic layer was dried over MgSO4, filtered and the solution was concentrated to afford a yellow solid. Solids were combined, triturated in CH2Cl2 and filtered Yield: 50%; appearance: yellow solid; 1H NMR (300 MHz, DMSO-d6, d in ppm): 8.74 (s, 1H); 9.07-9.09 (m, 2H); 9.21 (d, 1H, J = 2.7 Hz); 10.00 (s, 1H) | |
| Ex. 135 | (Z/E)-tert-butyl 3-(5-nitro-1H-pyrrolo[2,3-b]pyridin-3-yl)acrylate A solution of 5-nitro-1H-pyrrolo[2,3-b]pyridine-3-carbaldehyde Ex. 134 (0.350 g, 1.84 mmol) and tert-butyl 2-(triphenylphosphoranylidene)acetate (1.39 g, 3.68 mmol) in THF was heated at 90° C. for 6 h. The reaction mixture was cooled down to rt, diluted with EtOAc, washed with water and brine. The organic layer was dried over MgSO4, filtered and the solution was concentrated under reduced pressure. The crude oil was purified on silica gel column chromatography using DCM/MeOH/Et3N (96:4:0.1) as eluent followed by a second silica gel column chromatography using cyclohexane/EtOAc (60:40) as eluent to afford a yellow solid. The solid was triturated in cold MeOH and filtered Yield: 24%; appearance: yellow solid; 1H NMR (300 MHz, DMSO-d6, d in ppm): 1.50 (s, 9H); 6.47 (d, 1H, J = 16.2 Hz); 7.79 (d, 1H, J = 16.2 Hz); 8.35 (s, 1H); 9.09-9.15 (m, 2H). | |
| Ex. 136 | tert-butyl 3-(5-amino-1H-pyrrolo[2,3-b]pyridin-3-yl)propanoate A solution of (Z/E)-tert-butyl 3-(5-nitro-1H-pyrrolo[2,3-b]pyridin-3-yl)acrylate (540 mg, 1.87 mmol) and Pd(OH)2 (13 mg, 0.09 mmol) in CH2Cl2/EtOH (50:50) was stirred under H2 atmosphere at rt for 2 h. The reaction mixture was diluted with DCM/EtOH and filtered on Celite. The filtrate was concentrated under reduced pressure. The crude oil was purified on silica gel column chromatography using CH2Cl2/MeOH (95:5) as eluent to afford a brown solid. NMR showed the expected molecule with another product corresponding to compound with still the double bond (only NO2 was reduced). The solid was diluted with CH2Cl2/EtOH, Pd(OH)2 was added and the mixture was stirred again under hydrogen at rt for 3 h. The reaction mixture was diluted with CH2Cl2/EtOH and filtered on Celite. The filtrate was concentrated under reduced pressure. The crude oil was purified on silica gel column chromatography using CH2Cl2/MeOH (95:5) as eluent Yield: 60%; appearance: brown solid; 1H NMR (300 MHz, DMSO-d6, d in ppm): 1.35 (s, 9H); 2.50 (t, 2H, J = 7.5 Hz); 2.79 (t, 2H, J = 7.5 Hz); 4.76 (br s, 2H); 7.02 (d, 1H, J = 2.4 Hz); 7.06 (d, 1H, J = 2.4 Hz); 7.68 (d, 1H, J = 2.7 Hz); 10.75 (br s, 1H). | |

Figure 2G:
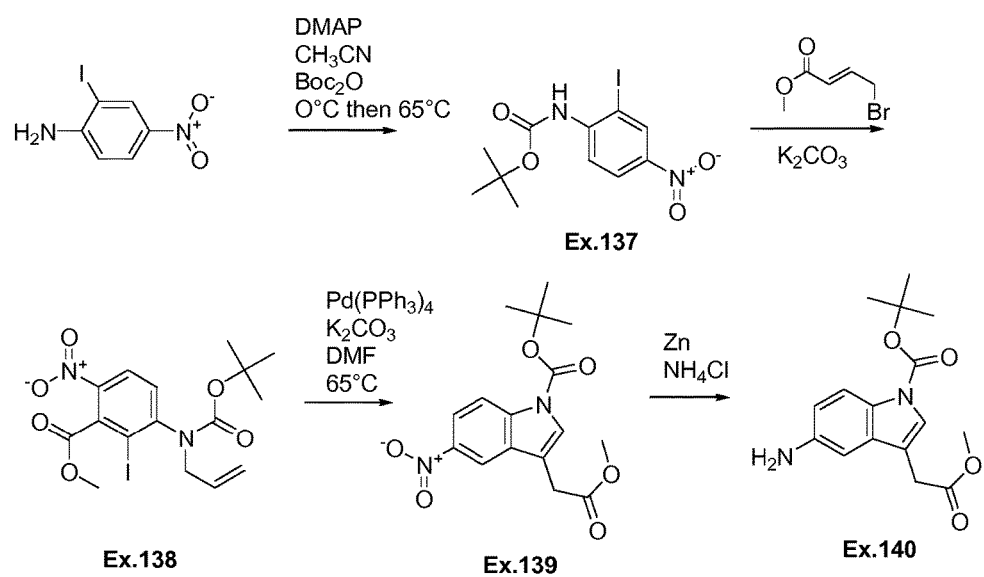

Intermediate Ex.140: tert-butyl 3-((methoxycarbonyl)methyl)-5-amino-1H-indole-1-carboxylate (FIG. 2G)

TABLE 1.8

| Cpd. | Starting compounds, Reaction conditions and purification, | Yield, Appearance, $^1$H NMR (solvent) data |
|---|---|---|
| Ex. 137 | tert-butyl 2-iodo-4-nitrophenylcarbamate To a solution of 2-iodo-4-nitrobenzenamine (2.00 g, 7.58 mmol) and DMAP (92 mg, 0.76 mmol) in acetonitrile was added Boc2O (3.64 g, 16.7 mmol) at 0° C. The solution was stirred 10 min at 0° C., let return to rt for 1 h and then heated at 65° C. for 1 h 30. The mixture was diluted with water and extracted with EtOAc. The combined organic layers were dried over MgSO4, filtered and the solution was concentrated to dryness. The residue was diluted with CH2Cl2, TFA (0.87 mL, 11.4 mmol) was added and the solution was stirred at rt overnight. The reaction was quenched with sat. NaHCO3. The two phases were separated. The organic layer was dried over MgSO4, filtered and the solution was concentrated under reduced pressure. The product was directly used in the next step without further purification. Yield: 92%; appearance: pale brown solid; 1H NMR (300 MHz, DMSO-d6, d in ppm): 1.48 (s, 9H); 1.80 (d, 1H, J = 9.0 Hz); 8.22 (dd, 1H, J = 9.0 Hz, J = 2.7 Hz); 8.58 (d, 1H, J = 2.7 Hz); 8.64 (br s, 1H). | |
| Ex. 138 | tert-butyl (E)-3-(methoxycarbonyl)allyl2-iodo-4-nitrophenylcarbamate A solution of tert-butyl 2-iodo-4-nitrophenylcarbamate Ex. 137 (1.50 g, 4.12 mmol), K2CO3 (2.28 g, 16.5 mmol) and methyl 4-bromobut-2-enoate (0.74 mL, 6.18 mmol) was stirred at rt for 3 h. The mixture was diluted with EtOAc and filtered. The filtrate was washed with brine. The two phases were separated. The organic layer was dried over MgSO4, filtered and the solution was concentrated under reduced pressure. The product which was directly used in the next step without further purification. Yield: 100%; appearance: brown oil; 1H NMR (300 MHz, DMSO-d6, d en ppm): 1.31-1.45 (m, 9H); 3.65 (s, 3H); 4.05-4.20 (m, 1H); 4.37-4.50 (m, 1H); 5.95-6.05 (m, 1H); 6.85-6.95 (m, 1H); 7.57 (d, 1H, J = 8.7 Hz); 8.25 (dd, 1H, J = 8.7 Hz, J = 2.7 Hz); 8.63 (d, 1H, J = 2.7 Hz). | |
| Ex. 139 | tert-butyl 3-((methoxycarbonyl)methyl)-5-nitro-1H-indole-1-carboxylate A solution of tert-butyl (E)-3-(methoxycarbonyl)allyl2-iodo-4-nitrophenylcarbamate Ex. 138 (1.90 g, 4.11 mmol), Pd(PPh3)4 (237 mg, 0.21 mmol) and K2CO3 (1.14 g, 8.22 mmol) in DMF was heated at 65° C. overnight. The solution was diluted with EtOAc and filtered. The filtrate was washed with brine. The two phases were separated. The organic layer was dried over MgSO4, filtered and the solution was concentrated under reduced pressure. The crude oil was purifiedon silica gel column chromatography using cyclohexane/EtOAc (80:20) as eluent Yield: 85%; appearance: pale brown oil; 1H NMR (300 MHz, DMSO-d6, d in ppm): 1.63 (s, 9H); 3.64 (s, 3H); 3.95 (s, 2H); 7.86 (s, 1H); 8.21-8.22 (m, 2H); 8.54-8.55 (m, 1H). | |
| Ex. 140 | tert-butyl 3-((methoxycarbonyl)methyl)-5-amino-1H-indole-1-carboxylate A solution of tert-butyl 3-((methoxycarbonyl)methyl)-5-nitro-1H-indole-1-carboxylate (400 mg, 1.20 mmol), Zn (313 mg, 4.79 mmol) and ammonium chloride (512 mg, 9.57 mmol) in acetone/water (10:2) was stirred at rt for 2 h. The reaction mixture was diluted with acetone and EtOAc and filtered. The filtrate was concentrated to dryness. EtOAc was added. The organic layer was washed with water and brine. The organic layer was dried over MgSO4, filtered and the solution was concentrated under reduced pressure. The compound was pure enough and used in the next step without further purification. Yield: 88%; appearance: pale brown oil; 1H NMR (300 MHz, DMSO-d6, d in ppm): 1.58 (s, 9H); 3.62 (s, 3H); 3.65 (s, 2H); 4.90 (br s, 2H); 6.59-6.62 (m, 2H); 7.42 (s, 1H); 7.68 (d, 1H, J = 9.3 Hz). | |

Example 2: Synthesis of the Compounds According to the Invention

Protocol D: To a solution of the substituted acid in DMF (0.15 mmol/mL) were added DMAP (2 to 4 equiv), EDCl·HCl (1 equiv) and the substituted amine (1 equiv). The reaction mixture was stirred at rt. After completion of the reaction (monitored by TLC), sat. NH4Cl or HCl 0.5N was added and the solution was extracted with EtOAc. The organic layer was washed with sat. NH4Cl, dried over MgSO4, filtered and evaporated to dryness under reduced pressure. (FIG. 3A)

Protocol E: To a solution of tert-butyl ester derivative in MeOH/THF, 2:1 (5 mmol/mL) was added NaOH 5N (5 equiv). The reaction mixture was reacted for 15-20 min at 100° C. under microwave conditions and evaporated to dryness under reduced pressure. The residue was taken up in water, acidified with citric acid 1N to pH 4-5, the precipitate was filtered, washed with water, dried under reduced pressure at 45° C. (FIG. 3B)

Protocol F: To a solution of methyl ester derivative in MeOH (5 mmol/mL) was added NaOH 5N (5 equiv). The reaction mixture was reacted overnight at 40° C. and evaporated to dryness under reduced pressure. The residue was taken up in water, acidified with citric acid 1N to pH 4-5, the precipitate was filtered, washed with water, dried under reduced pressure at 45° C. (FIG. 3C).

Protocol G: to a solution of amine 1 (1 equiv) at 0.025M in CH2Cl2 was added Et3N (10 equiv) and triphosgene (0.33 equiv) in CH2Cl2 at −78° C. The reaction mixture was stirred 10 min at −78° C. before addition of amine 2 (1 equiv) at 0.025M in CH2Cl2. The solution was then warmed to rt (ca 1 h). The reaction mixture was diluted with CH2Cl2, washed with sat. NaHCO3 and with NH4Cl. The two phases were partitionated. The organic layer was dried over MgSO4, filtered and the solution was concentrated to dryness. The crude was purified on silica gel column chromatography using the appropriate eluant (CH2Cl2/Cyclohexane/EtOAc (50:30:20) or CH2Cl2/MeOH (95:5)) or precipitate with the correct solvent (MeOH or DMF). The solid was triturated with Et2O, filtered off and dried under reduced pressure at 45° C. until constant weight. (FIG. 3D).

TABLE 2

All the NMR were performed in DMSO-d6

| | Cpd. | Starting compounds, Reaction conditions and purification Yield, MP, Appearance, $^1$H NMR (solvent) data, Mass (ES+ or ES−) data |
|---|---|---|
| 1 | 3-{5-[({phenyl[2-(piperidin-1-yl)phenyl]methyl}carbamoyl)methyl]-1H-indol-3-yl}propanoic acid | From tert-butyl 3-{5-[({phenyl[2-(piperidin-1-yl)phenyl]methyl}carbamoyl)methyl]-1H-indol-3-yl}propanoate Cpd. 2 following protocol E<br>Yield: 98%; p: 189, 193° C.; appearance: white solid; 1H NMR, d (ppm): 1.40-1.65 (m, 6H); 2.48 (m, 2H); 2.57 (t, 2H, J = 7.3 Hz); 2.88 (m, 4H); 3.58 (s, 2H); 6.64 (d, 1H, J = 8.7 Hz); 6.95-7.35 (m, 13H); 7.42 (s, 1H); 8.77 (m, 1H); 10.70 (br s, 1H); m/z: 496.25 [M + H]+ (calc. mass: 495.25). |
| 2 | tert-butyl 3-{5-[({phenyl[2-(piperidin-1-yl)phenyl]methyl}carbamoyl)methyl]-1H-indol-3-yl}propanoate | From phenyl[2-(piperidin-1-yl)phenyl]methanaminium chloride Ex. 9 and 2-{3-[3-(tert-butoxy)-3-oxopropyl]-1H-indol-5-yl}acetic acid Ex. 1 following protocol D, DMAP (2 equiv), 4 h at rt, purification with AutoPurification System 2767 Waters, Waters SymmetryPrep C18 column (7 μm, 19 × 150 mm), MeOH/H2O/HCOOH, 70:30:0.1 to 100:0:0.1<br>Yield: 63%; appearance: orange solid; 1H NMR, d (ppm): 1.39 (s, 9H); 1.40-1.65 (m, 6H); 2.48 (m, 2H); 2.52 (t, 2H, J = 7.3 Hz); 2.88 (m, 4H); 3.58 (s, 2H); 6.62 (d, 1H, J = 8.7 Hz); 6.88-7.40 (m, 13H); 7.41 (s, 1H); 8.74 (d, 1H, J = 8.7 Hz); 10.70 (br s, 1H).; m/z: 552.31 [M + H]+ (calc. mass: 551.31). |
| 3 | 3-[5-({[(3-fluorophenyl)[2-(piperidin-1-yl)phenyl]methyl]carbamoyl}methyl)-1H-indol-3-yl]propanoic acid | From tert-butyl 3-[5-({[(3-fluorophenyl)[2-(piperidin-1-yl)phenyl]methyl]carbamoyl}methyl)-1H-indol-3-yl]propanoate Cpd. 4 following protocol E<br>Yield: 93%; mp: 124, 140° C.; appearance: white solid; 1H NMR, d (ppm): 1.44-1.57 (m, 6H); 2.50-2.52 (m, 4H); 2.83-2.89 (m, 4H); 3.58 (s, 2H); 6.63 (d, 1H, J = 8.4 Hz); 6.93-7.31 (m, 11H); 7.40-7.42 (m, 1H); 8.78 (d, 1H, J = 8.7 Hz); 10.66 (s, 1H); 12.30 (br s, 1H); m/z: 514.24 [M + H]+ (calc. mass: 513.24). |
| 4 | tert-butyl 3-[5-({[(3-fluorophenyl)[2-(piperidin-1-yl)phenyl]methyl]carbamoyl}methyl)-1H-indol-3-yl]propanoate | From (3-fluorophenyl)[2-(piperidin-1-yl)phenyl]methanamine Ex. 10 and 2-{3-[3-(tert-butoxy)-3-oxopropyl]-1H-indol-5-yl}acetic acid Ex. 1 following protocol D, DMAP (2 equiv), 4 h at rt, purification with AutoPurification System 2767 Waters, Waters SymmetryPrep C18 column (7 μm, 19 × 150 mm), MeOH/H2O/HCOOH, 70:30:0.1 to 100:0:0.1<br>Yield: 15%; appearance: white solid; 1H NMR, d (ppm): 1.39 (s, 9H); 1.45-1.74 (m, 6H); 2.51-2.56 (m, 4H); 2.85-2.90 (m, 4H); 3.59 (s, 2H); 6.63 (d, 1H, J = 8.4 Hz); 6.95-7.36 (m, 11H); 7.41 (d, 1H, J = /Hz); 8.77 (d, 1H, J = 8.9 Hz); 10.70 (s, 1H) |
| 5 | 3-{5-[({[4-methyl-2-(pyrrolidin-1-yl)phenyl](phenyl)methyl}carbamoyl)methyl]-1H-indol-3-yl}propanoic acid | From tert-butyl 3-{5-[({[4-methyl-2-(pyrrolidin-1-yl)phenyl](phenyl)methyl}carbamoyl)methyl]-1H-indol-3-yl}propanoate Cpd. 6 following protocol E<br>Yield: 75%; mp: 160, 168° C.; appearance: white solid; 1H NMR, d (ppm): 1.70 (q, 4H, J = 4.6 Hz); 2.22 (s, 3H); 2.58 (t, 2H, J = 8.0 Hz); 2.74 (m, 2H); 2.88 (t, 2H, J = 8.0 Hz); 3.02 (m, 2H); 3.56 (s, 2H); 6.46 (d, 1H, J = 8.5 Hz); 6.75 (dd, 1H, J = 6.8 Hz, J = 1.0 Hz); 6.87 (s, 1H); 6.98 (dd, 1H, J = 6.8 Hz, J = 1.5 Hz); 7.09 (m, 5H); 7.21 (m, 3H); 7.41 (s, 1H); 8.68 (d, 1H, J = 8.5 Hz); 10.68 (d, 1H, J = 2.0 Hz); 12.10 (br s, 1H); m/z: 496.25 [M + H]+ (calc. mass: 495.25). |
| 6 | tert-butyl 3-{5-[({[4-methyl-2-(pyrrolidin-1-yl)phenyl](phenyl)methyl}carbamoyl)methyl]-1H-indol-3-yl}propanoate | From 4-methyl-2-(pyrrolidin-1-yl)phenyl](phenyl)methanamine Ex. 11 and 2-{3-[3-(tert-butoxy)-3-oxopropyl]-1H-indol-5-yl}acetic acid Ex. 1 following protocol D, DMAP (2 equiv), 5 days at rt, purification by column chromatography on silica gel (cyclohexane/EtOAc, 7:3)<br>Yield: 44%; appearance: white solid; 1H NMR, d (ppm): 1.38 (s, 9H); 1.69 (q, 4H, J = 4.5 Hz); 2.22 (s, 3H); 2.56 (t, 2H, J = 8.1 Hz); 2.72 (m, 2H); 2.86 (t, 2H, J = 8.1 Hz); 3.00 (m, 2H); 3.56 (s, 2H); 6.45 (d, 1H, J = 8.6 Hz); 6.75 (dd, 1H, J = 6.7 Hz, J = 1.0 Hz); 6.87 (d, 1H); 6.98 (dd, 1H, J = 6.9 Hz, J = 1.5 Hz); 7.07 (m, 5H); 7.21 (m, 3H); 7.40 (s, 1H); 8.67 (d, 1H, J = 8.6 Hz); 10.67 (d, 1H, J = 2.0 Hz) |

TABLE 2-continued

All the NMR were performed in DMSO-d6

| | Cpd. | Starting compounds, Reaction conditions and purification Yield, MP, Appearance, $^1$H NMR (solvent) data, Mass (ES+ or ES−) data |
|---|---|---|
| 7 | 3-[5-({[(2-chloro-4-methylphenyl)(phenyl)methyl]carbamoyl}methyl)-1H-indol-3-yl]propanoic acid | From tert-butyl 3-[5-({[(2-chloro-4-methylphenyl)(phenyl)methyl]carbamoyl}methyl)-1H-indol-3-yl]propanoate Cpd. 8 following protocol E<br>Yield: 65%; mp: 95-113° C.; appearance: white solid; 1H NMR, d (ppm): 2.26 (s, 3H); 2.56 (t, 2H, J = 7.2 Hz); 2.88 (t, 2H, J = 7.8 Hz); 3.55 (s, 2H); 6.37 (d, 1H, J = 8.4 Hz); 6.97 (dd, 1H, J = 8.4 Hz, J = 1.5 Hz); 7.06 (d, 1H, J = 2.1 Hz); 7.13-7.40 (m, 10H); 8.95 (d, 1H, J = 8.4 Hz); 10.68 (s, 1H); 12.10 (s, 1H); m/z: 461.15 [M + H]+ (calc. mass: 460.15) |
| 8 | tert-butyl 3-[5-({[(2-chloro-4-methylphenyl)(phenyl)methyl]carbamoyl}methyl)-1H-indol-3-yl]propanoate | From (2-chloro-4-methylphenyl)(phenyl)methanaminium chloride Ex. 12 and 2-{3-[3-(tert-butoxy)-3-oxopropyl]-1H-indol-5-yl}acetic acid Ex. 1 following protocol D, DMAP (2 equiv), 4 h at rt, purification by column chromatography on silica gel (CH2Cl2/EtOAc, 95:5)<br>Yield: 48%; appearance: white solid; 1H NMR, d (ppm): 1.38 (s, 9H); 2.26 (s, 3H); 2.54 (t, 2H, J = 8.1 Hz); 2.87 (t, 2H, J = 7.5 Hz); 3.55 (s, 2H); 6.36 (d, 1H, J = 8.4 Hz); 6.97 (dd, 1H, J = 8.4 Hz, J = 1.5 Hz); 7.07 (d, 1H, J = 2.1 Hz); 7.13-7.34 (m, 9H); 7.40 (m, 1H); 8.94 (d, 1H, J = 8.4 Hz); 10.69 (s, 1H) |
| 9 | 3-[5-({[(2-bromo-4-methylphenyl)(phenyl)methyl]carbamoyl}methyl)-1H-indol-3-yl]propanoic acid | From tert-butyl 3-[5-({[(2-bromo-4-methylphenyl)(phenyl)methyl]carbamoyl}methyl)-1H-indol-3-yl]propanoate Cpd. 10 following protocol E<br>Yield: 69%; mp: 102-126° C.; appearance: white solid; 1H NMR, d (ppm): 2.26 (s, 3H); 2.56 (t, 2H, J = 6.3 Hz); 2.88 (t, 2H, J = 7.5 Hz); 3.55 (s, 2H); 6.33 (d, 1H, J = 8.4 Hz); 6.97 (dd, 1H, J = 8.1 Hz, J = 1.5 Hz); 7.06 (d, 1H, J = 2.4 Hz); 7.12-7.42 (m, 10H); 8.96 (d, 1H, J = 8.4 Hz); 10.68 (s, 1H); 12.13 (s, 1H); m/z: 505.1 [M + H]+ (calc. mass: 504.1). |
| 10 | tert-butyl 3-[5-({[(2-bromo-4-methylphenyl)(phenyl)methyl]carbamoyl}methyl)-1H-indol-3-yl]propanoate | From (2-bromo-4-methylphenyl)(phenyl)methanamine Ex. 13 and 2-{3-[3-(tert-butoxy)-3-oxopropyl]-1H-indol-5-yl}acetic acid Ex. 1 following protocol D, DMAP (3 equiv), 48 h at rt, purification by column chromatography on silica gel (Cyclohexane/EtOAc, 7:3)<br>Yield: 53%; appearance: white solid; 1H NMR, d (ppm): 1.38 (s, 9H); 2.26 (s, 3H); 2.54 (t, 2H, J = 8.1 Hz); 2.87 (t, 2H, J = 7.5 Hz); 3.55 (s, 2H); 6.33 (d, 1H, J = 8.4 Hz); 6.97 (dd, 1H, J = 8.4 Hz, J = 1.5 Hz); 7.06 (d, 1H, J = 2.4 Hz); 7.12-7.34 (m, 8H); 7.40-7.42 (m, 2H); 8.95 (d, 1H, J = 8.4 Hz); 10.68 (s, 1H) |
| 11 | 3-[5-({[(2,4-dimethylphenyl)(phenyl)methyl]carbamoyl}methyl)-1H-indol-3-yl]propanoic acid | From tert-butyl 3-[5-({[(2,4-dimethylphenyl)(phenyl)methyl]carbamoyl}methyl)-1H-indol-3-yl]propanoate Cpd. 12 following protocol E<br>Yield: 76%; mp: 92-118° C.; appearance: white solid; 1H NMR, d (ppm): 2.14 (s, 3H); 2.21 (s, 3H); 2.56 (t, 2H, J = 6.9 Hz); 2.87 (t, 2H, J = 7.5 Hz); 3.54 (s, 2H); 6.19 (d, 1H, J = 8.4 Hz); 7.07 (m, 5H); 7.16-7.32 (m, 6H); 7.39-7.41 (m, 1H); 8.82 (d, 1H, J = 8.7 Hz); 10.67 (s, 1H); 12.10 (s, 1H); m/z: 441.2 [M + H]+ (calc. mass: 440.21) |
| 12 | tert-butyl 3-[5-({[(2,4-dimethylphenyl)(phenyl)methyl]carbamoyl}methyl)-1H-indol-3-yl]propanoate | From (2,4-dimethylphenyl)(phenyl)methanaminium chloride Ex. 14 and 2-{3-[3-(tert-butoxy)-3-oxopropyl]-1H-indol-5-yl}acetic acid Ex. 1 following protocol D, DMAP (3 equiv), 16 h at rt, purification by column chromatography on silica gel (CH2Cl2/EtOAc, 95:5)<br>Yield: 60%; appearance: white solid; 1H NMR, d (ppm): 1.39 (s, 9H); 2.15 (s, 3H); 2.22 (s, 3H); 2.54 (t, 2H, J = 7.5 Hz); 2.87 (t, 2H, J = 7.5 Hz); 3.54 (s, 2H); 6.20 (d, 1H, J = 8.4 Hz); 6.96-7.07 (m, 5H); 7.16-7.32 (m, 6H); 7.38-7.40 (m, 1H); 8.81 (d, 1H, J = 8.7 Hz); 10.68 (s, 1H) |
| 13 | 3-[5-({[(2,5-dimethylphenyl)(phenyl)methyl]carbamoyl}methyl)-1H-indol-3-yl]propanoic acid | From tert-butyl 3-[5-({[(2,5-dimethylphenyl)(phenyl)methyl]carbamoyl}methyl)-1H-indol-3-yl]propanoate Cpd. 14 following protocol E<br>Yield: 26%; mp: 103-108° C.; appearance: white solid; 1H NMR, d (ppm): 2.12 (s, 3H); 2.14 (s, 3H); 2.56 (t, 2H, J = 7.2 Hz); 2.88 (t, 2H, J = 7.4 Hz); 3.50-3.61 (m, 2H); 6.19 (d, 1H, J = 8.4 Hz); 6.93-7.07 (m, 5H); 7.16-7.34 (m, 6H); 7.42 (s, 1H); 8.82 (d, 1H, J = 8.4 Hz); 10.69 (d, 1H, J = 1.9 Hz), 12.19 (br s, 1H); m/z: 441.2 [M + H]+ (calc. mass: 440.21) |
| 14 | tert-butyl 3-[5-({[(2,5-dimethylphenyl)(phenyl)methyl]carbamoyl}methyl)-1H-indol-3-yl]propanoate | From (2,5-dimethylphenyl)(phenyl)methanaminium chloride Ex. 15 and 2-{3-[3-(tert-butoxy)-3-oxopropyl]-1H-indol-5-yl}acetic acid Ex. 1 following protocol D, DMAP (3 equiv), 16 h at rt, purification by column chromatography on silica gel (CH2Cl2/MeOH, 98:2)<br>Yield: 51%; appearance: colorless oil; 1H NMR, d (ppm): 1.38 (s, 9H); 2.13 (s, 3H); 2.14 (s, 3H); 2.54 (t, 2H, |

TABLE 2-continued

All the NMR were performed in DMSO-d6

| Cpd. | | Starting compounds, Reaction conditions and purification Yield, MP, Appearance, $^1$H NMR (solvent) data, Mass (ES+ or ES−) data |
|---|---|---|
| | | J = 7.4 Hz); 2.87 (t, 2H, J = 7.3 Hz); 3.54-3.57 (m, 2H); 6.19 (d, 1H, J = 8.3 Hz); 6.93-7.09 (m, 5H); 7.16-7.31 (m, 6H); 7.41 (s, 1H); 8.81 (d, 1H, J = 8.4 Hz); 10.69 (s, 1H) |
| 15 | 3-{5-[({[6-methyl-2-(pyrrolidin-1-yl)pyridin-3-yl](phenyl)methyl}carbamoyl)methyl]-1H-indol-3-yl}propanoic acid | From tert-butyl 3-{5-[({[6-methyl-2-(pyrrolidin-1-yl)pyridin-3-yl](phenyl)methyl}carbamoyl)methyl]-1H-indol-3-yl}propanoate Cpd. 16 following protocol E<br>Yield: 67%; mp: 115° C.; appearance: white solid; 1H NMR, d (ppm): 1.69-1.74 (m, 4H); 2.27 (s, 3H); 2.57 (t, 2H, J = 7.2 Hz); 2.89 (t, 2H, J = 7.4 Hz); 3.34-3.45 (m, 4H); 3.59 (m, 2H); 6.37 (d, 1H, J = 8.0 Hz); 6.56 (d, 1H, J = 7.7 Hz); 3.49-6.98 (dd, 1H, J = 8.4 Hz, J = 1.5 Hz); 7.07-7.31 (m, 8H); 7.39 (s, 1H); 8.85 (d, 1H, J = 8.0 Hz); 10.69 (d, 1H, J = 1.9 Hz); 12.12 (s, 1H); m/z: 497.24 [M + H]+ (calc. mass: 496.24) |
| 16 | tert-butyl 3-{5-[({[6-methyl-2-(pyrrolidin-1-yl)pyridin-3-yl](phenyl)methyl}carbamoyl)methyl]-1H-indol-3-yl}propanoate | From [6-methyl-2-(pyrrolidin-1-yl)pyridin-3-yl][(phenyl)methanamine Ex. 16 and 2-{3-[3-(tert-butoxy)-3-oxopropyl]-1H-indol-5-yl}acetic acid Ex. 1 following protocol D, DMAP (2 equiv), 16 h at rt, purification by column chromatography on silica gel (CH2Cl2/MeOH, 98:2; CH2Cl2/EtOAc, 5:5)<br>Yield: 60%; appearance: colorless oil; 1H NMR, d (ppm): 1.38 (s, 9H); 1.63-1.75 (m, 4H); 2.27 (s, 3H); 2.54 (t, 2H, J = 7.3 Hz); 2.87 (t, 2H, J = 7.4 Hz); 3.33-3.46 (m, 4H); 3.48-3.59 (m, 2H); 6.36 (d, 1H, J = 8.0 Hz); 6.55 (d, 1H, J = 7.7 Hz); 6.98 (dd, 1H, J = 8.3 Hz, J = 1.5 Hz); 7.07 (d, 1H, J = 2.3 Hz); 7.12-7.15 (m, 2H); 7.18-7.31 (m, 5H); 7.39 (s, 1H); 8.83 (d, 1H, J = 8.1 Hz); 10.69 (d, 1H, J = 1.9 Hz) |
| 17 | 3-[5-({[(2-fluoro-4-methylphenyl)(phenyl)methyl]carbamoyl}methyl)-1H-indol-3-yl]propanoic acid | From tert-butyl 3-[5-({[(2-fluoro-4-methylphenyl)(phenyl)methyl]carbamoyl}methyl)-1H-indol-3-yl]propanoate Cpd. 18 following protocol E<br>Yield: 88%; mp: 79-84° C.; appearance: white solid; 1H NMR, d (ppm): 2.27 (s, 3H); 2.56 (t, 2H, J = 9.0 Hz); 2.88 (t, 2H, J = 9.0 Hz); 3.56 (s, 2H); 6.30 (d, 1H, J = 9.0 Hz); 6.96-7.00 (m, 3H); 7.07 (d, 1H, J = 2.2 Hz); 7.19-7.34 (m, 7H); 7.41 (s, 1H); 8.95 (d, 1H, J = 9.0 Hz); 10.69 (d, 1H, J = 1.8 Hz); 12.04 (br s, 1H); m/z: 445.18 [M + H]+ (calc. mass: 444.18) |
| 18 | tert-butyl 3-[5-({[(2-fluoro-4-methylphenyl)(phenyl)methyl]carbamoyl}methyl)-1H-indol-3-yl]propanoate | From (2-fluoro-4-methylphenyl)(phenyl)methanaminium chloride Ex. 17 and 2-{3-[3-(tert-butoxy)-3-oxopropyl]-1H-indol-5-yl}acetic acid Ex. 1 following protocol D, DMAP (3 equiv), 6 h at rt, purification by column chromatography on silica gel (CH2Cl2/MeOH, 85:15)<br>Yield: 50%; appearance: yellow oil; 1H NMR, d (ppm): 1.38 (s, 9H); 2.27 (s, 3H); 2.54 (t, 2H, J = 7.2 Hz); 2.87 (t, 2H, J = 7.5 Hz); 3.56 (s, 2H); 6.29 (d, 1H, J = 8.6 Hz); 6.96-7.00 (m, 3H); 7.07 (d, 1H, J = 2.2 Hz); 7.19-7.34 (m, 7H); 7.40 (s, 1H); 8.93 (d, 1H, J = 8.6 Hz); 10.69 (d, 1H, J = 1.9 Hz) |
| 19 | 3-[5-({[(2-fluoro-5-methylphenyl)(phenyl)methyl]carbamoyl}methyl)-1H-indol-3-yl]propanoic acid | From tert-butyl 3-[5-({[(2-fluoro-5-methylphenyl)(phenyl)methyl]carbamoyl}methyl)-1H-indol-3-yl]propanoate Cpd. 20 following protocol E<br>Yeld 87%; mp: 80-85° C.; appearance: white solid; 1H NMR, d (ppm): 2.18 (s, 3H); 2.56 (t, 2H, J = 7.1 Hz); 2.88 (t, 2H, J = 7.4 Hz); 3.52-3.62 (m, 2H); 6.28 (d, 1H, J = 8.5 Hz); 6.98-7.08 (m, 4H); 7.12-7.15 (m, 1H); 7.20-7.34 (m, 6H); 7.44 (s, 1H); 8.93 (d, 1H, J = 8.5 Hz); 10.69 (d, 1H, J = 1.8 Hz); 12.13 (br s, 1H); m/z: 445.18 [M + H]+ (calc. mass: 444.18). |
| 20 | tert-butyl 3-[5-({[(2-fluoro-5-methylphenyl)(phenyl)methyl]carbamoyl}methyl)-1H-indol-3-yl]propanoate | From (2-fluoro-5-methylphenyl)(phenyl)methanaminium chloride Ex. 18 and 2-{3-[3-(tert-butoxy)-3-oxopropyl]-1H-indol-5-yl}acetic acid Ex. 1 following protocol D, DMAP (3 equiv), 6 h at rt, purification by column chromatography on silica gel (CH2Cl2/MeOH, 9:1)<br>Yield: 61%; appearance: yellow oil; -1H NMR, d (ppm): 1.38 (s, 9H); 2.27 (s, 3H); 2.54 (t, 2H, J = 7.2 Hz); 2.87 (t, 2H, J = 7.4 Hz); 3.52-3.62 (m, 2H); 6.28 (d, 1H, J = 8.5 Hz); 6.98-7.34 (m, 11H); 7.43 (s, 1H); 8.91 (d, 1H, J = 8.5 Hz); 10.69 (d, 1H, J = 1.7 Hz) |
| 21 | 3-[5-({[(2,4-dimethylphenyl)(pyridin-2-yl)methyl]carbamoyl}methyl)-1H-indol-3-yl]propanoic acid | From tert-butyl 3-[5-({[(2,4-dimethylphenyl)(pyridin-2-yl)methyl]carbamoyl}methyl)-1H-indol-3-yl]propanoate Cpd. 22 following protocol E<br>Yield: 63%; mp: 130-143° C.; appearance: white solid; 1H NMR, d (ppm): 2.22 (s, 3H); 2.24 (s, 3H); 2.53 (t, 2H, J = 8.0 Hz); 2.86 (t, 2H, J = 8.0 Hz); 3.56 (s, 2H); 6.23 (d, 1H, J = 8.3 Hz); 6.95 (m, 4H); 7.06 (d, 1H, J = 2.2 Hz); 7.23 (m, 2H); 7.33 (d, 1H); 7.40 (s, 1H); 7.74 (m, 1H); 8.48 (m, 1H); 7.79 (d, 1H, J = 8.4 Hz); 10.67 (d, 1H, J = 1.6 Hz); 12.13 (br s, |

TABLE 2-continued

All the NMR were performed in DMSO-d6

| Cpd. | | Starting compounds, Reaction conditions and purification Yield, MP, Appearance, $^1$H NMR (solvent) data, Mass (ES+ or ES−) data |
|---|---|---|
| 22 | tert-butyl 3-[5-({[(2,4-dimethylphenyl)(pyridin-2-yl)methyl]carbamoyl}methyl)-1H-indol-3-yl]propanoate | 1H); m/z: 442.2 [M + H]+ (calc. mass: 441.2).<br>From (2,4-dimethylphenyl)(pyridin-2-yl)methanamine Ex. 19 and 2-{3-[3-(tert-butoxy)-3-oxopropyl]-1H-indol-5-yl}acetic acid Ex. 1 following protocol D, DMAP (2 equiv), 5 days at rt, purification by column chromatography on silica gel (cyclohexane/EtOAc, 6:4)<br>Yield: 32%; appearance: yellow oil; 1H NMR, d (ppm):<br>1.38 (s, 9H); 2.20 (s, 3H); 2.24 (s, 3H); 2.54 (t, 2H, J = 7.9 Hz); 2.87 (t, 2H, J = 7.9 Hz); 3.56 (s, 2H); 6.23 (d, 1H, J = 8.2 Hz); 6.87-7.00 (m, 4H); 7.05-7.09 (m, 1H); 7.20-7.24 (m, 2H); 7.33 (d, 1H, J = 7.8 Hz); 7.39 (br s, 1H); 7.74 (dt, 1H, J = 7.7 Hz, J = 1.8 Hz); 8.48 (m, 1H); 8.79 (d, 1H, J = 8.2 Hz); 10.68 (d, 1H, J = 1.6 Hz) |
| 23 | 3-[5-({[phenyl({2-[2-(trifluoromethyl)piperidin-1-yl]phenyl})methyl]carbamoyl}methyl)-1H-indol-3-yl]propanoic acid | From tert-butyl 3-[5-({[phenyl({2-[2-(trifluoromethyl)piperidin-1-yl]phenyl})methyl]carbamoyl}methyl)-1H-indol-3-yl]propanoate Cpd. 24 following protocol E<br>Yield 89%; mp: 99-120° C.; appearance: white solid; 1H NMR, d (ppm): 1.22-1.51 (m, 2H); 1.65-1.69 (m, 1H); 1.86-1.90 (m, 1H); 2.53-2.59 (m, 4H); 2.66-2.73 (m, 2H); 2.88 (t, 2H, J = 7.8 Hz); 3.14-3.16 (m, 1H); 3.48-3.62 (m, 2H); 6.60 (d, 1H, J = 8.6 Hz); 6.98 (dd, 1H, J = 8.3 Hz, J = 1.5 Hz); 7.06-7.31 (m, 11H); 7.40-7.42 (m, 1H); 8.68 (d, 1H, J = 8.6 Hz); 10.68 (s, 1H); 12.04 (s, 1H); m/z: 564 [M + H]+ (calc. mass: 563.24). |
| 24 | 3-[5-({[phenyl({2-[2-(trifluoromethyl)piperidin-1-yl]phenyl})methyl]carbamoyl}methyl)-1H-indol-3-yl]propanoate | From phenyl({2-[2-(trifluoromethyl)piperidin-1-yl]phenyl})methanaminium chloride Ex. 20 and 2-{3-[3-(tert-butoxy)-3-oxopropyl]-1H-indol-5-yl}acetic acid Ex. 1 following protocol D, DMAP (3 equiv), 16 h at rt, purification by column chromatography on silica gel (CH2Cl2/EtOAc, 95:5)<br>Yield 39%; appearance: white solid; 1H NMR, d (ppm):<br>1.20-1.55 (m, 11H); 1.59-1.69 (m, 1H); 1.85-1.90 (m, 1H); 2.53-2.55 (m, 4H); 2.69-2.27 (m, 2H); 2.87 (t, 2H, J = 7.5 Hz); 3.14-3.17 (m, 1H); 3.48-3.55 (m, 2H); 6.60 (d, 1H, J = 8.4 Hz); 6.98 (dd, 1H, J = 8.4 Hz, J = 1.5 Hz); 7.06-7.30 (m, 11H); 7.40-7.42 (m, 1H); 8.68 (d, 1H, J = 8.7 Hz); 10.68 (s, 1H) |
| 25 | 3-{5-[({[2-(3,5-dimethylpiperidin-1-yl)phenyl](phenyl)methyl}carbamoyl)methyl]-1H-indol-3-yl}propanoic acid | From tert-butyl 3-{5-[({[2-(3,5-dimethylpiperidin-1-yl)phenyl](phenyl)methyl}carbamoyl)methyl]-1H-indol-3-yl}propanoate Cpd. 26 following protocol E, 40 min<br>Yield 85%; mp: 96-116° C.; appearance: white solid; 1H NMR, d (ppm): 0.51 (q, 1H, J = 11.9 Hz); 0.67 (d, 3H, J = 6.4 Hz); 0.72 (d, 3H, J = 6.5 Hz); 1.56-1.72 (m, 3H); 1.91 (t, 1H, J = 10.9 Hz); 2.17 (t, 1H, J = 10.7 Hz); 2.55-2.58 (m, 3H); 2.87 (t, 2H, J = 7.9 Hz); 2.94-2.98 (m, 1H); 3.57 (s, 2H); 6.57 (d, 1H, J = 8.7 Hz); 6.98 (dd, 1H, J = 8.4 Hz, J = 1.5 Hz); 7.03-7.27 (m, 10H); 7.32 (dd, 1H, J = 7.6 Hz, J = 1.5 Hz); 7.40-7.42 (m, 1H); 8.73 (d, 1H, J = 8.9 Hz); 10.67 (s, 1H); 12.04 (s, 1H); m/z: 524 [M + H]+ (calc. mass: 523.28). |
| 26 | tert-butyl 3-{5-[({[2-(3,5-dimethylpiperidin-1-yl)phenyl](phenyl)methyl}carbamoyl)methyl]-1H-indol-3-yl}propanoate | From [2-(3,5-dimethylpiperidin-1-yl)phenyl](phenyl)methanamine Ex. 21 and 2-{3-[3-(tert-butoxy)-3-oxopropyl]-1H-indol-5-yl}acetic acid Ex. 1following protocol D, DMAP (3 equiv), 16 h at rt, purification by column chromatography on silica gel (CH2Cl2/EtOAc, 9:1)<br>Yield 30%; appearance: white solid; 1H NMR, d (ppm):<br>0.54 (q, 1H, J = 12.1 Hz); 0.67 (d, 3H, J = 6.6 Hz); 0.72 (d, 3H, J = 6.6 Hz); 1.38 (s, 9H); 1.54-1.72 (m, 4H); 1.90 (t, 1H, J = 10.8 Hz); 2.17 (t, 1H, J = 10.7 Hz); 2.52-2.57 (m, 2H); 2.86 (t, 2H, J = 7.3 Hz); 2.94-2.97 (m, 1H); 3.57 (s, 2H); 6.58 (d, 1H, J = 8.7 Hz); 6.98 (dd, 1H, J = 8.4 Hz, J = 1.5 Hz); 7.06-27 (m, 10H); 7.32 (dd, 1H, J = 7.5 Hz, J = 1.5 Hz); 7.39-7.41 (m, 1H); 8.73 (d, 1H, J = 8.7 Hz); 10.67 (s, 1H) |
| 27 | 3-[5-({[(2,4-dimethylphenyl)(pyridin-3-yl)methyl]carbamoyl}methyl)-1H-indol-3-yl]propanoic acid | From tert-butyl 3-[5-({[(2,4-dimethylphenyl)(pyridin-3-yl)methyl]carbamoyl}methyl)-1H-indol-3-yl]propanoate Cpd. 28 following protocol E<br>Yield: 84%; mp: 108, 152° C.; appearance: white solid; 1H NMR, d (ppm): 2.17 (s, 3H); 2.22 (s, 3H); 2.56 (t, 2H, J = 7.2 Hz); 2.88 (t, 2H, J = 6.8 Hz); 3.55 (s, 2H); 6.24 (d, 1H, J = 8.2 Hz); 6.97-6.99 (m, 4H); 7.07 (d, 1H, J = 2.3 Hz); 7.22 (d, 1H, J = 8.5 Hz); 7.31-7.35 (m, 1H); 7.40 (s, 1H); 7.56 (dt, 1H, J = 7.9 Hz, J = 2.1 Hz); 8.41 (d, 1H, J = 2.3 Hz); 8.44 (dd, 1H, J = 4.7 Hz, J = 1.6 Hz); 8.90 (d, 1H, J = 8.3 Hz); 10.69 (s, 1H); |

TABLE 2-continued

All the NMR were performed in DMSO-d6

| Cpd. | | Starting compounds, Reaction conditions and purification Yield, MP, Appearance, $^1$H NMR (solvent) data, Mass (ES+ or ES−) data |
|---|---|---|
| 28 | tert-butyl 3-[5-({[(2,4-dimethylphenyl)(pyridin-3-yl)methyl]carbamoyl}methyl)-1H-indol-3-yl]propanoate | 12.06 (s, 1H); m/z: 442.2 [M + H]+ (calc. mass: 441.2). From (2,4-dimethylphenyl)(pyridin-3-yl)methanamine Ex. 22 and 2-{3-[3-(tert-butoxy)-3-oxopropyl]-1H-indol-5-yl}acetic acid Ex. 1 following protocol D, DMAP (4 equiv), 16 h at rt, purification by column chromatography on silica gel (CH2Cl2/EtOAc, 9:1) Yield: 68%; appearance: colorless oil; 1H NMR, d (ppm): 1.38 (s, 9H); 2.17 (s, 3H); 2.22 (s, 3H); 2.56 (t, 2H, J = 8.0 Hz); 2.87 (t, 2H, J = 7.9 Hz); 3.55 (s, 2H); 6.24 (d, 1H, J = 8.2 Hz); 6.97-6.99 (m, 4H); 7.07 (d, 1H, J = 2.3 Hz); 7.22 (d, 1H, J = 8.5 Hz); 7.31-7.35 (m, 1H); 7.39 (s, 1H); 7.54-7.57 (m, 1H); 8.41 (d, 1H, J = 2.3 Hz); 8.44 (dd, 1H, J = 4.7 Hz, J = 1.6 Hz); 8.89 (d, 1H, J = 8.4 Hz); 10.69 (s, 1H) |
| 29 | 3-{5-[({3-methyl-1-[2-(piperidin-1-yl)phenyl]butyl}carbamoyl)methyl]-1H-indol-3-yl}propanoic acid | From tert-butyl 3-{5-[({3-methyl-1-[2-(piperidin-1-yl)phenyl]butyl}carbamoyl)methyl]-1H-indol-3-yl}propanoate Cpd. 30 following protocol E Yield: 82%; mp: 80, 134° C.; appearance: white solid; 1H NMR, d (ppm): 0.88 (d, 3H, J = 6.4 Hz); 0.90 (d, 3H, J = 6.4 Hz); 1.22-1.34 (m, 2H); 1.38-1.90 (m, 8H); 2.55-2.58 (m, 3H); 2.88 (t, 2H, J = 7.5 Hz); 3.08 (m, 2H); 3.42-3.52 (m, 2H); 5.31-5.38 (m, 1H); 6.94 (dd, 1H, J = 8.3 Hz, J = 1.5 Hz); 7.02-7.15 (m, 4H); 7.21 (d, 1H, J = 8.3 Hz); 7.31 (dd, 1H, J = 7.5 Hz, J = 1.5 Hz); 7.38 (d, 1H); 8.33 (d, 1H, J = 8.4 Hz); 10.67 (s, 1H); 12.06 (br s, 1H); m/z: 476.28 [M + H]+ (calc. mass: 475.28). |
| 30 | tert-butyl 3-{5-[({3-methyl-1-[2-(piperidin-1-yl)phenyl]butyl}carbamoyl)methyl]-1H-indol-3-yl}propanoate | From 3-methyl-1-[2-(piperidin-1-yl)phenyl]butan-1-aminium chloride and 2-{3-[3-(tert-butoxy)-3-oxopropyl]-1H-indol-5-yl}acetic acid Ex. 1 following protocol D, DMAP (3 equiv), 16 h at rt, purification by column chromatography on silica gel (CH2Cl2/EtOAc, 9:1; Cyclohexane/EtOAc, 8:2) Yield: 38%; appearance: colorless oil; 1H NMR, d (ppm): 0.88 (d, 3H, J = 6.4 Hz); 0.90 (d, 3H, J = 6.4 Hz); 1.23-1.64 (m, 21H); 2.53 (t, 2H, J = 8.2 Hz); 2.87 (t, 2H, J = 7.7 Hz); 3.08 (br s, 2H); 3.44 (d, 1H, J = 13.6 Hz); 3.48 (d, 1H, J = 13.6 Hz); 5.33-5.35 (m, 1H); 6.95 (dd, 1H, J = 8.3 Hz, J = 1.4 Hz); 6.99-7.16 (m, 4H); 7.20 (d, 1H, J = 8.1 Hz); 7.31 (dd, 1H, J = 7.5 Hz, J = 1.5 Hz); 7.37 (s, 1H); 8.31 (d, 1H) |
| 31 | 3-[5-({[(5-methylquinolin-8-yl)(phenyl)methyl]carbamoyl}methyl)-1H-indol-3-yl]propanoic acid | From tert-butyl 3-[5-({[(5-methylquinolin-8-yl)(phenyl)methyl]carbamoyl}methyl)-1H-indol-3-yl]propanoate Cpd. 32 following protocol E Yield: 90%; mp: 101, 136° C.; appearance: light grey solid; 1H NMR, d (ppm): 2.56 (t, 2H, J = 7.7 Hz); 2.62 (s, 3H); 2.87 (t, 2H, J = 7.6 Hz); 3.59 (d, 2H, J = 2.3 Hz); 6.99 (dd, 1H, J = 8.3 Hz, J = 1.5 Hz); 7.08-7.15 (m, 2H); 7.20-7.25 (m, 6H); 7.41-7.46 (m, 2H); 7.47-7.52 (m, 1H); 7.75 (d, 1H, J = 7.3 Hz); 8.42 (dd, 1H, J = 8.5 Hz, J = 1.7 Hz); 8.68 (dd, 1H, J = 4.1 Hz, J = 1.7 Hz); 9.00 (d, 1H, J = 9.0 Hz); 10.70 (d, 1H, J = 1.9 Hz); 11.92 (br s, 1H); m/z: 478.2 [M + H]+ (calc. mass: 477.2) |
| 32 | tert-butyl 3-[5-({[(5-methylquinolin-8-yl)(phenyl)methyl]carbamoyl}methyl)-1H-indol-3-yl]propanoate | From (5-methylquinolin-8-yl)(phenyl)methanamine Ex. 24 and 2-{3-[3-(tert-butoxy)-3-oxopropyl]-1H-indol-5-yl}acetic acid Ex. 1 following protocol D, DMAP (2 equiv), 6 h at rt, purification by column chromatography on silica gel (CH2Cl2/EtOAc, 8:2) Yield: 45%; appearance: colorless oil; 1H NMR, d (ppm): 1.37 (s, 9H); 2.53 (t, 2H, J = 7.6 Hz); 2.62 (s, 3H); 2.85 (t, 2H, J = 7.7 Hz); 3.54-3.64 (m, 2H); 6.98 (dd, 1H, J = 8.3 Hz, J = 1.5 Hz); 7.08-7.24 (m, 8H); 7.41-7.44 (m, 2H); 7.49 (dd, 1H, J = 8.5 Hz, J = 4.1 Hz); 7.74 (d, 1H, J = 7.3 Hz); 8.42 (dd, 1H, J = 8.5 Hz, J = 1.7 Hz); 8.67 (dd, 1H, J = 4.1 Hz, J = 1.6 Hz); 8.99 (d, 1H, J = 8.9 Hz); 10.70 (d, 1H, J = 1.9 Hz) |
| 33 | 3-[5-({[(4-chloro-2-methylphenyl)(phenyl)methyl]carbamoyl}methyl)-1H-indol-3-yl]propanoic acid | From tert-butyl 3-[5-({[(4-chloro-2-methylphenyl)(phenyl)methyl]carbamoyl}methyl)-1H-indol-3-yl]propanoate Cpd. 34 following protocol E Yield: 87%; mp: 88, 140° C.; appearance: white solid; 1H NMR, d (ppm): 2.19 (s, 3H); 2.56 (t, 2H, J = 7.2 Hz); 2.88 (t, 2H, J = 7.5 Hz); 3.55 (s, 2H); 6.20 (d, 1H, J = 8.3 Hz); 6.97 (dd, 1H, J = 8.3 Hz, J = 1.5 Hz); 7.07 (d, 1H, J = 2.2 Hz); 7.13-7.35 (m, 9H); 7.40 (s, 1H); 8.92 (d, 1H, J = 8.4 Hz); 10.70 (d, 1H, J = 1.9 Hz); 11.99 (br s, 1H); m/z: 461.15, 463.15 [M + H]+ (calc. mass: 460.15). |

TABLE 2-continued

All the NMR were performed in DMSO-d6

| Cpd. | | Starting compounds, Reaction conditions and purification Yield, MP, Appearance, $^1$H NMR (solvent) data, Mass (ES+ or ES−) data |
|---|---|---|
| 34 | tert-butyl 3-[5-({[(4-chloro-2-methylphenyl)(phenyl)methyl]carbamoyl}methyl)-1H-indol-3-yl]propanoate following protocol E | From (4-chloro-2-methylphenyl)(phenyl)methanaminium chloride Ex. 25 and 2-{3-[3-(tert-butoxy)-3-oxopropyl]-1H-indol-5-yl}acetic acid Ex. 1 following protocol D, DMAP (3 equiv), 6 h at rt, purification by column chromatography on silica gel (CH2Cl2/EtOAc, 85:15) Yield: 62%; appearance: colorless oil; 1H NMR, d (ppm): 1.38 (s, 9H); 2.18 (s, 3H); 2.54 (t, 2H, J = 7.3 Hz); 2.87 (t, 2H, J = 7.4 Hz); 3.54 (s, 2H); 6.20 (d, 1H, J = 8.3 Hz); 6.84 (dd, 1H, J = 8.2 Hz, J = 1.4 Hz); 7.07 (d, 1H, J = 3.8 Hz); 7.13-7.35 (m, 9H); 7.39 (s, 1H); 8.90 (d, 1H, J = 8.3 Hz); 10.69 (d, 1H, J = 1.8 Hz) |
| 35 | 3-{5-[({[2-(azepan-1-yl)phenyl](phenyl)methyl}carbamoyl)methyl]-1H-indol-3-yl}propanoic acid | From tert-butyl 3-{5-[({[2-(azepan-1-yl)phenyl](phenyl)methyl}carbamoyl)methyl]-1H-indol-3-yl}propanoate Cpd. 36 following protocol E Yield: 86%; mp: 85, 122° C.; appearance: white solid; 1H NMR, d (ppm): 1.36-1.66 (m, 8H); 2.57 (t, 2H, J = 7.3 Hz); 2.75-2.82 (m, 2H); 2.88 (t, 2H, J = 7.2 Hz); 2.96-3.03 (m, 2H); 3.55 (s, 2H); 6.71 (d, 1H, J = 8.5 Hz); 6.98 (dd, 1H, J = 8.3 Hz, J = 1.5 Hz); 7.03-7.09 (m, 2H); 7.12-7.31 (m, 9H); 7.41 (s, 1H); 8.73 (d, 1H, J = 8.6 Hz); 10.68 (d, 1H, J = 1.8 Hz); 12.04 (br s, 1H); m/z: 510.26 [M + H]+ (calc. mass: 509.26) |
| 36 | tert-butyl 3-{5-[({[2-(azepan-1-yl)phenyl](phenyl)methyl}carbamoyl)methyl]-1H-indol-3-yl}propanoat | From [2-(azepan-1-yl)phenyl](phenyl)methanamine Ex. 26 and 2-{3-[3-(tert-butoxy)-3-oxopropyl]-1H-indol-5-yl}acetic acid Ex. 1 following protocol D, DMAP (2 equiv), 6 h at rt, purification by column chromatography on silica gel (CH2Cl2/EtOAc, 85:15) Yield: 69%; appearance: colorless oil; 1H NMR, d (ppm): 1.38 (s, 9H); 1.40-1.48 (m, 2H); 1.51-1.65 (m, 6H); 2.54 (t, 2H, J = 7.5 Hz); 2.75-2.82 (m, 2H); 2.87 (t, 2H, J = 7.5 Hz); 2.95-3.03 (m, 2H); 3.55 (s, 2H); 6.71 (d, 1H, J = 8.6 Hz); 6.98 (dd, 1H, J = 8.3 Hz, J = 1.5 Hz); 7.03-7.08 (m, 2H); 7.12-7.30 (m, 9H); 7.40 (s, 1H); 8.72 (d, 1H, J = 8.6 Hz); 10.68 (d, 1H, J = 2.0 Hz) |
| 37 | 3-[5-({[(4-methylnaphthalen-1-yl)(phenyl)methyl]carbamoyl}methyl)-1H-indol-3-yl]propanoic acid | From tert-butyl-3-[5-({[(4-methylnaphthalen-1-yl)(phenyl)methyl]carbamoyl}methyl)-1H-indol-3-yl]propanoate Cpd. 38 following protocol E Yield: 31%; mp: 198° C.; appearance: white solid; 1H NMR, d (ppm): 2.57 (t, 2H, J = 7.1 Hz); 2.62 (s, 3H); 2.87 (t, 2H, J = 7.4 Hz); 3.57 (s, 2H); 6.82 (d, 1H, J = 8.5 Hz); 6.98 (dd, 1H, J = 8.3 Hz, J = 1.4 Hz); 7.07 (d, 1H, J = 2.0 Hz); 7.17-7.34 (m, 8H); 7.40 (s, 1H); 7.43-7.56 (m, 2H); 7.99 (d, 1H, J = 8.3 Hz); 8.03 (d, 1H, J = 7.7 Hz); 9.04 (d, 1H, J = 8.4 Hz); 10.68 (s, 1H); 12.08 (s, 1H); m/z: 477.2 [M + H]+ (calc. mass: 477.2) |
| 38 | tert-butyl 3-[5-({[(4-methylnaphthalen-1-yl)(phenyl)methyl]carbamoyl}methyl)-1H-indol-3-yl]propanoate | From (4-methylnaphthalen-1-yl)(phenyl)methanaminium chloride Ex. 27 and 2-{3-[3-(tert-butoxy)-3-oxopropyl]-1H-indol-5-yl}acetic acid Ex. 1 following protocol D, DMAP (3 equiv), 16 h at rt, purification by column chromatography on silica gel (CH2Cl2/EtOAc, 85:15) Yield: 65%; appearance: colorless oil; 1H NMR, d (ppm): 1.38 (s, 9H); 2.54 (t, 2H, J = 7.5 Hz); 2.62 (s, 3H); 2.86 (t, 2H, J = 7.4 Hz); 3.57 (s, 2H); 6.82 (d, 1H, J = 8.4 Hz); 6.98 (dd, 1H, J = 8.3 Hz, J = 1.5 Hz); 7.07 (d, 1H, J = 2.2 Hz); 7.16-7.34 (m, 8H); 7.39-7.56 (m, 3H); 7.98 (d, 1H, J = 8.0 Hz); 8.04 (dd, 1H, J = 8.4 Hz, J = 1.0 Hz); 9.03 (d, 1H, J = 8.4 Hz); 10.69 (d, 1H, J = 1.9 Hz) |
| 39 | 2-{5-[({phenyl[2-(piperidin-1-yl)phenyl]methyl}carbamoyl)methyl]-1H-indol-3-yl}acetic acid | From methyl 2-{5-[({phenyl[2-(piperidin-1-yl)phenyl]methyl}carbamoyl)methyl]-1H-indol-3-yl}acetate Cpd. 40 following protocol E Yield: 91%; mp: 131, 136° C.; appearance: white solid; 1H NMR, d (ppm) (DMSO-d6): 1.40-1.65 (m, 6H); 2.48 (m, 2H); 2.87 (m, 4H); 3.58 (m, 4H); 6.62 (d, 1H, J = 8.7 Hz); 6.95-7.45 (m, 13H); 8.76 (d, 1H); 10.82 (br s, 1H); 12.05 (br s, 1H); m/z: 482.23 [M + H]+ (calc. mass: 481.23) |
| 40 | methyl 2-{5-[({phenyl[2-(piperidin-1-yl)phenyl]methyl}carbamoyl)methyl]-1H-indol-3-yl}acetate | From phenyl[2-(piperidin-1-yl)phenyl]methanamine Ex. 9 and 2-[3-(2-methoxy-2-oxoethyl)-1H-indol-5-yl]acetic acid Ex. 5 following protocol D Yield: 24%; appearance: white solid; 1H NMR, d (ppm): 1.40-1.65 (m, 6H); 2.48 (m, 2H); 2.88 (m, 2H); 3.59 (s, 5H); 3.69 (s, 2H); 6.62 (d, 1H, J = 8.4 Hz); 7.0-7.4 (m, 12H); 8.77 (m, 1H); 10.88 (br s, 1H) |

TABLE 2-continued

*All the NMR were performed in DMSO-d6*

| Cpd. | | Starting compounds, Reaction conditions and purification Yield, MP, Appearance, $^1$H NMR (solvent) data, Mass (ES+ or ES−) data |
|---|---|---|
| 41 | tert-butyl 3-[5-({[(2-chloro-5-methylphenyl)(phenyl)methyl]carbamoyl}methyl)-1H-indol-3-yl]propanoate | From (2-chloro-5-methylphenyl)(phenyl)methanamine Ex. 28 and 2-{3-[3-(tert-butoxy)-3-oxopropyl]-1H-indol-5-yl}acetic acid Ex. 1 following protocol D<br>Yield: 53%; mp: 71, 77° C.; appearance: white solid; 1H NMR, d (ppm): 2.19 (s, 3H); 2.56 (t, 2H, J = 7.2 Hz); 2.88 (t, 2H, J = 7.5 Hz); 3.55 (s, 2H); 6.20 (d, 1H, J = 8.3 Hz); 6.97 (dd, 1H, J = 8.3 Hz, J = 1.5 Hz); 7.07 (d, 1H, J = 2.2 Hz); 7.13-7.35 (m, 9H); 7.40 (s, 1H); 8.92 (d, 1H, J = 8.4 Hz); 10.70 (d, 1H, J = 1.9 Hz); m/z: 517.21 [M + H]+ (calc. mass: 516.21) |
| 42 | 3-[5-({[(2-chloro-5-methylphenyl)(phenyl)methyl]carbamoyl}methyl)-1H-indol-3-yl]propanoic acid | From tert-butyl 3-[5-({[(2-chloro-5-methylphenyl)(phenyl)methyl]carbamoyl}methyl)-1H-indol-3-yl]propanoate Cpd. 41 following protocol E<br>Yield: 100%; mp: 84, 116° C.; appearance: white solid; 1H NMR, d (ppm): 1.38 (s, 9H); 2.17 (s, 3H); 2.54 (t, 2H, J = 7.4 Hz); 2.87 (t, 2H, J = 7.5 Hz); 3.50-3.62 (m, 2H); 6.34 (d, 1H, J = 8.3 Hz); 7.01 (dd, 1H, J = 8.3 Hz, J = 1.5 Hz); 7.06-7.34 (m, 10H); 7.42 (s, 1H); 8.92 (d, 1H, J = 8.3 Hz); 10.69 (d, 1H, J = 1.8 Hz); m/z: 461.15 [M + H]+ (calc. mass: 460.15). |
| 43 | tert-butyl 3-[5-({[(4-bromo-2-methylphenyl)(phenyl)methyl]carbamoyl}methyl)-1H-indol-3-yl]propanoate | From (4-bromo-2-methylphenyl)(phenyl)methanamine Ex. 31 and 2-{3-[3-(tert-butoxy)-3-oxopropyl]-1H-indol-5-yl}acetic acid Ex. 1 following protocol D<br>Yield: 67%; mp: 68, 75° C.; appearance: white solid; 1H NMR, d (ppm): 1.38 (s, 9H); 2.18 (s, 3H); 2.54 (t, 2H, J = 7.3 Hz); 2.87 (t, 2H, J = 7.5 Hz); 3.54 (s, 2H); 6.18 (d, 1H, J = 8.2 Hz); 6.97 (dd, 1H, J = 8.3 Hz, J = 1.5 Hz); 7.07-7.09 (m, 2H); 7.17-7.39 (m, 9H); 8.90 (d, 1H, J = 8.4 Hz); 10.69 (d, 1H, J = 1.9 Hz); m/z: 561.16 [M + H]+ (calc. mass: 560.16). |
| 44 | 3-[5-({[(4-bromo-2-methylphenyl)(phenyl)methyl]carbamoyl}methyl)-1H-indol-3-yl]propanoic acid | From tert-butyl 3-[5-({[(4-bromo-2-methylphenyl)(phenyl)methyl]carbamoyl}methyl)-1H-indol-3-yl]propanoate Cpd. 43 following protocol E<br>Yield: 89%; mp: 90, 108° C.; appearance: white solid; 1H NMR, d (ppm): 1.38 (s, 9H); 2.20 (s, 3H); 2.54 (t, 2H, J = 7.2 Hz); 2.87 (t, 2H, J = 7.5 Hz); 3.55 (s, 2H); 6.21 (d, 1H, J = 8.4 Hz); 6.94-7.35 (m, 11H); 7.40 (s, 1H); 8.88 (d, 1H, J = 8.5 Hz); 10.69 (d, 1H, J = 2.0 Hz); m/z: 505.1 [M + H]+ (calc. mass: 504.1). |
| 45 | tert-butyl 3-[5-({[(4-fluoro-2-methylphenyl)(phenyl)methyl]carbamoyl}methyl)-1H-indol-3-yl]propanoate | From (4-fluoro-2-methylphenyl)(phenyl)methanamine Ex. 29 and 2-{3-[3-(tert-butoxy)-3-oxopropyl]-1H-indol-5-yl}acetic acid Ex. 1 following protocol D<br>Yield: 74%; mp: 58, 66° C.; appearance: white solid; 1H NMR, d (ppm): 2.18 (s, 3H); 2.57 (t, 2H, J = 7.1 Hz); 2.88 (t, 2H, J = 7.5 Hz); 3.55 (s, 2H); 6.18 (d, 1H, J = 8.3 Hz); 6.97 (dd, 1H, J = 8.3 Hz, J = 1.5 Hz); 7.07-7.10 (m, 2H); 7.17-7.40 (m, 9H); 8.91 (d, 1H, J = 8.4 Hz); 10.70 (d, 1H, J = 1.9 Hz); 12.04 (s, 1H); m/z: 501.24 [M + H]+ (calc. mass: 500.24). |
| 46 | 3-[5-({[(4-fluoro-2-methylphenyl)(phenyl)methyl]carbamoyl}methyl)-1H-indol-3-yl]propanoic acid | From tert-butyl 3-[5-({[(4-fluoro-2-methylphenyl)(phenyl)methyl]carbamoyl}methyl)-1H-indol-3-yl]propanoate Cpd. 45 following protocol E<br>Yield: 35%; mp: 148, 177° C.; appearance: white solid; 1H NMR, d (ppm): 2.57 (t, 2H, J = 7.1 Hz); 2.89 (t, 2H, J = 7.4 Hz); 3.54 (s, 2H); 6.14 (d, 1H, J = 8.1 Hz); 6.91-6.94 (m, 2H); 6.98 (dd, 1H, J = 8.3 Hz, J = 1.5 Hz); 7.07 (d, 1H, J = 2.2 Hz); 7.13-7.26 (m, 7H); 7.29-7.45 (m, 7H); 8.91 (d, 1H, J = 8.1 Hz); 10.69 (d, 1H, J = 2.0 Hz); 12.06 (s, 1H); m/z: 445.18 [M + H]+ (calc. mass: 444.18). |
| 47 | tert-butyl 3-{5-[({phenyl[2-(pyrrolidin-1-yl)-4-(trifluoromethyl)phenyl]methyl}carbamoyl)methyl]-1H-indol-3-yl}propanoate | From phenyl[2-(pyrrolidin-1-yl)-4-(trifluoromethyl)phenyl]methanamine Ex. 37 and 2-{3-[3-(tert-butoxy)-3-oxopropyl]-1H-indol-5-yl}acetic acid Ex. 1 following protocol D<br>Yield: 30%; mp: 76, 80° C.; appearance: white solid; 1H NMR, d (ppm): 1.36 (s, 9H); 1.72-1.76 (m, 4H); 2.53 (t, 2H, J = 8.1 Hz); 2.87 (t, 2H, J = 7.2 Hz); 2.95-2.99 (m, 2H); 3.13-3.18 (m, 2H); 3.56 (s, 2H); 6.53 (d, 1H, J = 8.2 Hz); 6.98 (dd, 1H, J = 8.1 Hz, J = 1.1 Hz); 7.07 (d, 1H, J = 2.3 Hz); 7.12-7.14 (m, 2H); 7.21-7.31 (m, 6H); 7.39-7.41 (m, 2H); 8.91 (d, 1H, J = 8.6 Hz); 10.69 (s, 1H); m/z: 606.28 [M + H]+ (calc. mass: 605.28). |
| 48 | 3-{5-[({phenyl[2-(pyrrolidin-1-yl)-4-(trifluoromethyl)phenyl]methyl}-carbamoyl)methyl]-1H-indol-3-yl}propanoic acid | From tert-butyl 3-{5-[({phenyl[2-(pyrrolidin-1-yl)-4-(trifluoromethyl)phenyl]methyl}-carbamoyl)methyl]-1H-indol-3-yl}propanoate Cpd. 47 following protocol E<br>Yield: 86%; mp: 123, 128° C.; appearance: white solid; 1H NMR, d (ppm): 1.73-1.78 (m, 4H); 2.56 (t, 2H, J = 8.3 Hz); 2.88 (t, 2H, J = 7.9 Hz); 2.95-2.98 (m, 2H); 3.13-3.18 (m, 2H); 3.56 (s, 2H); 6.53 (d, 1H, J = 8.6 Hz); 6.97 (dd, 1H, J = 8.4 Hz, |

TABLE 2-continued

*All the NMR were performed in DMSO-d6*

| Cpd. | | Starting compounds, Reaction conditions and purification Yield, MP, Appearance, $^1$H NMR (solvent) data, Mass (ES+ or ES−) data |
|---|---|---|
| | | J = 1.5 Hz); 7.06 (d, 1H, J = 2.3 Hz); 7.12-7.14 (m, 2H); 7.18-7.35 (m, 6H); 7.39-7.41 (m, 2H); 8.92 (d, 1H, J = 8.1 Hz); 10.69 (s, 1H); 12.04 (br s, 1H); m/z: 550.22 [M + H]+ (calc. mass: 549.22). |
| 49 | tert-butyl 3-{5-[({[4-bromo-2-(pyrrolidin-1-yl)phenyl](phenyl)methyl}carbamoyl)methyl]-1H-indol-3-yl}propanoate | From [4-bromo-2-(pyrrolidin-1-yl)phenyl](phenyl)methanamine Ex. 38 and 2-{3-[3-(tert-butoxy)-3-oxopropyl]-1H-indol-5-yl}acetic acid Ex. 1 following protocol D<br>Yield: 34%; mp: 78, 82° C.; appearance: white solid; 1H NMR, d (ppm): 1.38 (s, 9H); 1.69-1.74 (m, 4H); 2.54 (t, 2H, J = 7.9 Hz); 2.86 (t, 2H, J = 8.0 Hz); 2.87-2.91 (m, 2H); 3.07-3.12 (m, 2H); 3.55 (s, 2H); 6.43 (d, 1H, J = 8.4 Hz); 6.98 (dd, 1H, J = 8.2 Hz, J = 1.5 Hz); 7.05-7.12 (m, 6H); 7.16-7.29 (m, 4H); 7.40 (s, 1H); 8.82 (d, 1H, J = 8.2 Hz); 10.69 (s, 1H); m/z: 616.2 [M + H]+ (calc. mass: 615.2). |
| 50 | 3-{5-[({[4-bromo-2-(pyrrolidin-1-yl)phenyl](phenyl)methyl}carbamoyl)methyl]-1H-indol-3-yl}propanoic acid | From tert-butyl 3-{5-[({[4-bromo-2-(pyrrolidin-1-yl)phenyl](phenyl)methyl}carbamoyl)methyl]-1H-indol-3-yl}propanoate Cpd. 49 following protocol E<br>Yield: 98%; mp: 117, 120° C.; appearance: white solid; 1H NMR, d (ppm): 1.71-1.75 (m, 4H); 2.55 (t, 2H, J = 8.3 Hz); 2.85-2.91 (m, 4H); 3.07-3.14 (m, 2H); 3.55 (s, 2H); 6.43 (d, 1H, J = 8.3 Hz); 6.97 (dd, 1H, J = 8.3 Hz, J = 1.3 Hz); 7.05-7.28 (m, 10H); 7.41 (s, 1H); 8.83 (d, 1H, J = 8.3 Hz); 10.68 (s, 1H); 12.15 (br s, 1H); m/z: 560.14 [M + H]+ (calc. mass: 559.14). |
| 51 | tert-butyl 3-[5-({[(2-aminophenyl)(phenyl)methyl]carbamoyl}methyl)-1H-indol-3-yl]propanoate | From 2-[amino(phenyl)methyl]aniline Ex. 48 and 2-{3-[3-(tert-butoxy)-3-oxopropyl]-1H-indol-5-yl}acetic acid Ex. 1 following protocol D<br>Yield: 84%; mp: 71, 73° C.; appearance: white solid; 1H NMR, d (ppm): 1.38 (s, 9H); 2.54 (t, 2H, J = 8.1 Hz); 2.87 (t, 2H, J = 7.6 Hz); 3.51-3.61 (m, 2H); 4.83 (br s, 2H); 6.14 (d, 1H, J = 8.8 Hz); 6.47 (dt, 1H, J = 7.4 Hz, J = 1.1 Hz); 6.64 (dd, 1H, J = 7.9 Hz, J = 1.1 Hz); 6.77 (dd, 1H, J = 8.6 Hz, J = 1.4 Hz); 6.91-6.96 (m, 1H); 6.98 (dd, 1H, J = 8.4 Hz, J = 1.5 Hz); 7.06 (d, 1H, J = 2.3 Hz); 7.20-7.34 (m, 6H); 7.42 (s, 1H); 8.86 (d, 1H, J = 8.9 Hz); 10.68 (s, 1H); m/z: 484.25 [M + H]+ (calc. mass: 483.25). |
| 52 | 3-[5-({[(2-aminophenyl)(phenyl)methyl]carbamoyl}methyl)-1H-indol-3-yl]propanoic acid | From tert-butyl 3-[5-({[(2-aminophenyl)(phenyl)methyl]carbamoyl}methyl)-1H-indol-3-yl]propanoate Cpd. 51 following protocol E<br>Yield: 42%; mp: 173, 175° C.; appearance: white solid; 1H NMR, d (ppm): 2.29 (t, 2H, J = 7.6 Hz); 2.84 (t, 2H, J = 7.9 Hz); 3.56 (s, 2H); 5.02 (br s, 2H); 6.14 (d, 1H, J = 8.8 Hz); 6.44 (dt, 1H, J = 8.6 Hz, J = 1.3 Hz); 6.67-6.71 (m, 2H); 6.90-6.96 (m, 2H); 7.02 (d, 1H, J = 2.2 Hz); 7.20 (d, 1H, J = 8.3 Hz); 7.23-7.36 (m, 5H); 7.44 (s, 1H); 8.91 (d, 1H, J = 8.7 Hz); 10.58 (s, 1H); m/z: 428.18 [M + H]+ (calc. mass: 427.18). |
| 53 | tert-butyl 3-{5-[({[2-(dimethylamino)phenyl](phenyl)methyl}carbamoyl)methyl]-1H-indol-3-yl}propanoate | From 2-[amino(phenyl)methyl]-N,N-dimethylaniline Ex. 35 and 2-{3-[3-(tert-butoxy)-3-oxopropyl]-1H-indol-5-yl}acetic acid Ex. 1 following protocol D<br>Yield: 58%; mp: 56° C.; appearance: white solid; 1H NMR, d (ppm): 0.96-1.07 (m, 3H); 1.15-1.29 (m, 3H); 1.41 (s, 9H); 1.48-1.73 (m, 10H); 1.82-1.90 (m, 1H); 2.49-2.60 (m, 4H); 2.97 (t, 2H, J = 7.7 Hz); 3.01-3.14 (m, 2H); 3.58 (s, 2H); 5.24 (t, 1H, J = 9.0 Hz); 6.99-7.06 (m, 2H); 7.11-7.20 (m, 5H); 7.28 (d, 1H, J = 8.2 Hz); 7.48 (d, 1H, J = 0.6 Hz); 9.91 (br s, 1H); m/z: 512.28 [M + H]+ (calc. mass: 511.28). |
| 54 | 3-{5-[({[2-(dimethylamino)phenyl](phenyl)methyl}carbamoyl)methyl]-1H-indol-3-yl}propanoic acid | From tert-butyl 3-{5-[({[2-(dimethylamino)phenyl](phenyl)methyl}carbamoyl)methyl]-1H-indol-3-yl}propanoate Cpd. 53 following protocol E<br>Yield: 72%; mp: 85, 107° C.; appearance: white solid; 1H NMR, d (ppm): 1.38 (s, 9H); 2.50 (s, 6H); 2.53 (t, 2H, J = 7.3 Hz); 2.87 (t, 2H, J = 7.5 Hz); 3.57 (s, 2H); 6.64 (d, 1H, J = 8.8 Hz); 6.99 (dd, 1H, J = 8.2 Hz, J = 1.5 Hz); 7.04-7.32 (m, 11H); 7.41 (s, 1H); 8.80 (d, 1H, J = 8.8 Hz); 10.69 (d, 1H, J = 1.8 Hz); m/z: 456.22 [M + H]+ (calc. mass: 455.22). |
| 55 | tert-butyl 3-{5-[({phenyl[2-(piperidin-1-yl)phenyl]methyl}carbamoyl)amino]-1H-indol-3-yl}propanoate | From phenyl[2-(piperidin-1-yl)phenyl]methanamine Ex. 9 and tert-butyl 3-(5-amino-1H-indol-3-yl)propanoate Ex. 133 following protocol G<br>Yield: 50%; mp: 102, 250° C.; appearance: white solid; 1H NMR, d (ppm): 1.36 (s, 9H); 1.42-1.70 (m, 6H); 2.53 (t, 2H, J = 7.8 Hz); 2.83 (t, 2H, J = 7.8 Hz); 2.88-2.97 (m, 2H); 6.47 (d, 1H, J = 8.1 Hz); 6.83 (d, 1H, J = 8.4 Hz); 6.94 (dd, 1H, J = 8.7 Hz, J = 1.8 Hz); 7.03 (d, 1H, J = 2.4 Hz); 7.08-7.33 (m, 10H); 7.56 (d, |

TABLE 2-continued

*All the NMR were performed in DMSO-d6*

| Cpd. | | Starting compounds, Reaction conditions and purification Yield, MP, Appearance, $^1$H NMR (solvent) data, Mass (ES+ or ES−) data |
|---|---|---|
| | | 1H, J = 1.8 Hz); 8.23 (br s, 1H); 10.58 (br s, 1H); m/z: 553.31 [M + H]+ (calc. mass: 552.31). |
| 56 | 3-{5-[({phenyl[2-(piperidin-1-yl)phenyl]methyl}carbamoyl)amino]-1H-indol-3-yl}propanoic acid | From tert-butyl 3-{5-[({phenyl[2-(piperidin-1-yl)phenyl]methyl}carbamoyl)amino]-1H-indol-3-yl}propanoate Cpd. 53 following protocol E<br>Yield: 39%; mp: 223, 228° C.; appearance: white solid; 1H NMR, d (ppm): 1.50-1.63 (m, 6H); 2.49-2.52 (m, 2H); 2.53 (t, 2H, J = 7.2 Hz); 2.84 (t, 2H, J = 7.2 Hz); 2.87-2.94 (m, 2H); 6.47 (d, 1H, J = 8.1 Hz); 6.84 (d, 1H, J = 8.4 Hz); 6.96 (dd, 1H, J = 8.4 Hz, J = 1.5 Hz); 7.03 (s, 1H); 7.09-7.33 (m, 10H); 7.56 (s, 1H); 8.47 (br s, 1H); 10.58 (br s, 1H); m/z: 497.24 [M + H]+ (calc. mass: 496.24). |
| 57 | tert-butyl 3-{5-[({3-methyl-1-[2-(morpholin-4-yl)phenyl]butyl}carbamoyl)methyl]-1H-indol-3-yl}propanoate | From 3-methyl-1-[2-(morpholin-4-yl)phenyl]butan-1-amine Ex. 39 and 2-{3-[3-(tert-butoxy)-3-oxopropyl]-1H-indol-5-yl}acetic acid Ex. 1 following protocol D<br>Yield: 80%; mp: 67° C.; appearance: white solid; 1H NMR, d (ppm): 0.88 (s, 3H); 0.90 (s, 3H); 1.24-1.34 (m, 1H); 1.38 (s, 9H); 1.43-1.64 (m, 2H); 2.51-2.57 (m, 4H); 2.86 (t, 2H, J = 7.5 Hz); 3.14-3.21 (m, 2H); 3.40-3.51 (m, 2H); 3.59-3.63 (m, 2H); 3.68-3.77 (m, 2H); 5.35-5.43 (m, 1H); 6.94 (dd, 1H, J = 1.5 Hz, J = 8.3 Hz); 7.05-7.36 (m, 7H); 8.40 (d, 1H, J = 8.5 Hz); 10.68 (d, 1H, J = 1.8 Hz); m/z: 534.32 [M + H]+ (calc. mass: 533.32). |
| 58 | 3-{5-[({3-methyl-1-[2-(morpholin-4-yl)phenyl]butyl}carbamoyl)methyl]-1H-indol-3-yl}propanoic acid | From tert-butyl 3-{5-[({3-methyl-1-[2-(morpholin-4-yl)phenyl]butyl}carbamoyl)methyl]-1H-indol-3-yl}propanoate Cpd. 57 following protocol E<br>Yield: 50%; mp: 104, 130° C.; appearance: white solid; 1H NMR, d (ppm): 0.88 (s, 3H); 0.90 (s, 3H); 1.28-1.34 (m, 1H); 1.47-1.65 (m, 2H); 2.53-2.60 (m, 4H); 2.88 (t, 2H, J = 7.6 Hz); 3.14-3.22 (m, 2H); 3.41-3.51 (m, 2H); 3.68-3.77 (m, 4H); 5.37-5.43 (m, 1H); 6.94 (d, 1H, J = 8.9 Hz); 7.06-7.22 (m, 5H); 7.34-7.37 (m, 2H); 8.40 (d, 1H, J = 8.4 Hz); 10.67 (s, 1H); 12.09 (s, 1H); m/z: 478.26 [M + H]+ (calc. mass: 477.26). |
| 59 | tert-butyl 3-{5-[({[4-cyano-2-(pyrrolidin-1-yl)phenyl](phenyl)methyl}carbamoyl)methyl]-1H-indol-3-yl}propanoate | From 4-[amino(phenyl)methyl]-3-(pyrrolidin-1-yl)benzonitrile Ex. 47 and 2-{3-[3-(tert-butoxy)-3-oxopropyl]-1H-indol-5-yl}acetic acid Ex. 1 following protocol D<br>Yield: 83%; mp: 85, 88° C.; appearance: white solid; 1H NMR, d (ppm): 1.38 (s, 9H); 1.71-1.76 (m, 4H); 2.53 (t, 2H, J = 8.1 Hz); 2.87 (t, 2H, J = 7.5 Hz); 2.93-2.98 (m, 2H); 3.12-3.19 (m, 2H); 3.56 (s, 2H); 6.51 (d, 1H, J = 8.3 Hz); 6.97 (dd, 1H, J = 8.3 Hz, J = 1.5 Hz); 7.07 (d, 1H, J = 2.2 Hz); 7.10-7.13 (m, 2H); 7.18-7.39 (m, 8H); 8.94 (d, 1H, J = 8.3 Hz); 10.69 (s, 1H); m/z: 563.29 [M + H]+ (calc. mass: 562.29). |
| 60 | 3-{5-[({[4-cyano-2-(pyrrolidin-1-yl)phenyl](phenyl)methyl}carbamoyl)methyl]-1H-indol-3-yl}propanoic acid | From tert-butyl 3-{5-[({[4-cyano-2-(pyrrolidin-1-yl)phenyl](phenyl)methyl}carbamoyl)methyl]-1H-indol-3-yl}propanoate Cpd. 59 following protocol E<br>Yield: 10%; mp: 122, 128° C.; appearance: white solid; 1H NMR, d (ppm): 1.71-1.77 (m, 4H); 2.56 (t, 2H, J = 8.1 Hz); 2.88 (t, 2H, J = 7.7 Hz); 2.95-2.98 (m, 2H); 3.12-3.19 (m, 2H); 3.56 (s, 2H); 6.51 (d, 1H, J = 8.1 Hz); 6.97 (dd, 1H, J = 8.3 Hz, J = 1.4 Hz); 7.07 (d, 1H, J = 2.0 Hz); 7.11 (d, 2H, J = 7.2 Hz); 7.18-7.38 (m, 7H); 7.40 (s, 1H); 8.94 (d, 1H, J = 8.4 Hz); 10.69 (s, 1H); 12.40 (s, 1H); m/z: 507.23 [M + H]+ (calc. mass: 506.23). |
| 61 | tert-butyl 3-{5-[({[5-chloro-2-(piperidin-1-yl)phenyl](phenyl)methyl}carbamoyl)methyl]-1H-indol-3-yl}propanoate | From [5-chloro-2-(piperidin-1-yl)phenyl]methanamine Ex. 36 and 2-{3-[3-(tert-butoxy)-3-oxopropyl]-1H-indol-5-yl}acetic acid Ex. 1 following protocol D<br>Yield: 41%; mp: 85° C.; appearance: white speck solide;<br>1H NMR, d (ppm): 1.37 (s, 9H); 1.40-1.63 (m, 6H); 2.40-2.47 (m, 2H); 2.51-2.56 (m, 2H); 2.82-2.90 (m, 4H); 3.56 (s, 2H); 6.57 (d, 1H, J = 8.6 Hz); 6.99 (dd, 1H, J = 1.5 Hz, J = 8.3 Hz); 7.07 (d, 1H, J = 2.2 Hz); 7.13-7.33 (m, 9H); 7.40 (s, 1H); 8.82 (d, 1H, J = 8.7 Hz); 10.69 (d, 1H, J = 2.0 Hz); m/z: 586.27 [M + H]+ (calc. mass: 585.27). |
| 62 | 3-{5-[({[5-chloro-2-(piperidin-1-yl)phenyl](phenyl)methyl}carbamoyl)methyl]-1H-indol-3-yl}propanoic acid | From tert-butyl 3-{5-[({[5-chloro-2-(piperidin-1-yl)phenyl](phenyl)methyl}carbamoyl)methyl]-1H-indol-3-yl}propanoate Cpd. 61 following protocol E<br>Yield: 94%; mp: 108, 126° C.; appearance: white solid; 1H NMR, d (ppm): 1.39-1.57 (m, 6H); 2.42-2.46 (m, 2H); 2.55 (t, 2H, J = 8.3 Hz); 2.82-2.90 (m, 4H); 3.57 (s, 2H); 6.58 (d, 1H, J = 8.7 Hz); 6.99 (dd, 1H, J = 1.5 Hz, J = 8.3 Hz); 7.07 (d, 1H, |

TABLE 2-continued

All the NMR were performed in DMSO-d6

| Cpd. | | Starting compounds, Reaction conditions and purification Yield, MP, Appearance, ¹H NMR (solvent) data, Mass (ES+ or ES−) data |
|---|---|---|
| | | J = 2.2 Hz); 7.13-7.34 (m, 9H); 7.40 (s, 1H); 8.83 (d, 1H, J = 8.7 Hz); 10.69 (d, 1H, J = 1.9 Hz); 11.98 (s, 1H); m/z: 530.21 [M + H]+ (calc. mass: 529.21). |
| 63 | 3-{5-[({[4-carbamoyl-2-(pyrrolidin-1-yl)phenyl](phenyl)methyl}carbamoyl)methyl]-1H-indol-3-yl}propanoic acid By-product isolated from the synthesis of Cpd. 60 | From tert-butyl 3-{5-[({[4-cyano-2-(pyrrolidin-1-yl)phenyl](phenyl)methyl}carbamoyl)methyl]-1H-indol-3-yl}propanoate Cpd. 59 following protocol E. Yield: 34%; mp: 140, 143° C.; appearance: white solid; 1H NMR, d (ppm): 2.56 (t, 2H, J = 8.3 Hz); 2.88 (t, 2H, J = 8.0 Hz); 3.51-3.61 (m, 2H); 4.83 (br s, 2H); 6.14 (d, 1H, J = 8.8 Hz); 6.47 (dt, 1H, J = 7.4 Hz, J = 1.1 Hz); 6.64 (dd, 1H, J = 8.0 Hz, J = 1.1 Hz); 6.78 (dd, 1H, J = 7.7 Hz, J = 1.5 Hz); 6.92-6.96 (m, 1H); 6.99 (dd, 1H, J = 1.7 Hz); 7.07 (d, 1H, J = 2.2 Hz); 7.20-7.34 (m, 6H); 7.42 (s, 1H); 8.87 (d, 1H, J = 9.1 Hz); 10.69 (s, 1H); 12.02 (br s, 1H); m/z: 525.24 [M + H]+ (calc. mass: 524.24). |
| 64 | methyl 2-{5-[({[4-methyl-2-(pyrrolidin-1-yl)phenyl](phenyl)methyl}carbamoyl)methyl]-1H-indol-3-yl}acetate | From [4-methyl-2-(pyrrolidin-1-yl)phenyl](phenyl)methanamine Ex. 11 and 2-[3-(2-methoxy-2-oxoethyl)-1H-indol-5-yl]acetic acid Ex. 5 following protocol D Yield: 41%; mp: 78, 80° C.; appearance: yellow solid; 1H NMR, d (ppm): 1.67-1.72 (m, 4H); 2.21 (s, 3H); 2.72-2.79 (m, 2H); 3.00-3.05 (m, 2H); 3.55 (s, 2H); 3.57 (s, 3H); 3.68 (s, 2H); 6.45 (d, 1H, J = 8.5 Hz); 6.75 (d, 1H, J = 6.8 Hz); 6.87 (s, 1H); 7.01 (dd, 1H, J = 8.3 Hz, J = 1.5 Hz); 7.06 (d, 1H, J = 7.8 Hz); 7.09-7.26 (m, 7H); 7.34-7.36 (m, 1H); 6.68 (d, 1H, J = 8.5 Hz); 10.85 (br s, 1H); m/z: 496.25 [M + H]+ (calc. mass: 495.25). |
| 65 | 2-{5-[({[4-methyl-2-(pyrrolidin-1-yl)phenyl](phenyl)methyl}carbamoyl)methyl]-1H-indol-3-yl}acetic acid | From methyl 2-{5-[({[4-methyl-2-(pyrrolidin-1-yl)phenyl](phenyl)methyl}carbamoyl)methyl]-1H-indol-3-yl}acetate Cpd. 64 following protocol F Yield: 97%; mp: 101, 134° C.; appearance: white solid; 1H NMR, d (ppm): 1.67-1.73 (m, 4H); 2.22 (s, 3H); 2.73-2.80 (m, 2H); 3.01-3.08 (m, 2H); 3.55 (s, 2H); 3.58 (s, 2H); 6.45 (d, 1H, J = 8.5 Hz); 6.77 (d, 1H, J = 6.8 Hz); 6.87 (br s, 1H); 7.00 (dd, 1H, J = 8.3 Hz, J = 1.5 Hz); 7.05-7.26 (m, 8H); 7.37 (br s, 1H); 8.68 (d, 1H, J = 8.5 Hz); 10.82 (br s, 1H); 12.09 (br s, 1H) m/z: 482.23 [M + H]+ (calc. mass: 481.23). |
| 66 | methyl 2-{5-[({[4-bromo-2-(pyrrolidin-1-yl)phenyl](phenyl)methyl}carbamoyl)methyl]-1H-indol-3-yl}acetate | From [4-bromo-2-(pyrrolidin-1-yl)phenyl](phenyl)methanamine Ex. 38 and 2-[3-(2-methoxy-2-oxoethyl)-1H-indol-5-yl]acetic acid Ex. 5 following protocol D Yield: 27%; mp: 79, 81° C.; appearance: yellow solid; 1H NMR, d (ppm): 1.68-1.74 (m, 6H); 2.87-2.91 (m, 2H); 3.05-3.08 (m, 2H); 3.55 (s, 2H); 3.58 (s, 3H); 3.69 (s, 2H); 6.42 (d, 1H, J = 8.2 Hz); 7.00 (dd, 1H, J = 8.3 Hz, J = 1.5 Hz); 7.04-7.35 (m, 9H); 8.82 (d, 1H, J = 8.3 Hz); 10.86 (br s, 1H); m/z: 560.14 [M + H]+ (calc. mass: 559.14). |
| 67 | 2-{5-[({[4-bromo-2-(pyrrolidin-1-yl)phenyl](phenyl)methyl}carbamoyl)methyl]-1H-indol-3-yl}acetic acid | From methyl 2-{5-[({[4-bromo-2-(pyrrolidin-1-yl)phenyl](phenyl)methyl}carbamoyl)methyl]-1H-indol-3-yl}acetate Cpd. 66 following protocol F Yield: 88%; mp: 114, 136° C.; appearance: yellow solid; 1H NMR, d (ppm): 1.69-1.74 (m, 4H); 2.88-2.91 (m, 2H); 3.07-312 (m, 2H); 3.55 (s, 2H); 3.58 (s, 2H); 6.42 (d, 1H, J = 8.2 Hz); 7.00 (dd, 1H, J = 8.3 Hz, J = 1.5 Hz); 7.07-7.29 (m, 10H); 7.36 (br s, 1H); 8.83 (d, 1H, J = 8.2 Hz); 10.82 (br s, 1H); 12.07 (br s, 1H); m/z: 546.13 [M + H]+ (calc. mass: 545.13). |
| 68 | methyl 2-{5-[({phenyl[2-(piperidin-1-yl)phenyl]methyl}carbamoyl)amino]-1H-indol-3-yl}acetate | Step 1: From phenyl[2-(piperidin-1-yl)phenyl]methanamine Ex. 9 and tert-butyl 3-((methoxycarbonyl)methyl)-5-amino-1H-indole-1-carboxylate Ex. 140 following protocol G to afford tert-butyl 3-((methoxycarbonyl)methyl)-5-(3-(phenyl(2-(piperidin-1-yl)phenyl)methyl)ureido)-1H-indole-1-carboxylate Yield: 46%; appearance: pale brown solid; 1H NMR, d (ppm): 1.44-1.72 (m, 15H); 2.53-2.57 (m, 2H); 2.90-3.00 (m, 2H); 3.61 (s, 3H); 3.72 (s, 2H); 6.48 (d, 1H, J = 8.1 Hz); 6.95 (d, 1H, J = 8.1 Hz); 7.09-7.33 (m, 10H); 7.55 (s, 1H); 7.60 (d, 1H, J = 1.8 Hz); 7.87 (d, 1H, J = 9.0 Hz); 8.52 (s, 1H) Step 2: a mixture of urea previously obtained (60 mg, 0.10 mmol) and TFA (39 mL, 0.50 mmol) in CH2Cl2 was stirred at rt. After 2 h TLC showed only starting material, TFA (39 mL, 0.50 mmol) was added and the mixture was heated at 70° C. in a sealed tube. After 2 h at 70° C. TLC showed a new product with still some starting material. CH2Cl2 was removed under reduced pressure and TFA (1 mL) was added. The mixture was then heated at 70° C. for 1 h. The reaction mixture was cooled down, diluted with CH2Cl2 and washed with sat. NaHCO3. The two phases were separated. The organic layer was dried over MgSO4, filtered and the solution was |

TABLE 2-continued

All the NMR were performed in DMSO-d6

| Cpd. | | Starting compounds, Reaction conditions and purification Yield, MP, Appearance, ¹H NMR (solvent) data, Mass (ES+ or ES−) data |
|---|---|---|
| | | concentrated under reduced pressure. The crude oil was purified on silica gel column chromatography using CH2Cl2/MeOH/Et3N (94:6:0.1) as eluent. The solid obtained was triturated in Et2O, filtered and dried until constant weight.<br>Yield: 32%; mp: 172, 175° C.; appearance: white solid; 1H NMR, d (ppm): 1.48-1.64 (m, 6H); 2.53-2.56 (m, 2H); 2.92-2.97 (m, 2H); 3.58 (s, 3H); 3.65 (s, 2H); 6.47 (d, 1H, J = 8.4 Hz); 6.82 (d, 1H, J = 8.4 Hz); 7.03 (dd, 1H, J = 8.7 Hz, J = 1.8 Hz); 7.08-7.33 (m, 11H); 7.48 (d, 1H, J = 1.8 Hz); 8.25 (s, 1H); 10.76 (br s, 1H); m/z: 497.24 [M + H]+ (calc. mass: 496.24). |
| 69 | 2-{5-[({phenyl[2-(piperidin-1-yl)phenyl]methyl}carbamoyl)amino]-1H-indol-3-yl}acetic acid | From methyl 2-{5-[({phenyl[2-(piperidin-1-yl)phenyl]methyl}carbamoyl)amino]-1H-indol-3-yl}acetate Cpd. 68 following protocol F<br>Yield: 31%; mp: 186, 190° C.; appearance: white solid; 1H NMR, d (ppm): 1.48-1.64 (m, 6H); 2.53-2.56 (m, 2H); 2.93-2.96 (m, 2H); 3.54 (s, 2H); 6.46 (d, 1H, J = 8.2 Hz); 6.81 (d, 1H, J = 8.2 Hz); 7.03 (dd, 1H, J = 8.7 Hz, J = 1.8 Hz); 7.09-7.33 (m, 10H); 7.49 (d, 1H, J = 1.8 Hz); 8.25 (s, 1H); 10.70 (d, 1H, J = 1.8 Hz); 12.07 (br s, 1H); m/z: 483.23 [M + H]+ (calc. mass: 482.23). |
| 70 | methyl 2-{5-[({[2-(dimethylamino)phenyl](phenyl)methyl}carbamoyl)methyl]-1H-indol-3-yl}acetate | From 2-[amino(phenyl)methyl]-N,N-dimethylaniline Ex. 35 and 2-[3-(2-methoxy-2-oxoethyl)-1H-indol-5-yl]acetic acid Ex. 5 following protocol D<br>Yield: 42%; mp: 60, 63° C.; appearance: white solid; 1H NMR, d (ppm): 2.50 (s, 6H); 3.57-3.58 (m, 5H); 3.68 (s, 2H); 6.63 (d, 1H, J = 8.7 Hz); 7.01 (dd, 1H, J = 8.4 Hz, J = 1.5 Hz); 7.04-7.31 (m, 11H); 7.36 (br s, 1H); 8.79 (d, 1H, J = 8.8 Hz); 10.85 (br s, 1H); m/z: 456.22 [M + H]+ (calc. mass: 455.22). |
| 71 | 2-{5-[({[2-(dimethylamino)phenyl](phenyl)methyl}carbamoyl)methyl]-1H-indol-3-yl}acetic acid | From methyl 2-{5-[({[2-(dimethylamino)phenyl](phenyl)methyl}carbamoyl)methyl]-1H-indol-3-yl}acetate Cpd. 70 following protocol F<br>Yield: 80%; mp: 91, 123° C.; appearance: white solid; 1H NMR, d (ppm): 2.49 (s, 6H); 3.58-3.59 (m, 4H); 6.62 (d, 1H, J = 8.6 Hz); 7.00 (dd, 1H, J = 8.3 Hz, J = 1.5 Hz); 7.05-7.30 (m, 11H); 7.37 (br s, 1H); 8.82 (d, 1H, J = 8.2 Hz); 70.82 (br s, 1H); 12.09 (br s, 1H); m/z: 442.2 [M + H]+ (calc. mass: 441.2). |
| 72 | methyl 2-{5-[({phenyl[2-(pyrrolidin-1-yl)phenyl]methyl}carbamoyl)methyl]-1H-indol-3-yl}acetate | From phenyl[2-(pyrrolidin-1-yl)phenyl]methanamine Ex. 51 and 2-[3-(2-methoxy-2-oxoethyl)-1H-indol-5-yl]acetic acid Ex. 5 following protocol D<br>Yield: 57%; mp: 65, 67° C.; appearance: white solid; 1H NMR, d (ppm): 1.681.74 (m, 4H); 2.75-2.78 (m, 2H); 3.02-3.07 (m, 2H); 3.56 (s, 2H); 3.57 (s, 3H); 3.68 (s, 2H); 6.50 (d, 1H, J = 8.5 Hz); 6.92-7.27 (m, 12H); 7.36 (br s, 1H); 8.75 (d, 1H, J = 8.5 Hz); 10.86 (br s, 1H); m/z: 482.23 [M + H]+ (calc. mass: 481.23). |
| 73 | 2-{5-[({phenyl[2-(pyrrolidin-1-yl)phenyl]methyl}carbamoyl)methyl]-1H-indol-3-yl}acetic acid | From methyl 2-{5-[({phenyl[2-(pyrrolidin-1-yl)phenyl]methyl}carbamoyl)methyl]-1H-indol-3-yl}acetate Cpd. 72 following protocol F<br>Yield: 88%; mp: 97, 123° C.; appearance: white solid; 1H NMR, d (ppm): 1.67-1.76 (m, 4H); 2.74-2.81 (m, 2H); 3.05-3.09 (m, 2H); 3.56 (s, 2H); 3.58 (s, 2H); 6.50 (d, 1H, J = 8.5 Hz); 6.92-7.27 (m, 12H); 7.37 (br s, 1H); 8.75 (d, 1H, J = 8.5 Hz); 10.81 (br s, 1H); 12.09 (br s, 1H); m/z: 468.22 [M + H]+ (calc. mass: 467.22). |
| 74 | methyl 2-{5-[({[2-(azepan-1-yl)phenyl](phenyl)methyl}carbamoyl)methyl]-1H-indol-3-yl}acetate | From [2-(azepan-1-yl)phenyl](phenyl)methanamine Ex. 26 and 2-[3-(2-methoxy-2-oxoethyl)-1H-indol-5-yl]acetic acid Ex. 5 following protocol D<br>Yield: 33%; mp: 58, 61° C.; appearance: white solid; 1H NMR, d (ppm): 1.42-1.55 (m, 8H); 2.76-2.81 (m, 2H); 2.95-3.01 (m, 2H); 3.55 (s, 2H); 3.58 (s, 3H); 3.68 (s, 2H); 6.70 (d, 1H, J = 8.5 Hz); 7.00 (dd, 1H, J = 8.3 Hz, J = 1.5 Hz); 7.03-730 (m, 11H); 7.35 (br s, 1H); 8.72 (d, 1H, J = 8.5 Hz); 10.85 (br s, 1H); m/z: 510.26 [M + H]+ (calc. mass: 509.26). |
| 75 | 2-{5-[({[2-(azepan-1-yl)phenyl](phenyl)methyl}carbamoyl)methyl]-1H-indol-3-yl}acetic acid | From methyl 2-{5-[({[2-(azepan-1-yl)phenyl](phenyl)methyl}carbamoyl)methyl]-1H-indol-3-yl}acetate Cpd. 74 following protocol F<br>Yield: 85%; mp: 91, 113° C.; appearance: white solid; 1H NMR, d (ppm): 1.43-1.55 (m, 8H); 2.75-2.81 (m, 2H); 2.95-303 (m, 2H); 3.54 (s, 2H); 3.58 (s, 2H); 6.69-6.71 (d, 1H, |

TABLE 2-continued

*All the NMR were performed in DMSO-d6*

| Cpd. | | Starting compounds, Reaction conditions and purification Yield, MP, Appearance, $^1$H NMR (solvent) data, Mass (ES+ or ES−) data |
|---|---|---|
| | | J = 8.4 Hz); 7.00 (dd, 1H, J = 8.3 Hz, J = 1.5 Hz); 7.03-7.29 (m, 11H); 7.36 (br s, 1H); 8.72 (d, 1H, J = 8.4 Hz); 10.81 (br s, 1H); 12.08 (br s, 1H); m/z: 496.25 [M + H]+ (calc. mass: 495.25). |
| 76 | tert-butyl 3-{5-[({[4-methyl-2-(piperidin-1-yl)phenyl](phenyl)methyl}carbamoyl)methyl]-1H-indol-3-yl}propanoate | From [4-methyl-2-(piperidin-1-yl)phenyl](phenyl)methanamine Ex. 53 and 2-{3-[3-(tert-butoxy)-3-oxopropyl]-1H-indol-5-yl}acetic acid Ex. 1 following protocol D<br>Yield: 57%; mp: 74° C.; appearance: yellow solid; 1H NMR, d (ppm): 1.38 (s, 9H); 1.42-1.59 (m, 6H); 2.22 (s, 3H); 2.44-2.55 (m, 4H); 2.83-2.89 (m, 4H); 3.56 (s, 2H); 6.56 (d, 1H, J = 8.7 Hz); 6.86 (d, 1H, J = 7.9 Hz); 6.92 (s, 1H); 6.98 (dd, 1H, J = 1.5 Hz, J = 8.3 Hz); 7.06 (d, 1H, J = 2.3 Hz); 7.12-7.27 (m, 7H); 7.39 (s, 1H); 8.65 (d, 1H, J = 8.7 Hz); 10.68 (d, 1H, J = 2.1 Hz); m/z: 566.33 [M + H]+ (calc. mass: 565.33). |
| 77 | 3-{5-[({[4-methyl-2-(piperidin-1-yl)phenyl](phenyl)methyl}carbamoyl)methyl]-1H-indol-3-yl}propanoic acid | From tert-butyl 3-{5-[({[4-methyl-2-(piperidin-1-yl)phenyl](phenyl)methyl}carbamoyl)methyl]-1H-indol-3-yl}propanoate Cpd. 76 following protocol E<br>Yield: 87%; mp: 99, 115° C.; appearance: light yellow solid; 1H NMR, d (ppm): 1.43-1.56 (m, 6H); 2.22 (s, 3H); 2.47-2.58 (m, 4H); 2.83-2.90 (m, 4H); 3.56 (s, 2H); 6.56 (d, 1H, J = 8.3 Hz); 6.86 (d, 1H, J = 7.6 Hz); 6.93 (s, 1H); 6.98 (d, 1H, J = 8.1 Hz); 7.07 (s, 1H); 7.12-7.27 (m, 7H); 7.40 (s, 1H); 8.66 (d, 1H, J = 8.7 Hz); 10.68 (s, 1H); 11.96 (br s, 1H); m/z: 510.26 [M + H]+ (calc. mass: 509.26). |
| 78 | tert-butyl 3-{5-[({phenyl[2-(pyrrolidin-1-yl)phenyl]methyl}carbamoyl)methyl]-1H-indol-3-yl}propanoate | From phenyl[2-(pyrrolidin-1-yl)phenyl]methanamine Ex. 51 and 2-{3-[3-(tert-butoxy)-3-oxopropyl]-1H-indol-5-yl}acetic acid Ex. 1 following protocol D<br>Yield: 68%; mp: 70° C.; appearance: white solid; 1H NMR, d (ppm): 1.38 (s, 9H); 1.68-1.74 (m, 4H); 2.54 (t, 2H, J = 8.0 Hz); 2.76-2.80 (m, 2H); 2.87 (t, 2H, J = 7.8 Hz); 3.02-3.07 (m, 2H); 3.57 (s, 2H); 6.52 (d, 1H, J = 8.5 Hz); 6.92-7.00 (m, 2H); 7.05-7.08 (m, 2H); 7.11-7.27 (m, 8H); 7.41 (s, 1H); 8.75 (d, 1H, J = 8.6 Hz); 10.68 (s, 1H); m/z: 538.29 [M + H]+ (calc. mass: 537.29). |
| 79 | 3-{5-[({phenyl[2-(pyrrolidin-1-yl)phenyl]methyl}carbamoyl)methyl]-1H-indol-3-yl}propanoic acid | From tert-butyl 3-{5-[({phenyl[2-(pyrrolidin-1-yl)phenyl]methyl}carbamoyl)methyl]-1H-indol-3-yl}propanoate Cpd. 78 following protocol E<br>Yield: 85%; mp: 95, 112° C.; appearance: white solid; 1H NMR, d (ppm): 1.68-1.74 (m, 4H); 2.56 (t, 2H, J = 7.1 Hz); 2.74-2.81 (m, 2H); 2.88 (t, 2H, J = 7.4 Hz); 3.02-3.07 (m, 2H); 3.57 (s, 2H); 6.52 (d, 1H, J = 8.5 Hz); 6.95-7.00 (m, 2H); 7.07-7.25 (m, 10H); 7.41 (s, 1H); 7.75 (d, 1H, J = 8.6 Hz); 10.69 (d, 1H, J = 1.8 Hz); 12.06 (s, 1H); m/z: 482.23 [M + H]+ (calc. mass: 481.23). |
| 80 | tert-butyl 3-{5-[({[4-methyl-2-(morpholin-4-yl)phenyl](phenyl)methyl}carbamoyl)methyl]-1H-indol-3-yl}propanoate | From [4-methyl-2-(morpholin-4-yl)phenyl](phenyl)methanamine Ex. 57 and 2-{3-[3-(tert-butoxy)-3-oxopropyl]-1H-indol-5-yl}acetic acid Ex. 1 following protocol D<br>Yield: 63%; mp: 95, 100° C.; appearance: white solid; 1H NMR, d (ppm): 1.41 (s, 9H); 2.30 (s, 3H); 2.54-2.59 (m, 6H); 2.95 (t, 2H, J = 7.6 Hz); 3.68-3.72 (m, 4H); 6.63 (s, 1H); 6.93-6.96 (m, 1H); 7.01-7.30 (m, 12H); 7.48 (s, 1H); m/z: 568.3 [M + H]+ (calc. mass: 567.3). |
| 81 | 3-{5-[({[4-methyl-2-(morpholin-4-yl)phenyl](phenyl)methyl}carbamoyl)methyl]-1H-indol-3-yl}propanoic acid | From tert-butyl 3-{5-[({[4-methyl-2-(morpholin-4-yl)phenyl](phenyl)methyl}carbamoyl)methyl]-1H-indol-3-yl}propanoate Cpd. 80 following protocol E<br>Yield: 75%; mp: 141, 147° C.; appearance: white solid; 1H NMR, d (ppm): 2.24 (s, 3H); 2.48-2.49 (m, 2H); 2.53-2.56 (m, 2H); 2.84 (q, 4H, J = 8.1 Hz); 3.42-3.48 (m, 2H); 3.55-3.59 (m, 4H); 6.59 (d, 1H, J = 8.6 Hz); 6.90 (d, 1H, J = 7.9 Hz); 6.96-6.99 (m, 2H); 7.06 (d, 1H, J = 2.2 Hz); 7.14-7.28 (m, 7H); 7.40 (s, 1H); 8.70 (d, 1H, J = 8.9 Hz); 10.68 (d, 1H, J = 1.7 Hz); m/z: 512.24 [M + H]+ (calc. mass: 511.24). |
| 82 | tert-butyl 3-[5-({[(4-methoxy-2-methylphenyl)(phenyl)methyl]carbamoyl}methyl)-1H-indol-3-yl]propanoate | From (4-methoxy-2-methylphenyl)(phenyl)methanamine Ex. 55 and 2-{3-[3-(tert-butoxy)-3-oxopropyl]-1H-indol-5-yl}acetic acid Ex. 1 following protocol D<br>Yield: 40%; mp: 71, 72° C.; appearance: white solid; 1H NMR, d (ppm): 1.40 (s, 9H); 2.19 (s, 3H); 2.59 (t, 2H, J = 6.8 Hz); 3.01 (t, 2H, J = 7.6 Hz); 3.67 (s, 2H); 3.73-3.75 (m, 3H); 6.28 (s, 1H); 6.65 (dd, 1H, J = 8.3 Hz, J = 2.8 Hz); 6.73-6.74 (m, 1H); 6.94 (d, 1H, J = 8.5 Hz); 7.03 (s, 1H); 7.06 (dd, 1H, J = 8.5 Hz, J = 1.6 Hz); 7.14-7.16 (m, 2H); 7.22-7.31 (m, 4H); 7.48 (s, 1H); m/z: 513.26 [M + H]+ (calc. mass: 512.26). |

TABLE 2-continued

All the NMR were performed in DMSO-d6

| Cpd. | | Starting compounds, Reaction conditions and purification Yield, MP, Appearance, $^1$H NMR (solvent) data, Mass (ES+ or ES−) data |
|---|---|---|
| 83 | 3-[5-({[(4-methoxy-2-methylphenyl)(phenyl)methyl]carbamoyl}methyl)-1H-indol-3-yl]propanoic acid | From tert-butyl 3-[5-({[(4-methoxy-2-methylphenyl)(phenyl)methyl]carbamoyl}methyl)-1H-indol-3-yl]propanoate Cpd. 82 following protocol E<br>Yield: 72%; mp: 116, 143° C.; appearance: white solid; 1H NMR, d (ppm): 2.17 (s, 3H); 2.55 (t, 2H, J = 7.1 Hz); 2.88 (t, 2H, J = 7.1 Hz); 3.54 (s, 2H); 3.69 (s, 3H); 6.17 (d, 1H, J = 8.5 Hz); 6.69-6.74 (m, 2H); 6.96-7.01 (m, 2H); 7.06 (d, 1H, J = 2.0 Hz); 7.16-7.33 (m, 6H); 7.41 (s, 1H); 10.68 (d, 1H, J = 2.0 Hz); 12.10 (br s, 1H); m/z: 457.2 [M + H]+ (calc. mass: 456.2). |
| 84 | methyl 2-{5-[({[4-chloro-2-(pyrrolidin-1-yl)phenyl](phenyl)methyl}carbamoyl)methyl]-1H-indol-3-yl}acetate | From [4-chloro-2-(pyrrolidin-1-yl)phenyl](phenyl)methanamine Ex. 60 and 2-[3-(2-methoxy-2-oxoethyl)-1H-indol-5-yl]acetic acid Ex. 5 following protocol D<br>Yield: 51%; mp: 68, 83° C.; appearance: white solid; 1H NMR, d (ppm): 1.67-1.76 (m, 4H); 2.87-2.91 (m, 2H); 2.87-2.91 (m, 2H); 3.55 (s, 2H); 3.58 (s, 3H); 3.68 (s, 2H); 6.44 (d, 1H, J = 8.3 Hz); 6.91-7.02 (m, 3H); 7.09-7.29 (m, 8H); 7.35 (br s, 1H); 8.82 (d, 1H, J = 8.4 Hz); 10.86 (br s, 1H); m/z: 516.19 [M + H]+ (calc. mass: 515.19). |
| 85 | 2-{5-[({[4-chloro-2-(pyrrolidin-1-yl)phenyl](phenyl)methyl}carbamoyl)methyl]-1H-indol-3-yl}acetic acid | From methyl 2-{5-[({[4-chloro-2-(pyrrolidin-1-yl)phenyl](phenyl)methyl}carbamoyl) methyl]-1H-indol-3-yl}acetate Cpd. 84 following protocol F<br>Yield: 86%; mp: 101, 119° C.; appearance: white solid; 1H NMR, d (ppm): 1.68-1.75 (m, 4H); 2.87-2.92 (m, 2H); 308-3.13 (m, 2H); 3.54 (s, 2H); 3.58 (s, 2H); 6.44 (d, 1H, J = 8.3 Hz); 6.91-6.97 (m, 2H); 7.00 (dd, 1H, J = 8.3 Hz, J = 1.5 Hz); 7.09-7.29 (m, 8H); 7.36 (br s, 1H); 8.83 (d, 1H, J = 8.3 Hz); 10.82 (br s, 1H); 12.10 (br s, 1H); m/z: 502.18 [M + H]+ (calc. mass: 501.18). |
| 86 | methyl 2-{5-[({[4-methyl-2-(piperidin-1-yl)phenyl](phenyl)methyl}carbamoyl)methyl]-1H-indol-3-yl}acetate | From [4-methyl-2-(piperidin-1-yl)phenyl](phenyl)methanamine Ex. 53 and 2-[3-(2-methoxy-2-oxoethyl)-1H-indol-5-yl]acetic acid Ex. 5 following protocol D<br>Yield: 45%; mp: 66, 81° C.; appearance: white solid; 1H NMR, d (ppm): 1.42-1.53 (m, 6H); 2.22 (s, 3H); 2.48-2.50 (m, 2H); 2.81-2.83 (m, 2H); 3.55 (s, 2H); 3.59 (s, 3H); 3.68 (s, 2H); 6.54 (d, 1H, J = 8.7 Hz); 6.85-6.87 (m, 1H); 6.92 (br s, 1H); 7.00 (dd, 1H, J = 8.3 Hz, J = 1.4 Hz); 7.12-7.26 (m, 8H); 7.34 (br s, 1H); 8.66 (d, 1H, J = 8.7 Hz); 10.85 (br s, 1H); m/z: 510.26 [M + H]+ (calc. mass: 509.26). |
| 87 | 2-{5-[({[4-methyl-2-(piperidin-1-yl)phenyl](phenyl)methyl}carbamoyl)methyl]-1H-indol-3-yl}acetic acid | From methyl 2-{5-[({[4-methyl-2-(piperidin-1-yl)phenyl](phenyl)methyl}carbamoyl)methyl]-1H-indol-3-yl}acetate Cpd. 86 following protocol F<br>Yield: 80%; mp: 104, 123° C.; appearance: white solid; 1H NMR, d (ppm): 1.42-1.55 (m, 6H); 2.22 (s, 3H); 2.44-2.50 (m, 2H); 2.82-2.86 (m, 2H); 3.55 (s, 2H); 3.57 (s, 2H); 6.54 (d, 1H, J = 8.6 Hz); 6.85-6.88 (m, 1H); 6.92 (br s, 1H); 7.00 (dd, 1H, J = 8.3 Hz, J = 1.5 Hz); 7.12-7.27 (m, 8H); 7.35 (br s, 1H); 8.66 (d, 1H, J = 8.7 Hz); 10.80 (br s, 1H); 11.94 (br s, 1H); m/z: 496.25 [M + H]+ (calc. mass: 495.25). |
| 88 | methyl 2-{5-[({phenyl[2-(pyrrolidin-1-yl)-4-(trifluoromethyl)phenyl]methyl}carbamoyl)methyl]-1H-indol-3-yl}acetate | From phenyl[2-(pyrrolidin-1-yl)-4-(trifluoromethyl)phenyl]methanamine Ex. 37 and 2-[3-(2-methoxy-2-oxoethyl)-1H-indol-5-yl]acetic acid Ex. 5 following protocol D<br>Yield: 71%; mp: 68, 80° C.; appearance: white solid; 1H NMR, d (ppm): 1.71-1.76 (m, 4H); 2.92-2.97 (m, 2H); 3.12-3.18 (m, 2H); 3.56 (s, 2H); 3.57 (s, 3H); 3.68 (s, 2H); 6.52 (d, 1H, J = 8.2 Hz); 7.00 (dd, 1H, J = 8.3 Hz, J = 1.5 Hz); 7.11-7.40 (m, 11H); 8.92 (d, 1H, J = 8.2 Hz); 10.86 (br s, 1H); m/z: 550.22 [M + H]+ (calc. mass: 549.22). |
| 89 | 2-{5-[({phenyl[2-(pyrrolidin-1-yl)-4-(trifluoromethyl)phenyl]methyl}carbamoyl)methyl]-1H-indol-3-yl}acetic acid | From methyl 2-{5-[({phenyl[2-(pyrrolidin-1-yl)-4-(trifluoromethyl)phenyl]methyl}carbamoyl)methyl]-1H-indol-3-yl}acetate Cpd. 88 following protocol F<br>Yield: 81%; mp: 97, 129° C.; appearance: white solid; 1H NMR, d (ppm): 1.70-1.81 (m, 4H); 2.93-2.99 (m, 2H); 3.13-3.18 (m, 2H); 3.56 (s, 2H); 3.57 (s, 2H); 6.52 (d, 1H, J = 8.1 Hz); 7.00 (dd, 1H, J = 8.3 Hz, J = 1.5 Hz); 7.11-7.40 (m, 11H); 8.93 (d, 1H, J = 8.3 Hz); 10.82 (br s, 1H); 12.12 (br s, 1H); m/z: 536.2 [M + H]+ (calc. mass: 535.2). |

TABLE 2-continued

*All the NMR were performed in DMSO-d6*

| Cpd. | | Starting compounds, Reaction conditions and purification Yield, MP, Appearance, $^1$H NMR (solvent) data, Mass (ES+ or ES−) data |
|---|---|---|
| 90 | tert-butyl 3-{5-[({[4-chloro-2-(pyrrolidin-1-yl)phenyl](phenyl)methyl}carbamoyl)methyl]-1H-indol-3-yl}propanoate | From [4-chloro-2-(pyrrolidin-1-yl)phenyl](phenyl)methanamine Ex. 60 and 2-{3-[3-(tert-butoxy)-3-oxopropyl]-1H-indol-5-yl}acetic acid Ex. 1 following protocol D Yield: 61%; appearance: white solid 1H NMR, d (ppm): 1.36 (s, 9H); 1.72-1.76 (m, 4H); 2.53 (t, 2H, J = 8.1 Hz); 2.87 (t, 2H, J = 7.2 Hz); 2.95-2.99 (m, 2H); 3.13-3.18 (m, 2H); 3.56 (s, 2H); 6.53 (d, 1H, J = 8.2 Hz); 6.98 (dd, 1H, J = 8.1 Hz, J = 1.1 Hz); 7.07 (d, 1H, J = 2.3 Hz); 7.12-7.14 (m, 2H); 7.21-7.31 (m, 6H); 7.39-7.41 (m, 2H); 8.91 (d, 1H, J = 8.6 Hz); 10.69 (s, 1H); m/z: 572.26 [M + H]+ (calc. mass: 571.26). |
| 91 | 3-{5-[({[4-chloro-2-(pyrrolidin-1-yl)phenyl](phenyl)methyl}carbamoyl)methyl]-1H-indol-3-yl}propanoic acid | From tert-butyl 3-{5-[({[4-chloro-2-(pyrrolidin-1-yl)phenyl](phenyl)methyl}carbamoyl)methyl]-1H-indol-3-yl}propanoate Cpd. 90 following protocol E Yield: 80%; mp: 95, 117° C.; appearance: white solid; 1H NMR, d (ppm): 1.71-1.75 (m, 4H); 2.55 (t, 2H, J = 8.3 Hz); 2.85-2.91 (m, 4H); 3.07-3.14 (m, 2H); 3.55 (s, 2H); 6.43 (d, 1H, J = 8.3 Hz); 6.97 (dd, 1H, J = 8.3 Hz, J = 1.3 Hz); 7.05-7.28 (m, 10H); 7.41 (s, 1H); 8.83 (d, 1H, J = 8.3 Hz); 10.68 (s, 1H); 12.15 (br s, 1H); m/z: 516.19 [M + H]+ (calc. mass: 515.19). |
| 92 | tert-butyl 3-{5-[({[4-fluoro-2-(pyrrolidin-1-yl)phenyl](phenyl)methyl}carbamoyl)methyl]-1H-indol-3-yl}propanoate | From [4-fluoro-2-(pyrrolidin-1-yl)phenyl](phenyl)methanamine Ex. 66 and 2-{3-[3-(tert-butoxy)-3-oxopropyl]-1H-indol-5-yl}acetic acid Ex. 1 following protocol D Yield: 27%; appearance: white solid; 1H NMR, d (ppm): 1.36 (s, 9H); 1.72-1.76 (m, 4H); 2.53 (t, 2H, J = 8.1 Hz); 2.87 (t, 2H, J = 7.2 Hz); 2.95-2.99 (m, 2H); 3.13-3.18 (m, 2H); 3.56 (s, 2H); 6.53 (d, 1H, J = 8.2 Hz); 6.98 (dd, 1H, J = 8.1 Hz, J = 1.1 Hz); 7.07 (d, 1H, J = 2.3 Hz); 7.12-7.14 (m, 2H); 7.21-7.31 (m, 6H); 7.39-7.41 (m, 2H); 8.91 (d, 1H, J = 8.6 Hz); 10.69 (s, 1H); m/z: 556.28 [M + H]+ (calc. mass: 555.28). |
| 93 | 3-{5-[({[4-fluoro-2-(pyrrolidin-1-yl)phenyl](phenyl)methyl}carbamoyl)methyl]-1H-indol-3-yl}propanoic acid | From tert-butyl 3-{5-[({[4-fluoro-2-(pyrrolidin-1-yl)phenyl](phenyl)methyl}carbamoyl)methyl]-1H-indol-3-yl}propanoate Cpd. 92 following protocol E Yield: 98%; mp: 95, 114° C.; appearance: white solid; 1H NMR, d (ppm): 1.71-1.75 (m, 4H); 2.55 (t, 2H, J = 8.3 Hz); 2.85-2.91 (m, 4H); 3.07-3.14 (m, 2H); 3.55 (s, 2H); 6.43 (d, 1H, J = 8.3 Hz); 6.97 (dd, 1H, J = 8.3 Hz, J = 1.3 Hz); 7.05-7.28 (m, 10H); 7.41 (s, 1H); 8.83 (d, 1H, J = 8.3 Hz); 10.68 (s, 1H); 12.15 (br s, 1H); m/z: 500.22 [M + H]+ (calc. mass: 499.22). |
| 94 | tert-butyl 3-{5-[({phenyl[2-(piperidin-1-yl)phenyl]methyl}carbamoyl)amino]-1H-pyrrolo[2,3-b]pyridin-3-yl}propanoate | From phenyl[2-(piperidin-1-yl)phenyl]methanamine Ex. 9 and tert-butyl 3-(5-amino-1H-pyrrolo[2,3-b]pyridin-3-yl)propanoate Ex. 136 following protocol G Yield: 27%; mp: 247, 249° C.; appearance: white solid 1H NMR, d (ppm): 1.34 (s, 9H); 1.47-1.63 (m, 6H); 2.50-2.57 (m, 4H); 2.84 (t, 2H, J = 7.5 Hz); 2.89-2.97 (m, 2H); 6.49 (d, 1H, J = 8.2 Hz); 7.01 (d, 1H, J = 8.2 Hz); 7.09-7.33 (m, 10H); 8.00-8.03 (m, 2H); 8.38 (s, 1H); 11.13 (br s, 1H) m/z: 554.3 [M + H]+ (calc. mass: 553.3). |
| 95 | 3-{5-[({phenyl[2-(piperidin-1-yl)phenyl]methyl}carbamoyl)amino]-1H-pyrrolo[2,3-b]pyridin-3-yl}propanoic acid | From tert-butyl 3-{5-[({phenyl[2-(piperidin-1-yl)phenyl]methyl}carbamoyl)amino]-1H-pyrrolo[2,3-b]pyridin-3-yl}propanoate Cpd. 94 following protocol E Yield: 44%; mp: 231, 233° C.; appearance: white solid; 1H NMR, d (ppm): 1.50-1.62 (m, 6H); 2.50-2.56 (m, 4H); 2.85 (t, 2H, J = 7.5 Hz); 2.86-2.92 (m, 2H); 6.49 (d, 1H, J = 8.1 Hz); 7.02 (d, 1H, J = 8.4 Hz); 7.09-7.33 (m, 10H); 8.01-8.03 (m, 2H); 8.39 (br s, 1H); 11.13 (br s, 1H); m/z: 498.24 [M + H]+ (calc. mass: 497.24). |
| 96 | methyl 2-{5-[({[4-methyl-2-(morpholin-4-yl)phenyl](phenyl)methyl}carbamoyl)methyl]-1H-indol-3-yl}acetate | From [4-methyl-2-(morpholin-4-yl)phenyl](phenyl)methanamine Ex. 57 and 2-[3-(2-methoxy-2-oxoethyl)-1H-indol-5-yl]acetic acid Ex. 5 following protocol D Yield: 58%; mp: 79, 97° C.; appearance: white solid; 1H NMR, d (ppm): 2.24 (s, 3H); 2.49-2.51 (m, 2H); 2.82-2.88 (m, 2H); 3.41-3.48 (m, 2H); 3.54 (s, 2H); 3.57-3.60 (m, 5H); 3.67 (s, 2H); 6.58 (d, 1H, J = 8.7 Hz); 6.89-6.92 (m, 1H); 6.97 (br s, 1H); 7.00 (dd, 1H, J = 8.3 Hz, J = 1.5 Hz); 7.13-7.27 (m, 8H); 7.34 (br s, 1H); 8.68 (d, 1H, J = 8.7 Hz); 10.86 (br s, 1H); m/z: 512.24 [M + H]+ (calc. mass: 511.24). |

TABLE 2-continued

*All the NMR were performed in DMSO-d6*

| Cpd. | | Starting compounds, Reaction conditions and purification Yield, MP, Appearance, $^1$H NMR (solvent) data, Mass (ES+ or ES−) data |
|---|---|---|
| 97 | 2-{5-[({4-methyl-2-(morpholin-4-yl)phenyl](phenyl)methyl}carbamoyl)methyl]-1H-indol-3-yl}acetic acid | From methyl 2-{5-[({4-methyl-2-(morpholin-4-yl)phenyl](phenyl)methyl}carbamoyl)methyl]-1H-indol-3-yl}acetate Cpd. 96 following protocol F Yield: 83%; mp: 113, 141° C.; appearance: white solid; 1H NMR, d (ppm): 2.24 (s, 3H); 2.44-2.50 (m, 2H); 2.83-2.88 (m, 2H); 3.43-3.48 (m, 2H); 3.54 (s, 2H); 3.56-3.60 (m, 4H); 6.58 (d, 1H, J = 8.7 Hz); 6.89-6.92 (m, 1H); 6.97-7.01 (m, 2H); 7.13-7.28 (m, 8H); 7.35 (br s, 1H); 8.68 (d, 1H, J = 8.7 Hz); 10.81 (br s, 1H); 12.09 (br s, 1H); m/z: 498.23 [M + H]+ (calc. mass: 497.23). |
| 98 | tert-butyl 3-[5-({[(2-methoxy-4-methylphenyl)(phenyl)methyl]carbamoyl}methyl)-1H-indol-3-yl]propanoate | From (2-methoxy-4-methylphenyl)(phenyl)methanamine Ex. 56 and 2-{3-[3-(tert-butoxy)-3-oxopropyl]-1H-indol-5-yl}acetic acid Ex. 1 following protocol D Yield: 78%; mp: 74° C.; appearance: white solid; 1H NMR, d (ppm): 1.38 (s, 9H); 2.26 (s, 3H); 2.54 (t, 2H, J = 7.4 Hz); 2.87 (t, 2H, J = 7.7 Hz); 3.55 (s, 2H); 3.62 (s, 3H); 4.82 (d, 1H, J = 8.8 Hz); 6.71-6.76 (m, 2H); 6.98 (dd, 1H, J = 1.5 Hz, J = 8.3 Hz); 7.07 (d, 1H, J = 2.3 Hz); 7.13-7.28 (m, 7H); 7.41 (s, 1H); 8.63 (d, 1H, J = 8.8 Hz); 10.69 (d, 1H, J = 1.7 Hz); m/z: 513.26 [M + H]+ (calc. mass: 512.26). |
| 99 | 3-[5-({[(2-methoxy-4-methylphenyl)(phenyl)methyl]carbamoyl}methyl)-1H-indol-3-yl]propanoic acid | From tert-butyl 3-[5-({[(2-methoxy-4-methylphenyl)(phenyl)methyl]carbamoyl}methyl)-1H-indol-3-yl]propanoate Cpd. 98 following protocol E Yield: 92%; mp: 97, 115° C.; appearance: white solid; 1H NMR, d (ppm): 2.26 (s, 3H); 2.56 (t, 2H, J = 7.0 Hz); 2.88 (t, 2H, J = 7.3 Hz); 3.55 (s, 2H); 3.62 (s, 3H); 6.33 (d, 1H, J = 8.8 Hz); 6.72-6.76 (m, 2H); 6.98 (dd, 1H, J = 1.6 Hz, J = 8.3 Hz); 7.07 (d, 1H, J = 2.3 Hz); 7.13-7.27 (m, 7H); 7.41 (s, 1H); 8.64 (d, 1H, J = 9.0 Hz); 10.69 (d, 1H, J = 2.0 Hz); 12.08 (br s, 1H); m/z: 457.2 [M + H]+ (calc. mass: 456.2). |
| 100 | tert-butyl 3-[5-({[(2,4-dimethylphenyl)(5-methylthiophen-2-yl)methyl]carbamoyl}methyl)-1H-indol-3-yl]propanoate | From (2,4-dimethylphenyl)(5-methylthiophen-2-yl)methanamine Ex. 63 and 2-{3-[3-(tert-butoxy)-3-oxopropyl]-1H-indol-5-yl}acetic acid Ex. 1 following protocol D Yield: 86%; mp: 69, 77° C.; appearance: white foam; 1H NMR, d (ppm): 1.38 (s, 9H); 2.17 (s, 3H); 2.23 (s, 3H); 2.35 (s, 3H); 2.52 (t, 2H, J = 8.1 Hz); 2.87 (t, 2H, J = 8.1 Hz); 3.52 (s, 2H); 6.26 (d, 1H, J = 8.4 Hz); 6.44 (d, 1H, J = 3.4 Hz); 6.58 (dd, 1H, J = 3.4 Hz, J = 1.1 Hz); 6.95-6.99 (m, 3H); 7.06 (d, 1H, J = 2.2 Hz); 7.22 (t, 2H, J = 7.2 Hz); 7.40 (s, 1H); 8.98 (d, 1H, J = 8.6 Hz); 10.68 (br s, 1H); m/z: 517.24 [M + H]+ (calc. mass: 516.24). |
| 101 | 3-[5-({[(2,4-dimethylphenyl)(5-methylthiophen-2-yl)methyl]carbamoyl}methyl)-1H-indol-3-yl]propanoic acid | From tert-butyl 3-[5-({[(2,4-dimethylphenyl)(5-methylthiophen-2-yl)methyl]carbamoyl}methyl)-1H-indol-3-yl]propanoate Cpd. 100 following protocol E Yield: 59%; mp: 100, 122° C.; appearance: yellow solid; 1H NMR, d (ppm): 2.17 (s, 3H); 2.23 (s, 3H); 2.35 (s, 3H); 2.57 (t, 2H, J = 7.4 Hz); 2.89 (t, 2H, J = 7.4 Hz); 3.32 (s, 2H); 6.26 (d, 1H, J = 8.4 Hz); 6.44 (dd, 1H, J = 3.4 Hz, J = 0.9 Hz); 6.58 (dd, 1H, J = 3.4 Hz, J = 1.1 Hz); 6.95-7.00 (m, 3H); 7.06 (d, 1H, J = 2.2 Hz); 7.23 (t, 2H, J = 7.3 Hz); 7.41 (s, 1H); 9.00 (d, 1H, J = 8.4 Hz); 10.68 (d, 1H, J = 2.0 Hz); 12.15 (br s, 1H); m/z: 461.18 [M + H]+ (calc. mass: 460.18). |
| 102 | tert-butyl 3-{5-[({[4-methyl-2-(4-methylpiperazin-1-yl)phenyl](phenyl)methyl}carbamoyl)methyl]-1H-indol-3-yl}propanoate | From [4-methyl-2-(4-methylpiperazin-1-yl)phenyl](phenyl)methanamine Ex. 62 and 2-{3-[3-(tert-butoxy)-3-oxopropyl]-1H-indol-5-yl}acetic acid Ex. 1 following protocol D Yield: 64%; mp: 102, 110° C.; appearance: white foam; 1H NMR, d (ppm): 1.38 (s, 9H); 2.15 (s, 3H); 2.23 (s, 3H); 2.38 (br s, 2H); 2.51 (t, 2H, J = 7.1 Hz); 2.87 (t, 4H, J = 7.1 Hz); 3.55 (s, 2H); 6.55 (d, 1H, J = 8.7 Hz); 6.88 (d, 1H, J = 7.8 Hz); 6.94-6.99 (m, 2H); 7.07 (d, 1H, J = 2.2 Hz); 7.14-7.27 (m, 7H); 7.40 (s, 1H); 8.66 (d, 1H, J = 8.7 Hz); 10.68 (d, 1H, J = 1.7 Hz); m/z: 581.34 [M + H]+ (calc. mass: 580.34). |
| 103 | 3-{5-[({[4-methyl-2-(4-methylpiperazin-1-yl)phenyl](phenyl)methyl}carbamoyl)methyl]-1H-indol-3-yl}propanoic acid | From tert-butyl 3-{5-[({[4-methyl-2-(4-methylpiperazin-1-yl)phenyl](phenyl)methyl}carbamoyl)methyl]-1H-indol-3-yl}propanoate Cpd. 102 following protocol E Yield: 55%; mp: 182, 192° C.; appearance: white solid; 1H NMR, d (ppm): 2.21 (s, 3H); 2.23 (s, 3H); 2.38 (br s, 2H); 2.51 (t, 2H, J = 7.3 Hz); 2.87 (t, 4H, J = 7.3 Hz); 3.55 (s, 2H); 6.55 (d, 1H, J = 8.7 Hz); 6.88 (d, 1H, J = 8.1 Hz); 6.95-6.99 (m, 2H); 7.07 (d, 1H, J = 2.2 Hz); 7.15-7.27 (m, 7H); 7.41 (s, 1H); 8.68 (d, 1H, J = 8.7 Hz); 10.68 (br s, 1H); m/z: 525.27 [M + H]+ (calc. mass: 524.27). |

TABLE 2-continued

All the NMR were performed in DMSO-d6

| Cpd. | | Starting compounds, Reaction conditions and purification Yield, MP, Appearance, ¹H NMR (solvent) data, Mass (ES+ or ES−) data |
|---|---|---|
| 104 | tert-butyl 3-[5-({[3-methyl-1-(naphthalen-1-yl)butyl]carbamoyl}methyl)-1H-indol-3-yl]propanoate | From 3-methyl-1-(naphthalen-1-yl)butan-1-amine Ex. 32 and 2-{3-[3-(tert-butoxy)-3-oxopropyl]-1H-indol-5-yl}acetic acid Ex. 1 following protocol D<br>Yield: 43%; mp: 138, 140° C.; appearance: white solid; 1H NMR, d (ppm): 0.88 (d, 3H, J = 6.3 Hz); 0.99 (d, 3H, J = 6.3 Hz); 1.52-1.59 (m, 1H); 1.72-1.79 (m, 2H); 2.53 (t, 2H, J = 7.4 Hz); 2.86 (t, 2H, J = 7.4 Hz); 3.46-3.57 (m, 2H); 6.95 (dd, 1H, J = 8.3 Hz, J = 1.4 Hz); 7.06 (d, 1H, J = 2.3 Hz); 7.20 (d, 1H, J = 8.2 Hz); 7.38 (s, 1H); 7.43-7.56 (m, 4H); 7.78 (d, 1H, J = 8.2 Hz); 7.92 (dd, 1H, J = 7.8 Hz, J = 1.6 Hz); 8.10 (d, 1H, J = 8.3 Hz); 8.62 (d, 1H, J = 8.5 Hz); 10.67 (s, 1H); m/z: 499.28 [M + H]+ (calc. mass: 498.28). |
| 105 | 3-[5-({[3-methyl-1-(naphthalen-1-yl)butyl]carbamoyl}methyl)-1H-indol-3-yl]propanoic acid | From tert-butyl 3-[5-({[3-methyl-1-(naphthalen-1-yl)butyl]carbamoyl}methyl)-1H-indol-3-yl]propanoate Cpd. 104 following protocol E<br>Yield: 87%; mp: 154, 174° C.; appearance: white solid; 1H NMR, d (ppm): 0.88 (d, 3H, J = 6.3 Hz); 0.99 (d, 3H, J = 6.3 Hz); 1.56-1.79 (m, 3H); 2.55 (t, 2H, J = 7.5 Hz); 2.87 (t, 2H, J = 7.3 Hz); 3.46-3.56 (m, 2H); 5.67-5.73 (m, 1H); 6.95 (d, 1H, J = 8.1 Hz); 7.06 (s, 1H); 7.20 (d, 1H, J = 8.2 Hz); 7.39 (s, 1H); 7.43-7.57 (m, 4H); 7.78 (d, 1H, J = 8.1 Hz); 7.91 (d, 1H, J = 7.7 Hz); 8.10 (d, 1H, J = 8.1 Hz); 8.63 (d, 1H, J = 8.3 Hz); 10.67 (s, 1H); 12.20 (br s, 1H); m/z: 443.22 [M + H]+ (calc. mass: 442.22). |
| 106 | tert-butyl 3-{5-[({phenyl[2-(1H-pyrrol-1-yl)phenyl]methyl}carbamoyl)methyl]-1H-indol-3-yl}propanoate | From phenyl[2-(1H-pyrrol-1-yl)phenyl]methanamine Ex. 54 and 2-{3-[3-(tert-butoxy)-3-oxopropyl]-1H-indol-5-yl}acetic acid Ex. 1 following protocol D<br>Yield: 61%; mp: 76° C.; appearance: white solid; 1H NMR, d (ppm): 1.38 (s, 9H); 2.54 (t, 2H, J = 7.3 Hz); 2.88 (t, 2H, J = 7.5 Hz); 3.55 (s, 2H); 6.11 (d, 1H, J = 8.0 Hz); 6.15 (t, 2H, J = 2.1 Hz); 6.79 (t, 2H, J = 2.1 Hz); 6.94-6.99 (m, 3H); 7.07 (d, 1H, J = 2.2 Hz); 7.18-7.27 (m, 5H); 7.33-7.45 (m, 3H); 7.55 (dd, 1H, J = 1.6 Hz, J = 7.7 Hz); 8.99 (d, 1H, J = 8.0 Hz); 10.69 (d, 1H, J = 2.0 Hz); m/z: 534.26 [M + H]+ (calc. mass: 533.26). |
| 107 | 3-{5-[({phenyl[2-(1H-pyrrol-1-yl)phenyl]methyl}carbamoyl)methyl]-1H-indol-3-yl}propanoic acid | From tert-butyl 3-{5-[({phenyl[2-(1H-pyrrol-1-yl)phenyl]methyl}carbamoyl)methyl]-1H-indol-3-yl}propanoate Cpd. 106 following protocol E<br>Yield: 93%; mp: 115, 124° C.; appearance: white solid; 1H NMR, d (ppm): 2.53 (t, 2H, J = 7.1 Hz); 2.88 (t, 2H, J = 7.3 Hz); 3.55 (s, 2H); 6.12 (d, 1H, J = 8.0 Hz); 6.15 (t, 2H, J = 2.1 Hz); 6.79 (t, 2H, J = 2.1 Hz); 6.94-6.99 (m, 3H); 7.06 (d, 1H, J = 2.2 Hz); 7.15-7.27 (m, 5H); 7.35 (td, 1H, J = 1.7 Hz, J = 7.7 Hz); 7.40-7.46 (m, 2H); 7.57 (dd, 1H, J = 1.5 Hz, J = 7.7 Hz); 9.03 (d, 1H, J = 8.1 Hz); 10.68 (d, 1H, J = 2.0 Hz); m/z: 478.2 [M + H]+ (calc. mass: 477.2). |
| 108 | tert-butyl 3-{5-[({[4-methoxy-2-(pyrrolidin-1-yl)phenyl](phenyl)methyl}carbamoyl)methyl]-1H-indol-3-yl}propanoate | From [4-methoxy-2-(pyrrolidin-1-yl)phenyl](phenyl)methanamine Ex. 68 and 2-{3-[3-(tert-butoxy)-3-oxopropyl]-1H-indol-5-yl}acetic acid Ex. 1 following protocol D<br>Yield: 64%; mp: 71° C.; appearance: white solid; 1H NMR, d (ppm): 1.38 (s, 9H); 1.67-1.73 (m, 4H); 2.54 (t, 2H, J = 7.1 Hz); 2.78-2.90 (m, 4H); 3.03-3.10 (m, 2H); 3.56 (s, 2H); 3.69 (s, 3H); 6.41 (d, 1H, J = 8.4 Hz); 6.49-6.55 (m, 2H); 6.99 (dd, 1H, J = 1.5 Hz, J = 8.3 Hz); 7.04-7.26 (m, 8H); 7.40 (s, 1H); 8.69 (d, 1H, J = 8.5 Hz); 10.68 (d, 1H, J = 1.9 Hz); m/z: 568.3 [M + H]+ (calc. mass: 567.3). |
| 109 | 3-{5-[({[4-methoxy-2-(pyrrolidin-1-yl)phenyl](phenyl)methyl}carbamoyl)methyl]-1H-indol-3-yl}propanoic acid | From tert-butyl 3-{5-[({[4-methoxy-2-(pyrrolidin-1-yl)phenyl](phenyl)methyl}carbamoyl)methyl]-1H-indol-3-yl}propanoate Cpd. 108 following protocol E<br>Yield: 91%; mp: 94, 116° C.; appearance: white solid; 1H NMR, d (ppm): 1.68-1.73 (m, 4H); 2.56 (t, 2H, J = 7.1 Hz); 2.78-2.83 (m, 2H); 2.89 (t, 2H, J = 7.4 Hz); 3.03-3.08 (m, 2H); 3.56 (s, 2H); 3.69 (s, 3H); 6.41 (d, 1H, J = 8.4 Hz); 6.49-6.54 (m, 2H); 6.99 (dd, 1H, J = 1.5 Hz, J = 8.3 Hz); 7.04-7.27 (m, 8H); 7.41 (s, 1H); 8.68 (d, 1H, J = 8.5 Hz); 10.69 (d, 1H, J = 1.9 Hz); 12.07 (br s, 1H); m/z: 512.24 [M + H]+ (calc. mass: 511.24). |

TABLE 2-continued

_All the NMR were performed in DMSO-d6_

| Cpd. | | Starting compounds, Reaction conditions and purification Yield, MP, Appearance, ¹H NMR (solvent) data, Mass (ES+ or ES−) data |
|---|---|---|
| 110 | tert-butyl 3-{5-[({[4-methoxy-2-(piperidin-1-yl)phenyl](phenyl)methyl}carbamoyl)methyl]-1H-indol-3-yl}propanoate | From [4-methoxy-2-(piperidin-1-yl)phenyl](phenyl)methanamine Ex. 73 and 2-{3-[3-(tert-butoxy)-3-oxopropyl]-1H-indol-5-yl}acetic acid Ex. 1 following protocol D Yield: 38%; mp: 79° C.; appearance: white solid; 1H NMR, d (ppm): 1.38 (s, 9H); 1.43-1.59 (m, 6H); 2.45-2.56 (m, 4H); 2.79-2.89 (m, 4H); 3.56 (s, 2H); 3.69 (s, 3H); 6.51 (d, 1H); 6.62-6.66 (m, 2H); 6.97 (dd, 1H, J = 1.5 Hz, J = 8.3 Hz); 7.06 (d, 1H, J = 2.3 Hz); 7.15-7.27 (m, 7H); 7.39 (s, 1H); 8.65d (d, 1H, J = 8.7 Hz); 10.68 (d, 1H, J = 1.9 Hz); m/z: 582.32 [M + H]+ (calc. mass: 581.32). |
| 111 | 3-{5-[({[4-methoxy-2-(piperidin-1-yl)phenyl](phenyl)methyl}carbamoyl)methyl]-1H-indol-3-yl}propanoic acid | From tert-butyl 3-{5-[({[4-methoxy-2-(piperidin-1-yl)phenyl](phenyl)methyl}carbamoyl)methyl]-1H-indol-3-yl}propanoate Cpd. 110 following protocol E Yield: 88%; mp: 101, 113° C.; appearance: white solid; 1H NMR, d (ppm): 1.43-1.56 (m, 6H); 2.48-2.59 (m, 4H); 2.80-2.91 (m, 4H); 3.56 (s, 2H); 3.69 (s, 3H); 6.51 (d, 1H, J = 8.7 Hz); 6.63-6.66 (m, 2H); 6.98 (dd, 1H, J = 1.4 Hz, J = 8.3 Hz); 7.07 (d, 1H, J = 2.2 Hz); 7.12-7.27 (m, 7H); 7.41 (s, 1H); 8.65 (d, 1H, J = 8.6 Hz); 10.68 (d, 1H, J = 1.9 Hz); 12.05 (br s, 1H); m/z: 526.26 [M + H]+ (calc. mass: 525.26). |
| 112 | N,N-dimethyl-2-{5-[({[4-methyl-2-(morpholin-4-yl)phenyl](phenyl)methyl}carbamoyl)methyl]-1H-indol-3-yl}acetamide | From 2-{5-[({[4-methyl-2-(morpholin-4-yl)phenyl](phenyl)methyl}carbamoyl)methyl]-1H-indol-3-yl}acetic acid Cpd. 97 following protocol D Yield: 68%; mp: 109, 120° C.; appearance: white solid; 1H NMR, d (ppm): 2.24 (s, 3H); 2.42-2.44 (m, 2H); 2.80 (s, 3H); 2.83-2.86 (m, 2H); 2.98 (s, 3H); 3.41-3.47 (m, 2H); 3.54 (s, 2H); 3.56-3.58 (m, 2H); 3.60 (s, 2H); 6.57 (d, 1H, J = 8.7 Hz); 6.89-6.92 (m, 1H); 6.97-7.01 (m, 2H); 7.13-7.28 (m, 8H); 7.40 (m, 1H); 8.66 (d, 1H, J = 8.7 Hz); 10.79 (s, 1H); m/z: 525.27 [M + H]+ (calc. mass: 524.27). |
| 113 | tert-butyl 3-{5-[({[5-methyl-2-(piperidin-1-yl)phenyl](phenyl)methyl}carbamoyl)methyl]-1H-indol-3-yl}propanoate | From [5-methyl-2-(piperidin-1-yl)phenyl](phenyl)methanamine Ex. 112 and 2-{3-[3-(tert-butoxy)-3-oxopropyl]-1H-indol-5-yl}acetic acid Ex. 1 following protocol D Yield: 55%; mp: 83, 87° C.; appearance: white solid; 1H NMR, d (ppm): 1.37 (s, 9H); 1.40-1.58 (m, 6H); 2.17 (s, 3H); 2.40-2.48 (m, 2H); 2.53 (t, 2H, J = 8.1 Hz); 2.79-2.89 (m, 4H); 3.56 (s, 2H); 6.57 (d, 1H, J = 8.6 Hz); 6.98-7.04 (m, 3H); 7.07 (s, 2H); 7.13-7.27 (m, 6H); 7.41 (s, 1H); 8.64 (d, 1H, J = 8.8 Hz); 10.68 (s, 1H); m/z: 566.33 [M + H]+ (calc. mass: 565.33). |
| 114 | 3-{5-[({[5-methyl-2-(piperidin-1-yl)phenyl](phenyl)methyl}carbamoyl)methyl]-1H-indol-3-yl}propanoic acid | From tert-butyl 3-{5-[({[5-methyl-2-(piperidin-1-yl)phenyl](phenyl)methyl}carbamoyl)methyl]-1H-indol-3-yl}propanoate following Cpd. 113 protocol E Yield: 88%; mp: 115, 131° C.; appearance: white solid; 1H NMR, d (ppm): 1.41-1.54 (m, 6H); 2.16 (s, 3H); 2.39-2.50 (m, 2H); 2.55 (t, 2H, J = 8.2 Hz); 2.72-2.80 (m, 2H); 2.88 (t, 2H, J = 8.1 Hz); 3.52-3.62 (m, 2H); 6.57 (d, 1H, J = 8.6 Hz); 6.97-7.04 (m, 3H); 7.05-7.08 (m, 2H); 7.13-7.28 (m, 6H); 7.42 (s, 1H); 8.66 (d, 1H, J = 8.7 Hz); 10.68 (s, 1H); 12.07 (br s, 1H); m/z: 510.26 [M + H]+ (calc. mass: 509.26). |
| 115 | N-methyl-3-{5-[({phenyl[2-(piperidin-1-yl)phenyl]methyl}carbamoyl)methyl]-1H-indol-3-yl}propanamide | From 3-{5-[({phenyl[2-(piperidin-1-yl)phenyl]methyl}carbamoyl)methyl]-1H-indol-3-yl}propanoic acid Cpd. 1 and methylamine following protocol D Yield: 88%; mp: 99, 109° C.; appearance: white solid; 1H NMR, d (ppm): 1.40-1.65 (m, 6H); 2.45-2.5 (m, 4H); 2.57 (d, 3H, J = 0.3 Hz); 2.8-2.9 (m, 4H); 3.56 (s, 2H); 6.60 (d, 1H, J = 8.7 Hz); 6.95-7.35 (m, 12H); 7.39 (s, 1H); 7.75 (d, 1H, J = 0.3 Hz); 8.72 (d, 1H, J = 8.7 Hz); 10.63 (br s, 1H); m/z: 509.28 [M + H]+ (calc. mass: 508.28). |
| 116 | tert-butyl 3-{5-[({[5-bromo-2-(pyrrolidin-1-yl)phenyl](phenyl)methyl}carbamoyl)methyl]-1H-indol-3-yl}propanoate | From [5-bromo-2-(pyrrolidin-1-yl)phenyl](phenyl)methanamine Ex. 74 and 2-{3-[3-(tert-butoxy)-3-oxopropyl]-1H-indol-5-yl}acetic acid Ex. 1 following protocol D Yield: 70%; mp: 91, 100° C.; appearance: white foam; 1H NMR, d (ppm): 1.38 (s, 9H); 1.72 (q, 4H, J = 6.4 Hz); 2.54 (t, 2H, J = 7.2 Hz); 2.82-2.90 (m, 4H); 3.07-3.10 (m, 2H); 3.56 (s, 2H); 6.48 (d, 1H, J = 8.5 Hz); 6.97-7.01 (m, 2H); 7.07 (d, 1H, J = 2.3 Hz); 7.11-7.13 (m, 2H); 7.19-7.34 (m, 7H); 7.40 (s, 1H); 8.86 (d, 1H, J = 8.6 Hz); 10.70 (br s, 1H); m/z: 616.2 [M + H]+ (calc. mass: 615.2). |

TABLE 2-continued

*All the NMR were performed in DMSO-d6*

| Cpd. | | Starting compounds, Reaction conditions and purification Yield, MP, Appearance, $^1$H NMR (solvent) data, Mass (ES+ or ES−) data |
|---|---|---|
| 117 | 3-{5-[({[5-bromo-2-(pyrrolidin-1-yl)phenyl](phenyl)methyl}carbamoyl)methyl]-1H-indol-3-yl}propanoic acid | From tert-butyl 3-{5-[({[5-bromo-2-(pyrrolidin-1-yl)phenyl](phenyl)methyl}carbamoyl)methyl]-1H-indol-3-yl}propanoate Cpd. 116 following protocol E Yield: 93%; mp: 155, 161° C.; appearance: white powder; 1H NMR, d (ppm): 1.72 (q, 4H, J = 6.4 Hz); 2.54 (t, 2H, J = 7.2 Hz); 2.82-2.91 (m, 4H); 3.07-3.11 (m, 2H); 3.56 (s, 2H); 6.48 (d, 1H, J = 8.5 Hz); 6.97-7.01 (m, 2H); 7.07 (d, 1H, J = 2.3 Hz); 7.11-7.13 (m, 2H); 7.19-7.34 (m, 7H); 7.41 (s, 1H); 8.87 (d, 1H, J = 8.6 Hz); 10.69 (br s, 1H); 12.03 (br s, 1H); m/z: 560.14 [M + H]+ (calc. mass: 559.14). |
| 118 | 3-{5-[({phenyl[2-(piperidin-1-yl)phenyl]methyl}carbamoyl)methyl]-1H-indol-3-yl}-N-(propan-2-yl)propanamide | From 3-{5-[({phenyl[2-(piperidin-1-yl)phenyl]methyl}carbamoyl)methyl]-1H-indol-3-yl}propanoic acid Cpd. 1 and isopropylamine following protocol D Yield: 55%; mp: 92, 110° C.; appearance: white solid; 1H NMR, d (ppm): 1.02 (d, 6H, J = 6.6 Hz); 1.40-1.65 (m, 6H); 2.34 (t, 2H, J = 7.3 Hz); 2.45-2.5 (m, 2H); 2.82-2.88 (m, 4H); 3.57 (s, 2H); 3.83 (m, 1H); 6.60 (d, 1H, J = 8.7 Hz); 6.95-7.35 (m, 12H); 7.40 (s, 1H); 7.66 (d, 1H, J = 8.7 Hz); 8.72 (d, 1H, J = 8.7 Hz); 10.64 (br s, 1H); m/z: 537.31 [M + H]+ (calc. mass: 536.31). |
| 119 | tert-butyl 3-{5-[({[2-(ethylamino)-4-methylphenyl](phenyl)methyl}carbamoyl)methyl]-1H-indol-3-yl}propanoate | From 2-[amino(phenyl)methyl]-N-ethyl-5-methylaniline Ex. 76 and 2-{3-[3-(tert-butoxy)-3-oxopropyl]-1H-indol-5-yl}acetic acid Ex. 1 following protocol D Yield: 68%; mp: 130° C.; appearance: white solid; 1H NMR, d (ppm): 0.96 (t, 3H, J = 7.0 Hz); 1.38 (s, 9H); 2.18 (s, 3H); 2.53 (t, 2H, J = 7.5 Hz); 2.86 (t, 2H, J = 7.4 Hz); 2.90-3.02 (m, 2H); 3.55 (s, 2H); 4.50 (t, 1H, J = 5.1 Hz); 6.13 (d, 1H, J = 9.1 Hz); 6.30 (d, 1H, J = 7.7 Hz); 6.37 (s, 1H); 6.54 (d, 1H, J = 7.7 Hz); 6.98 (dd, 1H, J = 1.5 Hz, J = 8.3 Hz); 7.07 (d, 1H, J = 2.2 Hz); 7.20-7.35 (m, 6H); 7.40 (s, 1H); 8.87 (d, 1H, J = 9.1 Hz); 10.68 (d, 1H, J = 1.7 Hz); m/z: 526.29 [M + H]+ (calc. mass: 525.29). |
| 120 | 3-{5-[({[2-(ethylamino)-4-methylphenyl](phenyl)methyl}carbamoyl)methyl]-1H-indol-3-yl}propanoic acid | From tert-butyl 3-{5-[({[2-(ethylamino)-4-methylphenyl](phenyl)methyl}carbamoyl)methyl]-1H-indol-3-yl}propanoate Cpd. 119 following protocol E Yield: 77%; mp: 125° C.; appearance: white solid; 1H NMR, d (ppm): 0.97 (t, 3H, J = 7.0 Hz); 2.18 (s, 3H); 2.55 (t, 2H, J = 7.1 Hz); 2.87 (t, 2H, J = 7.5 Hz); 2.94-2.98 (m, 2H); 3.55 (s, 2H); 4.50 (m, 1H); 6.13 (d, 1H, J = 9.1 Hz); 6.30 (d, 1H, J = 7.7 Hz); 6.37 (s, 1H); 6.55 (d, 1H, J = 7.7 Hz); 6.98 (dd, 1H, J = 1.4 Hz, J = 8.3 Hz); 7.07 (d, 1H, J = 2.2 Hz); 7.20-7.33 (m, 6H); 7.41 (s, 1H); 8.89 (d, 1H, J = 9.1 Hz); 10.68 (d, 1H, J = 1.7 Hz); 12.15 (br s, 1H); m/z: 470.23 [M + H]+ (calc. mass: 469.23). |
| 121 | tert-butyl 3-(5-{[({2-[(dimethylamino)methyl]phenyl}(phenyl)methyl)carbamoyl]methyl}-1H-indol-3-yl)propanoate | From {2-[(dimethylamino)methyl]phenyl}(phenyl)methanamine Ex. 71 and 2-{3-[3-(tert-butoxy)-3-oxopropyl]-1H-indol-5-yl}acetic acid Ex. 1 following protocol D Yield: 46%; mp: 80, 83° C.; appearance: white solid; 1H NMR, d (ppm): 1.38 (s, 9H); 2.00 (s, 6H); 2.53 (t, 2H, J = 8.0 Hz); 2.84-2.89 (m, 3H); 3.42 (d, 1H, J = 12.6 Hz); 3.55 (s, 2H); 6.56 (d, 1H, J = 8.6 Hz); 6.98 (dd, 1H, J = 8.3 Hz, J = 1.5 Hz); 7.07 (d, 1H, J = 2.1 Hz); 7.14-7.7.17 (m, 3H); 7.19-7.30 (m, 7H); 7.40 (s, 1H); 9.22 (d, 1H, J = 8.5 Hz); 10.69 (s, 1H); m/z: 526.29 [M + H]+ (calc. mass: 525.29). |
| 122 | 3-(5-{[({2-[(dimethylamino)methyl]phenyl}(phenyl)methyl)carbamoyl]methyl}-1H-indol-3-yl)propanoic acid | From tert-butyl 3-{5-{[({2-[(dimethylamino)methyl]phenyl}(phenyl)methyl)carbamoyl]methyl}-1H-indol-3-yl)propanoate Cpd. 122 following protocol E Yield: 31%; mp: 111, 121° C.; appearance: white solid; 1H NMR, d (ppm): 2.00 (s, 6H); 2.53 (t, 2H, J = 7.3 Hz); 2.86-2.90 (m, 3H); 3.41-3.56 (m, 1H); 3.56 (s, 2H); 6.56 (d, 1H, J = 8.6 Hz); 6.98 (dd, 1H, J = 8.4 Hz, J = 1.3 Hz); 7.07 (d, 1H, J = 2.1 Hz); 7.14-7.30 (m, 10H); 7.41 (s, 1H); 8.20 (s, 1H); 9.22 (d, 1H, J = 9.0 Hz); 10.70 (s, 1H); m/z: 470.23 [M + H]+ (calc. mass: 469.23). |
| 123 | tert-butyl 3-{5-[({[2-(3-hydroxypiperidin-1-yl)phenyl](phenyl)methyl}carbamoyl)methyl]-1H-indol-3-yl}propanoate | From 1-{2-[amino(phenyl)methyl]phenyl}piperidin-3-ol Ex. 81 and 2-{3-[3-(tert-butoxy)-3-oxopropyl]-1H-indol-5-yl}acetic acid Ex. 1 following protocol D Yield: 70%; mp: 92, 96° C.; appearance: white solid; 1H NMR, d (ppm): 1.17-1.38 (m, 2H); 1.38 (s, 9H); 1.73-1.80 (m, 3H); 2.26-2.49 (m, 2H); 2.52-2.57 (m, 2H); 2.72-3.03 (m, 3H); 3.49-3.70 (m, 3H); 4.65 (d, 0.5H, J = 4.7 Hz); 4.77 (d, 0.5H, J = 4.8 Hz); 6.50 (d, 0.5H, J = 8.8 Hz); 6.60 (d, 0.5H, |

TABLE 2-continued

All the NMR were performed in DMSO-d6

| Cpd. | | Starting compounds, Reaction conditions and purification Yield, MP, Appearance, $^1$H NMR (solvent) data, Mass (ES+ or ES−) data |
|---|---|---|
| | | J = 8.9 Hz); 6.99 (dt, 1H, J = 8.4 Hz, J = 1.5 Hz); 7.04-7.28 (m, 10H); 7.34 (dd, 1H, J = 7.6 Hz, J = 1.4 Hz); 7.40 (s, .5H); 7.43 (s, .5H); 8.79 (d, 0.5H, J = 8.7 Hz); 8.88 (d, 0.5H, J = 8.8 Hz); 10.67 (s, 1H); m/z: 568.3 [M + H]+ (calc. mass: 567.3). |
| 124 | 3-{5-[({[2-(3-hydroxypiperidin-1-yl)phenyl](phenyl)methyl}carbamoyl)methyl]-1H-indol-3-yl}propanoic acid | From tert-butyl 3-{5-[({[2-(3-hydroxypiperidin-1-yl)phenyl](phenyl)methyl}carbamoyl)methyl]-1H-indol-3-yl}propanoate Cpd. 123 following protocol E Yield: 100%; mp: 122, 128° C.; appearance: white solid; 1H NMR, d (ppm): 1.17-1.38 (m, 2H); 1.38 (s, 9H); 1.73-1.80 (m, 3H); 2.26-2.49 (m, 2H); 2.52-2.57 (m, 2H); 2.72-3.03 (m, 3H); 3.49-3.70 (m, 3H); 4.65 (d, 0.5H, J = 4.7 Hz); 4.77 (d, 0.5H, J = 4.8 Hz); 6.50 (d, 0.5H, J = 8.8 Hz); 6.60 (d, 0.5H, J = 8.9 Hz); 6.99 (dt, 1H, J = 8.4 Hz, J = 1.5 Hz); 7.04-7.28 (m, 10H); 7.34 (dd, 1H, J = 7.6 Hz, J = 1.4 Hz); 7.40 (s, .5H); 7.43 (s, .5H); 8.79 (d, 0.5H, J = 8.7 Hz); 8.88 (d, 0.5H, J = 8.8 Hz); 10.67 (s, 1H); m/z: 512.24 [M + H]+ (calc. mass: 511.24). |
| 125 | tert-butyl 3-(5-{[({4-methyl-2-[(propan-2-yl)amino]phenyl}(phenyl)methyl)carbamoyl]methyl}-1H-indol-3-yl)propanoate | From 2-[amino(phenyl)methyl]-5-methyl-N-(propan-2-yl)aniline Ex. 77 and 2-{3-[3-(tert-butoxy)-3-oxopropyl]-1H-indol-5-yl}acetic acid Ex. 1 following protocol D Yield: 71%; mp: 83, 87° C.; appearance: white solid; 1H NMR, d (ppm): 0.92 (d, 3H, J = 6.2 Hz); 0.99 (d, 3H, J = 6.2 Hz); 1.38 (s, 9H); 2.18 (s, 3H); 2.55 (t, 2H, J = 7.2 Hz); 2.86 (t, 2H, J = 7.2 Hz); 3.54 (s, 2H); 4.28 (d, 1H, J = 7.5 Hz); 6.09 (d, 1H, J = 9.4 Hz); 6.24-6.28 (m, 1H); 6.40 (s, 1H); 6.48 (d, 1H, J = 7.7 Hz); 6.99 (dd, 1H, J = 8.4 Hz, J = 1.4 Hz); 7.06 (d, 1H, J = 2.1 Hz); 7.19-7.34 (m, 5H); 7.41 (s, 1H); 8.86 (d, 1H, J = 9.4 Hz); 10.68 (br s, 1H); m/z: 540.31 [M + H]+ (calc. mass: 539.31). |
| 126 | 3-(5-{[({4-methyl-2-[(propan-2-yl)amino]phenyl}(phenyl)methyl)carbamoyl]methyl}-1H-indol-3-yl)propanoic acid | From tert-butyl 3-(5-{[({4-methyl-2-[(propan-2-yl)amino]phenyl}(phenyl)methyl)carbamoyl]methyl}-1H-indol-3-yl)propanoate Cpd. 125 following protocol E Yield: 72%; mp: 114, 116° C.; appearance: white solid; 1H NMR, d (ppm): 0.92 (d, 3H, J = 6.2 Hz); 0.99 (d, 3H, J = 6.2 Hz); 2.17 (s, 3H); 2.55 (t, 2H, J = 7.2 Hz); 2.86 (t, 2H, J = 7.2 Hz); 3.54 (s, 2H); 4.28 (br s, 1H); 6.09 (d, 1H, J = 9.3 Hz); 6.24-6.28 (m, 1H); 6.40 (s, 1H); 6.48 (d, 1H, J = 7.7 Hz); 6.99 (dd, 1H, J = 8.3 Hz, J = 1.5 Hz); 7.06 (d, 1H, J = 2.2 Hz); 7.19-7.34 (m, 7H); 7.42 (s, 1H); 8.88 (d, 1H, J = 9.3 Hz); 10.68 (br s, 1H); m/z: 484.25 [M + H]+ (calc. mass: 483.25). |
| 127 | tert-butyl 3-{5-[({phenyl[2-(1,2,3,6-tetrahydropyridin-1-yl)phenyl]methyl}carbamoyl)methyl]-1H-indol-3-yl}propanoate | From phenyl[2-(1,2,3,6-tetrahydropyridin-1-yl)phenyl]methanamine Ex. 75 and 2-{3-[3-(tert-butoxy)-3-oxopropyl]-1H-indol-5-yl}acetic acid Ex. 1 following protocol D Yield: 35%; mp: 75° C.; appearance: white solid; 1H NMR, d (ppm): 1.38 (s, 9H); 1.94-2.00 (m, 1H); 2.12-2.18 (m, 1H); 2.53 (t, 2H, J = 7.5 Hz); 2.63-2.69 (m, 1H); 2.86 (t, 2H, J = 7.4 Hz); 2.96-3.01 (m, 1H); 3.03-3.10 (m, 1H); 3.49-3.57 (m, 3H); 5.66-5.76 (m, 1H); 6.60 (d, 2H, J = 8.6 Hz); 6.98 (dd, 1H, J = 1.5 Hz, J = 8.3 Hz); 6.96-7.27 (m, 10H); 7.34 (d, 1H, J = 7.3 Hz); 7.40 (s, 1H); 8.78 (d, 1H, J = 8.7 Hz); 10.68 (d, 1H, J = 1.9 Hz); m/z: 550.29 [M + H]+ (calc. mass: 549.29). |
| 128 | 3-{5-[({phenyl[2-(1,2,3,6-tetrahydropyridin-1-yl)phenyl]methyl}carbamoyl)methyl]-1H-indol-3-yl}propanoic acid | From tert-butyl 3-{5-[({phenyl[2-(1,2,3,6-tetrahydropyridin-1-yl)phenyl]methyl}carbamoyl)methyl]-1H-indol-3-yl}propanoate Cpd. 127 following protocol E Yield: 89%; mp: 89, 105° C.; appearance: white solid; 1H NMR, d (ppm): 1.95-2.00 (m, 1H); 2.13-2.19 (m, 1H); 2.56 (t, 2H, J = 7.2 Hz); 2.62-2.69 (m, 1H); 2.88 (t, 2H, J = 7.3 Hz); 2.96-3.01 (m, 1H); 3.03 (m, 1H); 3.49-3.57 (m, 3H); 5.66-5.76 (m, 1H); 6.60 (d, 1H, J = 8.6 Hz); 6.98 (dd, 1H, J = 1.5 Hz, J = 8.3 Hz); 7.06-7.36 (m, 11H); 7.41 (s, 1H); 8.79 (d, 1H, J = 8.7 Hz); 10.68 (d, 1H, J = 1.8 Hz); 12.10 (br s, 1H); m/z: 494.23 [M + H]+ (calc. mass: 493.23). |
| 129 | tert-butyl 3-{5-[({1-[2-(pyrrolidin-1-yl)phenyl]cyclopentyl}carbamoyl)methyl]-1H-indol-3-yl}propanoate | From 1-[2-(pyrrolidin-1-yl)phenyl]cyclopentan-1-amine Ex. 115 and 2-{3-[3-(tert-butoxy)-3-oxopropyl]-1H-indol-5-yl}acetic acid Ex. 1 following protocol D Yield: 74%; mp: 75, 80° C.; appearance: white solid; 1H NMR, d (ppm): 1.45 (s, 9H); 1.55-1.90 (m, 10H); 2.61 (t, 2H, J = 7.2 Hz); 2.68-2.72 (m, 2H); 2.80-2.85 (m, 4H); 3.03 (t, 2H, J = 7.2 Hz); 3.56 (s, 2H); 6.13 (br s, 1H); 7.03-7.06 (m, 2H); 7.12 (td, 1H, J = 7.8 Hz, J = 1.5 Hz); 7.22 (td, 1H, J = 7.8 Hz, |

TABLE 2-continued

All the NMR were performed in DMSO-d6

| Cpd. | | Starting compounds, Reaction conditions and purification Yield, MP, Appearance, $^1$H NMR (solvent) data, Mass (ES+ or ES−) data |
|---|---|---|
| | | J = 1.5 Hz); 7.26-7.32 (m, 1H); 7.41 (br s, 1H); 7.54 (dd, 1H, J = 7.8 Hz, J = 1.5 Hz); 8.02 (br s, 1H); m/z: 516.31 [M + H]+ (calc. mass: 515.31). |
| 130 | 3-{5-[({1-[2-(pyrrolidin-1-yl)phenyl]cyclopentyl}carbamoyl)methyl]-1H-indol-3-yl}propanoic acid | From tert-butyl 3-{5-[({1-[2-(pyrrolidin-1-yl)phenyl]cyclopentyl}carbamoyl)methyl]-1H-indol-3-yl}propanoate Cpd. 129 following protocol E Yield: 86%; mp: 130, 240° C.; appearance: white solid; 1H NMR, d (ppm): 1.62-1.92 (m, 10H); 2.68-2.72 (m, 4H); 2.78-2.87 (m, 4H); 3.05 (t, 2H, J = 7.2 Hz); 3.56 (s, 2H); 6.31 (br s, 1H); 6.97-7.03 (m, 2H); 7.10-7.15 (m, 1H); 7.20-7.30 (m, 2H); 7.40 (s, 1H); 7.53 (d, 1H, J = 7.8 Hz); 8.22 (br s, 1H); m/z: 460.25 [M + H]+ (calc. mass: 459.25). |
| 131 | tert-butyl 3-{5-[({[4-methyl-2-(piperidin-1-yl)phenyl](pyrimidin-2-yl)methyl}carbamoyl)methyl]-1H-indol-3-yl}propanoate | From [4-methyl-2-(piperidin-1-yl)phenyl](pyrimidin-2-yl)methanamine Ex. 88 and 2-{3-[3-(tert-butoxy)-3-oxopropyl]-1H-indol-5-yl}acetic acid Ex. 1 following protocol D Yield: 52%; mp: 88, 90° C.; appearance: white solid; 1H NMR, d (ppm): 1.30-1.55 (m, 15H); 2.48 (s, 3H); 2.55-2.60 (m, 4H); 2.69-2.73 (m, 2H); 2.86 (t, 2H, J = 7.5 Hz); 3.48-3.64 (m, 2H); 6.55 (d, 1H, J = 8.1 Hz); 6.81 (dd, 1H, J = 7.8 Hz, J = 1.0 Hz); 6.92 (m, 1H); 6.97 (dd, 1H, J = 8.3 Hz, J = 1.6 Hz); 7.05-7.10 (m, 2H); 7.20 (d, 1H, J = 8.3 Hz); 7.32 (t, 1H, J = 4.9 Hz); 7.38 (s, 1H); 8.52 (d, 1H, J = 8.1 Hz); 8.71 (d, 2H, J = 4.9 Hz); 10.66 (s, 1H); m/z: 568.32 [M + H]+ (calc. mass: 567.32). |
| 132 | 3-{5-[({[4-methyl-2-(piperidin-1-yl)phenyl](pyrimidin-2-yl)methyl}carbamoyl)methyl]-1H-indol-3-yl}propanoic acid | From tert-butyl 3-{5-[({[4-methyl-2-(piperidin-1-yl)phenyl](pyrimidin-2-yl)methyl}carbamoyl)methyl]-1H-indol-3-yl}propanoate Cpd. 131 following protocol E Yield: 88%; mp: 115, 143° C.; appearance: white solid; 1H NMR, d (ppm): 1.35-1.46 (m, 6H); 2.21 (s, 3H); 2.53-2.60 (m, 4H); 2.70-2.74 (m, 2H); 2.87 (t, 2H, J = 7.4 Hz); 3.49-3.64 (m, 2H); 6.55 (d, 1H, J = 8.1 Hz); 6.80 (d, 1H, J = 7.0 Hz); 6.92 (s, 1H); 6.97 (dd, 1H, J = 8.3 Hz, J = 1.4 Hz); 7.06 (d, 1H, J = 1.6 Hz); 7.08 (d, 1H, J = 7.9 Hz); 7.20 (d, 1H, J = 8.2 Hz); 7.32 (t, 1H, J = 4.9 Hz); 7.39 (s, 1H); 8.53 (d, 1H, J = 8.0 Hz); 8.72 (d, 2H, J = 4.9 Hz); 10.66 (d, 1H, J = 1.6 Hz); 12.08 (br s, 1H); m/z: 512.25 [M + H]+ (calc. mass: 511.25). |
| 133 | tert-butyl 3-{5-[({1-[2-(dimethylamino)-4-methylphenyl]-3-methylbutyl}carbamoyl)methyl]-1H-indol-3-yl}propanoate | From 2-(1-amino-3-methylbutyl)-N,N,5-trimethylaniline Ex. 82 and 2-{3-[3-(tert-butoxy)-3-oxopropyl]-1H-indol-5-yl}acetic acid Ex. 1 following protocol D Yield: 48%; mp: 46, 61° C.; appearance: white solid; 1H NMR, d (ppm): 0.82 (d, 3H, J = 6.3 Hz); 0.85 (d, 3H, J = 6.2 Hz); 1.31-.133 (m, 1H); 1.38 (s, 9H); 1.46-1.49 (m, 2H); 2.21 (s, 3H); 2.52 (t, 2H, J = 8.2 Hz); 2.58 (s, 6H); 2.86 (t, 2H, J = 7.4 Hz); 3.45 (s, 2H); 5.31 (m, 1H); 6.83 (d, 1H, J = 7.8 Hz); 6.88-6.90 (m, 1H); 6.93 (dd, 1H, J = 8.3 Hz, J = 1.5 Hz); 7.05 (d, 1H, J = 2.3 Hz); 7.18-7.21 (m, 2H); 7.35-7.37 (m, 1H); 8.23 (d, 1H, J = 8.5 Hz); 10.67 (s, 1H); m/z: 506.33 [M + H]+ (calc. mass: 505.33). |
| 134 | 3-{5-[({1-[2-(dimethylamino)-4-methylphenyl]-3-methylbutyl}carbamoyl)methyl]-1H-indol-3-yl}propanoic acid | From tert-butyl 3-{5-[({1-[2-(dimethylamino)-4-methylphenyl]-3-methylbutyl}carbamoyl)methyl]-1H-indol-3-yl}propanoate Cpd. 133 following protocol E Yield: 88%; mp: 82, 105° C.; appearance: white solid; 1H NMR, d (ppm): 0.82 (d, 3H, J = 6.4 Hz); 0.86 (d, 3H, J = 6.3 Hz); 1.23-1.38 (m, 1H); 1.49-1.51 (m, 2H); 2.22 (s, 3H); 2.53-2.60 (m, 8H); 2.87 (t, 2H, J = 7.3 Hz); 3.45 (s, 2H); 5.31 (m, 1H); 6.83-6.87 (m, 2H); 6.94 (dd, 1H, J = 8.2 Hz, J = 1.4 Hz); 7.05 (d, 1H, J = 2.2 Hz); 7.19-7.22 (m, 2H); 7.35-7.37 (m, 1H); 8.25 (m, 1H); 10.68 (s, 1H); 12.08 (br s, 1H); m/z: 450.26 [M + H]+ (calc. mass: 449.26). |
| 135 | tert-butyl 3-{5-[({[5-methoxy-2-(piperidin-1-yl)phenyl](phenyl)methyl}carbamoyl)methyl]-1H-indol-3-yl}propanoate | From [5-methoxy-2-(piperidin-1-yl)phenyl](phenyl)methanamine Ex. 89 and 2-{3-[3-(tert-butoxy)-3-oxopropyl]-1H-indol-5-yl}acetic acid Ex. 1 following protocol D Yield: 46%; mp: 69, 81° C.; appearance: white solid; 1H NMR, d (ppm): 1.37 (s, 9H); 1.40-1.51 (m, 6H); 2.37-2.41 (m, 2H); 2.52 (t, 2H, J = 8.1 Hz); 2.71-2.74 (m, 2H); 2.86 (t, 2H, J = 7.5 Hz); 3.56 (s, 2H); 3.62 (s, 3H); 6.58 (d, 1H, J = 8.7 Hz); 6.75 (dd, 1H, J = 8.7 Hz, J = 3.0 Hz); 6.88 (d, 1H, J = 3.0 Hz); 6.99 (dd, 1H, J = 8.4 Hz, J = 1.5 Hz); 7.05-7.28 (m, 8H); 7.38-7.40 (m, 1H); 8.68 (d, 1H, J = 8.9 Hz); 10.67 (s, 1H); m/z: 582.32 [M + H]+ (calc. mass: 581.32). |

TABLE 2-continued

All the NMR were performed in DMSO-d6

| Cpd. | | Starting compounds, Reaction conditions and purification Yield, MP, Appearance, $^1$H NMR (solvent) data, Mass (ES+ or ES−) data |
|---|---|---|
| 136 | 3-{5-[({[5-methoxy-2-(piperidin-1-yl)phenyl](phenyl)methyl}carbamoyl)methyl]-1H-indol-3-yl}propanoic acid | From tert-butyl 3-{5-[({[5-methoxy-2-(piperidin-1-yl)phenyl](phenyl)methyl}carbamoyl)methyl]-1H-indol-3-yl}propanoate Cpd. 135 following protocol E<br>Yield: 93%; mp: 94, 116° C.; appearance: white solid; 1H NMR, d (ppm): 1.40-1.51 (m, 6H); 2.35-2.38 (m, 2H); 2.55 (t, 2H, J = 6.6 Hz); 2.72-2.74 (m, 2H); 2.87 (t, 2H, J = 7.4 Hz); 3.56 (s, 2H); 3.63 (s, 3H); 6.58 (d, 1H, J = 8.7 Hz); 6.75 (dd, 1H, J = 8.7 Hz, J = 3.0 Hz); 6.88 (d, 1H, J = 3.0 Hz); 6.99 (dd, 1H, J = 8.3 Hz, J = 1.4 Hz); 7.06-7.09 (m, 2H); 7.14-7.28 (m, 6H); 7.39-7.41 (m, 1H); 8.70 (d, 1H, J = 8.6 Hz); 10.68 (s, 1H); 12.06 (br s, 1H); m/z: 526.26 [M + H]+ (calc. mass: 525.26). |
| 137 | tert-butyl 3-{5-[({[4-methyl-2-(piperidin-1-yl)phenyl](5-methylthiophen-2-yl)methyl}carbamoyl)methyl]-1H-indol-3-yl}propanoate | From [4-methyl-2-(piperidin-1-yl)phenyl](5-methylthiophen-2-yl)methanamine Ex. 90 and 2-{3-[3-(tert-butoxy)-3-oxopropyl]-1H-indol-5-yl}acetic acid Ex. 1 following protocol D<br>Yield: 60%; mp: 75° C.; appearance: light yellow solid; 1H NMR, d (ppm): 1.38 (s, 9H); 1.45-1.53 (m, 6H); 2.24 (s, 3H); 2.32 (s, 3H); 2.51-2.56 (m, 4H); 2.82-2.89 (m, 4H); 3.52 (s, 2H); 6.78 (dd, 1H, J = 0.8 Hz, J = 3.3 Hz); 6.54 (dd, 1H, J = 1.1 Hz, J = 3.4 Hz); 6.65 (d, 1H, J = 8.7 Hz); 6.88-6.98 (m, 3H); 7.06 (d, 1H, J = 2.2 Hz); 7.21 (d, 1H, J = 8.3 Hz); 7.31 (d, 1H, J = 7.7 Hz); 7.39 (s, 1H); 8.83 (d, 1H, J = 8.8 Hz); 10.68 (s, 1H); m/z: 586.3 [M + H]+ (calc. mass: 585.3). |
| 138 | 3-{5-[({[4-methyl-2-(piperidin-1-yl)phenyl](5-methylthiophen-2-yl)methyl}carbamoyl)methyl]-1H-indol-3-yl}propanoic acid | From tert-butyl 3-{5-[({[4-methyl-2-(piperidin-1-yl)phenyl](5-methylthiophen-2-yl)methyl}carbamoyl)methyl]-1H-indol-3-yl}propanoate Cpd. 137 following protocol E<br>Yield: 92%; mp: 93, 111° C.; appearance: beige solid; 1H NMR, d (ppm): 1.45-1.53 (m, 6H); 2.24 (s, 3H); 2.32 (s, 3H); 2.53-2.58 (m, 4H); 2.85-2.90 (m, 4H); 3.52 (s, 2H); 6.47 (dd, 1H, J = 0.9 Hz, J = 3.4 Hz); 6.54 (dd, 1H, J = 1.1 Hz, J = 3.4 Hz); 6.65 (d, 1H, J = 8.6 Hz); 6.88-6.92 (m, 2H); 6.96 (dd, 1H, J = 1.5 Hz, J = 8.3 Hz); 7.06 (d, 1H, J = 2.3 Hz); 7.21 (d, 1H, J = 8.3 Hz); 7.31 (d, 1H, J = 7.7 Hz); 7.40 (s, 1H); 8.84 (d, 1H, J = 8.9 Hz); 10.68 (d, 1H, J = 1.9 Hz); 12.17 (br s, 1H); m/z: 530.23 [M + H]+ (calc. mass: 529.23). |
| 139 | tert-butyl 3-{5-[({[4-methyl-2-(piperidin-1-yl)phenyl](1,3-thiazol-2-yl)methyl}carbamoyl)methyl]-1H-indol-3-yl}propanoate | From [4-methyl-2-(piperidin-1-yl)phenyl](1,3-thiazol-2-yl)methanamine Ex. 91 and 2-{3-[3-(tert-butoxy)-3-oxopropyl]-1H-indol-5-yl}acetic acid Ex. 1 following protocol D<br>Yield: 20%; mp: 76° C.; appearance: brown solid; -1H NMR, d (ppm): 1.38 (s, 9H); 1.44-1.54 (m, 6H); 2.24 (s, 3H); 2.53-2.63 (m, 4H); 2.84-2.89 (m, 4H); 3.58 (s, 2H); 6.78 (d, 1H, J = 8.2 Hz); 6.88 (d, 1H, J = 8.0 Hz); 6.96-7.00 (m, 2H); 7.06 (d, 1H, J = 2.2 Hz); 7.17-7.23 (m, 2H); 7.41 (s, 1H); 7.55 (d, 1H, J = 3.3 Hz); 7.67 (d, 1H, J = 3.3 Hz); 8.99 (d, 1H, J = 8.2 Hz); 10.68 (d, 1H, J = 1.9 Hz); m/z: 573.28 [M + H]+ (calc. mass: 572.28). |
| 140 | 3-{5-[({[4-methyl-2-(piperidin-1-yl)phenyl](1,3-thiazol-2-yl)methyl}carbamoyl)methyl]-1H-indol-3-yl}propanoic acid | From tert-butyl 3-{5-[({[4-methyl-2-(piperidin-1-yl)phenyl](1,3-thiazol-2-yl)methyl}carbamoyl)methyl]-1H-indol-3-yl}propanoate Cpd. 139 following protocol E<br>Yield: 54%; mp: 101, 115° C.; appearance: beige solid; 1H NMR, d (ppm): 1.44-1.55 (m, 6H); 2.24 (s, 3H); 2.53-2.63 (m, 4H); 2.85-2.91 (m, 4H); 3.59 (s, 2H); 6.78 (d, 1H, J = 8.2 Hz); 6.88 (d, 1H, J = 7.9 Hz); 6.97-7.00 (m, 2H); 7.07 (d, 1H, J = 2.2 Hz); 7.18 (d, 1H, J = 7.9 Hz); 7.22 (d, 1H, J = 8.3 Hz); 7.42 (s, 1H); 7.54 (d, 1H, J = 3.2 Hz); 7.67 (d, 1H, J = 3.2 Hz); 8.99 (d, 1H, J = 8.3 Hz); 10.68 (d, 1H, J = 1.8 Hz); 10.07 (br s, 1H); m/z: 517.21 [M + H]+ (calc. mass: 516.21). |
| 141 | tert-butyl 3-{5-[({[2-(azepan-1-yl)-4-methoxyphenyl](phenyl)methyl}carbamoyl)methyl]-1H-indol-3-yl}propanoate | From [2-(azepan-1-yl)-4-methoxyphenyl](phenyl)methanamine Ex. 92 and 2-{3-[3-(tert-butoxy)-3-oxopropyl]-1H-indol-5-yl}acetic acid Ex. 1 following protocol D<br>Yield: 60%; mp: 67, 80° C.; appearance: white solid; 1H NMR, d (ppm): 1.35 (s, 9H); 1.37-1.44 (m, 2H); 1.53-1.58 (m, 6H); 5.53 (t, 2H, J = 8.0 Hz); 2.79-2.89 (m, 4H); 2.94-2.98 (m, 2H); 3.54 (m, 2H); 3.69 (s, 3H); 6.59-6.67 (m, 3H); 6.98 (dd, 1H, J = 8.3 Hz, J = 1.5 Hz); 7.06 (d, 1H, J = 2.2 Hz); 7.10-7.27 (m, 7H); 7.38-7.40 (m, 1H); 8.63 (d, 1H, J = 8.5 Hz); 10.67 (s, 1H); m/z: 596.34 [M + H]+ (calc. mass: 595.34). |
| 142 | 3-{5-[({[2-(azepan-1-yl)-4-methoxyphenyl](phenyl)methyl}carbamoyl)methyl]-1H-indol-3-yl}propanoic acid | From tert-butyl 3-{5-[({[2-(azepan-1-yl)-4-methoxyphenyl](phenyl)methyl}carbamoyl)methyl]-1H-indol-3-yl}propanoate Cpd. 141 following protocol E<br>Yield: 99%; mp: 72, 125° C.; appearance: white solid; 1H NMR, d (ppm): 1.44-1.55 (m, 8H); 2.54 (t, 2H, J = 8.3 Hz); 2.78-2.90 (m, 4H); 2.94-3.02 (m, 2H); 3.32 (s, 2H); 3.54 (s, |

TABLE 2-continued

All the NMR were performed in DMSO-d6

| Cpd. | | Starting compounds, Reaction conditions and purification Yield, MP, Appearance, $^1$H NMR (solvent) data, Mass (ES+ or ES−) data |
|---|---|---|
| | | 3H); 6.59-6.67 (m, 3H); 6.97 (dd, 1H, J = 8.3 Hz, J = 1.4 Hz); 7.05 (d, 1H, J = 2.2 Hz); 7.10-7.27 (m, 7H); 7.39-7.41 (m, 1H); 8.65 (d, 1H, J = 8.5 Hz); 10.68 (s, 1H); 12.00 (br s, 1H); m/z: 540.27 [M + H]+ (calc. mass: 539.27). |
| 143 | tert-butyl 3-{5-[({1-[2-(piperidin-1-yl)phenyl]cyclohexyl}carbamoyl)methyl]-1H-indol-3-yl}propanoate | From 1-[2-(piperidin-1-yl)phenyl]cyclohexan-1-amine Ex. 114 and 2-{3-[3-(tert-butoxy)-3-oxopropyl]-1H-indol-5-yl}acetic acid Ex. 1 following protocol D Yield: 42%; mp: 164, 166° C.; appearance: white solid; 1H NMR, d (ppm): 1.27-1.80 (m, 12H); 1.37 (s, 9H); 1.96-2.03 (m, 2H); 2.37-2.45 (m, 2H); 2.53 (t, 2H, J = 8.1 Hz); 2.63-2.65 (m, 4H); 2.87 (t, 2H, J = 8.1 Hz); 3.53 (s, 2H); 6.99-7.06 (m, 3H); 7.14-7.35 (m, 5H); 7.44 (s, 1H); 10.71 (br s, 1H); m/z: 544.34 [M + H]+ (calc. mass: 543.34). |
| 144 | 3-{5-[({1-[2-(piperidin-1-yl)phenyl]cyclohexyl}carbamoyl)methyl]-1H-indol-3-yl}propanoic acid | From tert-butyl 3-{5-[({1-[2-(piperidin-1-yl)phenyl]cyclohexyl}carbamoyl)methyl]-1H-indol-3-yl}propanoate Cpd. 143 following protocol E Yield: 88%; mp: 113, 229° C.; appearance: white solid; 1H NMR, d (ppm): 1.24-1.75 (m, 12H); 1.97-2.04 (m, 2H); 2.40-2.45 (m, 2H); 2.55 (t, 2H, J = 7.8 Hz); 2.63-2.65 (m, 4H); 2.89 (t, 2H, J = 7.8 Hz); 3.54 (s, 2H); 7.00-7.34 (m, 7H); 7.45 (br s, 1H); 10.68 (br s, 1H); m/z: 488.28 [M + H]+ (calc. mass: 487.28). |
| 145 | tert-butyl 3-{5-[({[4-methyl-2-(propan-2-yloxy)phenyl](phenyl)methyl}carbamoyl)methyl]-1H-indol-3-yl}propanoate | From [4-methyl-2-(propan-2-yloxy)phenyl](phenyl)methanamine Ex. 95 and 2-{3-[3-(tert-butoxy)-3-oxopropyl]-1H-indol-5-yl}acetic acid Ex. 1 following protocol D Yield: 49%; mp: 47, 68° C.; appearance: white powder; 1H NMR, d (ppm): 0.92 (d, 3H, J = 6.0 Hz); 1.04 (d, 3H, J = 6.0 Hz); 1.38 (s, 9H); 2.23 (s, 3H); 2.73 (t, 2H, J = 8.2 Hz); 2.86 (t, 2H); 3.55 (s, 2H); 4.44-4.46 (m, 1H); 6.26 (d, 1H, J = 8.9 Hz); 6.67-6.73 (m, 2H); 6.98 (dd, 1H, J = 8.3 Hz, J = 1.5 Hz); 7.06 (d, 1H, J = 2.3 Hz); 7.12-7.23 (m, 7H); 7.40-7.42 (m, 1H); 8.43 (d, 1H, J = 8.8 Hz); 10.68 (s, 1H); m/z: 541.29 [M + H]+ (calc. mass: 540.29). |
| 146 | 3-{5-[({[4-methyl-2-(propan-2-yloxy)phenyl](phenyl)methyl}carbamoyl)methyl]-1H-indol-3-yl}propanoic acid | From tert-butyl 3-{5-[({[4-methyl-2-(propan-2-yloxy)phenyl](phenyl)methyl}carbamoyl)methyl]-1H-indol-3-yl}propanoate Cpd. 145 following protocol E Yield: 95%; mp: 61, 94° C.; appearance: white powder; 1H NMR, d (ppm): 0.92 (d, 3H, J = 6.0 Hz); 1.04 (d, 3H, J = 6.0 Hz); 2.23 (s, 3H); 2.56 (t, 2H, J = 6.5 Hz); 2.88 (t, 2H, J = 7.8 Hz); 3.55 (s, 2H); 4.43-4.47 (m, 1H); 6.27 (d, 1H, J = 8.8 Hz); 6.67-6.73 (m, 2H); 6.98 (dd, 1H, J = 8.3 Hz, J = 1.5 Hz); 7.06 (d, 1H, J = 2.2 Hz); 7.12-7.26 (m, 7H); 7.40-7.42 (m, 1H); 8.46 (d, 1H, J = 9.0 Hz); 10.70 (s, 1H); 12.04 (br s, 1H); m/z: 485.23 [M + H]+ (calc. mass: 484.23). |
| 147 | tert-butyl 3-[5-({[(5-methylfuran-2-yl)[2-(piperidin-1-yl)phenyl]methyl]carbamoyl}methyl)-1H-indol-3-yl]propanoate | From (5-methylfuran-2-yl)[2-(piperidin-1-yl)phenyl]methanamine Ex. 100 and 2-{3-[3-(tert-butoxy)-3-oxopropyl]-1H-indol-5-yl}acetic acid Ex. 1 following protocol D Yield: 70%; appearance: colorless oil; 1H NMR, d (ppm): 1.37 (s, 9H); 1.4-1.7 (m, 6H); 2.16 (s, 3H); 2.5-2.6 (m, 4H); 2.7-2.9 (m, 4H); 3.50 (s, 2H); 5.81 (d, 1H, J = 3.0 Hz); 5.93 (m, 1H); 6.53 (d, 1H, J = 8.7 Hz); 6.95 (dd, 1H, J = 8.3 Hz, J = 1.6 Hz); 7.03-7.15 (m, 3H); 7.15-7.25 (m, 2H); 7.3-7.4 (m, 2H); 8.72 (d, 1H, J = 8.7 Hz); 10.67 (s, 1H); m/z: 556.3 [M + H]+ (calc. mass: 555.3). |
| 148 | 3-[5-({[(5-methylfuran-2-yl)[2-(piperidin-1-yl)phenyl]methyl]carbamoyl}methyl)-1H-indol-3-yl]propanoic acid | From tert-butyl 3-[5-({[(5-methylfuran-2-yl)[2-(piperidin-1-yl)phenyl]methyl]carbamoyl}methyl)-1H-indol-3-yl]propanoate Cpd. 147 following protocol E Yield: 78%; mp: 88, 98° C.; appearance: white solid; 1H NMR, d (ppm): 1.4-1.7 (m, 6H); 2.17 (s, 3H); 2.5-2.6 (m, 4H); 2.70-2.8 (m, 2H); 2.87 (t, 2H, J = 7.3 Hz); 3.50 (s, 2H); 5.81 (d, 1H, J = 3.0 Hz); 5.92 (m, 1H); 6.53 (d, 1H, J = 8.7 Hz); 6.95 (dd, 1H, J = 8.3 Hz, J = 1.6 Hz); 7.03-7.15 (m, 3H); 7.15-7.25 (m, 2H); 7.3-7.4 (m, 2H); 8.73 (d, 1H, J = 8.7 Hz); 10.67 (s, 1H); 12.03 (br s, 1H); m/z: 500.24 [M + H]+ (calc. mass: 499.24). |
| 149 | tert-butyl 3-{5-[({[4-ethoxy-2-(piperidin-1-yl)phenyl](phenyl)methyl}carbamoyl)methyl]-1H-indol-3-yl}propanoate | From [4-ethoxy-2-(piperidin-1-yl)phenyl](phenyl)methanamine Ex. 98 and 2-{3-[3-(tert-butoxy)-3-oxopropyl]-1H-indol-5-yl}acetic acid Ex. 1 following protocol D Yield: 61%; mp: 67, 70° C.; appearance: white solid; 1H NMR, d (ppm): 1.25 (t, 3H, J = 7.0 Hz); 1.38 (s, 9H); 1.42-1.53 (m, 6H); 2.50-2.55 (m, 4H); 2.84-2.89 (m, 4H); 3.55 (s, |

TABLE 2-continued

All the NMR were performed in DMSO-d6

| Cpd. | | Starting compounds, Reaction conditions and purification Yield, MP, Appearance, $^1$H NMR (solvent) data, Mass (ES+ or ES−) data |
|---|---|---|
| | | 2H); 3.95 (q, 2H, J = 7.0 Hz); 6.50 (d, 1H, J = 8.6 Hz); 6.61-6.64 (m, 2H); 6.97 (dd, 1H, J = 1.5 Hz, J = 8.3 Hz); 7.06 (d, 1H, J = 2.3 Hz); 7.12-7.16 (m, 4H); 7.20-7.26 (m, 3H); 7.39 (s, 1H); 8.64 (d, 1H, J = 8.6 Hz); 10.68 (d, 1H, J = 1.9 Hz); m/z: 596.34 [M + H]+ (calc. mass: 595.34). |
| 150 | 3-{5-[({[4-ethoxy-2-(piperidin-1-yl)phenyl](phenyl)methyl}carbamoyl)methyl]-1H-indol-3-yl}propanoic acid | From tert-butyl 3-{5-[({[4-ethoxy-2-(piperidin-1-yl)phenyl](phenyl)methyl}carbamoyl)methyl]-1H-indol-3-yl}propanoate Cpd. 149 following protocol E Yield: 45%; mp: 96, 105° C.; appearance: white solid; 1H NMR, d (ppm): 1.28 (t, 3H, J = 6.9 Hz); 1.42-1.55 (m, 6H); 2.50-2.58 (m, 4H); 2.82-2.90 (m, 4H); 3.55 (s, 2H); 3.95 (q, 2H, J = 7.0 Hz); 6.50 (d, 1H, J = 8.6 Hz); 6.61-6.64 (m, 2H); 6.97 (dd, 1H, J = 1.4 Hz, J = 8.3 Hz); 7.06 (d, 1H, J = 2.2 Hz); 7.11-7.16 (m, 4H); 7.20-7.26 (m, 3H); 7.40 (s, 1H); 8.64 (d, 1H, J = 8.5 Hz); 10.67 (d, 1H, J = 1.8 Hz); 12.05 (br s, 1H); m/z: 540.27 [M + H]+ (calc. mass: 539.27). |
| 151 | tert-butyl 3-{5-[({phenyl[2-(piperidin-1-yl)-4-(propan-2-yloxy)phenyl]methyl}carbamoyl)methyl]-1H-indol-3-yl}propanoate | From phenyl[2-(piperidin-1-yl)-4-(propan-2-yloxy)phenyl]methanamine Ex. 99 and 2-{3-[3-(tert-butoxy)-3-oxopropyl]-1H-indol-5-yl}acetic acid Ex. 1 following protocol D Yield: %; appearance: pale yellow solid; 1H NMR, d (ppm): 1.22 (dd, 6H, J = 0.7 Hz, J = 6.0 Hz); 1.38 (s, 9H); 1.42-1.58 (m, 6H); 2.50-2.55 (m, 4H); 2.83-2.89 (m, 4H); 3.55 (s, 2H); 4.49-4.55 (m, 1H); 6.50 (d, 1H, J = 8.6 Hz); 6.58-6.63 (m, 2H); 6.97 (dd, 1H, J = 1.5 Hz, J = 8.3 Hz); 7.06 (d, 1H, J = 2.3 Hz); 7.11-7.27 (m, 7H); 7.39 (s, 1H); 8.64 (d, 1H, J = 8.7 Hz); 10.68 (d, 1H, J = 1.9 Hz); m/z: 610.35 [M + H]+ (calc. mass: 609.35). |
| 152 | 3-{5-[({phenyl[2-(piperidin-1-yl)-4-(propan-2-yloxy)phenyl]methyl}carbamoyl)methyl]-1H-indol-3-yl}propanoic acid | From tert-butyl 3-{5-[({phenyl[2-(piperidin-1-yl)-4-(propan-2-yloxy)phenyl]methyl}carbamoyl)methyl]-1H-indol-3-yl}propanoate Cpd. 151 following protocol E Yield: 43%; mp: 93, 111° C.; appearance: white solid; 1H NMR, d (ppm): 1.21 (dd, 6H, J = 1.0 Hz, J = 6.0 Hz); 1.42-1.55 (m, 6H); 2.50-2.58 (m, 4H); 2.82-2.90 (m, 4H); 3.55 (s, 2H); 4.49-4.57 (m, 1H); 6.50 (d, 1H, J = 8.6 Hz); 6.58-6.63 (m, 2H); 6.98 (dd, 1H, J = 1.5 Hz, J = 8.3 Hz); 7.06 (d, 1H, J = 2.2 Hz); 7.12-7.17 (m, 4H); 7.20-7.27 (m, 3H); 7.41 (s, 1H); 8.64 (d, 1H, J = 8.6 Hz); 10.67 (d, 1H, J = 1.9 Hz); 12.00 (br s, 1H); m/z: 554.29 [M + H]+ (calc. mass: 553.29). |
| 153 | tert-butyl 3-[5-({[(5-methyl-1,3-thiazol-2-yl)[2-(piperidin-1-yl)phenyl]methyl]carbamoyl}methyl)-1H-indol-3-yl]propanoate | From (5-methyl-1,3-thiazol-2-yl)[2-(piperidin-1-yl)phenyl]methanamine Ex. 106 and 2-{3-[3-(tert-butoxy)-3-oxopropyl]-1H-indol-5-yl}acetic acid Ex. 1 following protocol D Yield: 27%; appearance: colorless oil; 1H NMR, d (ppm): 1.38 (s, 9H); 1.4-1.7 (m, 6H); 2.34 (d, 3H, J = 1.0 Hz); 2.55-2.7 (m, 4H); 2.8-3.0 (m, 4H); 3.54 (s, 2H); 6.77 (d, 1H, J = 8.4 Hz); 6.95 (dd, 1H, J = 8.3 Hz, J = 1.6 Hz); 7.00-7.30 (m, 7H); 7.41 (s, 1H); 8.98 (d, 1H, J = 8.4 Hz); 10.67 (s, 1H); m/z: 573.28 [M + H]+ (calc. mass: 572.28). |
| 154 | 3-[5-({[(5-methyl-1,3-thiazol-2-yl)[2-(piperidin-1-yl)phenyl]methyl]carbamoyl}methyl)-1H-indol-3-yl]propanoic acid | From tert-butyl 3-[5-({[(5-methyl-1,3-thiazol-2-yl)[2-(piperidin-1-yl)phenyl]methyl]carbamoyl}methyl)-1H-indol-3-yl]propanoate Cpd. 153 following protocol E Yield: 97%; mp: 98, 128° C.; appearance: light yellow solid; 1H NMR, d (ppm): 1.4-1.7 (m, 6H); 2.26 (d, 3H, J = 1.0 Hz); 2.5-2.65 (m, 4H); 2.8-3.0 (m, 4H); 3.58 (s, 2H); 6.77 (d, 1H, J = 8.4 Hz); 6.95 (dd, 1H, J = 8.3 Hz, J = 1.6 Hz); 7.00-7.35 (m, 7H); 7.42 (s, 1H); 8.98 (d, 1H, J = 8.4 Hz); 10.67 (s, 1H); m/z: 517.21 [M + H]+ (calc. mass: 516.21). |
| 155 | tert-butyl 3-[5-({[(2-methyl-1,3-thiazol-5-yl)[2-(piperidin-1-yl)phenyl]methyl]carbamoyl}methyl)-1H-indol-3-yl]propanoate | From (2-methyl-1,3-thiazol-5-yl)[2-(piperidin-1-yl)phenyl]methanamine Ex. 105 and 2-{3-[3-(tert-butoxy)-3-oxopropyl]-1H-indol-5-yl}acetic acid Ex. 1 following protocol D Yield: 80%; appearance: white solid; 1H NMR, d (ppm): 1.39 (s, 9H); 1.4-1.7 (m, 6H); 2.5-2.6 (m, 7H); 2.8-3.0 (m, 4H); 3.54 (s, 2H); 6.77 (d, 1H, J = 8.4 Hz); 6.95 (dd, 1H, J = 8.3 Hz, J = 1.6 Hz); 7.00-7.30 (m, 6H); 7.38 (s, 1H); 7.44 (dd, 1H, J = 7.6 Hz, J = 1.5 Hz); 9.00 (d, 1H, J = 8.4 Hz); 10.67 (s, 1H); m/z: 573.28 [M + H]+ (calc. mass: 572.28). |
| 156 | 3-[5-({[(2-methyl-1,3-thiazol-5-yl)[2-(piperidin-1-yl)phenyl]methyl]carbamoyl}methyl)-1H-indol-3-yl]propanoic acid | From tert-butyl 3-[5-({[(2-methyl-1,3-thiazol-5-yl)[2-(piperidin-1-yl)phenyl]methyl]carbamoyl}methyl)-1H-indol-3-yl]propanoate Cpd. 155 following protocol E Yield: 92%; mp: 100, 130° C.; appearance: light yellow solid; 1H NMR, d (ppm): 1.4-1.7 (m, 6H); 2.5-2.6 (m, 7H); 2.8-3.0 (m, 4H); 3.54 (s, 2H); 6.77 (d, 1H, J = 8.4 Hz); 6.95 (dd, 1H, J = 8.3 Hz, J = 1.6 Hz); 7.05-7.30 (m, 6H); 7.40 (s, 1H); |

TABLE 2-continued

*All the NMR were performed in DMSO-d6*

| Cpd. | | Starting compounds, Reaction conditions and purification Yield, MP, Appearance, $^1$H NMR (solvent) data, Mass (ES+ or ES−) data |
|---|---|---|
| | | 7.44 (dd, 1H, J = 7.6 Hz, J = 1.5 Hz); 9.00 (d, 1H, J = 8.4 Hz); 10.67 (s, 1H); 12.00 (br s, 1H); m/z: 517.21 [M + H]+ (calc. mass: 516.21). |
| 157 | tert-butyl 3-[5-({[(3-methylphenyl)[2-(piperidin-1-yl)phenyl]methyl]carbamoyl}methyl)-1H-indol-3-yl]propanoate | From (3-methylphenyl)[2-(piperidin-1-yl)phenyl]methanamine Ex. 108 and 2-{3-[3-(tert-butoxy)-3-oxopropyl]-1H-indol-5-yl}acetic acid Ex. 1 following protocol D Yield: 50%; mp: 53, 71° C.; appearance: white solid; 1H NMR, d (ppm): 1.37 (s, 9H); 1.57-1.58 (m, 6H); 2.18 (s, 3H); 2.50-2.55 (m, 4H); 2.83-2.88 (m, 4H); 3.55 (s, 2H); 6.56 (d, 1H, J = 8.6 Hz); 6.94-7.22 (m, 10H); 7.29 (dd, 1H, J = 7.6 Hz, J = 1.5 Hz); 7.38-7.40 (m, 1H); 8.66 (d, 1H, J = 8.5 Hz); 10.67 (s, 1H); m/z: 566.33 [M + H]+ (calc. mass: 565.33). |
| 158 | 3-[5-({[(3-methylphenyl)[2-(piperidin-1-yl)phenyl]methyl]carbamoyl}methyl)-1H-indol-3-yl]propanoic acid | From tert-butyl 3-[5-({[(3-methylphenyl)[2-(piperidin-1-yl)phenyl]methyl]carbamoyl}methyl)-1H-indol-3-yl]propanoate Cpd. 157 following protocol E Yield: 79%; mp: 84, 110° C.; appearance: white solid; 1H NMR, d (ppm): 1.44-1.56 (m, 6H); 2.18 (s, 3H); 2.53-2.56 (m, 4H); 2.84-2.89 (m, 4H); 3.55 (s, 2H); 6.56 (d, 1H, J = 8.6 Hz); 6.94-7.22 (m, 10H); 7.29 (dd, 1H, J = 7.6 Hz, J = 1.5 Hz); 7.40-7.42 (m, 1H); 8.68 (d, 1H, J = 8.7 Hz); 10.67 (s, 1H); 12.10 (br s, 1H); m/z: 510.26 [M + H]+ (calc. mass: 509.26). |
| 159 | ethyl 3-{5-[({[4-methyl-2-(propan-2-yloxy)phenyl]phenyl}methyl}carbamoyl)methyl]-1H-indazol-3-yl}propanoate | Step 1: to a solution of 2-(1H-indazol-5-yl)acetic acid 137 mg, 0.78 mmol) in DMF (3 mL) were added DMAP (232 mg, 1.90 mmol), EDCl•HCl (182 mg, 0.95 mmol) and [4-methyl-2-(propan-2-yloxy)phenyl](phenyl)methanamine Ex. 95 (220 mg, 0.86 mmol). The reaction mixture was stirred at rt for 2 h. Sat. NH4Cl was added and the aqueous layer was extracted with EtOAc. The organic layer was washed with sat. NH4Cl, dried over MgSO4, filtered and the solution was concentrated to dryness. The crude material was purified on silica gel column chromatography using Cyclohexane/EtOAc (6:4) as eluent affording 2-(1H-indazol-5-yl)-N-((2-isopropoxy-4-methylphenyl)(phenyl)methyl) acetamide as white solid (yield: 81%). 1H NMR (300 MHz, DMSO-d6, d en ppm): 0.93 (d, 3H, J = 6.0 Hz); 1.06 (d, 3H, J = 6.0 Hz); 2.23 (s, 3H); 3.60 (s, 2H); 4.43-4.51 (m, 1H); 6.26 (d, 1H, J = 8.7 Hz); 6.67 (d, 1H, J = 7.8 Hz); 6.74 (s, 1H); 7.12-7.16 (m, 3H); 7.17-7.28 (m, 4H); 7.44 (d, 1H, J = 8.5 Hz); 7.60 (s, 1H); 7.99 (s, 1H); 8.56 (d, 1H, J = 8.7 Hz); 12.95 (s, 1H). Step 2: to a solution of 2-(1H-indazol-5-yl)-N-((2-isopropoxy-4-methylphenyl)(phenyl)methyl)acetamide (275 mg, 0.67 mmol) and KOH (138 mg, 2.46 mmol) in DMF (3 mL) was added iodine (169 mg, 0.67 mmol). The reaction mixture was stirred at rt for 18 h. Sodium thiosulfate 10% was added to quench the reaction. The precipitate formed was filtered-off, washed with water and dried under reduced pressure until constant weight affording 2-(3-iodo-1H-indazol-5-yl)-N-((2-isopropoxy-4-methylphenyl)(phenyl)methyl)acetamide as pale orange solid (yield: 84%). The compound was pure enough and used in the next step without further purification. 1H NMR (300 MHz, DMSO-d6, d in ppm): 0.95 (d, 3H, J = 6.0 Hz); 1.07 (d, 3H, J = 6.0 Hz); 2.24 (s, 3H); 3.64 (s, 2H); 4.44-4.52 (m, 1H); 6.27 (d, 1H, J = 8.7 Hz); 6.69 (d, 1H, J = 7.7 Hz); 6.78 (s, 1H); 7.13-7.19 (m, 4H); 7.23-7.28 (m, 2H); 7.32-7.35 (m, 2H); 7.44-7.48 (m, 1H); 8.64 (d, 1H, J = 8.8 Hz); 13.40 (br s, 1H). Step 3: to a solution of 2-(3-iodo-1H-indazol-5-yl)-N-((2-isopropoxy-4-methylphenyl)(phenyl)methyl)acetamide (290 mg, 0.54 mmol) in CH2Cl2 (20 mL) was added DMAP (10 mg, 0.08 mmol) followed by di-tert-butyl dicarbonate (123 mg, 0.57 mmol). The solution was stirred at rt for 2 h. Water was added to quench the reaction. The two phases were partitionated. The aqueous layer was extracted once more with CH2Cl2. The combined organic layers were dried over MgSO4, filtered and the solution was concentrated under reduced pressure. The crude material was triturated in Et2O and filtered-off to afford tert-butyl 5-(((2-isopropoxy-4-methylphenyl)(phenyl)methylcarbamoyl)methyl)-3-iodo-1H-indazole-1-carboxylate as yellow solid (yield: 94%). The compound was pure enough and used in the next step |

| Cpd. | Starting compounds, Reaction conditions and purification Yield, MP, Appearance, ¹H NMR (solvent) data, Mass (ES+ or ES−) data |
|---|---|
| | without further purification. 1H NMR (300 MHz, DMSO-d6, d in ppm): 0.97 (d, 3H, J = 6.0 Hz); 1.10 (d, 3H, J = 6.0 Hz); 1.63 (s, 9H); 2.24 (s, 3H); 3.70 (s, 2H); 4.45-4.54 (m, 1H); 6.27 (d, 1H, J = 8.6 Hz); 6.69 (d, 1H, J = 7.6 Hz); 7.76 (s, 1H); 7.11-7.2 (m, 4H); 7.24-7.29 (m, 2H); 7.48 (s, 1H); 7.58 (dd, 1H, J = 8.6 Hz, J = 1.5 Hz); 7.97 (d, 1H, J = 8.6 Hz); 7.73 (d, 1H, J = 8.6 Hz). Step 4: to a solution of tert-butyl 5-(((2-isopropoxy-4-methylphenyl)(phenyl)methylcarbamoyl) methyl)-3-iodo-1H-indazole-1-carboxylate (310 mg, 0.48 mmol), Pd(OAc)2 (3 mg, 0.012 mmol), triphenylphosphine (6 mg, 0.024 mmol) and triethylamine (390 mg, 3.9 mmol) in dry dioxane (3 mL) was added ethyl acrylate (390 mg, 3.9 mmol) under N2 atmosphere. The reaction mixture was stirred at 80° C. and under N2 atmosphere overnight. The solution was concentrated to dryness. The crude material was purified on silica gel column chromatography using Cyclohexane/EtOAc (9:1) as eluent affording tert-butyl 5-(((2-isopropoxy-4-methylphenyl)(phenyl)methylcarbamoyl) methyl)-3-(2-(ethoxycarbonyl)vinyl)-1H-indazole-1-carboxylate as yellow solid (yield: 95%). 1H NMR (300 MHz, DMSO-d6, d in ppm): 0.99 (d, 3H, J = 5.9 Hz); 1.09 (d, 3H, J = 6.0 Hz); 1.31 (t, 3H, J = 7.1 Hz); 1.66 (s, 9H); 2.24 (s, 3H); 3.73 (s, 2H); 4.27 (q, 2H, J = 7.1 Hz); 4.45-4.54 (m, 1H); 6.29 (d, 1H, J = 8.5 Hz); 6.67 (d, 1H, J = 7.9 Hz); 6.79 (s, 1H); 6.94 (d, 1H, J = 16.4 Hz); 7.11-7.28 (m, 6H); 7.58 (d, 1H); 7.83 (d, 1H, J = 16.4 Hz); 8.06 (d, 1H, J = 8.7 Hz); 8.15 (s, 1H); 8.70 (d, 1H, J = 8.7 Hz). Step 5: tert-butyl 5-(((2-isopropoxy-4-methylphenyl)(phenyl)methylcarbamoyl)methyl)-3-(2-(ethoxycarbonyl)vinyl)-1H-indazole-1-carboxylate (190 mg, 0.31 mmol) was dissolved in EtOH/THF (7 mL + 7 mL) with small amount of Pd/C 10%. The reaction mixture was stirred under H2 atmosphere at rt for 18 h. The reaction mixture was filtered-off on Celite. The solution was concentrated under reduced pressure and purified on silica gel column chromatography using Cyclohexane/EtOAc (95:5 to 7:3) as eluent to give tert-butyl 5-(((2-isopropoxy-4-methylphenyl)(phenyl)methylcarbamoyl)methyl)-3-(2-(ethoxycarbonyl)ethyl)-1H-indazole-1-carboxylate as white solid (yield: 78%). 1H NMR (300 MHz, DMSO-d6, d in ppm): 0.96 (d, 6H, J = 6.0 Hz); 1.11 (t, 3H, J = 7.0 Hz); 1.62 (s, 9H); 2.24 (s, 3H); 2.80 (t, 2H, J = 7.5 Hz); 3.15 (t, 2H, J = 7.1 Hz); 3.67 (s, 2H); 4.05 (q, 2H, J = 7.1 Hz); 4.45-4.53 (m, 1H); 6.28 (d, 1H, J = 8.8 Hz); 6.69 (d, 1H, J = 7.6 Hz); 6.67 (s, 1H); 7.13-7.28 (m, 6H); 7.49 (dd, 1H, J = 8.7 Hz, J = 1.5 Hz); 7.73 (s, 1H); 7.93 (d, 1H, J = 8.5 Hz); 8.67 (d, 1H, J = 8.7 Hz). Step 6: to a solution of tert-butyl 5-(((2-isopropoxy-4-methylphenyl)(phenyl)methylcarbamoyl)methyl)-3-(2-(ethoxycarbonyl)ethyl)-1H-indazole-1-carboxylate (150 mg, 0.24 mmol) in CH2Cl2 (2 mL) was added TFA (94 µL, 1.22 mmol). The reaction mixture was stirred at rt overnight. Additional TFA (94 µL, 1.22 mmol) was added to the reaction mixture. The reaction was monitored by TLC. Water was added to quench the reaction. The remaining TFA was neutralized with NaHCO3 10%. The aqueous layer was extracted with CH2Cl2. The combined organic layers were dried over MgSO4, filtered and the solution was concentrated to dryness. The crude material was purified on silica gel column chromatography using Cyclohexane/EtOAc (7:3) as eluent affording ethyl 3-(5-(((2-isopropoxy-4-methylphenyl)(phenyl)methylcarbamoyl)methyl)-1H-indazol-3-yl)propanoate Yield: 60%; mp: 68, 70° C.; appearance: white solid; 1H NMR, d (ppm): 0.94 (d, 3H, J = 6.0 Hz); 1.07 (d, 3H, J = 6.0 Hz); 1.14 (t, 3H, J = 7.1 Hz); 2.23 (s, 3H); 2.86 (t, 2H, J = 7.7 Hz); 3.11 (t, 2H, J = 7.3 Hz); 3.60 (s, 2H); 4.04 (q, 2H, J = 7.1 Hz); 4.44-4.50 (m, 1H); 6.58 (d, 1H, J = 8.8 Hz); 6.68 (d, 1H, J = 7.6 Hz); 6.75 (s, 1H); 7.13-7.27 (m, 7H); 7.36 (d, 1H, J = 8.5 Hz); 7.58 (s, 1H); 8.58 (d, 1H, J = 8.7 Hz); 12.59 (s, 1H); m/z: 514.26 [M + H]+ (calc. mass: 513.26). |

TABLE 2-continued

*All the NMR were performed in DMSO-d6*

| Cpd. | | Starting compounds, Reaction conditions and purification Yield, MP, Appearance, $^1$H NMR (solvent) data, Mass (ES+ or ES−) data |
|---|---|---|
| 160 | 3-{5-[({[4-methyl-2-(propan-2-yloxy)phenyl](phenyl)methyl}carbamoyl)methyl]-1H-indazol-3-yl}propanoic acid | From ethyl 3-{5-[({[4-methyl-2-(propan-2-yloxy)phenyl](phenyl)methyl}carbamoyl)methyl]-1H-indazol-3-yl}propanoate Cpd. 159 following protocol E<br>Yield: 81%; mp: 126, 132° C.; appearance: white solid; 1H NMR, d (ppm): 0.94 (d, 3H, J = 6.0 Hz); 1.06 (d, 3H, J = 6.0 Hz); 2.23 (s, 3H); 2.60 (t, 2H, J = 7.3 Hz); 3.06 (t, 2H, J = 7.3 Hz); 3.59 (s, 2H); 4.42-4.51 (m, 1H); 6.27 (d, 1H, J = 8.7 Hz); 6.68 (d, 1H, J = 7.7 Hz); 6.74 (s, 1H); 7.13-7.18 (m, 4H); 7.21-7.27 (m, 3H); 7.35 (d, 1H, J = 8.5 Hz); 7.60 (s, 1H); 8.59 (d, 1H, J = 8.8 Hz); 12.55 (br s, 1H); m/z: 486.23 [M + H]+ (calc. mass: 485.23). |
| 161 | tert-butyl 3-{5-[({2-cyclohexyl-1-[2-(piperidin-1-yl)phenyl]ethyl}carbamoyl)methyl]-1H-indol-3-yl}propanoate | From 2-cyclohexyl-1-[2-(piperidin-1-yl)phenyl]ethan-1-amine Ex. 41 and 2-{3-[3-(tert-butoxy)-3-oxopropyl]-1H-indol-5-yl}acetic acid Ex. 1 following protocol D<br>Yield: 66%; mp: 69° C.; appearance: white solid; 1H NMR, d (ppm): 0.78-1.13 (m, 6H); 1.21-1.29 (m, 1H); 1.38 (s, 9H); 1.42-1.76 (m, 12H); 2.47-2.57 (m, 4H); 2.88 (t, 2H, J = 7.6 Hz); 3.04-3.15 (m, 2H); 3.40-3.52 (m, 2H); 5.31-5.39 (m, 1H); 6.97-7.22 (m, 6H); 7.32 (dd, 1H, J = 1.4 Hz, J = 7.4 Hz); 7.38 (s, 1H); 8.31 (d, 1H, J = 8.6 Hz); 10.67 (d, 1H, J = 1.9 Hz); m/z: 572.37 [M + H]+ (calc. mass: 571.37). |
| 162 | 3-{5-[({2-cyclohexyl-1-[2-(piperidin-1-yl)phenyl]ethyl}carbamoyl)methyl]-1H-indol-3-yl}propanoic acid | From tert-butyl 3-{5-[({2-cyclohexyl-1-[2-(piperidin-1-yl)phenyl]ethyl}carbamoyl)methyl]-1H-indol-3-yl}propanoate Cpd. 161 following protocol E<br>Yield: 60%; mp: 101, 122° C.; appearance: white solid; 1H NMR, d (ppm): 0.78-1.76 (m, 21H); 2.53 (t, 2H, J = caché par solventHz); 2.88 (t, 2H, J = 7.3 Hz); 3.03-3.15 (m, 2H); 3.40-3.52 (m, 2H); 5.31-5.40 (m, 1H); 6.94-7.21 (m, 6H); 7.31-7.40 (m, 2H); 8.33 (d, 1H, J = 8.5 Hz); 10.66 (d, 1H, J = 1.6 Hz); m/z: 516.31 [M + H]+ (calc. mass: 515.31). |
| 163 | tert-butyl 3-[5-({[cyclopropyl(4-methylnaphthalen-1-yl)methyl]carbamoyl}methyl)-1H-indol-3-yl]propanoate | From cyclopropyl(4-methylnaphthalen-1-yl)methanamine Ex. 34 and 2-{3-[3-(tert-butoxy)-3-oxopropyl]-1H-indol-5-yl}acetic acid Ex. 1 following protocol D<br>Yield: 74%; mp: 75° C.; appearance: white solid; 1H NMR, d (ppm): 0.12-0.16 (m, 1H); 0.39-0.59 (m, 3H); 1.38 (s, 10H); 2.51 (t, 2H); 2.62 (s, 3H); 2.83 (t, 2H, J = 7.5 Hz); 3.45 (s, 2H); 5.28 (t, 1H, J = 7.9 Hz); 6.92 (dd, 1H, J = 1.5 Hz, J = 8.3 Hz); 7.05 (d, 1H, J = 2.2 Hz); 7.18 (d, 1H, J = 8.2 Hz); 7.32-7.36 (m, 2H); 7.44-7.53 (m, 2H); 7.67 (d, 1H, J = 7.3 Hz); 8.00-8.08 (m, 2H); 8.45 (d, 1H, J = 8.7 Hz); 10.66 (d, 1H, J = 1.8 Hz); m/z: 497.27 [M + H]+ (calc. mass: 496.27). |
| 164 | 3-[5-({[cyclopropyl(4-methylnaphthalen-1-yl)methyl]carbamoyl}methyl)-1H-indol-3-yl]propanoate acid | From tert-butyl 3-[5-({[cyclopropyl(4-methylnaphthalen-1-yl)methyl]carbamoyl}methyl)-1H-indol-3-yl]propanoate Cpd. 163 following protocol E<br>Yield: 89%; mp: 100, 121° C.; appearance: white solid; 1H NMR, d (ppm): 0.14-0.17 (m, 1H); 0.39-0.47 (m, 2H); 0.53-0.58 (m, 1H); 1.34-1.40 (m, 1H); 2.53 (t, 2H, J = 7.7 Hz); 2.81 (s, 3H); 2.83 (t, 2H, J = 7.6 Hz); 3.45 (s, 2H); 5.28 (t, 1H, J = 8.1 Hz); 6.91 (dd, 1H, J = 1.5 Hz, J = 8.3 Hz); 7.05 (d, 1H, J = 2.2 Hz); 7.18 (d, 1H, J = 8.3 Hz); 7.33-7.37 (m, 2H); 7.42-7.55 (m, 2H); 7.67 (d, 1H, J = 7.3 Hz); 8.01 (dd, 1H, J = 1.2 Hz, J = 8.4 Hz); 8.07 (d, 1H, J = 7.9 Hz); 8.45 (d, 1H, J = 8.7 Hz); 10.66 (d, 1H, J = 1.8 Hz); m/z: 441.2 [M + H]+ (calc. mass: 440.2). |
| 165 | methyl 2-{5-[({[5-chloro-2-(piperidin-1-yl)phenyl](phenyl)methyl}carbamoyl)methyl]-1H-indol-3-yl}acetate | From [5-chloro-2-(piperidin-1-yl)phenyl](phenyl)methanamine Ex. 36 and 2-[3-(2-methoxy-2-oxoethyl)-1H-indol-5-yl]acetic acid Ex. 5 following protocol D<br>Yield: 37%; mp: 71, 86° C.; appearance: white solid; 1H NMR, d (ppm): 1.43-1.57 (m, 6H); 2.42-2.50 (m, 2H); 2.85-2.88 (m, 2H); 3.56 (s, 2H); 3.57 (s, 3H); 3.69 (s, 2H); 6.57 (d, 1H, J = 8.7 Hz); 7.02 (dd, 1H, J = 8.4 Hz, J = 1.6 Hz); 7.13-7.33 (m, 10H); 7.35 (br s, 1H); 8.83 (d, 1H, J = 8.7 Hz); 10.86 (br s, 1H); m/z: 530.21 [M + H]+ (calc. mass: 529.21). |
| 166 | 2-{5-[({[5-chloro-2-(piperidin-1-yl)phenyl](phenyl)methyl}carbamoyl)methyl]-1H-indol-3-yl}acetic acid | From methyl 2-{5-[({[5-chloro-2-(piperidin-1-yl)phenyl](phenyl)methyl} carbamoyl)methyl]-1H-indol-3-yl}acetate Cpd. 165 following protocol F<br>Yield: 86%; mp: 103, 141° C.; appearance: white solid; 1H NMR, d (ppm): 1.43-1.56 (m, 6H); 2.48-2.50 (m, 2H); 2.85-2.88 (m, 2H); 3.56 (s, 2H); 3.58 (s, 2H); 6.57 (d, 1H, J = 8.6 Hz); 7.01 (dd, 1H, J = 8.3 Hz, J = 1.5 Hz); 7.13-7.33 (m, 10H); 7.36 (m, 1H); 8.83 (d, 1H, J = 9.3 Hz); 10.81 (br s, 1H); 12.03 (br s, 1H); m/z: 516.19 [M + H]+ (calc. mass: 515.19). |

TABLE 2-continued

All the NMR were performed in DMSO-d6

| Cpd. | | Starting compounds, Reaction conditions and purification Yield, MP, Appearance, $^1$H NMR (solvent) data, Mass (ES+ or ES−) data |
|---|---|---|
| 167 | tert-butyl 3-[5-({[1H-indol-7-yl(phenyl)methyl]carbamoyl}methyl)-1H-indol-3-yl]propanoate | From 1H-indol-7-yl(phenyl)methanamine Ex. 64 and 2-{3-[3-(tert-butoxy)-3-oxopropyl]-1H-indol-5-yl}acetic acid Ex. 1 following protocol D Yield: 83%; mp: 91° C.; appearance: beige solid; 1H NMR, d (ppm): 1.38 (s, 9H); 2.54 (t, 2H, J = 7.2 Hz); 2.87 (t, 2H, J = 7.4 Hz); 3.59 (s, 2H); 6.41-6.43 (m, 1H); 6.58 (d, 1H, J = 8.4 Hz); 6.94-7.44 (m, 13H); 9.01 (d, 1H, J = 8.4 Hz); 10.67 (d, 1H, J = 1.9 Hz); 11.00 (s, 1H); m/z: 508.25 [M + H]+ (calc. mass: 507.25). |
| 168 | 3-[5-({[1H-indol-7-yl(phenyl)methyl]carbamoyl}methyl)-1H-indol-3-yl]propanoic acid | From tert-butyl 3-[5-({[1H-indol-7-yl(phenyl)methyl]carbamoyl}methyl)-1H-indol-3-yl]propanoate Cpd. 167 following protocol D Yield: 65%; mp: 106, 130° C.; appearance: beige solid; 1H NMR, d (ppm): 2.57 (t, 2H, J = 7.1 Hz); 2.88 (t, 2H, J = 7.3 Hz); 3.59 (s, 2H); 6.42-6.43 (m, 1H); 6.58 (d, 1H, J = 8.5 Hz); 6.95-7.43 (m, 13H); 9.02 (d, 1H, J = 8.4 Hz); 10.67 (s, 1H); 11.00 (s, 1H); 12.08 (br s, 1H); m/z: 452.18 [M + H]+ (calc. mass: 451.18). |
| 169 | tert-butyl 3-[5-({[(1-methyl-1H-indol-7-yl)(phenyl)methyl]carbamoyl}methyl)-1H-indol-3-yl]propanoate | From (1-methyl-1H-indol-7-yl)(phenyl)methanamine Ex. 65 and 2-{3-[3-(tert-butoxy)-3-oxopropyl]-1H-indol-5-yl}acetic acid Ex. 1 following protocol D Yield: 81%; mp: 92° C.; appearance: beige solid; 1H NMR, d (ppm): 1.38 (s, 9H); 2.54 (t, 2H, J = 7.2 Hz); 2.87 (t, 2H, J = 7.4 Hz); 3.57-3.58 (m, 2H); 3.87 (s, 3H); 6.41 (d, 1H, J = 3.1 Hz); 6.81 (d, 1H, J = 6.5 Hz); 6.91-7.00 (m, 3H); 7.07 (d, 1H, J = 2.3 Hz); 7.20-7.34 (m, 7H); 7.41 (s, 1H); 7.44 (dd, 1H, J = 1.1 Hz, J = 7.7 Hz); 9.08 (d, 1H, J = 8.2 Hz); 10.69 (d, 1H, J = 1.9 Hz); m/z: 522.26 [M + H]+ (calc. mass: 521.26). |
| 170 | 3-[5-({[(1-methyl-1H-indol-7-yl)(phenyl)methyl]carbamoyl}methyl)-1H-indol-3-yl]propanoic acid | From tert-butyl 3-[5-({[(1-methyl-1H-indol-7-yl)(phenyl)methyl]carbamoyl}methyl)-1H-indol-3-yl]propanoate Cpd. 169 following protocol E Yield: 66%; mp: 211° C.; appearance: white solid; 1H NMR, d (ppm): 2.57 (t, 2H, J = 7.2 Hz); 2.88 (t, 2H, J = 7.4 Hz); 3.57-3.58 (m, 2H); 3.88 (s, 3H); 6.41 (d, 1H, J = 3.1 Hz); 6.81 (d, 1H, J = 6.6 Hz); 6.91-7.00 (m, 3H); 7.07 (d, 1H, J = 2.1 Hz); 7.20-7.46 (m, 9H); 9.09 (d, 1H, J = 8.1 Hz); 10.69 (s, 1H); 12.08 (br s, 1H); m/z: 466.2 [M + H]+ (calc. mass: 465.2). |
| 171 | tert-butyl 3-{5-[({1-[2-(piperidin-1-yl)phenyl]pentyl}carbamoyl)methyl]-1H-indol-3-yl}propanoate | From 1-[2-(piperidin-1-yl)phenyl]pentan-1-amine Ex. 110 and 2-{3-[3-(tert-butoxy)-3-oxopropyl]-1H-indol-5-yl}acetic acid Ex. 1 following protocol D Yield: 67%; appearance: white solid; 1H NMR, d (ppm): 1.36 (s, 9H); 1.72-1.76 (m, 4H); 2.53 (t, 2H, J = 8.1 Hz); 2.87 (t, 2H, J = 7.2 Hz); 2.95-2.99 (m, 2H); 3.13-3.18 (m, 2H); 3.56 (s, 2H); 6.53 (d, 1H, J = 8.2 Hz); 6.98 (dd, 1H, J = 8.1 Hz, J = 1.1 Hz); 7.07 (d, 1H, J = 2.3 Hz); 7.12-7.14 (m, 2H); 7.21-7.31 (m, 6H); 7.39-7.41 (m, 2H); 8.91 (d, 1H, J = 8.6 Hz); 10.69 (s, 1H); m/z: 532.34 [M + H]+ (calc. mass: 531.34). |
| 172 | 3-{5-[({1-[2-(piperidin-1-yl)phenyl]pentyl}carbamoyl)methyl]-1H-indol-3-yl}propanoic acid | From tert-butyl 3-{5-[({1-[2-(piperidin-1-yl)phenyl]pentyl}carbamoyl)methyl]-1H-indol-3-yl}propanoate Cpd. 171 following protocol E Yield: 93%; mp: 76, 94° C.; appearance: white solid; 1H NMR, d (ppm): 0.88 (dd, 6H, J = 6.4 Hz, J = 1.6 Hz); 1.22-1.34 (m, 2H); 1.38-4.90 (m, 8H); 2.55-2.58 (m, 3H); 2.88 (t, 2H, J = 7.5 Hz); 3.08 (m, 2H); 3.42-3.52 (m, 2H); 5.31-5.38 (m, 1H); 6.94 (dd, 1H, J = 8.3 Hz, J = 1.5 Hz); 7.02-7.15 (m, 4H); 7.21 (d, 1H, J = 8.3 Hz); 7.31 (dd, 1H, J = 7.5 Hz, J = 1.5 Hz); 7.38 (s, 1H); 8.33 (d, 1H, J = 8.4 Hz); 10.67 (s, 1H); 12.06 (s(I), 1H); m/z: 476.28 [M + H]+ (calc. mass: 475.28). |
| 173 | tert-butyl 3-{5-[({1-[2-(diethylamino)phenyl]-3-methylbutyl}carbamoyl)methyl]-1H-indol-3-yl}propanoate | From 2-(1-amino-3-methylbutyl)-N,N-diethylaniline Ex. 43 and 2-{3-[3-(tert-butoxy)-3-oxopropyl]-1H-indol-5-yl}acetic acid Ex. 1 following protocol D Yield: 43%; mp: 50, 52° C.; appearance: white solid; 1H NMR, d (ppm): 0.85-0.93 (m, 12H); 1.24-1.36 (m, 1H); 1.38 (s, 9H); 1.45-1.68 (m, 2H); 2.52-2.55 (m, 4H); 2.84-3.03 (m, 5H); 3.41-3.52 (m, 2H); 6.94 (dd, 1H, J = 8.2 Hz, J = 1.5 Hz); 7.01-7.17 (m, 4H); 7.20 (d, 1H, J = 8.2 Hz); 7.34-7.37 (m, 2H); 8.27 (d, 1H, J = 8.5 Hz); 10.67 (s, 1H); m/z: 520.34 [M + H]+ (calc. mass: 519.34). |

TABLE 2-continued

_All the NMR were performed in DMSO-d6_

| Cpd. | | Starting compounds, Reaction conditions and purification Yield, MP, Appearance, $^1$H NMR (solvent) data, Mass (ES+ or ES−) data |
|---|---|---|
| 174 | 3-{5-[({1-[2-(diethylamino)phenyl]-3-methylbutyl}carbamoyl)methyl]-1H-indol-3-yl}propanoic acid | From tert-butyl 3-{5-[({1-[2-(diethylamino)phenyl]-3-methylbutyl}carbamoyl)methyl]-1H-indol-3-yl}propanoate Cpd. 173 following protocol E<br>Yield: 92%; mp: 71, 88° C.; appearance: white solid; 1H NMR, d (ppm): 0.85-0.93 (m, 12H); 1.24-1.35 (m, 1H); 1.46-1.62 (m, 2H); 2.55 (t, 2H, J = 8.3 Hz); 2.85-3.01 (m, 6H); 3.41-3.52 (m, 2H); 5.38-5.45 (m, 1H); 6.94 (dd, 1H, J = 8.3 Hz, J = 1.4 Hz); 7.01-7.16 (m, 4H); 7.20 (d, 1H, J = 8.1 Hz); 7.34-7.38 (m, 2H); 8.27 (d, 1H, J = 8.6 Hz); 10.67 (s, 1H); 12.06 (br s, 1H); m/z: 464.28 [M + H]+ (calc. mass: 463.28). |
| 175 | tert-butyl 3-[5-({[2-(3-methylphenyl)-1-[2-(piperidin-1-yl)phenyl]ethyl]carbamoyl}methyl)-1H-indol-3-yl]propanoate | From 2-(3-methylphenyl)-1-[2-(piperidin-1-yl)phenyl]ethan-1-amine Ex. 44 and 2-{3-[3-(tert-butoxy)-3-oxopropyl]-1H-indol-5-yl}acetic acid Ex. 1 following protocol D<br>Yield: 54%; mp: 64, 66° C.; appearance: white solid; 1H NMR, d (ppm): 1.38 (s, 9H); 1.52-1.65 (m, 6H); 2.22 (s, 3H); 2.40-2.48 (m, 2H); 2.53 (t, 2H, J = 8.3 Hz); 2.69-2.80 (m, 2H); 2.83 (t, 2H, J = 8.6 Hz); 3-3.12 (m, 2H); 3.41 (s, 2H); 5.40-5.47 (m, 1H); 6.82 (dd, 1H, J = 8.3 Hz, J = 1.6 Hz); 6.94-6.99 (m, 2H); 7.01-7.19 (m, 7H); 7.28 (s, 1H); 7.39-7.42 (m, 1H); 8.43 (d, 1H, J = 8.6 Hz); 10.65 (s, 1H); m/z: 580.34 [M + H]+ (calc. mass: 579.34). |
| 176 | 3-[5-({[2-(3-methylphenyl)-1-[2-(piperidin-1-yl)phenyl]ethyl]carbamoyl}methyl)-1H-indol-3-yl]propanoic acid | From tert-butyl 3-[5-({[2-(3-methylphenyl)-1-[2-(piperidin-1-yl)phenyl]ethyl]carbamoyl}methyl)-1H-indol-3-yl]propanoate Cpd. 175 following protocol E<br>Yield: 92%; mp: 95, 121° C.; appearance: white solid; 1H NMR, d (ppm): 1.52-1.65 (m, 6H); 2.22 (s, 3H); 2.40-2.48 (m, 2H); 2.54 (t, 2H, J = 7.3 Hz); 2.69-2.80 (m, 2H); 2.87 (t, 2H, J = 7.4 Hz); 2.99-3.14 (m, 2H); 3.41 (s, 2H); 5.40-5.47 (m, 1H); 8.81 (dd, 1H, J = 8.3 Hz, J = 1.4 Hz); 6.94-7.18 (m, 9H); 7.30 (s, 1H); 7.39-7.43 (m, 1H); 8.45 (d, 1H, J = 8.3 Hz); 10.65 (s, 1H); 12.23 (br s, 1H); m/z: 524.28 [M + H]+ (calc. mass: 523.28). |
| 177 | tert-butyl 3-{5-[({3-methyl-1-[2-(piperidin-1-yl)phenyl]butyl}carbamoyl)amino]-1H-pyrrolo[2,3-b]pyridin-3-yl}propanoate | From 3-methyl-1-[2-(piperidin-1-yl)phenyl]butan-1-amine Ex. 23 and tert-butyl 3-(5-amino-1H-pyrrolo[2,3-b]pyridin-3-yl)propanoate Ex. 136 following protocol G<br>Yield: 23%; mp: 248, 250° C.; appearance: light pink solid; 1H NMR, d (ppm): 0.91-0.97 (m, 6H); 1.34 (s, 9H); 1.46-1.70 (m, 9H); 2.50 (t, 2H, J = 7.5 Hz); 2.53-2.59 (m, 2H); 2.83 (t, 2H, J = 7.5 Hz); 3.05-3.15 (m, 2H); 5.26 (m, 1H); 6.56 (d, 1H, J = 8.4 Hz); 7.05-7.20 (m, 4H); 7.28-7.31 (m, 1H); 7.97-8.00 (m, 2H); 8.23 (br s, 1H); m/z: 534.33 [M + H]+ (calc. mass: 533.33). |
| 178 | 3-{5-[({3-methyl-1-[2-(piperidin-1-yl)phenyl]butyl}carbamoyl)amino]-1H-pyrrolo[2,3-b]pyridin-3-yl}propanoic acid | From tert-butyl 3-{5-[({3-methyl-1-[2-(piperidin-1-yl)phenyl]butyl}carbamoyl)amino]-1H-pyrrolo[2,3-b]pyridin-3-yl}propanoate Cpd. 177 following protocol E<br>Yield: 37%; mp: 227, 229° C.; appearance: white solid; 1H NMR, d (ppm): 0.94 (dd, 6H, J = 12.9 Hz, J = 6.6 Hz); 1.39-1.70 (m, 9H); 2.51-2.60 (m, 4H); 2.84 (t, 2H, J = 7.2 Hz); 3.05-3.15 (m, 2H); 5.22-5.30 (m, 1H); 6.55 (d, 1H, J = 8.4 Hz); 7.06-7.21 (m, 4H); 7.29 (dd, 1H, J = 7.5 Hz, J = 1.5 Hz); 7.99 (dd, 2H, J = 11.4 Hz, J = 2.1 Hz); 8.21 (s, 1H); 11.11 (br s, 1H); 11.90 (br s, 1H); m/z: 478.27 [M + H]+ (calc. mass: 477.27). |
| 179 | tert-butyl 3-{5-[({[2-(4,4-difluoropiperidin-1-yl)phenyl](phenyl)methyl}carbamoyl)methyl]-1H-indol-3-yl}propanoate | From [2-(4,4-difluoropiperidin-1-yl)phenyl](phenyl)methanamine Ex. 78 and 2-{3-[3-(tert-butoxy)-3-oxopropyl]-1H-indol-5-yl}acetic acid Ex. 1 following protocol D<br>Yield: 66%; mp: 83, 90° C.; appearance: white solid; 1H NMR, d (ppm): 1.38 (s, 9H); 1.83-1.97 (m, 4H); 2.52 (t, 2H, J = 8.1 Hz); 2.63-2.66 (m, 2H); 2.86 (t, 2H, J = 8.0 Hz); 2.94-2.98 (m, 2H); 3.56 (s, 2H); 6.63 (d, 1H, J = 8.7 Hz); 6.98 (dd, 1H, J = 8.1 Hz, J = 1.2 Hz); 7.07 (d, 1H, J = 2.1 Hz); 7.08-7.13 (m, 1H); 7.16-7.30 (m, 9H); 7.40 (s, 1H); 8.76 (d, 1H, J = 8.6 Hz); 10.68 (s, 1H); m/z: 588.29 [M + H]+ (calc. mass: 587.29). |
| 180 | 3-{5-[({[2-(4,4-difluoropiperidin-1-yl)phenyl](phenyl)methyl}carbamoyl)methyl]-1H-indol-3-yl}propanoic acid | From tert-butyl 3-{5-[({[2-(4,4-difluoropiperidin-1-yl)phenyl](phenyl)methyl}carbamoyl)methyl]-1H-indol-3-yl}propanoate Cpd. 179 following protocol E<br>Yield: 98%; mp: 114, 121° C.; appearance: white solid; 1H NMR, d (ppm): 1.81-2.05 (m, 4H); 2.55 (t, 2H, J = 7.0 Hz); 2.62-2.67 (m, 2H); 2.87 (t, 2H, J = 7.6 Hz); 2.93-2.98 (m, 2H); 3.56 (s, 2H); 6.62 (d, 1H, J = 8.5 Hz); 6.98 (dd, 1H, J = 8.3 Hz, J = 1.5 Hz); 7.07 (d, 1H, J = 2.3 Hz); 7.08-7.14 (m, 2H); |

TABLE 2-continued

All the NMR were performed in DMSO-d6

| Cpd. | | Starting compounds, Reaction conditions and purification Yield, MP, Appearance, $^1$H NMR (solvent) data, Mass (ES+ or ES−) data |
|---|---|---|
| | | 7.16-7.31 (m, 9H); 7.41 (s, 1H); 8.77 (d, 1H, J = 8.7 Hz); 10.68 (br s, 1H); m/z: 532.23 [M + H]+ (calc. mass: 531.23). |
| 181 | tert-butyl 3-{5-[({1-[4-bromo-2-(pyrrolidin-1-yl)phenyl]-3-methylbutyl}carbamoyl)methyl]-1H-indol-3-yl}propanoate | From 1-[4-bromo-2-(pyrrolidin-1-yl)phenyl]-3-methylbutan-1-amine Ex. 122 and 2-{3-[3-(tert-butoxy)-3-oxopropyl]-1H-indol-5-yl}acetic acid Ex. 1 following protocol D Yield: 53%; mp: 65° C.; appearance: light yellow solid; 1H NMR, d (ppm): 0.83 (dd, 6H, J = 6.4 Hz, J = 8.9 Hz); 1.29-1.35 (m, 1H); 1.38 (s, 9H); 1.46-1.59 (m, 2H); 1.75-1.86 (m, 4H); 2.53 (t, 2H, J = 7.5 Hz); 2.84-2.89 (m, 4H); 3.25-3.27 (m, 2H); 3.46 (s, 2H); 5.23-5.31 (m, 1H); 6.94 (dd, 1H, J = 1.5 Hz, J = 8.3 Hz); 7.06-7.10 (m, 3H); 7.21 (d, 1H, J = 8.2 Hz); 7.26 (d, 1H, J = 8.5 Hz); 7.36 (s, 1H); 8.37 (d, 1H, J = 8.4 Hz); 10.68 (s, 1H); m/z: 596.24 [M + H]+ (calc. mass: 595.24). |
| 182 | 3-{5-[({1-[4-bromo-2-(pyrrolidin-1-yl)phenyl]-3-methylbutyl}carbamoyl)methyl]-1H-indol-3-yl}propanoic acid | From tert-butyl 3-{5-[({1-[4-bromo-2-(pyrrolidin-1-yl)phenyl]-3-methylbutyl}carbamoyl)methyl]-1H-indol-3-yl}propanoate Cpd. 181 following protocol E Yield: 85%; mp: 87, 102° C.; appearance: white solid; 1H NMR, d (ppm): 0.83 (dd, 6H, J = 6.4 Hz, J = 9.1 Hz); 1.23-1.38 (m, 1H); 1.45-1.54 (m, 2H); 1.72-1.89 (m, 4H); 2.55 (t, 2H, J = 7.2 Hz); 2.85-2.92 (m, 4H); 3.25-3.27 (m, 2H); 3.42-3.50 (m, 2H); 5.23-5.31 (m, 1H); 6.94 (dd, 1H, J = 1.5 Hz, J = 8.3 Hz); 7.06-7.11 (m, 3H); 7.21 (d, 1H, J = 8.2 Hz); 7.26 (d, 1H, J = 8.1 Hz); 7.38 (s, 1H); 8.38 (d, 1H, J = 8.4 Hz); 10.68 (d, 1H, J = 2.1 Hz); 12.16 (br s, 1H); m/z: 540.17 [M + H]+ (calc. mass: 539.17). |
| 183 | tert-butyl 3-[5-({[(2-amino-4-methylphenyl)(phenyl)methyl]carbamoyl}methyl)-1H-indol-3-yl]propanoate | From 2-[amino(phenyl)methyl]-5-methylaniline Ex. 123 and 2-{3-[3-(tert-butoxy)-3-oxopropyl]-1H-indol-5-yl}acetic acid Ex. 1 following protocol D Yield: 43%; mp: 86, 88° C.; appearance: white foam; 1H NMR, d (ppm): 1.38 (s, 9H); 2.12 (s, 3H); 2.54 (t, 2H, J = 7.3 Hz); 2.87 (t, 2H, J = 7.3 Hz); 3.55 (d, 2H, J = 3.9 Hz); 4.74 (s, 2H); 6.09 (d, 1H, J = 8.9 Hz); 6.29 (d, 1H, J = 7.8 Hz); 6.45 (s, 1H); 6.65 (d, 1H, J = 7.8 Hz); 6.98 (dd, 1H, J = 8.3 Hz, J = 1.4 Hz); 7.06 (d, 1H, J = 2.1 Hz); 7.20-7.30 (m, 6H); 7.41 (s, 1H); 8.79 (d, 1H, J = 8.9 Hz); 10.68 (s, 1H); m/z: 498.26 [M + H]+ (calc. mass: 497.26). |
| 184 | 3-[5-({[(2-amino-4-methylphenyl)(phenyl)methyl]carbamoyl}methyl)-1H-indol-3-yl]propanoic acid | From tert-butyl 3-[5-({[(2-amino-4-methylphenyl)(phenyl)methyl]carbamoyl}methyl)-1H-indol-3-yl]propanoate Cpd. 183 following protocol E Yield: 39%; mp: 212, 218° C.; appearance: white solid; 1H NMR, d (ppm): 2.13 (s, 3H); 2.56 (t, 2H, J = 7.5 Hz); 2.89 (t, 2H, J = 7.5 Hz); 3.56 (d, 2H, J = 2.6 Hz); 4.78 (br s, 2H); 6.11 (d, 1H, J = 8.9 Hz); 6.30 (d, 1H, J = 7.8 Hz); 6.47 (s, 1H); 6.65 (d, 1H, J = 7.8 Hz); 6.99 (dd, 1H, J = 6.8 Hz, J = 1.6 Hz); 7.07 (d, 1H, J = 2.2 Hz); 7.21-7.32 (m, 6H); 7.43 (s, 1H); 8.82 (d, 1H, J = 8.9 Hz); 10.69 (s, 1H); m/z: 442.2 [M + H]+ (calc. mass: 441.2). |
| 185 | tert-butyl 3-{5-[({3,3-dimethyl-1-[2-(piperidin-1-yl)phenyl]butyl}carbamoyl)methyl]-1H-indol-3-yl}propanoate | From 3,3-dimethyl-1-[2-(piperidin-1-yl)phenyl]butan-1-amine Ex. 101 and 2-{3-[3-(tert-butoxy)-3-oxopropyl]-1H-indol-5-yl}acetic acid Ex. 1 following protocol D Yield: 49%; mp: 50, 67° C.; appearance: white solid; 1H NMR, d (ppm): 0.84 (s, 9H); 1.38 (s, 9H); 1.49-1.57 (m, 6H); 1.66-1.68 (m, 2H); 2.52-2.54 (m, 4H); 2.85 (t, 2H, J = 7.0 Hz); 3.11-3.15 (m, 2H); 3.44 (d, 2H, J = 3.0 Hz); 5.45-5.42 (m, 1H); 6.92 (dd, 1H, J = 8.3 Hz, J = 1.4 Hz); 7.00-7.14 (m, 4H); 7.18 (d, 1H, J = 8.2 Hz); 7.34-7.36 (m, 2H); 8.26 (d, 1H, J = 8.5 Hz); 10.66 (s, 1H); m/z: 546.36 [M + H]+ (calc. mass: 545.36). |
| 186 | 3-{5-[({3,3-dimethyl-1-[2-(piperidin-1-yl)phenyl]butyl}carbamoyl)methyl]-1H-indol-3-yl}propanoic acid | From tert-butyl 3-{5-[({3,3-dimethyl-1-[2-(piperidin-1-yl)phenyl]butyl}carbamoyl)methyl]-1H-indol-3-yl}propanoate Cpd. 185 following protocol E Yield: 86%; mp: 77, 114° C.; appearance: white solid; 1H NMR, d (ppm): 0.88 (s, 9H); 1.49-1.60 (m, 6H); 1.66-1.68 (m, 2H); 2.52-2.57 (m, 4H); 2.86 (t, 2H, J = 7.2 Hz); 3.09-3.11 (m, 2H); 3.43 (s, 2H); 5.45-5.40 (m, 1H); 6.92 (dd, 1H, J = 8.2 Hz, J = 1.3 Hz); 7.00-7.14 (m, 4H); 7.18 (d, 1H, J = 8.2 Hz); 7.35-7.37 (m, 2H); 8.27 (d, 1H, J = 8.4 Hz); 10.66 (s, 1H); 12.05 (br s, 1H); m/z: 490.29 [M + H]+ (calc. mass: 489.29). |

TABLE 2-continued

All the NMR were performed in DMSO-d6

| Cpd. | | Starting compounds, Reaction conditions and purification Yield, MP, Appearance, $^1$H NMR (solvent) data, Mass (ES+ or ES−) data |
|---|---|---|
| 187 | tert-butyl 3-[5-({[(4-methylphenyl)[2-(piperidin-1-yl)phenyl]methyl]carbamoyl}methyl)-1H-indol-3-yl]propanoate | From (4-methylphenyl)[2-(piperidin-1-yl)phenyl]methanamine Ex. 107 and 2-{3-[3-(tert-butoxy)-3-oxopropyl]-1H-indol-5-yl}acetic acid Ex. 1 following protocol D Yield: 54%; mp: 55, 72° C.; appearance: white solid; 1H NMR, d (ppm): 1.37 (s, 9H); 1.56-1.58 (m, 6H); 2.20 (s, 3H); 2.50-2.55 (m, 4H); 2.88-2.83 (m, 4H); 3.54 (s, 2H); 6.55 (d, 1H, J = 8.6 Hz); 6.97 (dd, 1H, J = 8.4 Hz, J = 1.5 Hz); 7.02-7.22 (m, 9H); 7.29 (dd, 1H, J = 7.6 Hz, J = 1.5 Hz); 7.37-7.39 (m, 1H); 8.66 (d, 1H, J = 8.7 Hz); 10.66 (s, 1H); m/z: 566.33 [M + H]+ (calc. mass: 565.33). |
| 188 | 3-[5-({[(4-methylphenyl)[2-(piperidin-1-yl)phenyl]methyl]carbamoyl}methyl)-1H-indol-3-yl]propanoic acid | From tert-butyl 3-[5-({[(4-methylphenyl)[2-(piperidin-1-yl)phenyl]methyl]carbamoyl}methyl)-1H-indol-3-yl]propanoate Cpd. 187 following protocol E Yield: 86%; mp: 91, 120° C.; appearance: white solid; 1H NMR, d (ppm): 1.43-1.65 (m, 6H); 2.21 (s, 3H); 2.50-2.57 (m, 4H); 2.84-2.87 (m, 4H); 3.54 (s, 2H); 6.57 (d, 1H, J = 8.6 Hz); 6.97 (dd, 1H, J = 8.3 Hz, J = 1.5 Hz); 7.02-7.22 (m, 9H); 7.30 (dd, 1H, J = 7.6 Hz, J = 1.5 Hz); 7.38-7.40 (m, 1H); 8.68 (d, 1H, J = 8.6 Hz); 10.67 (s, 1H); 12.04 (br s, 1H); m/z: 510.26 [M + H]+ (calc. mass: 509.26). |
| 189 | tert-butyl 3-[5-({[2-(oxan-4-yl)-1-[2-(piperidin-1-yl)phenyl]ethyl]carbamoyl}methyl)-1H-indol-3-yl]propanoate | From 2-(oxan-4-yl)-1-[2-(piperidin-1-yl)phenyl]ethan-1-amine Ex. 109 and 2-{3-[3-(tert-butoxy)-3-oxopropyl]-1H-indol-5-yl}acetic acid Ex. 1 following protocol D Yield: 37%; mp: 58, 74° C.; appearance: white solid; 1H NMR, d (ppm): 0.81-0.87 (m, 1H); 1.12-1.22 (m, 3H); 1.40 (s, 9H); 1.44-1.64 (m, 9H); 2.53-2.56 (m, 4H); 2.87 (t, 2H, J = 7.4 Hz); 3.05-308 (m, 4H); 3.46 (q, 2H, J = 9.4 Hz); 3.72 (d, 2H, J = 10.6 Hz); 5.32-5.37 (m, 1H); 6.96 (dd, 1H, J = 8.3 Hz, J = 1.5 Hz); 7.03-7.13 (m, 4H); 7.20 (d, 1H, J = 8.3 Hz); 7.33 (dd, 1H, J = 7.5 Hz, J = 1.5 Hz); 7.38-7.39 (m, 1H); 8.33 (d, 1H, J = 8.4 Hz); 10.67 (s, 1H); m/z: 574.35 [M + H]+ (calc. mass: 573.35). |
| 190 | 3-[5-({[2-(oxan-4-yl)-1-[2-(piperidin-1-yl)phenyl]ethyl]carbamoyl}methyl)-1H-indol-3-yl]propanoic acid | From tert-butyl 3-[5-({[2-(oxan-4-yl)-1-[2-(piperidin-1-yl)phenyl]ethyl]carbamoyl}methyl)-1H-indol-3-yl]propanoate Cpd. 189 following protocol E Yield: 70%; mp: 105, 123° C.; appearance: white solid; 1H NMR, d (ppm): 1.10-1.12 (m, 2H); 1.37-1.63 (m, 11H); 2.47-2.50 (m, 2H); 2.56 (t, 2H, J = 8.3 Hz); 2.91 (t, 2H, J = 7.5 Hz); 3.04-3.11 (m, 4H); 3.45 (q, 2H, J = 9.9 Hz); 3.70-3.74 (m, 2H); 5.35-5.37 (m, 1H); 6.96 (dd, 1H, J = 8.3 Hz, J = 1.5 Hz); 7.00-7.16 (m, 4H); 7.22 (d, 1H, J = 8.3 Hz); 7.34 (dd, 1H, J = 7.5 Hz, J = 1.4 Hz); 7.39-7.41 (m, 1H); 8.34 (d, 1H, J = 8.6 Hz); 10.67 (s, 1H); 12.09 (br s, 1H); m/z: 518.29 [M + H]+ (calc. mass: 517.29). |
| 191 | tert-butyl 3-{5-[({[2-(dimethylamino)-4-methylphenyl](phenyl)methyl}carbamoyl)methyl]-1H-indol-3-yl}propanoate | From 2-[amino(phenyl)methyl]-N,N,5-trimethylaniline Ex. 46 and 2-{3-[3-(tert-butoxy)-3-oxopropyl]-1H-indol-5-yl}acetic acid Ex. 1 following protocol D Yield: 81%; appearance: colorless oil; 1H NMR, d (ppm): 1.38 (s, 9H); 2.25 (s, 3H); 2.48 (s, 6H); 2.54 (t, 2H, J = 7.3 Hz); 2.87 (t, 2H, J = 7.3 Hz); 3.58 (s, 2H); 6.59 (d, 1H, J = 8.7 Hz); 6.87 (dd, 1H, J = 7.9 Hz, J = 1.1 Hz); 6.95-7.00 (m, 2H); 7.00-7.40 (m, 8H); 7.41 (s, 1H); 8.74 (d, 1H, J = 8.7 Hz); 10.68 (br s, 1H); m/z: ND (calc. mass: 525.29). |
| 192 | 3-{5-[({[2-(dimethylamino)-4-methylphenyl](phenyl)methyl}carbamoyl)methyl]-1H-indol-3-yl}propanoic acid | From tert-butyl 3-{5-[({[2-(dimethylamino)-4-methylphenyl](phenyl)methyl}carbamoyl)methyl]-1H-indol-3-yl}propanoate Cpd. 191 following protocol E Yield: 85%; mp: 198, 208° C.; appearance: white solid; 1H NMR, d (ppm): 2.25 (s, 3H); 2.50 (s, 6H); 2.56 (t, 2H, J = 7.3 Hz); 2.77 (t, 2H, J = 7.3 Hz); 3.56 (s, 2H); 6.55 (d, 1H, J = 8.7 Hz); 6.95 (dd, 1H, J = 7.9 Hz, J = 1.1 Hz); 6.95-7.00 (m, 2H); 7.00-7.50 (m, 11H); 9.08 (br s, 1H); 10.71 (s, 1H); m/z: 470.23 [M + H]+ (calc. mass: 469.23). |
| 193 | methyl 2-{5-[({3-methyl-1-[2-(piperidin-1-yl)phenyl]butyl}carbamoyl)methyl]-1H-indol-3-yl}acetate | From 3-methyl-1-[2-(piperidin-1-yl)phenyl]butan-1-aminium chloride Ex. 23 and 2-[3-(2-methoxy-2-oxoethyl)-1H-indol-5-yl]acetic acid Ex. 5 following protocol D Yield: 34%; appearance: pale yellow solid; 1H NMR, d (ppm): 0.88 (d, 6H, J = 6.5 Hz); 1.22-1.43 (m, 4H); 1.62-1.69 (m, 7H); 3.14-3.16 (m, 2H); 3.43-3.50 (m, 2H); 3.58 (s, 3H); 3.67 (s, 2H); 5.08-5.43 (m, 1H); 6.96 (d, 1H, J = 8.2 Hz); 7.03-7.64 (m, 6H); 8.06-8.08 (m, 1H); 8.24-8.73 (m, 1H); 10.88 (br s, 1H); m/z: ND (calc. mass: 475.28). |

TABLE 2-continued

All the NMR were performed in DMSO-d6

| Cpd. | | Starting compounds, Reaction conditions and purification Yield, MP, Appearance, $^1$H NMR (solvent) data, Mass (ES+ or ES−) data |
|---|---|---|
| 194 | 2-{5-[({3-methyl-1-[2-(piperidin-1-yl)phenyl]butyl}carbamoyl)methyl]-1H-indol-3-yl}acetic acid | From methyl 2-{5-[({3-methyl-1-[2-(piperidin-1-yl)phenyl]butyl}carbamoyl)methyl]-1H-indol-3-yl}acetate Cpd. 193 following protocol F Yield: 62%; mp: 78, 100° C.; appearance: white solid; 1H NMR, d (ppm): 0.88 (d, 6H, J = 6.5 Hz); 1.16-1.29 (m, 1H); 1.49-1.64 (m, 8H); 2.49-2.51 (m, 2H); 3.08 (m, 2H); 3.46 (d, 2H, J = 4.8 Hz); 3.57 (s, 2H); 5.32 (m, 1H); 6.97 (dd, 1H, J = 8.3 Hz, J = 1.4 Hz); 7.02-7.33 (m, 7H); 8.32 (d, 1H, J = 8.2 Hz); 10.80 (br s, 1H); 12.00 (br s, 1H); m/z: 462.26 [M + H]+ (calc. mass: 461.26). |
| 195 | tert-butyl 3-{5-[({[2-(morpholin-4-yl)phenyl](phenyl)methyl}carbamoyl)methyl]-1H-indol-3-yl}propanoate | From [2-(morpholin-4-yl)phenyl](phenyl)methanaminium chloride Ex. 52 and 2-{3-[3-(tert-butoxy)-3-oxopropyl]-1H-indol-5-yl}acetic acid Ex. 1 following protocol D Yield: 67%; appearance: yellow oil; 1H NMR, d (ppm): 1.38 (s, 9H); 2.55 (t, 2H, J = 7.1 Hz); 2.86 (t, 2H, J = 7.1 Hz); 3.31-3.47 (m, 2H); 3.56-3.58 (m, 4H); 6.65 (d, 1H, J = 8.7 Hz); 6.97 (dd, 1H, J = 8.3 Hz, J = 1.5 Hz); 7.06-7.31 (m, 11H); 7.39 (s, 1H); 8.75 (d, 1H, J = 8.7 Hz); 10.68 (d, 1H, J = 1.9 Hz); m/z: ND (calc. mass: 553.29). |
| 196 | 3-{5-[({[2-(morpholin-4-yl)phenyl](phenyl)methyl}carbamoyl)methyl]-1H-indol-3-yl}propanoic acid | From tert-butyl 3-{5-[({[2-(morpholin-4-yl)phenyl](phenyl)methyl}carbamoyl)methyl]-1H-indol-3-yl}propanoate Cpd. 195 following protocol E Yield: 73%; mp: 146, 169° C.; appearance: white solid 1H NMR, d (ppm): 2.49-2.50 (m, 2H); 2.87 (t, 4H, J = 7.3 Hz); 3.44-3.50 (m, 2H); 3.56-3.61 (m, 4H); 6.65 (d, 1H, J = 8.8 Hz); 6.97 (dd, 1H, J = 8.3 Hz, J = 1.5 Hz); 7.06-7.32 (m, 11H); 7.41 (s, 1H); 8.76 (d, 1H, J = 8.7 Hz); 10.68 (d, 1H, J = 2.1 Hz); 12.10 (br s, 1H); m/z: 498.23 [M + H]+ (calc. mass: 497.23). |
| 197 | tert-butyl 3-{5-[({1-[2-(azepan-1-yl)phenyl]-3-methylbutyl}carbamoyl)methyl]-1H-indol-3-yl}propanoate | From 1-[2-(azepan-1-yl)phenyl]-3-methylbutan-1-amine Ex. 40 and 2-{3-[3-(tert-butoxy)-3-oxopropyl]-1H-indol-5-yl}acetic acid Ex. 1 following protocol D Yield: 16%; appearance: white solid; 1H NMR, d (ppm): 0.87-0.90 (m, 6H); 1.34-1.39 (m, 10H); 1.48-1.78 (m, 11H); 2.53 (t, 2H, J = 7.3 Hz); 2.79-2.89 (m, 4H); 3.1-3.17 (m, 2H); 3.41-3.51 (m, 2H); 6.94 (dd, 1H, J = 8.3 Hz, J = 1.4 Hz); 6.99-7.15 (m, 4H); 7.20 (d, 1H, J = 8.2 Hz); 7.31 (dd, 1H, J = 7.4 Hz, J = 1.4 Hz); 7.37 (s, 1H); 8.31 (d, 1H, J = 8.5 Hz); 10.67 (s, 1H); m/z: ND (calc. mass: 545.36). |
| 198 | 3-{5-[({1-[2-(azepan-1-yl)phenyl]-3-methylbutyl}carbamoyl)methyl]-1H-indol-3-yl}propanoic acid | From tert-butyl 3-{5-[({1-[2-(azepan-1-yl)phenyl]-3-methylbutyl}carbamoyl)methyl]-1H-indol-3-yl}propanoate Cpd. 197 following protocol E Yield: 84%; mp: 81, 105° C.; appearance: white solid; 1H NMR, d (ppm): 0.87-0.90 (m, 6H); 1.22-1.37 (m, 1H); 1.48-1.97 (m, 10H); 2.56 (t, 2H, J = 8.3 Hz); 2.78-2.90 (m, 4H); 3.10-3.17 (m, 2H); 3.41-3.51 (m, 2H); 5.41-5.48 (m, 1H); 6.94 (dd, 1H, J = 8.4 Hz, J = 1.3 Hz); 6.99-7.15 (m, 4H); 7.20 (d, 1H, J = 8.2 Hz); 7.30-7.33 (m, 1H); 7.38 (s, 1H); 8.31 (d, 1H, J = 8.7 Hz); 10.67 (s, 1H); 12.05 (br s, 1H); m/z: 490.29 [M + H]+ (calc. mass: 489.29). |
| 199 | tert-butyl 3-{5-[({[2-(2,5-dihydro-1H-pyrrol-1-yl)-4-methylphenyl](phenyl)methyl}carbamoyl)methyl]-1H-indol-3-yl}propanoate | From [2-(2,5-dihydro-1H-pyrrol-1-yl)-4-methylphenyl](phenyl)methanaminium chloride Ex. 61 and 2-{3-[3-(tert-butoxy)-3-oxopropyl]-1H-indol-5-yl}acetic acid Ex. 1 following protocol D Yield: 38%; appearance: white solid; 1H NMR, d (ppm): 1.38 (s, 9H); 2.22 (s, 3H); 2.54 (t, 2H, J = 7.2 Hz); 2.87 (t, 2H, J = 7.2 Hz); 3.56 (s, 2H); 3.76 (d, 2H, J = 9.8 Hz); 4.01 (d, 2H, J = 9.8 Hz); 5.79 (s, 2H); 6.52 (d, 1H, J = 8.8 Hz); 6.75 (d, 1H, J = 8.8 Hz); 6.92 (s, 1H); 6.98 (d, 1H, J = 9.3 Hz); 7.06-7.27 (m, 9H); 7.40 (s, 1H); 8.74 (d, 1H, J = 8.8 Hz); 10.68 (br s, 1H); m/z: ND (calc. mass: 549.29). |
| 200 | 3-{5-[({[2-(2,5-dihydro-1H-pyrrol-1-yl)-4-methylphenyl](phenyl)methyl}carbamoyl)methyl]-1H-indol-3-yl}propanoic acid | From tert-butyl 3-{5-[({[2-(2,5-dihydro-1H-pyrrol-1-yl)-4-methylphenyl](phenyl)methyl}carbamoyl)methyl]-1H-indol-3-yl}propanoate Cpd. 199 following protocol E Yield: 35%; mp: 170, 180° C.; appearance: white solid; 1H NMR, d (ppm): 2.22 (s, 3H); 2.56 (t, 2H, J = 7.4 Hz); 2.88 (t, 2H, J = 7.4 Hz); 3.56 (s, 2H); 3.74-3.79 (m, 2H); 3.98-4.03 (m, 2H); 5.79 (s, 2H); 6.53 (d, 1H, J = 8.5 Hz); 6.75 (d, 1H, J = 7.0 Hz); 6.92 (s, 1H); 6.98 (dd, 1H, J = 8.3 Hz, J = 1.5 Hz); 7.06-7.27 (m, 8H); 7.41 (s, 1H); 8.74 (d, 1H, J = 8.5 Hz); 10.69 (br s, 1H); m/z: 494.23 [M + H]+ (calc. mass: 493.23). |

TABLE 2-continued

All the NMR were performed in DMSO-d6

| Cpd. | | Starting compounds, Reaction conditions and purification Yield, MP, Appearance, ¹H NMR (solvent) data, Mass (ES+ or ES−) data |
|---|---|---|
| 201 | tert-butyl 3-{5-[({[3-methyl-2-(piperidin-1-yl)phenyl](phenyl)methyl}carbamoyl)methyl]-1H-indol-3-yl}propanoate | From [3-methyl-2-(piperidin-1-yl)phenyl](phenyl)methanaminium chloride Ex. 111 and 2-{3-[3-(tert-butoxy)-3-oxopropyl]-1H-indol-5-yl}acetic acid Ex. 1 following protocol D Yield: 28%; appearance: white solid; 1H NMR, d (ppm): 1.17-1.20 (m, 2H); 1.36 (s, 9H); 1.44-1.59 (m, 3H); 2.27 (s, 3H); 2.48-2.52 (m, 2H); 2.53 (t, 2H, J = 7.3 Hz); 2.87 (t, 2H, J = 7.8 Hz); 2.99-3.01 (m, 2H); 3.53 (s, 3H); 6.68 (d, 1H, J = 8.2 Hz); 6.97 (dd, 1H, J = 8.3 Hz, J = 1.6 Hz); 7.01-7.29 (m, 10H); 7.39 (s, 1H); 8.64 (d, 1H, J = 8.4 Hz); 10.68 (s, 1H); m/z: ND (calc. mass: 565.33). |
| 202 | 3-{5-[({[3-methyl-2-(piperidin-1-yl)phenyl](phenyl)methyl}carbamoyl)methyl]-1H-indol-3-yl}propanoic acid | From tert-butyl 3-{5-[({[3-methyl-2-(piperidin-1-yl)phenyl](phenyl)methyl}carbamoyl)methyl]-1H-indol-3-yl}propanoate Cpd. 201 following protocol E Yield: 76%; mp: 114, 121° C.; appearance: white solid; 1H NMR, d (ppm): 1.13-1.59 (m, 6H); 2.48 (m, 1H); 2.27 (s, 3H); 2.56 (t, 2H, J = 7.6 Hz); 2.88 (t, 2H, J = 7.6 Hz); 2.88-3.02 (m, 3H); 3.53 (s, 2H); 6.69 (d, 1H, J = 8.6 Hz); 6.98 (dd, 1H, J = 8.2 Hz, J = 1.4 Hz); 7.01 (s, 1H); 7.02 (d, 1H, J = 7.0 Hz); 7.06-7.13 (m, 4H); 7.15-7.29 (m, 4H); 7.40 (s, 1H); 8.65 (d, 1H, J = 8.5 Hz); 10.67 (s, 1H); 12.18 (br s, 1H); m/z: 510.26 [M + H]+ (calc. mass: 509.26). |
| 203 | tert-butyl 3-{5-[({[4-methyl-2-(methylamino)phenyl](phenyl)methyl}carbamoyl)methyl]-1H-indol-3-yl}propanoate | From [4-methyl-2-(methylamino)phenyl](phenyl)methanaminium chloride Ex. 80 and 2-{3-[3-(tert-butoxy)-3-oxopropyl]-1H-indol-5-yl}acetic acid Ex. 1 following protocol D Yield: 71%; mp: 97, 100° C.; appearance: white solid; 1H NMR, d (ppm) 1H NMR (300 MHz, CDCl3, d in ppm): 1.44 (s, 9H); 2.28 (s, 3H); 2.60 (t, 2H, J = 6.9 Hz); 2.67 (s, 3H); 3.02 (t, 2H, J = 6.1 Hz); 3.76 (q, 2H, J = 8.9 Hz); 6.31-6.33 (m, 2H); 6.39-6.46 (m, 2H); 6.55 (d, 1H, J = 7.7 Hz); 7.03-7.09 (m, 3H); 7.21-7.34 (m, 4H); 7.47-7.49 (m, 1H); 8.00 (s, 1H); m/z: ND (calc. mass: 511.28). |
| 204 | 3-{5-[({[4-methyl-2-(methylamino)phenyl](phenyl)methyl}carbamoyl)methyl]-1H-indol-3-yl}propanoic acid | From tert-butyl 3-{5-[({[4-methyl-2-(methylamino)phenyl](phenyl)methyl}carbamoyl)methyl]-1H-indol-3-yl}propanoate Cpd. 203 following protocol E Yield: 51%; mp: 102, 132° C.; appearance: white solid; 1H NMR, d (ppm): 2.19 (s, 3H); 2.56 (t, 2H, J = 7.2 Hz); 2.61 (d, 3H, J = 0.8 Hz); 2.88 (t, 2H, J = 7.4 Hz); 3.54 (s, 2H); 4.84 (br s, 1H); 6.12 (d, 1H, J = 8.8 Hz); 6.33-6.34 (m, 2H); 6.70 (d, 1H, J = 8.1 Hz); 6.67 (dd, 1H, J = 8.3 Hz, J = 1.5 Hz); 7.07 (d, 1H, J = 2.3 Hz); 7.20-7.32 (m, 6H); 7.40-7.42 (m, 1H); 8.83 (d, 1H, J = 8.8 Hz); 10.68 (s, 1H); 12.08 (br s, 1H); m/z: 456.22 [M + H]+ (calc. mass: 455.22). |
| 205 | methyl 5-[({phenyl[2-(piperidin-1-yl)phenyl]methyl}carbamoyl)methyl]-1H-indole-3-carboxylate | Step 1: to a solution of phenyl[2-(piperidin-1-yl)phenyl]methanamine Ex. 9 (1.16 g, 4.36 mmol) in CH2Cl2 (13 mL) was added DCC (943 mg, 4.57 mmol), HOBt (700 mg, 4.57 mmol) followed by 2-(1H-indol-5-yl)acetic acid (763 mg, 4.36 mmol) dissolved in DMF (2 mL). The reaction was stirred at rt and monitored by TLC. After completion, the reaction mixture was cooled down at −30° C. and filtered off. The solution was concentrated under reduced pressure. The crude material was purified on silica gel column chromatography using CH2Cl2/EtOAc (96:4) as eluent. (yield 65%; mp: 181° C.; appearance: white solid; 1H NMR, d (ppm): 1.4-1.7 (m, 6H); 2.50 (m, 2H); 2.86 (m, 2H); 3.58 (s, 2H); 6.33 (m, 1H); 6.61 (d, 1H, J = 8.7 Hz); 6.95-7.35 (m, 13H); 7.41 (d, 1H, J = 7.6 Hz); 8.71 (d, 1H, J = 8.7 Hz); 10.97 (br s, 1H); -m/z: 424.14[M + H]+ (calc. mass: 423.23)) Step 2: to a solution of dry DMF (3 mL) was added dropwise phosphorus oxychloride (267 µL, 2.87 mmol) at 0° C. After addition, the ice bath was removed and the reaction was kept under stirring at rt for 15 minutes. 2-(1H-indol-5-yl)-N-{phenyl[2-(piperidin-1-yl)phenyl]methyl}acetamide (405 mg, 0.96 mmol) dissolved in DMF (2 mL) was introduced dropwise. The reaction mixture was stirred at rt for 3 h. Brine was added to quench the reaction. The pH was adjusted to pH = 5-6 with a solution of NaOH 2N. The aqueous layer was extracted twice with EtOAc. The combined organic layer was washed once with brine, dried over MgSO4, filtered and the solution was concentrated under reduced pressure. The crude material was purified on silica gel column chromatography |

TABLE 2-continued

All the NMR were performed in DMSO-d6

| Cpd. | | Starting compounds, Reaction conditions and purification Yield, MP, Appearance, $^1$H NMR (solvent) data, Mass (ES+ or ES−) data |
|---|---|---|
| | | using CH2Cl2/MeOH (95:5) as eluent to afford 2-(3-formyl-1H-indol-5-yl)-N-{phenyl[2-(piperidin-1-yl)phenyl]methyl}acetamide (yield 50%; mp: 203° C.; appearance: pale yellow solid; 1H NMR, d (ppm): 1.4-1.7 (m, 6H); 2.50 (m, 2H); 2.86 (m, 2H); 3.63 (s, 2H); 6.61 (d, 1H, J = 8.7 Hz); 6.95-7.35 (m, 12H); 8.07 (s, 1H); 8.82 (d, 1H, J = 8.7 Hz); 9.91 (s, 1H); 12.06 (br s, 1H); m/z: 452.23[M + H]+ (calc. mass: 451.22)) Step 3: to a solution of 2-(3-formyl-1H-indol-5-yl)-N-{phenyl[2-(piperidin-1-yl)phenyl]methyl}acetamide (130 mg, 0.29 mmol) in methanol (7 mL) was added KCN (94 mg, 1.44 mmol). Then, activated MnO2 (500 mg, 5.76 mmol) was introduced portionwise. CH2Cl2 (2 mL) was added to increase the solubility. The reaction mixture was stirred at rt for 96 h. The solution was diluted with CH2Cl2 and filtered-off on Celite. The filtrate was concentrated to dryness. Water was added to dissolve inorganic salts. The aqueous layer was extracted with EtOAc. The combined organic layers were dried over MgSO4, filtered and the solution was concentrated to dryness. The crude material was purified on silica gel column chromatography using CH2Cl2/MeOH (98:2) as eluent. Yield: 47%; appearance: white solid; 1H NMR, d (ppm): 1.40-1.65 (m, 6H); 2.48 (m, 2H); 2.88 (m, 2H); 3.58 (s, 2H); 3.78 (s, 3H); 6.62 (d, 1H, J = 8.7 Hz); 6.88-7.40 (m, 11H); 7.92 (s, 1H); 8.02 (d, 1H, J = 3.0 Hz); 8.80 (d, 1H, J = 8.7 Hz); 11.82 (br s, 1H); m/z: 482.36[M + H]+ (calc. mass: 481.23). |
| 206 | 1-(2-{[2-(3-carboxy-1H-indol-5-yl)acetamido](phenyl)methyl}phenyl)piperidin-1-ium chloride | From methyl 5-[({phenyl[2-(piperidin-1-yl)phenyl]methyl}carbamoyl)methyl]-1H-indole-3-carboxylate Cpd. 205 following protocol E Yield: 26%; mp: 188, 198° C.; appearance: white solid; 1H NMR, d (ppm): 1.40-1.65 (m, 6H); 2.48 (m, 2H); 2.88 (m, 2H); 3.60 (s, 2H); 6.59 (d, 1H, J = 8.7 Hz); 6.88-7.40 (m, 11H); 7.90-7.95 (m, 2H); 8.80 (d, 1H, J = 8.7 Hz); 11.71 (br s, 1H); m/z: 468.33 [M + H]+ (calc. mass: 503.19). |
| 207 | 5-({[(2-bromo-4-methylphenyl)(phenyl)methyl]carbamoyl}methyl)-1H-indole-3-carboxylic acid | Step 1: synthesis of N-[(2-bromo-4-methylphenyl)(phenyl)methyl]-2-(3-formyl-1H-indol-5-yl)acetamide: (2-bromo-4-methylphenyl)(phenyl)methanamine Ex. 13 and 2-(3-formyl-1H-indol-5-yl)acetic acid following protocol D (yield 18%; appearance: colorless oil; 1H NMR, d (ppm): 2.26 (s, 3H); 3.60 (s, 2H); 6.30 (d, 1H, J = 8.2 Hz); 7.24-7.33 (m, 8H); 7.39-7.41 (m, 2H); 8.05 (m, 1H); 8.24 (d, 1H, J = 3.1 Hz); 9.02 (d, 1H, J = 8.2 Hz); 9.90 (s, 1H); 12.04 (s, 1H); m/z: ND (calc. mass: 460.07)) Step 2: the titled compound was synthesized following the procedure described in (Showalter et al, 1997) from N-[(2-bromo-4-methylphenyl)(phenyl)methyl]-2-(3-formyl-1H-indol-5-yl)acetamide. Yield: 16%; mp: 132, 220° C.; appearance: white solid; 1H NMR, d (ppm): 2.26 (s, 3H); 3.58 (s, 2H); 6.30 (d, 1H, J = 8.2 Hz); 7.09-7.36 (m, 9H); 7.41-7.42 (m, 1H); 7.94-7.95 (m, 2H); 9.00 (d, 1H, J = 8.3 Hz); 11.71 (s, 1H); 11.85 (br s, 1H); m/z: 477.07 [M + H]+ (calc. mass: 476.07). |
| 208 | tert-butyl 3-[5-({2-[4-methyl-2-(piperidin-1-yl)phenyl]-2-phenylacetamido}methyl)-1H-indol-3-yl]propanoate | From 2-[4-methyl-2-(piperidin-1-yl)phenyl]-2-phenylacetic acid Ex. 128 and {3-[3-(tert-butoxy)-3-oxopropyl]-1H-indol-5-yl}methanaminium chloride Ex. 131 following protocol D Yield: 54%; mp: 166, 176° C.; appearance: white solid; 1H NMR, d (ppm): 1.38 (s, 9H); 1.40-1.65 (m, 6H); 2.26 (m, 3H); 2.48 (m, 2H); 2.5-2.7 (m, 4H); 2.72 (m, 2H); 4.36 (m, 2H); 5.47 (s, 1H); 6.8-7.35 (m, 11H); 7.75 (m, 1H); 8.51 (t, 1H); 10.80 (br s, 1H); m/z: 566.33 [M + H]+ (calc. mass: 565.33). |
| 209 | 3-[5-({2-[4-methyl-2-(piperidin-1-yl)phenyl]-2-phenylacetamido}methyl)-1H-indol-3-yl]propanoic acid | From tert-butyl 3-[5-({2-[4-methyl-2-(piperidin-1-yl)phenyl]-2-phenylacetamido}methyl)-1H-indol-3-yl]propanoate Cpd. 208 following protocol E Yield: 84%; mp: 115, 125° C.; appearance: white solid; 1H NMR, d (ppm): 1.40-1.65 (m, 6H); 2.26 (m, 3H); 2.5-2.7 (m, 4H); 2.72 (m, 2H); 2.84 (t, 2H, J = 7.3 Hz); 4.36 (d, 2H, J = 4.7 Hz); 5.47 (s, 1H); 6.8-7.35 (m, 11H); 7.75 (m, 1H); 8.51 (t, 1H, J = 4.7 Hz); 10.69 (br s, 1H); 12.00 (br s, 1H); m/z: 510.26 [M + H]+ (calc. mass: 509.26). |

TABLE 2-continued

All the NMR were performed in DMSO-d6

| Cpd. | | Starting compounds, Reaction conditions and purification Yield, MP, Appearance, 1H NMR (solvent) data, Mass (ES+ or ES−) data |
|---|---|---|
| 210 | ethyl 4-oxo-4-{5-[({phenyl[2-(piperidin-1-yl)phenyl]methyl}carbamoyl)methyl]-1H-indol-3-yl}butanoate | Aluminum chloride (35 mg, 0.26 mmol) was suspended in dry CH2Cl2 (1.5 mL) and cooled to 0° C. Ethyl-4-chloro-4-oxobutyrate (37 µL, 0.26 mmol) was then slowly added to the solution. After 30 min, 2-(1H-indol-5-yl)-N-{phenyl[2-(piperidin-1-yl)phenyl]methyl}acetamide (see Step 1 of synthesis of Cpd. 205) (100 mg, 0.24 mmol) dissolved in in dry CH2Cl2 (1.5 mL) was slowly introduced. The reaction proceeded for 2 h, gradually warming to rt (4 h). The TLC showed still starting material. The reaction was cooled down to 0° C. and additional aluminum chloride (35 mg, 0.26 mmol) was added to the reaction mixture. The reaction proceeded for 2 h, gradually warming to rt. The TLC showed the completion of the reaction after 3 h. The reaction mixture was slowly quenched with sat. NH4Cl. The pH was ajusted to pH = 5-6 with NaHCO3 10%. The aqueous layer was extracted with CH2Cl2. The combined organic layers were washed with brine, dried over MgSO4, the solution was concentrated to dryness. The crude material was purified on preparative HPLC. Yield: 46%; mp: 80, 85° C.; appearance: white solid; 1H NMR, d (ppm): 1.17 (t, 3H, J = 7.3 Hz); 1.30-1.65 (m, 6H); 2.48 (m, 2H); 2.61 (t, 2H, J = 7.3 Hz); 2.82 (m, 2H); 3.15 (t, 2H, J = 7.3 Hz); 3.59 (s, 2H); 4.04 (q, 2H, J = 7.3 Hz); 6.60 (d, 1H, J = 8.7 Hz); 7.0-7.40 (m, 11H); 8.12 (s, 1H); 8.30 (d, 1H, J = 3.1 Hz); 8.78 (d, 1H, J = 8.7 Hz); 11.84 (br s, 1H); m/z: 552.27 [M + H]+ (calc. mass: 551.27). |
| 211 | ethyl 4-{5-[({phenyl[2-(piperidin-1-yl)phenyl]methyl}carbamoyl)methyl]-1H-indol-3-yl}butanoate | From ethyl 4-oxo-4-{5-[({phenyl[2-(piperidin-1-yl)phenyl]methyl}carbamoyl)methyl]-1H-indol-3-yl}butanoate Cpd. 210 following protocol E Yield: 60%; mp: 105, 110° C.; appearance: white solid; 1H NMR, d (ppm): 1.16 (t, 3H, J = 7.3 Hz); 1.30-1.65 (m, 6H); 1.86 (st, 2H, J = 7.3 Hz); 2.28 (t, 2H, J = 7.3 Hz); 2.48 (m, 2H); 2.64 (t, 2H, J = 7.3 Hz); 2.84 (m, 2H); 3.56 (s, 2H); 4.01 (q, 2H, J = 7.3 Hz); 6.59 (d, 1H, J = 8.7 Hz); 7.0-7.40 (m, 12H); 7.37 (s, 1H); 8.70 (d, 1H, J = 8.7 Hz); 10.67 (br s, 1H); m/z: 538.29 [M + H]+ (calc. mass: 537.29). |
| 212 | 4-{5-[({phenyl[2-(piperidin-1-yl)phenyl]methyl}carbamoyl)methyl]-1H-indol-3-yl}butanoic acid | From ethyl 4-{5-[({phenyl[2-(piperidin-1-yl)phenyl]methyl}carbamoyl)methyl]-1H-indol-3-yl}butanoate Cpd. 211 following protocol E Yield: 74%; mp: 88, 108° C.; appearance: white solid; 1H NMR, d (ppm): 1.30-1.65 (m, 6H); 1.86 (st, 2H, J = 7.3 Hz); 2.24 (t, 2H, J = 7.3 Hz); 2.45 (m, 2H); 2.64 (t, 2H, J = 7.3 Hz); 2.84 (m, 2H); 3.56 (s, 2H); 6.59 (d, 1H, J = 8.7 Hz); 7.0-7.40 (m, 12H); 7.38 (s, 1H); 8.72 (d, 1H, J = 8.7 Hz); 10.67 (br s, 1H); 12.00 (br s, 1H); m/z: 510.26 [M + H]+ (calc. mass: 509.26). |
| 213 | 4-oxo-4-{5-[({phenyl[2-(piperidin-1-yl)phenyl]methyl}carbamoyl)methyl]-1H-indol-3-yl}butanoic acid | From ethyl 4-oxo-4-{5-[({phenyl[2-(piperidin-1-yl)phenyl]methyl}carbamoyl)methyl]-1H-indol-3-yl}butanoate Cpd. 210 following protocol E Yield: 63%; mp: 125, 135° C.; appearance: white solid; 1H NMR, d (ppm): 1.30-1.65 (m, 6H); 2.48 (m, 2H); 2.58 (t, 2H, J = 7.3 Hz); 2.85 (m, 2H); 3.10 (t, 2H, J = 7.3 Hz); 3.59 (s, 2H); 6.59 (d, 1H, J = 8.7 Hz); 7.0-7.40 (m, 11H); 8.12 (s, 1H); 8.30 (d, 1H, J = 2.5 Hz); 8.78 (d, 1H, J = 8.7 Hz); 11.82 (br s, 1H); m/z: 524.24 [M + H]+ (calc. mass: 523.24). |
| 214 | ethyl 5-oxo-5-{5-[({phenyl[2-(piperidin-1-yl)phenyl]methyl}carbamoyl)methyl]-1H-indol-3-yl}pentanoate | Aluminum chloride (165 mg, 1.24 mmol) was suspended in dry CH2Cl2 (1.5 mL) and cooled to 0° C. Ethyl 4-(chlorocarbonyl)butanoate (0.106 mL, 0.71 mmol) was then slowly added to the solution. After 30 min, 2-(1H-indol-5-yl)-N-{phenyl[2-(piperidin-1-yl)phenyl]methyl}acetamide (see Step 1 of synthesis of Cpd. 205) (150 mg, 0.35 mmol) dissolved in in dry CH2Cl2 (1.5 mL) was slowly introduced. The reaction proceeded for 2 h, gradually warming to rt (48 h). The TLC showed the completion of the reaction after 3 h. The reaction mixture was slowly quenched with sat. NH4Cl. The pH was ajusted to pH = 5-6 with NaHCO3 10%. The aqueous layer was extracted with EtOAc. The combined organic layers were washed with brine, dried over MgSO4, the solution was concentrated to dryness. The crude material was purified on silica gel column chromatography using CH2Cl2/MeOH (97:3) as eluent. Yield: 80%; appearance: ocher solid; 1H NMR, d (ppm): 1.17 (t, 3H, J = 7.3 Hz); 1.30-1.65 (m, 6H); 1.90 (m, 2H); |

TABLE 2-continued

All the NMR were performed in DMSO-d6

| Cpd. | | Starting compounds, Reaction conditions and purification Yield, MP, Appearance, $^1$H NMR (solvent) data, Mass (ES+ or ES−) data |
|---|---|---|
| | | 2.37 (t, 2H, J = 7.3 Hz); 2.48 (m, 2H); 2.86 (m, 4H); 3.60 (s, 2H); 4.04 (q, 2H, J = 7.3 Hz); 6.60 (d, 1H, J = 8.7 Hz); 7.0-7.40 (m, 11H); 8.16 (d, 1H, J = 1.0 Hz); 8.24 (s, 1H); 8.80 (d, 1H, J = 8.7 Hz); 11.84 (br s, 1H); m/z: 566.29 [M + H]+ (calc. mass: 565.29). |
| 215 | 5-oxo-5-{5-[({phenyl[2-(piperidin-1-yl)phenyl]methyl}carbamoyl)methyl]-1H-indol-3-yl}pentanoic acid | From ethyl 5-oxo-5-{5-[({phenyl[2-(piperidin-1-yl)phenyl]methyl}carbamoyl)methyl]-1H-indol-3-yl}pentanoate Cpd. 214 following protocol E Yield: 81%; mp: 123, 130° C.; appearance: pinkish solid; 1H NMR, d (ppm): 1.30-1.65 (m, 6H); 1.87 (m, 2H); 2.26 (t, 2H, J = 7.3 Hz); 2.48 (m, 2H); 2.86 (m, 4H); 3.60 (s, 2H); 6.60 (d, 1H, J = 8.7 Hz); 7.0-7.40 (m, 11H); 8.16 (s, 1H); 8.24 (d, 1H, J = 3.1 Hz); 8.78 (d, 1H, J = 8.7 Hz); 11.82 (d, 1H, J = 3.1 Hz); m/z: 538.26 [M + H]+ (calc. mass: 537.26). |
| 216 | ethyl 5-{5-[({phenyl[2-(piperidin-1-yl)phenyl]methyl}carbamoyl)methyl]-1H-indol-3-yl}pentanoate | To a solution of ethyl 5-oxo-5-{5-[({phenyl[2-(piperidin-1-yl)phenyl]methyl}carbamoyl)methyl]-1H-indol-3-yl}pentanoate Cpd. 214 (140 mg, 0.25 mmol) and NaBH4 (19 mg, 0.50 mmol) in dry THF (2 mL) was added dropwise BF3•E2tO (70 µL, 0.57 mmol) at rt. The reaction was stirred at rt for 6 h. The reaction was quenched with water. The pH was adjusted tp pH = 5-6 with citric acid 10% and NaHCO3 10%. The aqueous layer was extracted with EtOAc. The combined organic layers were washed with brine, dried over MgSO4, filtered and the solution was concentrated under reduced pressure. The crude material was purified on silica gel column chromatography using CH2Cl2/MeOH (97:3) as eluent. The material was not pure enough and purified on another silica gel column chromatography using cyclohexane/EtOAc (7:3) as eluent. Yield: 7%; mp: ND; appearance: white solid; 1H NMR, d (ppm): 1.15 (t, 3H); 1.30-1.70 (m, 10H); 2.30 (t, 2H, J = 7.3 Hz); 2.48 (m, 2H); 2.58 (t, 2H, J = 7.3 Hz); 2.85 (m, 2H); 3.56 (s, 2H); 4.04 (q, 2H, J = 7.3 Hz); 6.61 (d, 1H, J = 8.7 Hz); 6.9-7.40 (m, 13H); 8.70 (d, 1H, J = 8.7 Hz); 10.62 (br s, 1H); m/z: 552.31 [M + H]+ (calc. mass: 551.31). |
| 217 | 5-{5-[({phenyl[2-(piperidin-1-yl)phenyl]methyl}carbamoyl)methyl]-1H-indol-3-yl}pentanoic acid | To a solution of ethyl 5-{5-[({phenyl[2-(piperidin-1-yl)phenyl]methyl}carbamoyl)methyl]-1H-indol-3-yl}pentanoate Cpd. 216 (10 mg, 0.02 mmol) in MeOH/THF (1.5 mL/1 mL) was added NaOH 5N (11 µL, 0.05 mmol). The reaction mixture was stirred at rt overnight. Excess of solvent was removed under vacuo. Water was added to the mixture and the solution was acidified with citric acid 10% up to pH = 4-5. The precipitate was collected by filtration and dried until constant weight. Yield: 74%; mp: 83, 103° C.; appearance: white solid; 1H NMR, d (ppm): 1.30-1.70 (m, 10H); 2.22 (t, 2H, J = 7.3 Hz); 2.48 (m, 2H); 2.62 (t, 2H, J = 7.3 Hz); 2.85 (m, 2H); 3.56 (s, 2H); 6.61 (d, 1H, J = 8.7 Hz); 6.9-7.40 (m, 13H); 8.70 (d, 1H, J = 8.7 Hz); 10.62 (br s, 1H); -m/z: 524.28 [M + H]+ (calc. mass: 523.28). |
| 218 | tert-butyl 3-{5-[({1-[2-(diethylamino)phenyl]pentyl}carbamoyl)methyl]-1H-indol-3-yl}propanoate | From 2-(1-aminopentyl)-N,N-diethylaniline Ex. 42 and 2-{3-[3-(tert-butoxy)-3-oxopropyl]-1H-indol-5-yl}acetic acid Ex. 1 following protocol D Yield: 74%; mp: 40° C.; appearance: white solid; 1H NMR, d (ppm): 0.78-0.82 (m, 3H); 0.88 (t, 6H, J = 7.0 Hz); 1.19-1.29 (m, 4H); 1.38 (s, 9H); 1.53-1.55 (m, 2H); 2.53 (t, 2H, J = 7.1 Hz); 2.84-3.01 (m, 6H); 3.47 (m, 2H); 5.27-5.35 (m, 1H); 6.95 (dd, 1H, J = 1.5 Hz, J = 8.3 Hz); 7.01-7.22 (m, 5H); 7.34-7.37 (m, 2H); 8.24 (d, 1H, J = 8.6 Hz); 10.67 (d, 1H, J = 1.9 Hz); m/z: 520.34 [M + H]+ (calc. mass: 519.34). |
| 219 | 3-{5-[({1-[2-(diethylamino)phenyl]pentyl}carbamoyl)methyl]-1H-indol-3-yl}propanoic acid | From tert-butyl 3-{5-[({1-[2-(diethylamino)phenyl]pentyl}carbamoyl)methyl]-1H-indol-3-yl}propanoate Cpd. 218 following protocol E Yield: 46%; mp: 70, 86° C.; appearance: white solid; 1H NMR, d (ppm): 0.80 (t, 3H, J = 6.7 Hz); 0.89 (t, 6H, J = 6.9 Hz); 1.14-1.33 (m, 4H); 1.49-1.59 (m, 2H); 2.56 (t, 2H, J = 7.2 Hz); 2.83-3.00 (m, 6H); 3.42-3.52 (m, 2H); 5.26-5.36 (m, 1H); 6.95 (dd, 1H, J = 1.2 Hz, J = 8.2 Hz); 7.00-7.23 (m, 5H); 7.33-7.41 (m, 2H); 8.25 (d, 1H, J = 8.2 Hz); 10.67 (s, 1H); 12.07 (br s, 1H); m/z: 464.28 [M + H]+ (calc. mass: 463.28). |

TABLE 2-continued

All the NMR were performed in DMSO-d6

| Cpd. | | Starting compounds, Reaction conditions and purification Yield, MP, Appearance, $^1$H NMR (solvent) data, Mass (ES+ or ES−) data |
|---|---|---|
| 220 | methyl 2-[5-({[(2-bromo-4-methylphenyl)(phenyl)methyl]carbamoyl}methyl)-1H-indol-3-yl]acetate | From (2-bromo-4-methylphenyl)(phenyl)methanamine Ex. 13 and 2-[3-(2-methoxy-2-oxoethyl)-1H-indol-5-yl]acetic acid Ex. 5 following protocol D<br>Yield: 43%; mp: 134, 136° C.; appearance: white solid; 1H NMR, d (ppm): 2.27 (s, 3H); 3.55 (s, 2H); 3.59 (s, 3H); 3.69 (s, 2H); 6.32 (d, 1H, J = 8.2 Hz); 7.00 (dd, 1H, J = 8.3 Hz, J = 1.6 Hz); 7.12-7.42 (m, 11H); 8.95 (d, 1H, J = 8.3 Hz); 10.86 (br s, 1H); m/z: 505.1 [M + H]+ (calc. mass: 504.1). |
| 221 | 2-[5-({[(2-bromo-4-methylphenyl)(phenyl)methyl]carbamoyl}methyl)-1H-indol-3-yl]acetic acid | From methyl 2-[5-({[(2-bromo-4-methylphenyl)(phenyl)methyl]carbamoyl}methyl)-1H-indol-3-yl]acetate Cpd. 220 following protocol F<br>Yield: 84%; mp: 101, 125° C.; appearance: white solid; 1H NMR, d (ppm): 2.26 (s, 3H); 3.55 (s, 2H); 3.58 (s, 2H); 6.32 (d, 1H, J = 8.2 Hz); 6.99 (dd, 1H, J = 8.3 Hz, J = 1.5 Hz); 7.12-7.36 (m, 10H); 7.42 (br s, 1H); 8.96 (d, 1H, J = 8.3 Hz); 10.81 (br s, 1H); 12.12 (br s, 1H); m/z: 491.08 [M + H]+ (calc. mass: 490.08). |
| 222 | methyl 2-[5-({[(2,4-dimethylphenyl)(5-methylthiophen-2-yl)methyl]carbamoyl}methyl)-1H-indol-3-yl]acetate | From (2,4-dimethylphenyl)(5-methylthiophen-2-yl)methanamine Ex. 63 and 2-[3-(2-methoxy-2-oxoethyl)-1H-indol-5-yl]acetic acid Ex. 5 following protocol D<br>Yield: 71%; mp: 58, 67° C.; appearance: white solid; 1H NMR, d (ppm): 2.16 (s, 3H); 2.23 (s, 3H); 2.35 (s, 3H); 3.52 (s, 2H); 3.59 (s, 3H); 3.69 (s, 2H); 6.27 (d, 1H, J = 8.3 Hz); 6.45 (dd, 1H, J = 3.4 Hz, J = 0.8 Hz); 6.58 (dd, 1H, J = 3.4 Hz, J = 1.1 Hz); 6.95-7.01 (m, 3H); 7.20-7.24 (m, 3H); 7.35 (br s, 1H); 8.98 (d, 1H, J = 8.4 Hz); 10.81 (br s, 1H); m/z: 461.18 [M + H]+ (calc. mass: 460.18). |
| 223 | 2-[5-({[(2,4-dimethylphenyl)(5-methylthiophen-2-yl)methyl]carbamoyl}methyl)-1H-indol-3-yl]acetic acid | From methyl 2-[5-({[(2,4-dimethylphenyl)(5-methylthiophen-2-yl)methyl]carbamoyl}methyl)-1H-indol-3-yl]acetate Cpd. 222 following protocol F<br>Yield: 81%; mp: 88, 107° C.; appearance: white solid; 1H NMR, d (ppm): 2.16 (s, 3H); 2.23 (s, 3H); 2.35 (s, 3H); 3.51 (s, 2H); 3.57 (s, 2H); 6.27 (d, 1H, J = 8.3 Hz); 6.44 (dd, 1H, J = 3.4 Hz, J = 0.9 Hz); 6.58 (dd, 1H, J = 3.4 Hz, J = 1.1 Hz); 6.95-7.00 (m, 3H); 7.17-7.24 (m, 3H); 7.36 (br s, 1H); 8.97 (d, 1H, J = 8.4 Hz); 10.80 (br s, 1H); 12.15 (br s, 1H); m/z: 447.16 [M + H]+ (calc. mass: 446.16). |
| 224 | methyl 2-{5-[({[2-(morpholin-4-yl)phenyl](phenyl)methyl}carbamoyl)methyl]-1H-indol-3-yl}acetate | From [2-(morpholin-4-yl)phenyl](phenyl)methanamine Ex. 52 and 2-[3-(2-methoxy-2-oxoethyl)-1H-indol-5-yl]acetic acid Ex. 5 following protocol D<br>Yield: 48%; mp: 74, 88° C.; appearance: white solid; 1H NMR, d (ppm): 2.49-2.51 (m, 2H); 2.84-2.89 (m, 2H); 3.43-3.50 (m, 2H); 3.55 (s, 2H); 3.57-3.62 (m, 5H); 3.67 (s, 2H); 6.64 (d, 1H, J = 8.7 Hz); 7.00 (dd, 1H, J = 8.3 Hz, J = 1.5 Hz); 7.07-7.30 (m, 11H); 7.35 (br s, 1H); 8.75 (d, 1H, J = 8.7 Hz); 10.85 (br s, 1H); m/z: 498.23 [M + H]+ (calc. mass: 497.23). |
| 225 | 2-{5-[({[2-(morpholin-4-yl)phenyl](phenyl)methyl}carbamoyl)methyl]-1H-indol-3-yl}acetic acid | From methyl 2-{5-[({[2-(morpholin-4-yl)phenyl](phenyl)methyl}carbamoyl)methyl]-1H-indol-3-yl}acetate Cpd. 224 following protocol F<br>Yield: 80%; mp: 107, 130° C.; appearance: white solid; 1H NMR, d (ppm): 2.45-2.50 (m, 2H); 2.86-2.90 (m, 2H); 3.45-3.50 (m, 2H); 3.55 (s, 2H); 3.57-3.63 (m, 4H); 6.64 (d, 1H, J = 8.7 Hz); 7.00 (dd, 1H, J = 8.4 Hz, J = 1.6 Hz); 7.08-7.30 (m, 11H); 7.36 (br s, 1H); 8.75 (d, 1H, J = 8.7 Hz); 10.81 (br s, 1H); 12.09 (br s, 1H); -m/z: 484.21 [M + H]+ (calc. mass: 483.21). |
| 226 | tert-butyl 3-[5-({[(2-bromo-4-methylphenyl)(pyrimidin-2-yl)methyl]carbamoyl}methyl)-1H-indol-3-yl]propanoate | From (2-bromo-4-methylphenyl)(pyrimidin-2-yl)methanamine Ex. 69 and 2-{3-[3-(tert-butoxy)-3-oxopropyl]-1H-indol-5-yl}acetic acid Ex. 1 following protocol D<br>Yield: 71%; mp: 78° C.; appearance: white solid; 1H NMR, d (ppm): 1.38 (s, 9H); 2.25 (s, 3H); 2.54 (t, 2H, J = 7.5 Hz); 2.87 (t, 2H, J = 7.3 Hz); 3.52-3.64 (m, 2H); 6.47 (d, 1H, J = 8.0 Hz); 6.97 (dd, 1H, J = 1.5 Hz, J = 8.3 Hz); 7.06 (d, 1H, J = 2.2 Hz); 7.12 (d, 1H, J = 8.2 Hz); 7.20 (d, 1H, J = 4.0 Hz); 7.23 (d, 1H, J = 3.6 Hz); 7.39-7.42 (m, 3H); 8.77 (d, 2H, J = 4.9 Hz); 8.94 (d, 1H, J = 8.0 Hz); 10.68 (s, 1H); m/z: 563.15 [M + H]+ (calc. mass: 562.15). |
| 227 | 3-[5-({[(2-bromo-4-methylphenyl)(pyrimidin-2-yl)methyl]carbamoyl}methyl)-1H- | From tert-butyl 3-[5-({[(2-bromo-4-methylphenyl)(pyrimidin-2-yl)methyl]carbamoyl}methyl)-1H-indol-3-yl]propanoate Cpd. 226 following protocol E<br>Yield: 88%; mp: 106, 126° C.; appearance: white solid; 1H NMR, d (ppm): 2.25 (s, 3H); 2.56 (t, 2H, J = 7.1 Hz); 2.88 (t, 2H, J = 7.4 Hz); 3.58 (dd, 2H, J = 13.8 Hz, J = 21.9 Hz); 6.47 (d, |

TABLE 2-continued

All the NMR were performed in DMSO-d6

| Cpd. | Starting compounds, Reaction conditions and purification Yield, MP, Appearance, $^1$H NMR (solvent) data, Mass (ES+ or ES−) data |
|---|---|
| indol-3-yl]propanoic acid | 1H, J = 8.0 Hz); 6.98 (dd, 1H, J = 1.5 Hz, J = 8.3 Hz); 7.07 (d, 1H, J = 2.2 Hz); 7.12 (dd, 1H, J = 1.3 Hz, J = 8.1 Hz); 7.21 (d, 1H, J = 4.4 Hz); 7.13 (d, 1H, J = 4.1 Hz); 7.38-7.41 (m, 3H); 8.77 (d, 2H, J = 4.9 Hz); 8.95 (d, 1H, J = 8.0 Hz); 10.68 (d, 1H, J = 1.8 Hz); 12.05 (br s, 1H); m/z: 507.09 [M + H]+ (calc. mass: 506.09). |
| 228 tert-butyl 3-[5-({[(4-methyl-1H-indol-7-yl)(phenyl)methyl]carbamoyl}methyl)-1H-indol-3-yl]propanoate | From (4-methyl-1H-indol-7-yl)(phenyl)methanamine Ex. 97 and 2-{3-[3-(tert-butoxy)-3-oxopropyl]-1H-indol-5-yl}acetic acid Ex. 1 following protocol D Yield: 64%; mp: 68, 88° C.; appearance: white solid; 1H NMR, d (ppm): 1.38 (s, 9H); 2.41 (s, 3H); 2.53 (t, 2H, J = 8.0 Hz); 2.86 (t, 2H, J = 7.3 Hz); 3.57 (s, 2H); 6.42-6.43 (m, 1H); 6.53 (d, 1H, J = 8.5 Hz); 6.76 (d, 1H, J = 7.4 Hz); 6.94-6.99 (m, 2H); 7.06 (d, 1H, J = 2.1 Hz); 7.18-7.33 (m, 7H); 7.40-7.42 (m, 1H); 8.94 (d, 1H, J = 8.4 Hz); 10.66 (s, 1H); 10.95 (s, 1H); m/z: 522.26 [M + H]+ (calc. mass: 521.26). |
| 229 3-[5-({[(4-methyl-1H-indol-7-yl)(phenyl)methyl]carbamoyl}methyl)-1H-indol-3-yl]propanoic acid | From tert-butyl 3-[5-({[(4-methyl-1H-indol-7-yl)(phenyl)methyl]carbamoyl}methyl)-1H-indol-3-yl]propanoate Cpd. 228 following protocol E Yield: 94%; mp: 80, 125° C.; appearance: white solid; 1H NMR, d (ppm): 2.41 (s, 3H); 2.55 (t, 2H, J = 8.3 Hz); 2.87 (t, 2H, J = 7.3 Hz); 3.57 (s, 2H); 6.42-6.43 (m, 1H); 6.52 (d, 1H, J = 8.4 Hz); 6.76 (d, 1H, J = 8.0 Hz); 6.95-6.99 (m, 2H); 7.05 (d, 1H, J = 2.2 Hz); 7.18-7.33 (m, 7H); 7.41-7.43 (m, 1H); 9.94 (d, 1H, J = 8.0 Hz); 10.66 (s, 1H); 10.95 (s, 1H); 12.04 (br s, 1H); m/z: 466.2 [M + H]+ (calc. mass: 465.2). |
| 230 tert-butyl 3-{5-[({1-[4-methyl-2-(piperidin-1-yl)phenyl]pentyl}carbamoyl)methyl]-1H-indol-3-yl}propanoate | From 1-[4-methyl-2-(piperidin-1-yl)phenyl]pentan-1-amine Ex. 102 and 2-{3-[3-(tert-butoxy)-3-oxopropyl]-1H-indol-5-yl}acetic acid Ex. 1 following protocol D Yield: 76%; mp: 56-58° C.; appearance: white solid; 1H NMR, d (ppm): 0.80 (t, 3H, J = 7.1 Hz); 1.16-1.31 (m, 5H); 1.37 (s, 9H); 1.44-1.68 (m, 9H); 2.20 (s, 3H); 2.53 (t, 2H, J = 8.3 Hz); 2.86 (t, 2H, J = 7.9 Hz); 3-3.08 (m, 2H); 3.45 (s, 2H); 5.12-5.19 (m, 1H); 6.82 (d, 1H, J = 7.7 Hz); 6.85 (s, 1H); 6.94 (dd, 1H, J = 8.1 Hz, J = 1.5 Hz); 7.05 (d, 1H, J = 2.3 Hz); 7.16-7.21 (m, 2H); 7.36 (s, 1H); 8.23 (d, 1H, J = 8.5 Hz); 10.66 (s, 1H); m/z: 546.36 [M + H]+ (calc. mass: 545.36). |
| 231 3-{5-[({1-[4-methyl-2-(piperidin-1-yl)phenyl]pentyl}carbamoyl)methyl]-1H-indol-3-yl}propanoic acid | From tert-butyl 3-{5-[({1-[4-methyl-2-(piperidin-1-yl)phenyl]pentyl}carbamoyl)methyl]-1H-indol-3-yl}propanoate Cpd. 230 following protocol E Yield: 89%; mp: 95-99° C.; appearance: light yellow solid; 1H NMR, d (ppm): 0.80 (t, 3H, J = 7.1 Hz); 1.18-1.63 (m, 13H); 2.20 (s, 3H); 2.53 (t, 2H, J = 8.2 Hz); 2.86 (t, 2H, J = 8.2 Hz); 3-3.10 (m, 2H); 3.45 (s, 2H); 5.12-5.19 (m, 1H); 6.82 (d, 2H, J = 8.2 Hz); 6.85 (s, 1H); 6.94 (dd, 1H, J = 8.3 Hz, J = 1.4 Hz); 7.05 (d, 1H, J = 2.2 Hz); 7.17 (d, 1H, J = 5.1 Hz); 7.19 (d, 1H, J = 5.6 Hz); 7.38 (s, 1H); 8.24 (d, 1H, J = 8.5 Hz); 10.64 (s, 1H); m/z: 490.29 [M + H]+ (calc. mass: 489.29). |
| 232 tert-butyl 3-{5-[({[2-(3,3-difluoropiperidin-1-yl)phenyl](phenyl)methyl}carbamoyl)methyl]-1H-indol-3-yl}propanoate | From [2-(3,3-difluoropiperidin-1-yl)phenyl](phenyl)methanamine Ex. 79 and 2-{3-[3-(tert-butoxy)-3-oxopropyl]-1H-indol-5-yl}acetic acid Ex. 1 following protocol D Yield: 75%; mp: 77, 81° C.; appearance: white solid; 1H NMR, d (ppm): 1.38 (s, 9H); 1.58-1.73 (m, 2H); 1.93-2 (m, 2H); 2.41-2.48 (m, 1H); 2.53 (t, 2H, J = 8.0 Hz); 2.87 (t, 2H, J = 8.0 Hz); 2.89-2.95 (m, 2H); 3.34-3.38 (m, 1H); 3.56 (s, 2H); 6.56 (d, 1H, J = 8.4 Hz); 6.97 (dd, 1H, J = 8.3 Hz, J = 1.5 Hz); 7.06 (d, 1H, J = 2.2 Hz); 7.11-7.28 (m, 9H); 7.38-7.42 (m, 2H); 8.80 (d, 1H, J = 8.5 Hz); 10.68 (s, 1H); m/z: 588.29 [M + H]+ (calc. mass: 587.29). |
| 233 3-{5-[({[2-(3,3-difluoropiperidin-1-yl)phenyl](phenyl)methyl}carbamoyl)methyl]-1H-indol-3-yl}propanoic acid | From tert-butyl 3-{5-[({[2-(3,3-difluoropiperidin-1-yl)phenyl](phenyl)methyl}carbamoyl)methyl]-1H-indol-3-yl}propanoate Cpd. 232 following protocol E Yield 90%; mp: 103, 113° C.; appearance: white solid; 1H NMR, d (ppm): 1.53-1.76 (m, 2H); 1.89-2 (m, 2H); 2.39-2.48 (m, 2H); 2.56 (t, 2H, J = 7.2 Hz); 2.88 (t, 2H, J = 7.4 Hz); 2.90-2.96 (m, 1H); 3.30-3.42 (m, 1H); 3.56 (s, 2H); 6.57 (d, 1H, J = 8.5 Hz); 6.98 (dd, 1H, J = 8.3 Hz, J = 1.5 Hz); 7.06 (d, 1H, J = 2.3 Hz); 7.11-7.28 (m, 9H); 7.39-7.41 (m, 2H); 8.81 (d, 1H, J = 8.5 Hz); 10.68 (d, 1H, J = 2.1 Hz); 12.06 (br s, 1H); - m/z: 532.23 [M + H]+ (calc. mass: 531.23). |

| Cpd. | | Starting compounds, Reaction conditions and purification Yield, MP, Appearance, $^1$H NMR (solvent) data, Mass (ES+ or ES−) data |
|---|---|---|
| 234 | tert-butyl N-[(3-{5-[({phenyl[2-(piperidin-1-yl)phenyl]methyl}carbamoyl)methyl]-1H-indol-3-yl}propanamido)methanimidoyl]carbamate | From 3-{5-[({phenyl[2-(piperidin-1-yl)phenyl]methyl}carbamoyl)methyl]-1H-indol-3-yl}propanoic acid Cpd. 1 and 1-(tert-Butoxycarbonyl)guanidine following protocol D<br>Yield: 71%; mp: 128-130° C.; appearance: white solid; 1H NMR, d (ppm): 1.38 (s, 9H); 1.40-1.65 (m, 6H); 2.45 (m, 2H); 2.66 (t, 2H, J = 7.3 Hz); 2.8-3.0 (m, 4H); 3.57 (s, 2H); 6.62 (d, 1H, J = 8.7 Hz); 6.95-7.35 (m, 12H); 7.40 (s, 1H); 8.72 (d, 1H, J = 8.7 Hz); 8.76 (br s, 1H); 8.90 (br s, 1H); 10.69 (s, 1H); 10.85 (br s, 1H); m/z: 637.34 [M + H]+ (calc. mass: 636.34). |
| 235 | 1-{2-[(2-{3-[2-(carbamimidoylcarbamoyl)ethyl]-1H-indol-5-yl}acetamido)(phenyl)methyl]phenyl}piperidin-1-ium chloride | tert-butyl N-[(3-{5-[({phenyl[2-(piperidin-1-yl)phenyl]methyl}carbamoyl)methyl]-1H-indol-3-yl}propanamido)methanimidoyl]carbamate Cpd. 234 (55 mg, 0.09 mmol) was dissolved in a minimum of CH2Cl2. TFA (64 µL, 0.90 mmol) was added to the mixture. The solution was stirred at rt and monitored by TLC. After completion, water was added to quench the reaction and pH was adjusted to pH = 8 with NaHCO3 10%. The precipitate formed was collected by filtration and washed with Et2O. Hydrochloride was performed and the salt was triturated with Et2O and small amount of EtOH.<br>Yield: 62%; mp: 167, 177° C.; appearance: white solid; 1H NMR, d (ppm): 1.40-1.65 (m, 6H); 2.45 (m, 2H); 2.75 (t, 2H, J = 7.3 Hz); 2.85 (m, 2H); 2.87 (t, 2H, J = 7.3 Hz); 3.58 (s, 2H); 6.62 (d, 1H, J = 8.7 Hz); 6.95-7.35 (m, 12H); 7.42 (s, 1H); 8.22 (br s, 3H); 8.77 (br s, 1H); 8.90 (br s, 1H); 10.75 (s, 1H); 10.65 (br s, 1H); m/z: 537.28 [M + H]+ (calc. mass: 536.28). |
| 236 | ethyl 3-{5-[({phenyl[2-(piperidin-1-yl)phenyl]methyl}carbamoyl)methyl]-1H-indazol-3-yl}propanoate | Step 1: to a solution of 2-(1H-indazol-5-yl)acetic acid (100 mg, 0.57 mmol) and KOH (118 mg, 2.10 mmol) in DMF (1 mL) was added iodine (144 mg, 0.57 mmol). The reaction mixture was stirred at rt for 4 h. Sodium thiosulfate 10% was added to quench the reaction. The aqueous layer was extracted with EtOAc. The combined organic layers were dried over MgSO4, filtered and the solution was concentrated under reduced pressure to afford 2-(3-iodo-1H-indazol-5-yl)acetic acid as white solid (yield: 79%). The compound was pure enough and used in the next step without further purification. 1H NMR, d (ppm): 3.70 (s, 2H); 7.30-7.34 (m, 2H); 7.48 (dd, 1H, J = 8.4 Hz, J = 0.8 Hz); 12.30 (br s, 1H); 13.44 (s, 1H).<br>Step 2: to a solution of 2-(3-iodo-1H-indazol-5-yl)acetic acid (130 mg, 0.43 mmol) in DMF (1 mL) were added DMAP (116 mg, 0.95 mmol), EDCl•HCl (91 mg, 0.47 mmol) and phenyl(2-(piperidin-1-yl)phenyl)methanamine Ex. 9 (115 mg, 0.43 mmol). The reaction mixture was stirred at rt for 2 h. Sat. NH4Cl was added and the aqueous layer was extracted with EtOAc. The organic layer was washed with sat. NH4Cl, dried over MgSO4, filtered and the solution was concentrated to dryness. The crude material was purified on silica gel column chromatography using Cyclohexane/EtOAc (8:2) as eluent affording 2-(3-iodo-1H-indazol-5-yl)-N-(phenyl(2-(piperidin-1-yl)phenyl)methyl)acetamide as white solid (yield: 70%). 1H NMR, d (ppm): 1.35-1.56 (m, 6H); 2.47-2.51 (m, 2H); 2.83-2.88 (m, 2H); 3.65 (s, 2H); 6.61 (d, 1H, J = 8.5 Hz); 7.07 (dt, 1H, J = 7.5 Hz, J = 1.2 Hz); 7.12-7.21 (m, 8H); 7.23-7.36 (m, 2H); 7.46 (d, 1H, J = 5.0 Hz); 8.84 (d, 1H, J = 8.5 Hz); 13.41 (s, 1H).<br>Step 3: to a solution of 2-(3-iodo-1H-indazol-5-yl)-N-(phenyl(2-(piperidin-1-yl)phenyl)methyl)acetamide (130 mg, 0.24 mmol) in CH2Cl2 was added DMAP (4 mg, 0.04 mmol) followed by di-tert-butyl dicarbonate (54 mg, 0.25 mmol). The solution was stirred at rt for 2 h. Water was added to quench the reaction. The two phases were partitionated. The aqueous layer was extracted once more with CH2Cl2. The combined organic layers were dried over MgSO4, filtered and the solution was concentrated under reduced pressure to afford tert-butyl 5-((phenyl(2-(piperidin-1-yl)phenyl)methylcarbamoyl)methyl)-3-iodo-1H-indazole-1-carboxylate as white solid (yield: 98%). The compound was pure enough and used in the next step without further |

TABLE 2-continued

All the NMR were performed in DMSO-d6

TABLE 2-continued

*All the NMR were performed in DMSO-d6*

| Cpd. | Starting compounds, Reaction conditions and purification Yield, MP, Appearance, $^1$H NMR (solvent) data, Mass (ES+ or ES−) data |
|---|---|
| | purification. 1H NMR, d (ppm): 1.40-1.56 (m, 6H); 1.63 (s, 9H); 2.48-2.5 (m, 2H); 2.85-2.88 (m, 2H); 3.72 (s, 2H); 6.61 (d, 1H, J = 8.4 Hz); 7.06 (dt, 1H, J = 7.4 Hz, J = 1.3 Hz); 7.12-7.30 (m, 8H); 7.47 (s, 1H); 7.58 (dd, 1H, J = 8.7 Hz, J = 1.6 Hz); 7.97 (d, 1H, J = 8.6 Hz); 8.90 (d, 1H, J = 8.5 Hz). Step 4: to a solution of tert-butyl 5-((phenyl(2-(piperidin-1-yl)phenyl)methylcarbamoyl)methyl)-3-iodo-1H-indazole-1-carboxylate (110 mg, 0.17 mmol), Pd(OAc)2 (1 mg, 0.004 mmol), triphenylphosphine (2 mg, 0.009 mmol) and triethylamine (140 mg, 1.4 mmol) in dry dioxane (1.5 mL) was added ethyl acrylate (140 mg, 1.4 mmol) under N2 atmosphere. The reaction mixture was stirred at 80° C. and under N2 atmosphere overnight. The solution was concentrated to dryness. The crude material was purified on silica gel column chromatography using Cyclohexane/EtOAc (7:3) as eluent affording tert-butyl 3-(2-(ethoxycarbonyl)vinyl)-5-((phenyl(2-(piperidin-1-yl)phenyl)methylcarbamoyl)methyl)-1H-indazole-1-carboxylate as white solid (yield: 95%). 1H NMR, d (ppm): 1.30 (t, 3H, J = 7.3 Hz); 1.40-1.60 (m, 8H); 1.65 (s, 9H); 2.84-2.89 (m, 2H); 3.74 (s, 2H); 4.26 (q, 2H, J = 7.1 Hz); 6.62 (d, 1H, J = 8.6 Hz); 6.93 (d, 1H, J = 16.4 Hz); 7.05 (dt, 1H, J = 8.6 Hz, J = 1.4 Hz); 7.12-7.30 (m, 8H); 7.57 (dd, 1H, J = 8.8 Hz, J = 1.4 Hz); 8.80 (d, 1H, J = 16.4 Hz); 8.05 (d, 1H, J = 8.7 Hz); 8.12 (s, 1H); 8.88 (d, 1H, J = 8.5 Hz). Step 5: tert-butyl 3-(2-(ethoxycarbonyl)vinyl)-5-((phenyl(2-(piperidin-1-yl)phenyl)methylcarbamoyl)methyl)-1H-indazole-1-carboxylate (100 mg, 0.16 mmol) was dissolved in EtOH/THF (2 mL + 1 mL) with small amount of Pd/C 10%. The reaction mixture was stirred under H2 atmosphere at rt for 18 h. The reaction mixture was filtered-off on Celite. The solution was concentrated under reduced pressure and purified on silica gel column chromatography using Cyclohexane/EtOAc (8:2) as eluent to give tert-butyl 3-(2-(ethoxycarbonyl)ethyl)-5-((phenyl(2-(piperidin-1-yl)phenyl)methylcarbamoyl)methyl)-1H-indazole-1-carboxylate as pale yellow solid (yield: 51%). 1H NMR (300 MHz, DMSO-d6, d in ppm): 1.16 (t, 3H, J = 7.1 Hz); 1.40-1.60 (m, 6H); 1.63 (s, 9H); 2.50 (m, 2H); 2.79-2.86 (m, 4H); 3.16 (t, 2H, J = 7.2 Hz); 3.70 (s, 2H); 4.07 (q, 2H, J = 7.1 Hz); 6.64 (d, 1H, J = 8.6 Hz); 7.08 (dt, 1H, J = 7.2 Hz, J = 1.4 Hz); 7.14-7.22 (m, 5H); 7.26-7.32 (m, 3H); 7.50 (dd, 1H, J = 8.6 Hz, J = 1.4 Hz); 7.73 (s, 1H); 7.94 (d, 1H, J = 8.7 Hz); 8.86 (d, 1H, J = 8.7 Hz). Step 6: tert-butyl 3-(3-ethoxy-3-oxopropyl)-5-[({phenyl[2-(piperidin-1-yl)phenyl]methyl}carbamoyl)methyl]-1H-indazole-1-carboxylate (48 mg, 0.08 mmol) was dissolved in a minimum of CH2Cl2. TFA (60 µL, 0.76 mmol) was added to the mixture. The solution was stirred at rt and monitored by TLC. After completion, water was added to quench the reaction and pH was adjusted to pH = 8 with NaHCO3 10%. The aqueous solution was extracted with CH2Cl2. The combined organic layers were dried over MgSO4, filtered and the solution was concentrated under reduced pressure to afford Cpd. 236. Yield: 94%; mp: 114, 178° C.; appearance: white solid; 1H NMR, d (ppm): 1.14 (t, 3H, J = 7.1 Hz); 1.40-1.56 (m, 6H); 2.45-2.55 (m, 2H); 2.76 (t, 2H, J = 7.4 Hz); 2.8-2.9 (m, 2H); 3.11 (t, 2H, J = 7.3 Hz); 3.61 (s, 2H); 4.04 (q, 2H, J = 7.1 Hz); 6.62 (d, 1H, J = 8.5 Hz); 7.06 (td, 1H, J = 7.5 Hz, J = 1.4 Hz); 7.12-7.30 (m, 9H); 7.36 (d, 1H, J = 8.5 Hz); 7.57 (s, 1H); 8.79 (d, 1H, J = 8.5 Hz); 12.59 (s, 1H); m/z: 525.27 [M + H]+ (calc. mass: 524.27). |
| 237  3-{5-[({phenyl[2-(piperidin-1-yl)phenyl]methyl}carbamoyl)methyl]-1H-indazol-3-yl}propanoic acid | From ethyl 3-{5-[({phenyl[2-(piperidin-1-yl)phenyl]methyl}carbamoyl)methyl]-1H-indazol-3-yl}propanoate Cpd. 236 following protocol E Yield: 83%; mp: 111, 121° C.; appearance: white solid; 1H NMR, d (ppm): 1.40-1.60 (m, 6H); 2.45-2.55 (m, 2H); 2.66 (t, 2H, J = 7.2 Hz); 2.80-2.90 (m, 2H); 3.07 (t, 2H, J = 7.3 Hz); 3.61 (s, 2H); 6.62 (d, 1H, J = 8.7 Hz); 7.03-7.30 (m, 10H); 7.35 (d, 1H, J = 8.6 Hz); 7.58 (s, 1H); 8.79 (d, 1H, J = 8.1 Hz); 12.56 (br s, 1H); m/z: 497.24 [M + H]+ (calc. mass: 496.24). |

TABLE 2-continued

All the NMR were performed in DMSO-d6

| Cpd. | | Starting compounds, Reaction conditions and purification Yield, MP, Appearance, ¹H NMR (solvent) data, Mass (ES+ or ES−) data |
|---|---|---|
| 238 | methyl 2-{5-[({phenyl[3-(piperidin-1-yl)phenyl]methyl}carbamoyl)methyl]-1H-indol-3-yl}acetate | From phenyl[3-(piperidin-1-yl)phenyl]methanamine Ex. 49 and and 2-[3-(2-methoxy-2-oxoethyl)-1H-indol-5-yl]acetic acid Ex. 5 following protocol D Yield: 64%; mp: 62, 74° C.; appearance: white solid; 1H NMR, d (ppm): 1.50-1.52 (m, 6H); 2.49-2.51 (m, 2H); 2.99-2.301 (m, 2H); 3.55 (s, 2H); 3.56 (s, 3H); 3.68 (s, 2H); 6.00 (d, 1H, J = 8.7 Hz); 6.60 (d, 1H, J = 7.3 Hz); 6.73-6.75 (m, 1H); 6.83 (br s, 1H); 7.02-7.11 (m, 2H); 7.18-7.32 (m, 7H); 7.37 (br s, 1H); 8.88 (d, 1H, J = 8.7 Hz); 10.86 (br s, 1H); m/z: 496.25 [M + H]+ (calc. mass: 495.25). |
| 239 | 2-{5-[({phenyl[3-(piperidin-1-yl)phenyl]methyl}carbamoyl)methyl]-1H-indol-3-yl}acetic acid | From methyl 2-{5-[({phenyl[3-(piperidin-1-yl)phenyl]methyl}carbamoyl)methyl]-1H-indol-3-yl}acetate Cpd. 238 following protocol F Yield: 74%; mp: 102, 129° C.; appearance: white solid; 1H NMR, d (ppm): 1.49-1.51 (m, 6H); 2.49-2.51 (m, 2H); 3.01-3.03 (m, 2H); 3.50-3.58 (m, 4H); 6.00 (d, 1H, J = 8.7 Hz); 6.62-6.85 (m, 3H); 7.03 (dd, 1H, J = 8.4 Hz, J = 1.5 Hz); 7.09-7.11 (m, 1H); 7.18-7.33 (m, 7H); 7.39 (br s, 1H); 8.97 (d, 1H, J = 8.8 Hz); 10.82 (br s, 1H); 12.11 (br s, 1H); m/z: 482.23 [M + H]+ (calc. mass: 481.23). |
| 240 | tert-butyl 3-{5-[({3-methyl-1-[2-(propan-2-yloxy)phenyl]butyl}carbamoyl)methyl]-1H-indol-3-yl}propanoate | From 3-methyl-1-[2-(propan-2-yloxy)phenyl]butan-1-amine Ex. 117 and 2-{3-[3-(tert-butoxy)-3-oxopropyl]-1H-indol-5-yl}acetic acid Ex. 1 following protocol D Yield: 70%; mp: 54, 61° C.; appearance: white solid; 1H NMR, d (ppm): 0.87 (dd, 6H, J = 6.4 Hz, J = 5.3 Hz), 1.21 (dd, 6H, J = 5.9 Hz, J = 2.6 Hz), 1.38 (m, 11H), 1.57-1.60 (m, 1H), 2.50-2.56 (m, 2H), 2.87 (t, 2H, J = 7.5 Hz), 3.49 (s, 2H), 4.54-4.62 (m, 1H), 5.15-5.22 (m, 1H), 6.81 (m, 1H), 6.89 (d, 1H, J = 7.8 Hz), 6.95 (dd, 1H, J = 8.3 Hz, J = 1.5 Hz), 7.06-7.13 (m, 2H), 7.22 (d, 1H, J = 8.3 Hz), 7.23 (dd, 1H, J = 7.5 Hz, J = 1.6 Hz), 7.38 (s, 1H), 8.18 (d, 1H, J = 8.8 Hz), 10.68 (d, 1H, J = 1.9 Hz); m/z: 507.38 [M + H]+ (calc. mass: 506.31). |
| 241 | 3-{5-[({3-methyl-1-[2-(propan-2-yloxy)phenyl]butyl}carbamoyl)methyl]-1H-indol-3-yl}propanoic acid | From tert-butyl 3-{5-[({3-methyl-1-[2-(propan-2-yloxy)phenyl]butyl}carbamoyl)methyl]-1H-indol-3-yl}propanoate Cpd. 240 following protocol E Yield: 93%; mp: 72, 86° C.; appearance: white solid; 1H NMR, d (ppm): 0.88 (dd, 6H, J = 6.4 Hz, J = 5.3 Hz), 1.23 (dd, 6H, J = 6.0 Hz, J = 2.6 Hz), 1.32-1.51 (m, 2H), 1.58-1.62 (m, 1H), 2.57 (t, 2H, J = 6.9 Hz), 2.90 (t, 2H), 3.51 (s, 2H), 4.57-4.63 (m, 1H), 5.16-5.22 (m, 1H), 6.80-6.85 (m, 1H), 6.91 (d, 1H, J = 7.7 Hz), 6.97 (dd, 1H, J = 8.3 Hz, J = 1.5 Hz), 7.08-7.15 (m, 2H), 7.22-7.27 (m, 2H), 7.42 (s, 1H), 8.21 (d, 1H, J = 8.9 Hz), 10.69 (d, 1H, J = 2.1 Hz); m/z: 451.3 [M + H]+ (calc. mass: 450.25). |
| 242 | tert-butyl 3-[5-({[1-(2-ethoxyphenyl)-3-methylbutyl]carbamoyl}methyl)-1H-indol-3-yl]propanoate | From 1-(2-ethoxyphenyl)-3-methylbutan-1-amine Ex. 119 and 2-{3-[3-(tert-butoxy)-3-oxopropyl]-1H-indol-5-yl}acetic acid Ex. 1 following protocol D Yield: 82%; mp: 42, 53° C.; appearance: white solid; 1H NMR, d (ppm): 0.87 (dd, 6H, J = 6.5 Hz, J = 3.9 Hz), 1.28 (t, 3H, J = 6.9 Hz), 1.38-1.46 (m, 11H), 1.57-1.66 (m, 1H), 2.53 (t, 2H, J = 7.4 Hz), 2.87 (t, 2H, J = 7.5 Hz), 3.49 (s, 2H), 3.97 (q, 2H, J = 7.0 Hz), 5.16-5.24 (m, 1H), 6.81-6.89 (m, 2H), 6.96 (dd, 1H, J = 8.3 Hz, J = 1.5 Hz), 7.07 (dd, 1H, J = 2.3 Hz), 7.09-7.15 (m, 1H), 7.21 (d, 1H, J = 8.3 Hz), 7.23 (dd, 1H, J = 7.4 Hz, J = 1.6 Hz), 7.38 (s, 1H), 8.22 (d, 1H, J = 8.7 Hz), 10.68 (d, 1H, J = 1.6 Hz); m/z: 493.33 [M + H]+ (calc. mass: 492.29). |
| 243 | 3-[5-({[1-(2-ethoxyphenyl)-3-methylbutyl]carbamoyl}methyl)-1H-indol-3-yl]propanoic acid | From tert-butyl 3-[5-({[1-(2-ethoxyphenyl)-3-methylbutyl]carbamoyl}methyl)-1H-indol-3-yl]propanoate Cpd. 242 following protocol E Yield: 93%; mp: 67, 80° C.; appearance: white solid; 1H NMR, d (ppm): 0.85-0.88 (m, 6H), 1.28 (t, 3H, J = 7.0 Hz), 1.33-1.51 (m, 2H), 1.55-1.66 (m, 1H), 2.54 (t, 2H, J = 7.2 Hz), 2.89 (t, 2H, J = 7.5 Hz), 3.34 (s, 2H), 3.97 (q, 2H, J = 7.0 Hz), 5.16-5.24 (m, 1H), 6.81-6.89 (m, 2H), 6.95 (dd, 1H, J = 8.3 Hz, J = 1.5 Hz), 7.06 (d, 1H, J = 2.2 Hz), 7.09-7.14 (m, 1H), 7.21 (d, 1H, J = 8.1 Hz), 7.23 (dd, 1H, J = 7.4 Hz, J = 1.6 Hz), 7.40 (s, 1H), 8.23 (d, 1H, J = 8.9 Hz), 10.67 (d, 1H, J = 1.6 Hz); m/z: 437.29 [M + H]+ (calc. mass: 436.23). |

TABLE 2-continued

All the NMR were performed in DMSO-d6

| Cpd. | | Starting compounds, Reaction conditions and purification Yield, MP, Appearance, ¹H NMR (solvent) data, Mass (ES+ or ES−) data |
|---|---|---|
| 244 | tert-butyl 3-{5-[({4-methyl-1-[2-(piperidin-1-yl)phenyl]pentyl}carbamoyl)methyl]-1H-indol-3-yl}propanoate | From 4-methyl-1-[2-(piperidin-1-yl)phenyl]pentan-1-amine Ex. 120 and 2-{3-[3-(tert-butoxy)-3-oxopropyl]-1H-indol-5-yl}acetic acid Ex. 1 following protocol D Yield: 85%; mp: 49, 58° C.; appearance: white solid; 1H NMR, d (ppm): 0.80 (dd, 6H, J = 10.8 Hz, J = 6.6 Hz), 1.05-1.25 (m, 2H), 1.38 (s, 9H), 1.44-1.61 (m, 9H), 2.50-2.56 (m, 4H), 2.87 (t, 2H, J = 7.6 Hz), 3.04-3.09 (m, 2H), 3.42-3.53 (m, 2H), 5.13-5.20 (m, 1H), 6.96 (dd, 1H, J = 8.3 Hz, J = 1.5 Hz), 6.99-7.07 (m, 3H), 7.10-7.16 (m, 1H), 7.21 (d, 1H, J = 8.2 Hz), 7.30 (dd, 1H, J = 7.5 Hz, J = 1.5 Hz), 7.38 (s, 1H), 8.30 (d, 1H, J = 8.3 Hz), 10.67 (d, 1H, J = 1.5 Hz); m/z: 546.37 [M + H]+ (calc. mass: 545.36). |
| 245 | 3-{5-[({4-methyl-1-[2-(piperidin-1-yl)phenyl]pentyl}carbamoyl)methyl]-1H-indol-3-yl}propanoic acid | From tert-butyl 3-{5-[({4-methyl-1-[2-(piperidin-1-yl)phenyl]pentyl}carbamoyl)methyl]-1H-indol-3-yl}propanoate Cpd. 244 following protocol E Yield: 91%; mp: 75, 93° C.; appearance: white solid; 1H NMR, d (ppm): 0.77-0.83 (m, 6H), 1.02-1.27 (m, 2H), 1.47-1.61 (m, 9H), 2.50-2.58 (m, 4H), 2.88 (t, 2H, J = 7.5 Hz), 3.05-3.07 (m, 2H), 3.42-3.52 (m, 2H), 5.13-5.20 (m, 1H), 6.96 (dd, 1H, J = 8.3 Hz, J = 1.5 Hz), 6.99-7.06 (m, 3H), 7.10-7.16 (m, 1H), 7.20 (d, 1H, J = 8.2 Hz), 7.30 (dd, 1H, J = 7.5 Hz, J = 1.5 Hz), 7.39 (s, 1H), 8.31 (d, 1H, J = 8.5 Hz), 10.67 (d, 1H, J = 2.0 Hz); -m/z: 490.34 [M + H]+ (calc. mass: 489.29). |
| 246 | tert-butyl 3-[5-({[(2,4-diethoxyphenyl)(phenyl)methyl]carbamoyl}methyl)-1H-indol-3-yl]propanoate | From (2,4-diethoxyphenyl)(phenyl)methanamine Ex. 121 and 2-{3-[3-(tert-butoxy)-3-oxopropyl]-1H-indol-5-yl}acetic acid Ex. 1 following protocol D Yield: 80%; mp: 57, 67° C.; appearance: white solid; 1H NMR, d (ppm): 1.08 (t, 3H, J = 6.9 Hz), 1.28 (t, 3H, J = 7.0 Hz), 1.38 (s, 9H), 2.53 (t, 2H, J = 7.6 Hz), 2.87 (t, 2H, J = 7.5 Hz), 3.55 (s, 2H), 3.81-3.91 (m, 2H), 3.93-4.00 (m, 2H), 6.26 (d, 1H, J = 8.8 Hz), 6.44-6.47 (m, 2H), 6.98 (dd, 1H, J = 8.3 Hz, J = 1.5 Hz), 7.07 (d, 1H, J = 2.3 Hz), 7.13-7.18 (m, 4H), 7.21-7.27 (m, 3H), 7.40 (s, 1H), 8.52 (d, 1H, J = 8.8 Hz), 10.69 (d, 1H, J = 2.0 Hz); m/z: 557.38 [M + H]+ (calc. mass: 556.29). |
| 247 | 3-[5-({[(2,4-diethoxyphenyl)(phenyl)methyl]carbamoyl}methyl)-1H-indol-3-yl]propanoic acid | From tert-butyl 3-[5-({[(2,4-diethoxyphenyl)(phenyl)methyl]carbamoyl}methyl)-1H-indol-3-yl]propanoate Cpd. 246 following protocol E Yield: 90%; mp: 76, 97° C.; appearance: white solid; 1H NMR, d (ppm): 1.08 (t, 3H, J = 6.9 Hz), 1.28 (t, 3H, J = 7.0 Hz), 2.55 (t, 2H, J = 7.1 Hz), 2.88 (t, 2H, J = 7.4 Hz), 3.55 (s, 2H), 3.81-3.91 (m, 2H), 3.93-4.00 (m, 2H), 6.27 (d, 1H, J = 8.7 Hz), 6.44-6.48 (m, 2H), 6.97 (dd, 1H, J = 8.3 Hz, J = 1.5 Hz), 7.06 (d, 1H, J = 2.3 Hz), 7.13-7.19 (m, 4H), 7.21-7.27 (m, 3H), 7.42 (s, 1H), 8.54 (d, 1H, J = 8.8 Hz), 10.68 (d, 1H, J = 1.9 Hz); m/z: 501.32 [M + H]+ (calc. mass: 500.23). |
| 248 | tert-butyl 3-{5-[({3-methyl-1-[4-methyl-2-(propan-2-yloxy)phenyl]butyl}carbamoyl)methyl]-1H-indol-3-yl}propanoate | From 3-methyl-1-[4-methyl-2-(propan-2-yloxy)phenyl]butan-1-amine Ex. 118 and 2-{3-[3-(tert-butoxy)-3-oxopropyl]-1H-indol-5-yl}acetic acid Ex. 1 following protocol D Yield: 89%; mp: 47, 56° C.; appearance: white solid; 1H NMR, d (ppm): 0.86 (dd, 6H, J = 6.5 Hz, J = 3.8 Hz), 1.20 (dd, 6H, J = 6.0 Hz, J = 3.5 Hz), 1.31-1.44 (m, 11H), 1.51-1.59 (m, 1H), 2.21 (s, 3H), 2.53 (t, 2H, J = 7.7 Hz), 2.87 (t, 2H, J = 7.5 Hz), 3.48 (s, 2H), 4.51-4.59 (m, 1H), 5.09-5.17 (m, 1H), 6.62 (d, 1H, J = 7.6 Hz), 6.71 (s, 1H), 6.95 (dd, 1H, J = 8.3 Hz, J = 1.5 Hz), 7.06 (d, 1H, J = 2.3 Hz), 7.09 (d, 1H, J = 7.7 Hz), 7.21 (d, 1H, J = 8.3 Hz), 7.38 (s, 1H), 8.09 (d, 1H, J = 8.9 Hz), 10.68 (d, 1H, J = 1.8 Hz); m/z: 521.37 [M + H]+ (calc. mass: 520.33). |
| 249 | 3-{5-[({3-methyl-1-[4-methyl-2-(propan-2-yloxy)phenyl]butyl}carbamoyl)methyl]-1H-indol-3-yl}propanoic acid | From tert-butyl 3-{5-[({3-methyl-1-[4-methyl-2-(propan-2-yloxy)phenyl]butyl}carbamoyl)methyl]-1H-indol-3-yl}propanoate Cpd. 248 following protocol E Yield: 91%; mp: 82, 90° C.; appearance: white solid; 1H NMR, d (ppm): 0.84-0.87 (m, 6H), 1.18-121 (m, 6H), 1.34-1.42 (m, 2H), 1.53-1.57 (m, 1H), 2.21 (s, 3H), 2.55 (t, 2H, J = 7.1 Hz), 2.88 (t, 2H, J = 7.4 Hz), 3.48 (s, 2H), 4.51-4.59 (m, 1H), 5.09-5.17 (m, 1H), 6.62 (d, 1H, J = 7.7 Hz), 6.71 (s, 1H), 6.95 (dd, 1H, J = 8.3 Hz, J = 1.5 Hz), 7.06 (d, 1H, J = 2.2 Hz), 7.09 (d, 1H, J = 7.7 Hz), 7.20 (d, 1H, J = 8.3 Hz), 7.39 (s, 1H), 8.11 (d, 1H, J = 9.0 Hz), 10.67 (d, 1H, J = 1.9 Hz); m/z: 465.33 [M + H]+ (calc. mass: 464.26). |

TABLE 2-continued

All the NMR were performed in DMSO-d6

| Cpd. | | Starting compounds, Reaction conditions and purification Yield, MP, Appearance, $^1$H NMR (solvent) data, Mass (ES+ or ES−) data |
|---|---|---|
| 250 | tert-butyl 3-{5-[({[2-(azepan-1-yl)-4-methylphenyl](phenyl)methyl}carbamoyl)methyl]-1H-indol-3-yl}propanoate | From [2-(azepan-1-yl)-4-methylphenyl](phenyl)methanamine Ex. 142 and 2-{3-[3-(tert-butoxy)-3-oxopropyl]-1H-indol-5-yl}acetic acid Ex. 1 following protocol D<br>Yield: 47%; mp: 73, 76° C.; appearance: white solid; 1H NMR, d (ppm): 1.38 (s, 9H), 1.39-1.47 (m, 2H), 1.49-1.65 (m, 6H), 2.22 (s, 3H), 2.53 (t, 2H, J = 8.2 Hz), 2.73-2.90 (m, 4H), 2.92-3.03 (m, 2H), 3.54 (s, 2H), 6.65 (d, 1H, J = 8.5 Hz), 6.85 (d, 1H, J = 9.1 Hz), 6.92-7.01 (m, 2H), 7.06 (d, 1H, J = 2.3 Hz), 7.09-7.28 (m, 7H), 7.39 (s, 1H), 8.64 (d, 1H, J = 8.5 Hz), 10.67 (d, 1H, J = 1.7 Hz); -m/z: 580.27 [M + H]+ (calc. mass: 579.34). |
| 251 | 3-{5-[({[2-(azepan-1-yl)-4-methylphenyl](phenyl)methyl}carbamoyl)methyl]-1H-indol-3-yl}propanoic acid | From tert-butyl 3-{5-[({[2-(azepan-1-yl)-4-methylphenyl](phenyl)methyl}carbamoyl)methyl]-1H-indol-3-yl}propanoate Cpd. 250 following protocol E<br>Yield: 42%; mp: 118, 123° C.; appearance: white solid; 1H NMR, d (ppm): 1.34-1.48 (m, 2H), 1.48-1.66 (m, 6H), 2.22 (s, 3H), 2.50-2.53 (m, 2H), 2.73-2.90 (m, 4H), 2.91-3.03 (m, 2H), 3.54 (s, 2H), 6.65 (d, 1H, J = 8.5 Hz), 6.85 (d, 1H, J = 7.9 Hz), 6.92-7.01 (m, 2H), 7.05 (d, 1H, J = 2.2 Hz), 7.08-7.30 (m, 7H), 7.41 (s, 1H), 8.67 (d, 1H, J = 8.6 Hz), 10.65 (d, 1H, J = 1.9 Hz); -m/z: 524.23 [M + H]+ (calc. mass: 523.28). |
| 252 | tert-butyl 3-[5-({[(4,5-dimethylfuran-2-yl)[2-(piperidin-1-yl)phenyl]methyl]carbamoyl}methyl)-1H-indol-3-yl]propanoate | From (4,5-dimethylfuran-2-yl)[2-(piperidin-1-yl)phenyl]methanamine Ex. 143 and 2-{3-[3-(tert-butoxy)-3-oxopropyl]-1H-indol-5-yl}acetic acid Ex. 1 following protocol D<br>Yield: 52%; mp: 55, 65° C.; appearance: pale yellow solid; 1H NMR, d (ppm): 1.38 (s, 9H), 1.40-1.65 (m, 6H), 1.80 (s, 3H), 2.07 (s, 3H), 2.50-2.60 (m, 4H), 2.75-2.80 (m, 2H), 2.85 (t, 2H, J = 8.0 Hz), 3.49 (s, 2H), 5.72 (s, 1H), 6.48 (d, 1H, J = 8.4 Hz), 6.96 (dd, 1H, J = 8.3 Hz, J = 2.4 Hz), 7.0-7.15 (m, 3H), 7.15-7.25 (m, 2H), 7.3-7.4 (m, 2H), 8.67 (d, 1H, J = 8.5 Hz), 10.67 (d, 1H, J = 1.8 Hz); m/z: 570.36 [M + H]+ (calc. mass: 569.32). |
| 253 | 3-[5-({[(4,5-dimethylfuran-2-yl)[2-(piperidin-1-yl)phenyl]methyl]carbamoyl}methyl)-1H-indol-3-yl]propanoic acid | From tert-butyl 3-[5-({[(4,5-dimethylfuran-2-yl)[2-(piperidin-1-yl)phenyl]methyl]carbamoyl}methyl)-1H-indol-3-yl]propanoate Cpd. 252 following protocol E<br>Yield: 95%; mp: 105, 115° C.; appearance: white solid; 1H NMR, d (ppm): 1.35-1.60 (m, 6H), 1.80 (d, 3H, J = 0.5 Hz), 2.07 (s, 3H), 2.5-2.6 (m, 4H), 2.75-2.80 (m, 2H), 2.87 (t, 2H, J = 8.4 Hz), 3.49 (s, 2H), 5.72 (s, 1H), 6.49 (d, 1H, J = 8.3 Hz), 6.96 (dd, 1H, J = 8.3 Hz, J = 1.6 Hz), 7.00-7.15 (m, 3H), 7.15-7.25 (m, 2H), 7.30-7.40 (m, 2H), 8.67 (d, 1H, J = 8.6 Hz), 10.67 (d, 1H, J = 2.1 Hz); -m/z: 514.3 [M + H]+ (calc. mass: 513.26). |
| 254 | tert-butyl 3-[5-({[(5-methylfuran-2-yl)[2-(propan-2-yloxy)phenyl]methyl]carbamoyl}methyl)-1H-indol-3-yl]propanoate | From (5-methylfuran-2-yl)[2-(propan-2-yloxy)phenyl]methanamine Ex. 141 and 2-{3-[3-(tert-butoxy)-3-oxopropyl]-1H-indol-5-yl}acetic acid Ex. 1 following protocol D<br>Yield: 25%; mp: 57, 59° C.; appearance: yellow solid; 1H NMR, d (ppm): 1.06 (d, 3H, J = 6.0 Hz), 1.13 (d, 3H, J = 6.0 Hz), 1.38 (s, 9H), 2.18 (s, 3H), 2.54 (t, 2H, J = 7.5 Hz), 2.87 (t, 2H, J = 7.7 Hz), 3.52 (d, 2H, J = 2.6 Hz), 4.46-4.59 (m, 1H), 5.75-5.80 (m, 1H), 5.90-5.95 (m, 1H), 6.32 (d, 1H, J = 8.6 Hz), 6.84-6.92 (m, 1H), 6.93-7.01 (m, 2H), 7.05-7.1 (d, 1H, J = 2.3 Hz), 7.16-7.24 (m, 2H), 7.29 (dd, 1H, J = 7.5 Hz, J = 1.7 Hz), 7.39 (s, 1H), 8.65 (d, 1H, J = 8.8 Hz), 10.69 (br s, 1H); m/z: 531.36 [M + H]+ (calc. mass: 530.27). |
| 255 | 3-[5-({[(5-methylfuran-2-yl)[2-(propan-2-yloxy)phenyl]methyl]carbamoyl}methyl)-1H-indol-3-yl]propanoic acid | From tert-butyl 3-[5-({[(5-methylfuran-2-yl)[2-(propan-2-yloxy)phenyl]methyl]carbamoyl}methyl)-1H-indol-3-yl]propanoate Cpd. 254 following protocol E<br>Yield: 79%; mp: 90, 92° C.; appearance: yellow solid; 1H NMR, d (ppm): 1.06 (d, 3H, J = 6.0 Hz), 1.14 (d, 3H, J = 6.0 Hz), 2.18 (s, 3H), 2.55 (t, 2H, J = 8.3 Hz), 2.88 (t, 2H, J = 7.5 Hz), 3.53 (d, 2H, J = 2.1 Hz), 4.45-4.58 (m, 1H), 5.75-5.80 (m, 1H), 5.89-5.95 (m, 1H), 6.31 (d, 1H, J = 9.0 Hz), 6.84-6.92 (m, 1H), 6.92-7.01 (m, 2H), 7.07 (d, 1H, J = 2.2 Hz), 7.16-7.25 (m, 2H), 7.29 (dd, 1H, J = 7.6 Hz, J = 1.6 Hz), 7.40 (s, 1H), 8.66 (d, 1H, J = 8.7 Hz), 10.69 (br s, 1H), 11.85 (br s, 1H); m/z: 475.29 [M + H]+ (calc. mass: 474.21). |

TABLE 2-continued

_All the NMR were performed in DMSO-d6_

| Cpd. | | Starting compounds, Reaction conditions and purification Yield, MP, Appearance, $^1$H NMR (solvent) data, Mass (ES+ or ES−) data |
|---|---|---|
| 256 | methyl 2-[5-({[(2-bromo-4-methylphenyl)(pyrimidin-2-yl)methyl]carbamoyl}methyl)-1H-indol-3-yl]acetate | From (2-bromo-4-methylphenyl)(pyrimidin-2-yl)methanamine Ex. 69 and 2-[3-(2-methoxy-2-oxoethyl)-1H-indol-5-yl]acetic acid Ex. 5 following protocol D<br>Yield: 85%; mp: 75, 89° C.; appearance: white solid; 1H NMR, d (ppm): 2.25 (s, 3H); 3.57 (m, 2H); 3.58 (s, 3H); 3.69 (s, 2H); 6.46 (d, 1H, J = 7.9 Hz); 7.01 (dd, 1H, J = 8.3 Hz, J = 1.6 Hz); 7.111-7.14 (m, 1H); 7.19-7.25 (m, 3H); 7.34 (m, 1H); 7.38-7.42 (m, 2H); 8.77 (d, 2H, J = 4.9 Hz); 8.93 (d, 1H, J = 8.0 Hz); 10.85 (s, 1H); m/z: 507.09 [M + H]+ (calc. mass: 506.09). |
| 257 | 2-[5-({[(2-bromo-4-methylphenyl)(pyrimidin-2-yl)methyl]carbamoyl}methyl)-1H-indol-3-yl]acetic acid | From methyl 2-[5-({[(2-bromo-4-methylphenyl)(pyrimidin-2-yl)methyl]carbamoyl}methyl)-1H-indol-3-yl]acetate Cpd. 256 following protocol F<br>Yield: 69%; mp: 113, 120° C.; appearance: white solid; 1H NMR, d (ppm): 2.25 (s, 3H), 3.58 (d, 2H), 6.47 (d, 1H, J = 8.0 Hz), 7.00 (dd, 1H, J = 8.3 Hz, J = 1.5 Hz), 7.10-7.16 (m, 1H), 7.18 (d, 1H, J = 2.3 Hz), 7.19-7.26 (m, 2H), 7.36 (s, 1H), 7.38-7.44 (m, 2H), 8.77 (d, 2H, J = 4.9 Hz), 8.95 (d, 1H, J = 8.0 Hz), 10.81 (br s, 1H), 12.13 (br s, 1H); m/z: 493.32 [M + H]+ (calc. mass: 492.07). |
| 258 | N-methoxy-N-methyl-2-{5-[({phenyl[2-(piperidin-1-yl)phenyl]methyl}carbamoyl)methyl]-1H-indol-3-yl}acetamide | From 2-{5-[({phenyl[2-(piperidin-1-yl)phenyl]methyl}carbamoyl)methyl]-1H-indol-3-yl}acetic acid Cpd. 39 and N,O-dimethylhydroxylamine following protocol D<br>Yield: 42%; mp: 80, 94° C.; appearance: white solid; 1H NMR, d (ppm): 1.43-1.56 (m, 6H); 2.48-2.50 (m, 2H); 2.84-2.88 (m, 2H); 3.09 (s, 3H); 3.56 (s, 2H); 3.64 (s, 3H); 3.74 (s, 2H); 6.60 (d, 1H, J = 8.6 Hz); 6.98-7.31 (m, 12H); 7.37-7.39 (m, 1H); 8.70 (d, 1H, J = 8.7 Hz); 10.78 (br s, 1H); m/z: 525.27 [M + H]+ (calc. mass: 524.27). |
| 259 | 2-[3-(3-oxobutyl)-1H-indazol-5-yl]-N-{phenyl[2-(piperidin-1-yl)phenyl]methyl}acetamide | To a solution of 2-(1H-indazol-5-yl)acetic acid (100 mg, 0.57 mmol) dissolved in acetonitrile (2 mL) was added bismuth (III) trifluomethanesulfonate (11 mg, 0.02 mmol) followed by but-3-en-2-one (40 mg, 0.57 mmol). The reaction mixture was stirred at rt for 18 h. The excess of solvent was removed under reduced pressure and the crude material was purified on silica gel column chromatography using CH2Cl2/MeOH (9:1) as eluent affording 2-(3-(3-oxobutyl)-1H-indazol-5-yl)acetic acid as white solid (yield: 40%). 1H NMR (300 MHz, DMSO-d6, d in ppm): 1.12 (s, 3H); 3.18 (t, 2H, J = 6.7 Hz); 3.59 (s, 2H); 4.59 (t, 2H, J = 6.7 Hz); 7.12 (dd, 1H, J = 9.1 Hz, J = 1.5 Hz); 7.50-7.53 (m, 2H); 8.28 (d, 1H, J = 0.7 Hz); 12.33 (br s, 1H).<br>From phenyl[2-(piperidin-1-yl)phenyl]methanamine Ex. 9 and 2-(3-(3-oxobutyl)-1H-indazol-5-yl)acetic acid following protocol D<br>Yield: 66%; mp: 158, 160° C.; appearance: white solid; 1H NMR, d (ppm): 1.40-1.58 (m, 6H); 2.10 (s, 3H); 2.46-2.51 (m, 2H); 2.84-2.88 (m, 2H); 3.15 (t, 2H, J = 6.7 Hz); 3.56 (s, 2H); 4.57 (t, 2H, J = 6.7 Hz); 6.61 (d, 1H, J = 8.5 Hz); 7.03 (dt, 1H, J = 7.4 Hz, J = 1.5 Hz); 7.11-7.46 (m, 9H); 7.45-7.49 (m, 2H); 8.25 (d, 1H, J = 0.7 Hz); 8.76 (d, 1H, J = 8.6 Hz); -m/z: 495.26 [M + H]+ (calc. mass: 494.26). |
| 260 | tert-butyl 3-{5-[({1-[2-(piperidin-1-yl)phenyl]but-3-yn-1-yl}carbamoyl)methyl]-1H-indol-3-yl}propanoate | From 1-[2-(piperidin-1-yl)phenyl]but-3-yn-1-amine Ex. 72 and 2-{3-[3-(tert-butoxy)-3-oxopropyl]-1H-indol-5-yl}acetic acid Ex. 1 following protocol D<br>Yield: 47%; mp: 61° C.; appearance: light yellow solid; 1H NMR, d (ppm): 1.38 (s, 9H); 1.44-1.59 (m, 6H); 2.45-2.61 (m, 6H); 2.73 (t, 1H, J = 2.5 Hz); 2.87 (t, 2H, J = 7.5 Hz); 2.98-3.00 (m, 2H); 3.51 (s, 2H); 5.41 (dd, 1H, J = 8.2 Hz, J = 14.1 Hz); 6.97 (dd, 1H, J = 1.5 Hz, J = 8.4 Hz); 7.01-7.11 (m, 3H); 7.16-7.22 (m, 2H); 7.33-7.37 (m, 2H); 8.45 (d, 1H, J = 8.3 Hz); 10.67 (s, 1H); m/z: 514.29 [M + H]+ (calc. mass: 513.29). |
| 261 | 3-{5-[({1-[2-(piperidin-1-yl)phenyl]but-3-yn-1-yl}carbamoyl)methyl]-1H-indol-3-yl}propanoic acid | From tert-butyl 3-{5-[({1-[2-(piperidin-1-yl)phenyl]but-3-yn-1-yl}carbamoyl)methyl]-1H-indol-3-yl}propanoate Cpd. 260 following protocol E<br>Yield: 25%; mp: 104° C.; appearance: white solid; 1H NMR, d (ppm): 1.49-1.60 (m, 6H); 2.42-2.61 (m, 6H); 2.73 (t, 1H, J = 2.5 Hz); 2.88 (t, 2H, J = 7.5 Hz); 2.92-3.03 (m, 2H); 3.51 (s, 2H); 5.41 (dd, 1H, J = 8.2 Hz, J = 14.1 Hz); 6.97 (dd, 1H, J = 1.5 Hz, J = 8.3 Hz); 7.01-7.11 (m, 3H); 7.16-7.22 (m, 2H); 7.34 (dd, 1H, J = 1.5 Hz, J = 7.6 Hz); 7.38 (s, 1H); 8.45 (d, |

TABLE 2-continued

All the NMR were performed in DMSO-d6

| Cpd. | | Starting compounds, Reaction conditions and purification Yield, MP, Appearance, $^1$H NMR (solvent) data, Mass (ES+ or ES−) data |
|---|---|---|
| | | 1H, J = 8.3 Hz); 10.68 (d, 1H, J = 1.8 Hz); 12.02 (br s, 1H); m/z: 458.23 [M + H]+ (calc. mass: 457.23). |
| 262 | tert-butyl 3-{5-[({3-methyl-1-[2-(piperidin-1-yl)phenyl]butyl}carbamoyl)amino]-1H-indol-3-yl}propanoate | From 3-methyl-1-[2-(piperidin-1-yl)phenyl]butan-1-amine Ex. 23 and tert-butyl 3-(5-amino-1H-indol-3-yl)propanoate Ex. 133 and following protocol G Yield: 9%; mp: 134, 137° C.; appearance: white solid; 1H NMR, d (ppm): 0.91-0.97 (m, 6H); 1.36 (s, 9H); 1.40-1.71 (m, 8H); 2.50 (t, 2H, J = 7.5 Hz); 2.54-2.60 (m, 2H); 2.83 (t, 2H, J = 7.5 Hz); 3.02-3.11 (m, 2H); 5.21-5.28 (m, 1H); 6.38 (d, 1H, J = 8.4 Hz); 6.94 (dd, 1H, J = 8.7 Hz, J = 1.8 Hz); 7.01-7.20 (m, 4H); 7.27 (dd, 1H, J = 7.5 Hz, J = 1.5 Hz); 7.50 (d, 1H, J = 1.5 Hz); 8.06 (s, 1H); 10.56 (br s, 1H); m/z: 533.34 [M + H]+ (calc. mass: 532.34). |
| 263 | tert-butyl 3-{5-[({[2-(4-benzylpiperazin-1-yl)-4-methylphenyl](phenyl)methyl}carbamoyl)methyl]-1H-indol-3-yl}propanoate | From [2-(4-benzylpiperazin-1-yl)-4-methylphenyl](phenyl)methanamine Ex. 70 and 2-{3-[3-(tert-butoxy)-3-oxopropyl]-1H-indol-5-yl}acetic acid Ex. 1 following protocol D -Yield: 55%; mp: 87, 90° C.; appearance: white solid -1H NMR, d (ppm): 1.39 (s, 9H); 2.22 (s, 3H); 2.26-2.48 (m, 4H); 2.49-2.55 (m, 4H); 2.83-2.88 (m, 4H); 3.43 (s, 2H); 3.55 (s, 2H); 6.57 (d, 1H, J = 8.8 Hz); 6.88 (d, 1H, J = 8.0 Hz); 6.95-6.98 (m, 2H); 7.06 (d, 1H, J = 2.2 Hz); 7.12-7.33 (m, 12H); 7.39 (s, 1H); 8.66 (d, 1H, J = 8.8 Hz); 10.68 (d, 1H, J = 2.0 Hz); m/z: 657.37 [M + H]+ (calc. mass: 656.37). |
| 264 | tert-butyl 3-{5-[({[4-hydroxy-2-(piperidin-1-yl)phenyl](phenyl)methyl}carbamoyl)methyl]-1H-indol-3-yl}propanoate | From 4-[amino(phenyl)methyl]-3-(piperidin-1-yl)phenol Ex. 87 and 2-{3-[3-(tert-butoxy)-3-oxopropyl]-1H-indol-5-yl}acetic acid Ex. 1 following protocol D Yield: 13%; mp: 70, 76° C.; appearance: white solid; 1H NMR, d (ppm): 1.37 (s, 9H); 1.41-1.58 (m, 6H); 2.48-2.50 (m, 2H); 2.53 (t, 2H, J = 8.1 Hz); 2.71-81 (m, 2H); 2.86 (t, 2H, J = 7.8 Hz); 3.55 (s, 2H); 6.42-6.50 (m, 3H); 6.96-7.25 (m, 9H); 7.38-7.40 (m, 1H); 8.57 (d, 1H, J = 8.6 Hz); 9.24 (s, 1H); 10.67 (s, 1H); m/z: 568.3 [M + H]+ (calc. mass: 567.3). |
| 265 | 3-{5-[({[4-hydroxy-2-(piperidin-1-yl)phenyl](phenyl)methyl}carbamoyl)methyl]-1H-indol-3-yl}propanoic acid | From tert-butyl 3-{5-[({[4-hydroxy-2-(piperidin-1-yl)phenyl](phenyl)methyl}carbamoyl)methyl]-1H-indol-3-yl}propanoate following protocol E Yield: 74%; mp: 156, 177° C.; appereence: white solid; 1H NMR, d (ppm): 1.41-1.54 (m, 6H); 2.47-2.50 (m, 2H); 2.54 (t, 2H, J = 8.1 Hz); 2.76-2.78 (m, 2H); 2.57 (t, 2H, J = 7.3 Hz); 3.54 (s, 2H); 6.42-6.49 (m, 3H); 6.97 (dd, 1H, J = 8.3 Hz, J = 1.4 Hz); 7.00 (d, 1H, J = 8.4 Hz); 7.05 (d, 1H, J = 2.2 Hz); 7.12-725 (m, 5H); 7.38-7.40 (m, 2H); 8.58 (d, 1H, J = 8.7 Hz); 10.66 (s, 1H); 12.00 (br s, 1H); m/z: 512.41 [M + H]+ |
| 266 | 3-(hexadecanoyloxy)-2-[(3-{5-[({phenyl[2-(piperidin-1-yl)phenyl]methyl}carbamoyl)methyl]-1H-indol-3-yl}propanoyl)oxy]propyl hexadecanoate | From 3-{5-[({phenyl[2-(piperidin-1-yl)phenyl]methyl}carbamoyl)methyl]-1H-indol-3-yl}propanoic acid Cpd. 1 and 1,3-dihexadecanoylglycerol following protocol D Yield: 14%; appearance: colorless oil; 1H NMR, d (ppm): 0.85-0.95 (m, 6H); 1.2-1.4 (m, 52H); 1.5-1.7 (m, 6H); 2.30 (t, 4H, J = 7.6 Hz); 2.3-2.4 (m, 2H); 2.45-2.55 (m, 2H); 2.71 (t, 2H, J = 7.4 Hz); 3.06 (t, 2H, J = 7.4 Hz); 3.80 (m, 2H); 4.1-4.3 (m, 4H); 5.27 (qt, 1H); 6.56 (d, 1H, J = 8.7 Hz); 7.0-7.4 (m, 13H); 7.51 (br s, 1H); 7.97 (br s, 1H); m/z: 1046.74 [M + H]+ (calc. mass: 1045.74). |
| 267a | tert-butyl 3-{5-[({[4-methyl-2-(piperidin-1-yl)phenyl](5-methylfuran-2-yl)methyl}carbamoyl)methyl]-1H-indol-3-yl}propanoate (R or S) | From [4-methyl-2-(piperidin-1-yl)phenyl](5-methylfuran-2-yl)methanamine Ex. 144a and and 2-{3-[3-(tert-butoxy)-3-oxopropyl]-1H-indol-5-yl}acetic acid Ex. 1 following protocol D Yield: 43%; mp: 69, 71° C.; appearance: white solid; 1H NMR, d (ppm): 1.38 (s, 9H), 1.40-1.60 (m, 6H), 2.16 (s, 3H), 2.24 (s, 3H), 2.53-2.60 (m, 4H), 2.74-2.80 (m, 2H), 2.86 (t, 2H, J = 8.4 Hz), 3.49 (s, 2H), 5.80-5.84 (m, 1H), 5.89-5.94 (m, 1H), 6.48 (d, 1H, J = 8.6 Hz), 6.88 (d, 1H, J = 7.8 Hz), 6.92 (s, 1H), 6.96 (dd, 1H, J = 8.2 Hz, J = 1.7 Hz), 7.06 (d, 1H, J = 2.4 Hz), 7.18-7.23 (m, 2H), 7.36 (s, 1H), 8.66 (d, 1H, J = 8.5 Hz), 10.67 (br s, 1H); m/z: 570.86 [M + H]+ (calc. mass: 569.32). |
| 268a | 3-{5-[({[4-methyl-2-(piperidin-1-yl)phenyl](5-methylfuran-2-yl)methyl}carbamoyl)methyl]-1H-indol-3- | From tert-butyl 3-{5-[({[4-methyl-2-(piperidin-1-yl)phenyl](5-methylfuran-2-yl)methyl}carbamoyl)methyl]-1H-indol-3-yl}propanoate Cpd. 267a following protocol E. Yield: 63% (ee>96%); mp: 105, 110° C.; appearance: white solid; 1H NMR, d (ppm): 1.38-1.63 (m, 6H), 2.17 (s, 3H), 2.25 (s, 3H), 2.57 (m, 4H), 2.73-2.84 (m, 2H), 2.88 (t, 2H, J = 7.9 Hz), 3.51 (s, 2H), 5.82 (d, 1H, J = 3.4 Hz), 5.90-5.94 (m, |

TABLE 2-continued

All the NMR were performed in DMSO-d6

| Cpd. | | Starting compounds, Reaction conditions and purification Yield, MP, Appearance, $^1$H NMR (solvent) data, Mass (ES+ or ES−) data |
|---|---|---|
| | yl}propanoic acid (R or S) | 1H), 6.49 (d, 1H, J = 8.4 Hz), 6.89 (d, 1H, J = 7.6 Hz), 6.93 (s, 1H), 6.96 (dd, 1H, J = 8.3 Hz, J = 1.5 Hz), 7.07 (d, 1H, J = 2.3 Hz), 7.22 (m, 2H), 7.38 (s, 1H), 8.67 (d, 1H, J = 8.6 Hz), 10.68 (d, 1H, J = 2.0 Hz), 12.06 (br s, 1H); m/z: 514.75 [M + H]+ (calc. mass: 513.26). |
| 267b | tert-butyl 3-{5-[({[4-methyl-2-(piperidin-1-yl)phenyl](5-methylfuran-2-yl)methyl}carbamoyl)methyl]-1H-indol-3-yl}propanoate (R or S) | From [4-methyl-2-(piperidin-1-yl)phenyl](5-methylfuran-2-yl)methanamine Ex. 144b and and 2-{3-[3-(tert-butoxy)-3-oxopropyl]-1H-indol-5-yl}acetic acid Ex. 1 following protocol D.<br>Yield 47%; mp: 69, 71° C.; appearance: white solid; 1H NMR, d (ppm): 1.38 (s, 9H), 1.41-1.57 (m, 6H), 2.16 (s, 3H), 2.24 (s, 3H), 2.53-2.59 (m, 4H), 2.75-2.82 (m, 2H), 2.86 (t, 2H, J = 8.1 Hz), 3.50 (s, 2H), 5.80-5.83 (m, 1H), 5.89-5.93 (m, 1H), 6.48 (d, 1H, J = 8.4 Hz), 6.88 (d, 1H, J = 8.6 Hz), 6.92 (s, 1H), 6.95 (dd, 1H, J = 9.9 Hz, J = 1.5 Hz), 7.06 (d, 1H, J = 2.3 Hz), 7.18-7.23 (m, 2H), 7.36 (s, 1H), 8.66 (d, 1H, J = 8.8 Hz), 10.67 (br s, 1H); m/z: 571.86 [M + H]+ (calc. mass: 569.32). |
| 268b | 3-{5-[({[4-methyl-2-(piperidin-1-yl)phenyl](5-methylfuran-2-yl)methyl}carbamoyl)methyl]-1H-indol-3-yl}propanoic acid (R or S) | From tert-butyl 3-{5-[({[4-methyl-2-(piperidin-1-yl)phenyl](5-methylfuran-2-yl)methyl}carbamoyl)methyl]-1H-indol-3-yl}propanoate Cpd. 267b following protocol E<br>Yield: 67% (ee>96%); mp: 105, 110° C.; appearance: white solid; 1H NMR, d (ppm): 1.38-1.61 (m, 6H), 2.17 (s, 3H), 2.25 (s, 3H), 2.53-2.61 (m, 4H), 2.72-2.84 (m, 2H), 2.88 (t, 2H, J = 7.8 Hz), 3.51 (s, 2H), 5.83 (d, 1H, J = 3.0 Hz), 5.90-5.95 (m, 1H), 6.49 (d, 1H, J = 8.4 Hz), 6.89 (d, 1H, J = 7.9 Hz), 6.93 (s, 1H), 6.97 (dd, 1H, J = 8.3 Hz, J = 1.4 Hz), 7.07 (d, 1H, J = 2.2 Hz), 7.22 (m, 2H), 7.38 (s, 1H), 8.68 (d, 1H, J = 8.5 Hz), 10.68 (d, 1H, J = 2.1 Hz), 12.07 (br s, 1H); m/z: 515.75 [M + H]+ (calc. mass: 513.26). |

For comparative biological activities, the compound 2-(2-(hydroxy(3,5-dimethylisoxazol-4-yl)methyl)benzofuran-5-yl)-N-((2,4-dimethylphenyl)(phenyl)methyl)acetamide (noted compound T) disclosed in (Skepner et al, 2014) was synthesized following the protocol of PCT application WO 2013/019682. (analyses were performed to ensure the structure of the compound: 1H NMR (300 MHz, CDCl3, d in ppm): 2.19 (s, 3H); 2.23 (s, 3H); 2.31 (s, 3H); 2.37 (s, 3H); 3.15 (s, 1H); 3.68 (s, 2H); 5.83 (s large, 1H); 6.02 (d, 1H, J=8.1 Hz); 6.35 (d, 1H, J=8.1 Hz); 6.53 (s, 1H); 6.76 (d, 1H, J=7.9 Hz); 6.96 (s, 1H); 7.04-7.07 (m, 2H); 7.16 (dd, 1H, J=8.4 Hz J=1.8 Hz); 7.20-7.27 (m, 3H); 7.35-7.45 (m, 2H); appearance: white solid; M=517 [M+Na]+)

Separation of 4 diastereoisomers was realized by Chiral Technologies.

| Chiral Tech code | HPLC Chiral Tech | dr Chiral Tech |
|---|---|---|
| T-1 | >99% | 100% |
| T-2 | >99% | 98.32% |
| T-3 | >99% | 97.77% |
| T-4 | >99% | 99.76% |

Example 3: RORE Luciferase/RORγt Transactivation Assay

It is well known that RORγ binds to a conserved non-coding sequence (CNS) enhancer element in the IL-17 promoter. Accordingly, we have used in this assay a luciferase reporter gene construct that contains the human IL-17 promoter fragment with RORγ-specific CNS enhancer element and a RORγt overexpressing plasmid, to indirectly assess the effect of compounds on RORγ activity. Inhibition of RORγ activity by test compounds will result in a decrease in luciferase activity in COS-7 cells transfected with the reporter construct.

COS-7 Cell Line Culture

Monkey Kidney COS-7 cell line are maintained in a standard culture medium Dulbecco's modified Eagle's minimal (DMEM) medium supplemented with 10% fetal calf serum, 1% sodium pyruvate, 1% essential amino acids and 1% antibiotics at 37° C. in a humidified atmosphere of 5% $CO_2$ and 95% air. Culture medium was changed every 2 days.

Construct Descriptions

The 4.3 Kb human IL-17 promoter containing the RORγ-specific CNS enhancer element was PCR amplified from human genomic DNA and cloned into a pGL3-TKLuc2Cp reporter plasmid. To overexpress RORγt, the full-length cDNA of human RORγt (identical to published sequence NM 001001523) was cloned without any restriction into pcdna3.1DV5-His-topo to generate the RORγt overexpression plasmid "RORγt_FL_h_pcDNA3.1DV5-His-TOPO_1".

COS-7 Cell Transfection

The luciferase reporter plasmid and the RORγt overexpression plasmid were transfected into COS-7 cell line using 4 µLJetPEITM/µg of DNA. Briefly, 150 ng of DNA (ration ½ between RORE-Tk Luc2Cp and cDNA RORγt or the empty vector for the negative control) was served to transfect adherent COS-7 cells in a 225 cm3 culture flask, in complete medium (see cos-7 cell line culture). Cells were incubated for 24 hours in a humidified atmosphere of 5% $CO_2$ and 95% air Cells were then detached (using trypsin) and washed by centrifugation at 300 g for 10 minutes. Cell pellet was resuspended in serum free/phenol red free DMEM and seeded in 384 well plates at a density of 10000 cells/well and then incubated for 4 h at 37° C.

Assay

Compounds were dissolved in 100% DMSO to obtain 10 mM stock solutions. For each compound, test concentrations were diluted in serum free/phenol red free DMEM using the Genesis Freedom 200™ (TECAN) and added to the cells to obtain a 0.3% DMSO final concentration (in a final volume of 40 µL per well). T091317 was used as reference compound. Cells were incubated in presence of compounds for an additional 20 h at 37° C. in a humidified atmosphere of 5% CO2 and 95% air The luciferase activity was then measured with 40 µL/well steady-Glo Luciferase assay system (Promega, Madison, Wis.) and after incubation at room temperature for 30 minutes. The luminescence was estimated using the Ultra384 reader (TECAN). Data were collected and analyzed using GraphPad Prism software (GraphPad Software V5.02, San Diego Calif. USA). IC50 in µM and Emax in % were reported for each compound.

Results:

Effect of reference compound on RORγt activity: in this assay, reference compound T091317 showed on RORγt activity inhibition with $IC_{50}$ of 0.2 µM and an Emax of 83.7%

Several compounds belonging to formula (I) inhibit the high transcriptional activity of RORγ at different levels. These compounds displayed an $IC_{50}$ comprised between 1 and 10 µM in particular Cpds 7, 9, 11, 13, 15, 23, 33, 37, and 39. Cpds 17, 19, 21, 25, 27, and 31 displayed an $IC_{50}$ superior to 10 µM. Best compounds (such as Cpds. 1, 3, 5, 29, 35 and 268) displayed an $IC_{50}$ inferior to 1 µM.

Further, the major part of compounds from this chemical series showed no cytotoxic effect at 30 µM as judged from the reporter signal obtained from cells transfected with the empty vector that was used as negative control in this experiment.

Example 4: FRET

General Considerations

Time-resolved FRET (TR-FRET) RORγt coactivator assay was used to identify RORγ modulator compounds with ligand-dependent coactivator displacement. The assay uses a d2-labeled anti-GST antibody, synthetic N-terminally biotinylated peptide which is derived from nuclear receptor coactivator protein RIP140, and a RORγt ligand-binding domain (RORγt-LBD) that is tagged with glutathione-S-transferase (GST). The influence of compounds on the RORγ-peptide interaction relies on the binding dependent energy transfer from a donor to an acceptor fluorophore attached to the binding partner of interest. Because RORγ is constitutively active, streptavidin-terbium conjugate labeled-coactivator peptide is recruited in the absence of ligand and the terbium d2 on the anti-GST antibody is excited at 340 nm, energy is transferred to the terbium label on the coactivator peptide and detected as emission at 665 nm. For reduction of background from compound fluorescence, TR-FRET method makes use of generic fluorophore labels and time resolved detection.

Assay

The assays were done in a final volume of 20 µl in a 384 well plate in a CHAPS buffer (2 mM CHAPS; 1 mM DTT, 2 mM EDTA; 0.1% BSA), containing 20 nM recombinantly expressed RORγ-LBD fused to GST, 30 nM N-terminally biotinylated peptide, 1 nM streptavidin-terbium conjugate and 20 nM d2 labeled-anti-GST. Test compounds were diluted using 10 mM stock solution. The range of the final compound concentrations used in this test was from 0.3 nM to 30 µM (logarithmic scale). DMSO content of the samples was kept at 1%. The assay was equilibrated for 2 hours in the dark at room temperature in 384 well plates (Falcon). The signal was detected by an Ultra384 reader (TECAN). The results were visualized by plotting the ratio between the emitted light at 665 nm and 620 nm. A basal level of RORγ-peptide formation is observed in the absence of added compound. Compounds that promote coactivator displacement induce a concentration-dependent decrease in time-resolved fluorescent signal. Data were collected and analyzed using GraphPad Prism software (GraphPad Software V5.02, San Diego Calif. USA). IC50 in µM and Emax in % were reported for each compound.

Results:

Effect of reference compound on RORγt activity: in this assay, reference compound T091317 showed on RORγt activity inhibition with $IC_{50}$ of 0.097 µM and an Emax of 37%

Several compounds belonging to formula (I) inhibit the ligand-dependent coactivator-RORγt binding.

These compounds displayed an $IC_{50}$ comprised between 1 and 10 µM in particular Cpds 45, 55, and 178 displayed an $IC_{50}$ comprised between 10 µM and 30 µM. Cpds 2, 17, 19, 27, 34, 39, 41, 43, 47, 49, 51, 52, 53, 57, 61, 63, 68, 69, 71, 73, 75, 78, 92, 94, 95, 97, 100, 102, 103, 104, 106, 113, 116, 121, 123, 124, 127, 129, 133, 135, 137, 143, 149, 156, 162, 166, 168, 172, 174, 176, 180, 183, 184, 194, 196, 206, 207, 214, 218, 222, 228, 229, 230, 234, 235, 238, 248, 252, 256, 260, 262, and 264 displayed an IC50 comprised between 1 µM and 10 µM.

Best compounds (such as Cpds. 1, 3, 5, 7, 9, 11, 13, 15, 21, 29, 31, 33, 35, 37, 40, 42, 44, 46, 48, 50, 54, 56, 58, 59, 60, 62, 64, 65, 66, 67, 70, 72, 74, 76, 77, 79, 80, 81, 82, 83, 84, 85, 86, 87, 88, 89, 90, 91, 93, 96, 98, 99, 101, 105, 107, 108, 109, 110, 111, 112, 114, 115, 117, 118, 119, 120, 122, 125, 126, 128, 130, 131, 132, 134, 136, 138, 139, 140, 141, 142, 144, 145, 146, 148, 150, 152, 154, 157, 158, 159, 160, 164, 170, 182, 186, 188, 190, 192, 198, 200, 202, 204, 208, 209, 211, 212, 213, 215, 216, 217, 220, 224, 226, 232, 236, 237, 240, 241, 243, 245, 246, 247, 250, 251, 253, 254, 255, 258, 259, 263, and 268) displayed an $IC_{50}$ inferior to 1 µM.

Example 5: IL-17 Secretion from EL4 Murine Lymphoma

Murine EL-4 lymphoma cell line overexpressing human RORγt was used in this functional assay to assess compound ability to inhibit IL-17 cytokine secretion.

EL-4 Cell Transfection

EL-4 cells are maintained in a standard culture medium RPMI supplemented with 10% fetal calf serum, 1% sodium pyruvate, 1% essential amino acids and 1% antibiotics at 37° C. in a humidified atmosphere of 5% CO2 and 95% air. Culture medium was changed every 2 days. EL4 cells were transfected with a plasmid encoding hRORγt (sequence identical to published sequence NM 001001523). Transfection of EL4 cells was achieved with Amaxa electroporation apparatus (Amaxa Biosystems, Germany), as per the manufacturer's protocols, for the EL4 cells (Amaxa Cell Line Nucleofector Kit L, Amaxa Biosystems). Briefly, 1 µg of DNA/1 million cells was served to transfect EL-4 cells. Cell/DNA suspension was transferred into certified cuvette and the electroporation of RORγt plasmid was carried out using appropriate Nucleofector® program.

IL-17 Secretion Assay

Cells were seeded in 96 well plates at a density of 150000 cells/well then treated with compounds of this invention at indicated concentrations and incubated for 24 hours at 37° C. in a humidified atmosphere of 5% CO2 and 95% air. EL-4 cells were pretreated with test compounds (RORγ modulators) and stimulated with PMA (10 ng/mL) and ionomycin (1 μM final concentration) in the presence of test compound concentrations for additional 24 h at 37° C. in a humidified atmosphere of 5% CO2 and 95% air. Subsequently, supernatants were collected (after centrifugation at 300 g for 10 minutes) to determine the concentrations of IL-17 by HTRF (CisBio, France) or ELISA (R&D Systems Europe) according to the manufacturer's protocols.

Results:

Effect of reference compound T091317 on RORγt activity: in this experiment, the effect of the reference compound T091317 on RORγt activity showed an $IC_{50}$ of 0.8 μM and an Emax of 93.5%

Many of the compounds listed above were evaluated for IL-17 secretion inhibition in human RORγt-transfected EL4 Tcells. Data from this assay correlate with the activity observed in RORE Tk luc/RORγt assay.

Cpds 15, 37, 43, 90, 117, 152, 160, and 188 displayed an $IC_{50}$ comprised between 10 μM and 30 μM.

Cpd. 1, 3, 29, 35, 47, 48, 49, 55, 59, 62, 65, 76, 78, 82, 84, 87, 88, 91, 96, 98, 105, 109, 110, 111, 112, 114, 115, 119, 120, 125, 126, 136, 138, 140, 141, 142, 144, 145, 146, 148, 150, 158, 159, 162, 172, 174, 186, 198, 200, 202, 209, 211, 212, 216, 217, 259, and 264 displayed an IC50 comprised between 1 μM and 10 μM.

Best compounds (such as Cpds. 5, 50, 64, 77, 86, 108, and 192) displayed an $IC_{50}$ inferior to 1 μM.

Example 6: eADME Assays

All the assays were conducted at CEREP (CEREP, France and USA). Metabolic compound stability was tested in human (CEREP, Ref 607) and mouse (CEREP, Ref: 806) microsomes. Inhibition of human drug-metabolizing cytochromes P450 was tested on the five most commonly responsible enzymes of metabolism of xenobiotics, CYP1A2 (CEREP, Ref 389), CYP2C9 (CEREP, Ref 412), CYP2C19 (CEREP, Ref 390), CYP2D6 (CEREP, Ref 1338) and CYP3A4 (CEREP, Ref 391).

Microsomal Stability

Briefly, the standard conditions for CEREP's stability assays include incubation of test compound at 0.1 μM with human or mouse microsomes for 60 minutes in duplicate. The protein concentration of microsomes is 0.1 mg/mL. The parent compound is detected by HPLC-MS/MS analysis. The quantity of the parent compound that remains intact upon 60 minutes of microsome exposure (% remaining) is calculated by comparing the peak area of the parent compound at 60 minutes of exposure to the time zero.

CYPs Inhibition

Briefly, CEREP's CYP inhibition assay uses traditional probe substrates, which are specific to individual CYP isoforms. 3-cyano-7-ethoxycoumarin is mainly catalyzed by CYP1A2 and CYP2C19, 3-[2-(N,N-diethyl-N-methylammonium)ethyl]-7-methoxy-4-methylcoumarin for CYP2C9 and CYP2D6 and finally, 7-benzyloxy-4-trifluoromethyl-coumarin is pathway catalyzed predominantly by CYP3A4. The inhibition assays were performed with human recombinant CYP isoforms preparations. HPLC MS/MS methods are used to detect metabolites in these assays. Compounds were tested at single concentrations (typically 10 μM) and data were expressed as percent of control inhibition.

Results

TABLE 4

Representative data from eADME analyses.

| | Human microsomes (% Cpd. remaining at 60 min) | Mouse microsomes | CYP 1A2 | CYP 2C9 | CYP 2C19 | CYP 2D6 | CYP 3A4 |
|---|---|---|---|---|---|---|---|
| | | | (% inhibition of Control) | | | | |
| Cpd. T-3 | 0 | 0 | −5 | 75 | 92 | 19 | 93 |
| Cpd. T-4 | 0 | 0 | −3 | 73 | 85 | 31 | 82 |
| Cpd. 1 | 54 | 35 | 1 | 12 | 13 | 49 | 19 |
| Cpd. 3 | 36 | 22 | 2.9 | 52.7 | 58.8 | −2 | 60.9 |
| Cpd. 5 | 89 | 50 | 4.4 | 35.9 | 25 | 13.5 | 25.8 |
| Cpd. 29 | 23 | 20 | −8.2 | 14.9 | 14.1 | 18.2 | 47.2 |
| Cpd. 48 | 83 | 53 | 10.7 | 24.6 | 35 | 78.9 | 33.7 |
| Cpd. 50 | 92 | 38 | 0.9 | 15.8 | 32.3 | 26.5 | 36.8 |
| Cpd. 77 | 88 | 31 | −0.9 | 23.2 | 28.1 | 6.2 | 31.3 |
| Cpd. 111 | 88 | 37 | −12.4 | 28.2 | 29.4 | 7.5 | 40.1 |
| Cpd. 192 | 79 | 66 | −1.9 | 28.6 | 31.2 | 4.3 | 30.9 |
| Cpd. 212 | 26 | 11 | −5.4 | 29.5 | 32.2 | −6.3 | 31 |

Compounds according to the invention showed a significantly better eADME profile compared to T-3 and T-4 compounds. In particular, Cpd.1 showed a good metabolic stability and had no or a minor effect on cytochromes P450 metabolism (except for CYP2D6, 49% inhibition) compared to T-3 and T-4 compounds.

Example 7: Inhibition of IL-17 Secretion and the Development of EAE in a Mouse Model 8-10 week old, male C57BL/6 mice were purchased from Janvier Lab (St Berthevin, France) and housed in a specific pathogen free (SPF) animal facility for one week before the start of the studies. Peptide antigen MOG35-55 (Myelin Oligodendrocyte Glycoprotein) (MMEVGWYRSPFSRV-VHLYRNG, SEQ ID NO:1, Polypeptide group, France) was dissolved in PBS and emulsified with an equal volume of Complete Freund's Adjuvant (CFA) containing 5 mg/mL of mycobacteria and administrated by subcutaneous injection at the dorsal flanks on day 0 at 200 μg/mouse. To ensure induction of reliable EAE, 200 ng of *Bordetella pertussis* toxin (Sigma) was given via intraperitoneal injection at day 0 and 2 (Cua, Sherlock et al. 2003; Zhang, Gran et al. 2003). Animals were treated with drug beginning 2 days before peptide injection. Animals were randomized into groups for treatment by weight, so that the average weight of each group was similar. The groups were segregated by cage. Compounds according to the invention were suspended in Carboxymethyl Cellulose (CMC) 1% (Sigma) and Tween80 0.1% (Sigma) by sonication and animals were dosed daily by gavage with 10 mL/kg body weight. The daily dose of Cpd. 1 was 30 mg/kg and vidofludimus (reference compound) at 60 mg/kg in protocol 1 to assess IL-17 A and IL-17F secretion from splenocytes ex vivo. In protocol 2, mice were treated with Cpd. 1 at 3 and 10 mg/Kg or T4 compound at 1 and 10 mg/kg daily by gavage to assess the clinical score. Clinical assessment of EAE was performed daily according to the following criteria: 0) no disease, 1) limp tail, 2) weak/partially paralyzed hind legs, 3) completely paralyzed hind legs, 4) complete hind and partial front leg paralysis, and 5) complete paralysis/death. For Cytokine quantifications, mice were euthanized 20 days after EAE induction. Spleen-isolated cells were collected and adjusted to 2×10 6 cells/mL. Cells were cultured in complete RPMI medium (RPMI supplemented with 10% of fetal calf serum, 1% glutamine, and 1% penicillin/streptomycin). Spleen cells were stimulated with MOG (20 μg/mL) (Polypeptide group, France). Cytokine levels were evaluated 48 h later by ELISA (R&D Systems Europe) or HTRF (CisBio, France) in culture supernatants using IL-17A and IL-17-F according to the manufacturer's protocols. The statistical significance was based on Student's t test (p<0.05, unpaired test).

Results (IL-17 Secretion Ex Vivo)

Figure 4A:
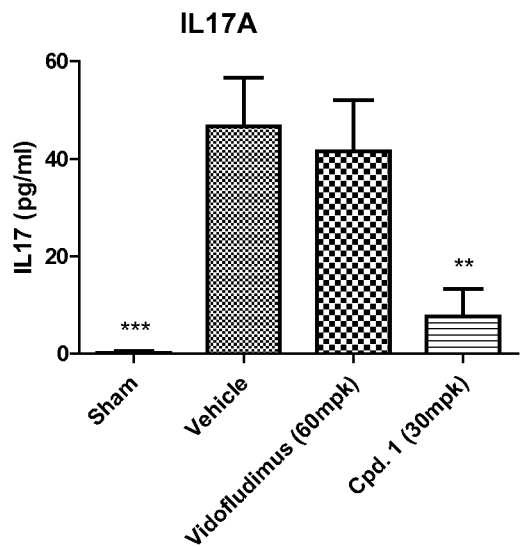
Figure 4B:
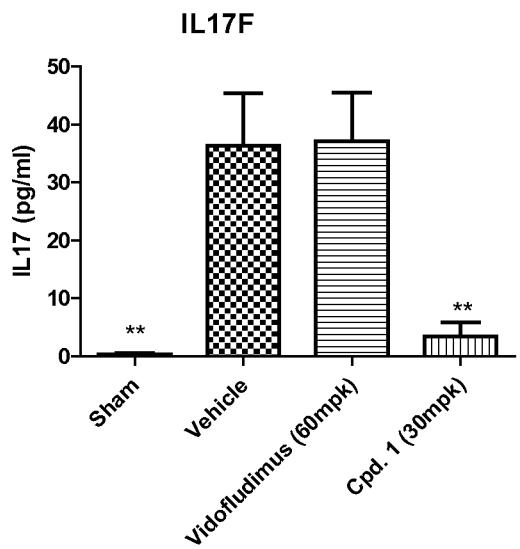

The example in FIGS. 4A and 4B shows that RORγ modulator according to the invention are able to inhibit drastically the secretion of both proinflammatory forms of IL-17 cytokine in vivo.

Results (Clinical Score)

This example shows that Cpd.1 RORγ modulator is able to delay the onset of EAE when the compound was administered p/os for 20 days. Clinical disease score improvement was apparent with compound 1 by day 15 and maintained through in vivo protocol duration. In this protocol, compound T-4 wasn't effective in decreasing EAE clinical score.

REFERENCES

Armarego W L F, Chai C L L (2009) *Purification of Laboratory Chemicals (Sixth Edition)*: ELSEVIER.

Asada M, Obitsu T, Nagase T, Tanaka M, Yamaura Y, Takizawa H, Yoshikawa K, Sato K, Narita M, Ohuchida S, Nakai H, Toda M (2010) 3-(2-Aminocarbonylphenyl) propanoic acid analogs as potent and selective EP3 receptor antagonists. Part 1: discovery and exploration of the carboxyamide side chain. *Bioorg Med Chem* 18: 80-90

Bauer M (2004) *Polymorphisme et stabilité*, Paris, FRANCE: Editions de santé.

Crispin J C, Oukka M, Bayliss G, Cohen R A, Van Beek C A, Stillman I E, Kyttaris V C, Juang Y-T, Tsokos G C (2008) Expanded Double Negative T Cells in Patients with Systemic Lupus Erythematosus Produce IL-17 and Infiltrate the Kidneys. *The Journal of Immunology* 181: 8761-8766

Dang Eric V, Barbi J, Yang H-Y, Jinasena D, Yu H, Zheng Y, Bordman Z, Fu J, Kim Y, Yen H-R, Luo W, Zeller K, Shimoda L, Topalian Suzanne L, Semenza Gregg L, Dang Chi V, Pardoll Drew M, Pan F (2011) Control of TH17/Treg Balance by Hypoxia-Inducible Factor 1. *Cell* 146: 772-784

Dubrovskiy A V, Larock R C (2012) Synthesis of o-(dimethylamino)aryl ketones, acridones, acridinium salts, and 1H-indazoles by the reaction of hydrazones and arynes. *J Org Chem* 77: 11232-11256

Eberl G, Marmon S, Sunshine M J, Rennert P D, Choi Y, Littman D R (2004) An essential function for the nuclear receptor RORgamma(t) in the generation of fetal lymphoid tissue inducer cells. *Nat Immunol* 5: 64-73

Erdemir D, Lee A Y, Myerson A S (2007) Polymorph selection: the role of nucleation, crystal growth and molecular modeling. *Curr Opin Drug Discov Devel* 10: 746-755

Furuzawa-Carballeda J, Vargas-Rojas M I, Cabral A R (2007) Autoimmune inflammation from the Th17 perspective. *Autoimmunity Reviews* 6: 169-175

Gennaro A (2000) *Remington: The Science and Practice of Pharmacy—20th edition:* Baltimore, Md.; Lippincott Williams & Wilkins.

Grell W, Hurnaus R, Griss G, Sauter R, Rupprecht E, Mark M, Luger P, Nar H, Wittneben H, Muller P (1998) Repaglinide and related hypoglycemic benzoic acid derivatives. *J Med Chem* 41: 5219-5246

He Y-W, Deftos M L, Ojala E W, Bevan M J (1998) RORγt, a Novel Isoform of an Orphan Receptor, Negatively Regulates Fas Ligand Expression and IL-2 Production in T Cells. *Immunity* 9: 797-806

Hirose T, Smith R J, Jetten A M (1994) ROR-γ: The Third Member of ROR/RZR Orphan Receptor Subfamily That Is Highly Expressed in Skeletal Muscle. *Biochemical and Biophysical Research Communications* 205: 1976-1983

Korn T, Bettelli E, Oukka M, Kuchroo V K (2009) IL-17 and Th17 Cells. *Annual Review of Immunology* 27: 485-517

Kumar L, Amin A, Bansal A K (2007) An overview of automated systems relevant in pharmaceutical salt screening. *Drug Discov Today* 12: 1046-1053

Lipp M, Muller G (2004) Lymphoid organogenesis: getting the green light from RORgamma(t). *Nat Immunol* 5: 12-14

Liu S-J, Tsai J-P, Shen C-R, Sher Y-P, Hsieh C-L, Yeh Y-C, Chou A-H, Chang S-R, Hsiao K-N, Yu F-W, Chen H-W (2007) Induction of a distinct CD8 Tnc17 subset by transforming growth factor-β and interleukin-6. *Journal of Leukocyte Biology* 82: 354-360

Lubberts E, Koenders M I, Oppers-Walgreen B, van den Bersselaar L, Coenen-de Roo C J J, Joosten L A B, van den Berg W B (2004) Treatment with a neutralizing anti-murine interleukin-17 antibody after the onset of collagen-induced arthritis reduces joint inflammation, cartilage destruction, and bone erosion. *Arthritis & Rheumatism* 50: 650-659

Mahato R, Narang A (2011) *Pharmaceutical Dosage Forms and Drug Delivery, Second Edition*: CRC Press.

Morissette S L, Almarsson O, Peterson M L, Remenar J F, Read M J, Lemmo A V, Ellis S, Cima M J, Gardner C R (2004) High-throughput crystallization: polymorphs, salts, co-crystals and solvates of pharmaceutical solids. *Adv Drug Deliv Rev* 56: 275-300

Murdoch J R, Lloyd C M (2010) Resolution of Allergic Airway Inflammation and Airway Hyperreactivity Is Mediated by IL-17-producing γδT Cells. *American Journal of Respiratory and Critical Care Medicine* 182: 464-476

Mutlib A E (2008) Application of stable isotope-labeled compounds in metabolism and in metabolism-mediated toxicity studies. *Chem Res Toxicol* 21: 1672-1689

Ortiz M A, Piedrafita F J, Pfahl M, Maki R (1995) TOR: a new orphan receptor expressed in the thymus that can modulate retinoid and thyroid hormone signals. *Molecular Endocrinology* 9: 1679-1691

Rachitskaya A V, Hansen A M, Horai R, Li Z, Villasmil R, Luger D, Nussenblatt R B, Caspi R R (2008) Cutting Edge: NKT Cells Constitutively Express IL-23 Receptor and RORγt and Rapidly Produce IL-17 upon Receptor Ligation in an IL-6-Independent Fashion. *Journal of immunology* (Baltimore, Md.: 1950) 180: 5167-5171

Reddy I K, Mehvar R (2004) *Chirality in Drug Design and Development*: CRC Press.

Robak M T, Herbage M A, Ellman J A (2010) Synthesis and applications of tert-butanesulfinamide. *Chem Rev* 110: 3600-3740

Rowe R, Sheskey P, Weller P, Rowe R, Sheskey P, Weller P (2003) *Handbook of Pharmaceutical Excipients, 4th Edition.*

Showalter H D, Sercel A D, Leja B M, Wolfangel C D, Ambroso L A, Elliott W L, Fry D W, Kraker A J, Howard C T, Lu G H, Moore C W, Nelson J M, Roberts B J, Vincent P W, Denny W A, Thompson A M (1997) Tyrosine kinase inhibitors. 6. Structure-activity relationships among N- and 3-substituted 2,2'-diselenobis(1H-indoles) for inhibition of protein tyrosine kinases and comparative in vitro and in vivo studies against selected sulfur congeners. *J Med Chem* 40: 413-426

Skepner J, Ramesh R, Trocha M, Schmidt D, Baloglu E, Lobera M, Carlson T, Hill J, Orband-Miller L A, Barnes A, Boudjelal M, Sundrud M, Ghosh S, Yang J (2014) Pharmacologic inhibition of RORgammat regulates Th17 signature gene expression and suppresses cutaneous inflammation in vivo. *J Immunol* 192: 2564-2575

Solt L A, Kumar N, Nuhant P, Wang Y, Lauer J L, Liu J, Istrate M A, Kamenecka T M, Roush W R, Vidovic D, Schurer S C, Xu J, Wagoner G, Drew P D, Griffin P R, Burris T P (2011) Suppression of TH17 differentiation and autoimmunity by a synthetic ROR ligand. *Nature* 472: 491-494

Stahl P, Wermuth C (2002) *Handbook of Pharmaceutical Salts: Properties, Selection, and Use*: Verlag Helvetica Chimica Acta, Zürich, Switzerland, and Wiley-VCH, Weinheim, Germany.

Stockinger B, Veldhoen M, Martin B (2007) Th17 T cells: Linking innate and adaptive immunity. *Seminars in Immunology* 19: 353-361

Tuskey A, Behm B W (2014) Profile of ustekinumab and its potential in patients with moderate-to-severe Crohn's disease. *Clinical and Experimental Gastroenterology* 7: 173-179

Wuts P G M, Greene T W (2007) *Greene's Protective Groups in Organic Synthesis, Fourth Edition*: John Wiley & Sons.

Yamashita T, Iwakura T, Matsui K, Kawaguchi H, Obana M, Hayama A, Maeda M, Izumi Y, Komuro I, Ohsugi Y, Fujimoto M, Naka T, Kishimoto T, Nakayama H, Fujio Y (2011) *IL-6-mediated Th17 differentiation through RORγt is essential for the initiation of experimental autoimmune myocarditis*, Vol. 91.

Yang X O, Pappu B, Nurieva R, Akimzhanov A, Kang H S, Chung Y, Ma L, Shah B, Panopoulos A D, Schluns K, Watowich S S, Tian Q, Jetten A M, Dong C (2008) TH17 lineage differentiation is programmed by orphan nuclear receptors RORα and RORγ. *Immunity* 28: 29-39

Yin S X, Grosso J A (2008) Selecting and controlling API crystal form for pharmaceutical development—strategies and processes. *Curr Opin Drug Discov Devel* 11: 771-777

The invention claimed is:

1. A compound of formula (I)

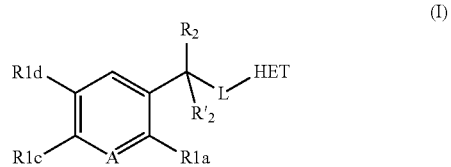

in which,

A is a C-R1b group or a nitrogen atom;

R1a is a hydrogen atom, a halogen atom, a nitrile group, a nitro group ($NO_2$), an alkyl group, an alkyloxy group, an alkylthio group, an amino group, an alkylamino group, a dialkylamino group or a heterocyclic group;

R1b is a hydrogen atom, an alkyloxy group, an alkyl group or a heterocyclic group;

or R1a and R1b can form, together with the carbon atoms to which they are attached, an aryl group or a heterocyclic group;

R1c is a hydrogen atom, a halogen atom, an alkyl group, an alkyloxy group, an alkylthio group, a heterocyclic group, a cyano group, an amido group or a hydroxyl group;

R1d is a hydrogen atom, a halogen atom, an alkyloxy group or an alkyl group;

R2 and R'2 are independently a hydrogen atom, an alkyl group, an alkynyl group, a cycloalkyl group, an aryl group or a heterocyclic group, with the proviso that R2 and R'2 are not simultaneously a hydrogen atom, or R2 and R2' can form, together with the carbon atom to which they are attached, a cycloalkyl group or a heterocycloalkyl group;

L is a $NR7\text{-}CO\text{-}CH_2$, $NR7\text{-}CO\text{-}NH$, $NR7\text{-}CO\text{-}C(CH_3)_2$, $NR7\text{-}CS\text{-}CH_2$, $NR7\text{-}CS\text{-}NH$, $NR7\text{-}CS\text{-}C(CH_3)_2$, $NR7\text{-}SO_2\text{-}CH_2$, $NR7\text{-}SO_2\text{-}C(CH_3)_2$, $CO\text{-}NH\text{-}CH_2$ or $CO\text{-}NH\text{-}C(CH_3)_2$ group;

SEQUENCE LISTING

<160> NUMBER OF SEQ ID NOS: 1

<210> SEQ ID NO 1
<211> LENGTH: 21
<212> TYPE: PRT
<213> ORGANISM: Artificial sequence
<220> FEATURE:
<223> OTHER INFORMATION: Peptide antigen MOG35-55

<400> SEQUENCE: 1

```
Met Met Glu Val Gly Trp Tyr Arg Ser Pro Phe Ser Arg Val Val His
1               5                   10                  15

Leu Tyr Arg Asn Gly
            20
```

HET is a heterocyclic group selected from:

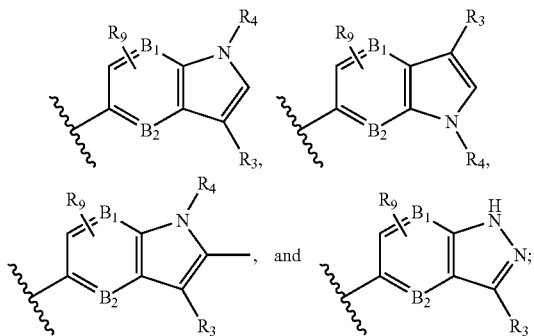

B1 and B2 are independently a nitrogen atom or a carbon atom;
R3 is a COR5 group, a CO-Alkyl-COR5 group or an alkyl group substituted by a COR5 group;
R4 is a hydrogen atom, an alkyl group or a hydroxyl group;
R5 is a hydroxyl group, an alkyloxy group, an alkyl group, a NR8R8' group or a —O—CH—(CH$_2$—O—CO—R6)$_2$ group;
R6 is a long chain alkyl group;
R7 is a hydrogen atom or an alkyl group;
R8 is a hydrogen atom or an alkyl group;
R8' is a hydrogen atom, an alkyl group, a C(=NH)NH$_2$ group, a C(=NH)NHCOOtBu group or an alkoxy group; and
R9 is a hydrogen atom, an alkyl group or a halogen atom.

2. The compound according to claim 1, wherein:
A is a C-R1b group or a nitrogen atom;
R1a is a hydrogen atom, a halogen atom, an alkyl group, an alkyloxy group, an amino group, an alkylamino group, a dialkylamino group or a heterocyclic group;
R1b is hydrogen, an alkyl group or a heterocyclic group;
R1a and R1b can form, together with the carbon atoms to which they are attached, an aryl group or a heterocyclic group;
R1c is a hydrogen atom, a halogen atom, an alkyl group, an alkyloxy group, a cyano group, an amido group or a hydroxyl group;
R1d is a hydrogen atom, a halogen atom, an alkyloxy group or an alkyl group;
R2 and R'2 are independently a hydrogen atom, an alkyl group, an alkynyl group, a cycloalkyl group, an aryl group or a heterocyclic group, with the proviso that R2 and R'2 are not simultaneously a hydrogen atom,
or R2 and R2' can form, together with the carbon atom to which they are attached, a cycloalkyl group;
L is a NR7-CO—CH$_2$, NR7-CO—NH, or CO—NH—CH$_2$ group;
HET is a heterocyclic group selected from:

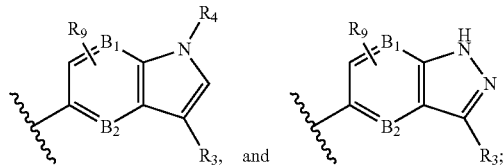

B1 and B2 are independently a nitrogen atom or a carbon atom;
R3 is a COR5 group, or a CO-Alkyl-COR5 group or an alkyl group substituted by a COR5 group;
R4 is a hydrogen atom or an alkyl group;
R5 is a hydroxyl group, an alkyloxy group, an alkyl group, a NR8R8'group or a —O—CH—(CH$_2$—O—CO—R6)$_2$ group;
R6 is a long chain alkyl group;
R7 is a hydrogen atom;
R8 is a hydrogen atom or an alkyl group;
R8' is a hydrogen atom, an alkyl group, a C(=NH)NH$_2$ group or a C(=NH)NHCOOtBu group; and
R9 is a hydrogen atom.

3. The compound according to claim 1, wherein:
A is a C-R1b group or a nitrogen atom;
R1a is a halogen atom, a nitrile group, a nitro group (NO$_2$), an alkyl group, an alkyloxy group, an alkylthio group, an amino group, an alkylamino group, a dialkylamino group or a heterocyclic group;
R1b is a hydrogen atom or a heterocyclic group;
wherein R1a and R1b can optionally form, together with the carbon atoms to which they are attached, an aryl group or a heterocyclic group;
R1c is a hydrogen atom, a halogen atom, an alkyl group, an alkyloxy group, an alkylthio or a heterocyclic group;
R1d is a hydrogen atom, a halogen atom or an alkyl group;
R2 and R'2 are independently a hydrogen atom, an alkyl group, a cycloalkyl group, an aryl group, or a heterocyclic group, with the proviso that R2 and R'2 are not simultaneously a hydrogen atom,
or R2 and R2' can form, together with the carbon atom to which they are attached, a cycloalkyl group or a heterocycloalkyl group;
L is a NR7-CO—CH$_2$, NR7-CO—NH, NR7-CO—C(CH$_3$)$_2$, NR7-CS—CH$_2$, NR7-CS—NH, NR7-CS—C(CH$_3$)$_2$, NR7-SO$_2$—CH$_2$, NR7-SO$_2$—C(CH$_3$)$_2$, CO—NH—CH$_2$ or CO—NH—C(CH$_3$)$_2$ group;
HET is a heterocyclic group selected from:

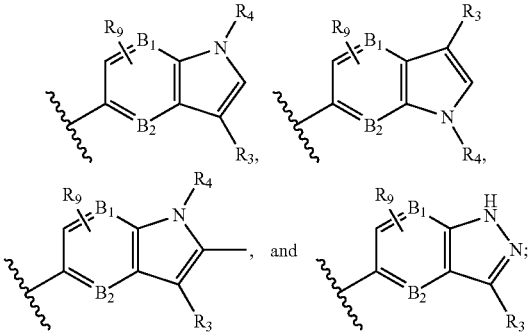

B1 and B2 are independently a nitrogen atom or a carbon atom;
R3 is a COR5 group or an alkyl group substituted by a COR5 group;
R4 is a hydrogen atom or a hydroxyl group;
R5 is a hydroxyl group, an alkyloxy group, a NR8R8'group or a —O—CH—(CH$_2$—O—CO—R6)$_2$ group;
R6 is a long chain alkyl group;
R7 is a hydrogen atom or an alkyl group;
R8 and R8' are independently a hydrogen atom or an alkyl group; and R9 is a hydrogen atom, an alkyl group or a halogen atom.
4. The compound according to claim 1, wherein:
A is a C-R1b group;
R1a is a halogen atom, a nitrile group, a nitro group (NO$_2$), an alkyl group, an alkyloxy group, an alkylthio group, an alkylamino group, a dialkylamino group, a 1-pyrrolidinyl group, a 1-azepanyl group, a 4-morpholinyl group, a 1-piperidinyl group, a 1-piperazinyl group, wherein said piperidinyl or piperazinyl group can be optionally substituted by one or more alkyl groups;
R1b is hydrogen, a 1-pyrrolidinyl group, a 1-azepanyl group, a 4-morpholinyl group, a 1-piperidinyl group or a 1-piperazinyl group;
R1c is hydrogen, a halogen atom, an alkyl group or an alkyloxy group;
R2 is an alkyl group, a cycloalkyl group, an aryl group or a heteroaryl group, and
R'2 is a hydrogen atom.
5. The compound according to claim 1, wherein B1 and B2 are carbon atoms.
6. The compound according to claim 1, wherein L is NH—CO—CH$_2$, NH—CO—NH, NH—SO$_2$—CH$_2$, CO—NH—CH$_2$, N(CH$_3$)—CO—CH$_2$ or NH—CO—C(CH$_3$)$_2$.
7. The compound according to claim 1, wherein
A is a CH group,
R1a is a heterocycloalkyl group,
R1c is a hydrogen atom or an alkyl group,
R2 is a phenyl group or an alkyl group,
L represents a NH—CO—CH$_2$ group or a NH—CO—NH group,
HET has the following structure

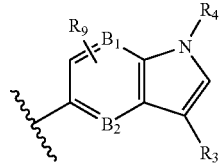

in which B1 and B2 are carbon atoms,
R4 is a hydrogen atom; and
R3 represents a CH$_2$—CH$_2$—COR5 group, wherein R5 is a hydroxyl group or an alkyloxy group
R9 is a hydrogen atom.
8. The compound according to claim 1, wherein:
A is a CH group;
R1a is a piperidinyl group;
R1c is a hydrogen atom or an alkyl group;
R2 is a heterocyclic group, substituted or not by an alkyl group;
L represents a NH—CO—CH$_2$ group,
HET has the following structure

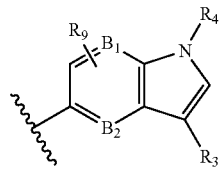

in which B1 and B2 are carbon atoms;
R9 is a hydrogen atom;
R4 is a hydrogen atom; and
R3 represents a CH$_2$—CH$_2$—COR5 group, wherein R5 is a hydroxyl group or an alkyloxy group.
9. The compound according to claim 1, characterized in that it is selected from:
3-{5-[({phenyl[2-(piperidin-1-yl)phenyl]methyl}carbamoyl)methyl]-1H-indol-3-yl}propanoic acid;
tert-butyl 3-{5-[({phenyl[2-(piperidin-1-yl)phenyl]methyl}carbamoyl)methyl]-1H-indol-3-yl}propanoate;
3-[5-({[(3-fluorophenyl)[2-(piperidin-1-yl)phenyl]methyl]carbamoyl}methyl)-1H-indol-3-yl]propanoic acid;
tert-butyl 3-[5-({[(3-fluorophenyl)[2-(piperidin-1-yl)phenyl]methyl]carbamoyl}methyl)-1H-indol-3-yl]propanoate;
3-{5-[({[4-methyl-2-(pyrrolidin-1-yl)phenyl](phenyl)methyl}carbamoyl)methyl]-1H-indol-3-yl}propanoic acid;
tert-butyl 3-{5-[({[4-methyl-2-(pyrrolidin-1-yl)phenyl](phenyl)methyl}carbamoyl)methyl]-1H-indol-3-yl}propanoate;
3-[5-({[(2-chloro-4-methylphenyl)(phenyl)methyl]carbamoyl}methyl)-1H-indol-3-yl]propanoic acid;
tert-butyl 3-[5-({[(2-chloro-4-methylphenyl)(phenyl)methyl]carbamoyl}methyl)-1H-indol-3-yl]propanoate;
3-[5-({[(2-bromo-4-methylphenyl)(phenyl)methyl]carbamoyl}methyl)-1H-indol-3-yl]propanoic acid;
tert-butyl 3-[5-({[(2-bromo-4-methylphenyl)(phenyl)methyl]carbamoyl}methyl)-1H-indol-3-yl]propanoate;
3-[5-({[(2,4-dimethylphenyl)(phenyl)methyl]carbamoyl}methyl)-1H-indol-3-yl]propanoic acid;
tert-butyl 3-[5-({[(2,4-dimethylphenyl)(phenyl)methyl]carbamoyl}methyl)-1H-indol-3-yl]propanoate;
3-[5-({[(2,5-dimethylphenyl)(phenyl)methyl]carbamoyl}methyl)-1H-indol-3-yl]propanoic acid;
tert-butyl 3-[5-({[(2,5-dimethylphenyl)(phenyl)methyl]carbamoyl}methyl)-1H-indol-3-yl]propanoate;
3-{5-[({[6-methyl-2-(pyrrolidin-1-yl)pyridin-3-yl](phenyl)methyl}carbamoyl)methyl]-1H-indol-3-yl}propanoic acid;
tert-butyl 3-{5-[({[6-methyl-2-(pyrrolidin-1-yl)pyridin-3-yl](phenyl)methyl}carbamoyl)methyl]-1H-indol-3-yl}propanoate;
3-[5-({[(2-fluoro-4-methylphenyl)(phenyl)methyl]carbamoyl}methyl)-1H-indol-3-yl]propanoic acid;
tert-butyl 3-[5-({[(2-fluoro-4-methylphenyl)(phenyl)methyl]carbamoyl}methyl)-1H-indol-3-yl]propanoate;
3-[5-({[(2-fluoro-5-methylphenyl)(phenyl)methyl]carbamoyl}methyl)-1H-indol-3-yl]propanoic acid;
tert-butyl 3-[5-({[(2-fluoro-5-methylphenyl)(phenyl)methyl]carbamoyl}methyl)-1H-indol-3-yl]propanoate;
3-[5-({[(2,4-dimethylphenyl)(pyridin-2-yl)methyl]carbamoyl}methyl)-1H-indol-3-yl]propanoic acid;
tert-butyl 3-[5-({[(2,4-dimethylphenyl)(pyridin-2-yl)methyl]carbamoyl}methyl)-1H-indol-3-yl]propanoate;
3-[5-({[phenyl({2-[2-(trifluoromethyl)piperidin-1-yl]phenyl})methyl]carbamoyl}-methyl)-1H-indol-3-yl]propanoic acid;
tert-butyl 3-[5-({[phenyl({2-[2-(trifluoromethyl)piperidin-1-yl]phenyl})methyl]carbamoyl}methyl)-1H-indol-3-yl]propanoate;
3-{5-[({[2-(3,5-dimethylpiperidin-1-yl)phenyl](phenyl)methyl}carbamoyl)methyl]-1H-indol-3-yl}propanoic acid;

tert-butyl 3-{5-[({[2-(3,5-dimethylpiperidin-1-yl)phenyl](phenyl)methyl}carbamoyl)methyl]-1H-indol-3-yl}propanoate;
3-[5-({[(2,4-dimethylphenyl)(pyridin-3-yl)methyl]carbamoyl}methyl)-1H-indol-3-yl]propanoic acid;
tert-butyl 3-[5-({[(2,4-dimethylphenyl)(pyridin-3-yl)methyl]carbamoyl}methyl)-1H-indol-3-yl]propanoate;
3-{5-[({3-methyl-1-[2-(piperidin-1-yl)phenyl]butyl}carbamoyl)methyl]-1H-indol-3-yl}propanoic acid;
tert-butyl 3-{5-[({3-methyl-1-[2-(piperidin-1-yl)phenyl]butyl}carbamoyl)methyl]-1H-indol-3-yl}propanoate;
3-[5-({[(5-methylquinolin-8-yl)(phenyl)methyl]carbamoyl}methyl)-1H-indol-3-yl]propanoic acid;
tert-butyl 3-[5-({[(5-methylquinolin-8-yl)(phenyl)methyl]carbamoyl}methyl)-1H-indol-3-yl]propanoate;
3-[5-({[(4-chloro-2-methylphenyl)(phenyl)methyl]carbamoyl}methyl)-1H-indol-3-yl]propanoic acid;
tert-butyl 3-[5-({[(4-chloro-2-methylphenyl)(phenyl)methyl]carbamoyl}methyl)-1H-indol-3-yl]propanoate;
3-{5-[({[2-(azepan-1-yl)phenyl](phenyl)methyl}carbamoyl)methyl]-1H-indol-3-yl}propanoic acid;
tert-butyl 3-{5-[({[2-(azepan-1-yl)phenyl](phenyl)methyl}carbamoyl)methyl]-1H-indol-3-yl}propanoate;
3-[5-({[(4-methylnaphthalen-1-yl)(phenyl)methyl]carbamoyl}methyl)-1H-indol-3-yl]propanoic acid;
tert-butyl 3-[5-({[(4-methylnaphthalen-1-yl)(phenyl)methyl]carbamoyl}methyl)-1H-indol-3-yl]propanoate;
2-{5-[({phenyl[2-(piperidin-1-yl)phenyl]methyl}carbamoyl)methyl]-1H-indol-3-yl}acetic acid;
methyl 2-{5-[({phenyl[2-(piperidin-1-yl)phenyl]methyl}carbamoyl)methyl]-1H-indol-3-yl}acetate;
tert-butyl 3-[5-({[(2-chloro-5-methylphenyl)(phenyl)methyl]carbamoyl}methyl)-1H-indol-3-yl]propanoate;
3-[5-({[(2-chloro-5-methylphenyl)(phenyl)methyl]carbamoyl}methyl)-1H-indol-3-yl]propanoic acid;
tert-butyl 3-[5-({[(4-bromo-2-methylphenyl)(phenyl)methyl]carbamoyl}methyl)-1H-indol-3-yl]propanoate;
3-[5-({[(4-bromo-2-methylphenyl)(phenyl)methyl]carbamoyl}methyl)-1H-indol-3-yl]propanoic acid;
tert-butyl 3-[5-({[(4-fluoro-2-methylphenyl)(phenyl)methyl]carbamoyl}methyl)-1H-indol-3-yl]propanoate;
3-[5-({[(4-fluoro-2-methylphenyl)(phenyl)methyl]carbamoyl}methyl)-1H-indol-3-yl]propanoic acid;
tert-butyl 3-{5-[({phenyl[2-(pyrrolidin-1-yl)-4-(trifluoromethyl)phenyl]methyl}carbamoyl)methyl]-1H-indol-3-yl}propanoate;
3-{5-[({phenyl[2-(pyrrolidin-1-yl)-4-(trifluoromethyl)phenyl]methyl}carbamoyl)methyl]-1H-indol-3-yl}propanoic acid;
tert-butyl 3-{5-[({[4-bromo-2-(pyrrolidin-1-yl)phenyl](phenyl)methyl}carbamoyl)methyl]-1H-indol-3-yl}propanoate;
3-{5-[({[4-bromo-2-(pyrrolidin-1-yl)phenyl](phenyl)methyl}carbamoyl)methyl]-1H-indol-3-yl}propanoic acid;
tert-butyl 3-[5-({[(2-aminophenyl)(phenyl)methyl]carbamoyl}methyl)-1H-indol-3-yl]propanoate;
3-[5-({[(2-aminophenyl)(phenyl)methyl]carbamoyl}methyl)-1H-indol-3-yl]propanoic acid;
tert-butyl 3-[5-({[(2-dimethylamino)phenyl](phenyl)methyl}carbamoyl)methyl]-1H-indol-3-yl}propanoate;
3-{5-[({[2-(dimethylamino)phenyl](phenyl)methyl}carbamoyl)methyl]-1H-indol-3-yl}propanoic acid;
tert-butyl 3-{5-[({phenyl[2-(piperidin-1-yl)phenyl]methyl}carbamoyl)amino]-1H-indol-3-yl}propanoate;
3-{5-[({phenyl[2-(piperidin-1-yl)phenyl]methyl}carbamoyl)amino]-1H-indol-3-yl}propanoic acid;
tert-butyl 3-{5-[({3-methyl-1-[2-(morpholin-4-yl)phenyl]butyl}carbamoyl)methyl]-1H-indol-3-yl}propanoate;
3-{5-[({3-methyl-1-[2-(morpholin-4-yl)phenyl]butyl}carbamoyl)methyl]-1H-indol-3-yl}propanoic acid;
tert-butyl 3-{5-[({[4-cyano-2-(pyrrolidin-1-yl)phenyl](phenyl)methyl}carbamoyl)methyl]-1H-indol-3-yl}propanoate;
3-{5-[({[4-cyano-2-(pyrrolidin-1-yl)phenyl](phenyl)methyl}carbamoyl)methyl]-1H-indol-3-yl}propanoic acid;
tert-butyl 3-{5-[({[5-chloro-2-(piperidin-1-yl)phenyl](phenyl)methyl}carbamoyl)methyl]-1H-indol-3-yl}propanoate;
3-{5-[({[5-chloro-2-(piperidin-1-yl)phenyl](phenyl)methyl}carbamoyl)methyl]-1H-indol-3-yl}propanoic acid;
3-{5-[({[4-carbamoyl-2-(pyrrolidin-1-yl)phenyl](phenyl)methyl}carbamoyl)methyl]-1H-indol-3-yl}propanoic acid;
methyl 2-{5-[({[4-methyl-2-(pyrrolidin-1-yl)phenyl](phenyl)methyl}carbamoyl)methyl]-1H-indol-3-yl}acetate;
2-{5-[({[4-methyl-2-(pyrrolidin-1-yl)phenyl](phenyl)methyl}carbamoyl)methyl]-1H-indol-3-yl}acetic acid;
methyl 2-{5-[({[4-bromo-2-(pyrrolidin-1-yl)phenyl](phenyl)methyl}carbamoyl)methyl]-1H-indol-3-yl}acetate;
2-{5-[({[4-bromo-2-(pyrrolidin-1-yl)phenyl](phenyl)methyl}carbamoyl)methyl]-1H-indol-3-yl}acetic acid;
methyl 2-{5-[({phenyl[2-(piperidin-1-yl)phenyl]methyl}carbamoyl)amino]-1H-indol-3-yl}acetate;
2-{5-[({phenyl[2-(piperidin-1-yl)phenyl]methyl}carbamoyl)amino]-1H-indol-3-yl}acetic acid;
methyl 2-{5-[({[2-(dimethylamino)phenyl](phenyl)methyl}carbamoyl)methyl]-1H-indol-3-yl}acetate;
2-{5-[({[2-(dimethylamino)phenyl](phenyl)methyl}carbamoyl)methyl]-1H-indol-3-yl}acetic acid;
methyl 2-{5-[({phenyl[2-(pyrrolidin-1-yl)phenyl]methyl}carbamoyl)methyl]-1H-indol-3-yl}acetate;
2-{5-[({phenyl[2-(pyrrolidin-1-yl)phenyl]methyl}carbamoyl)methyl]-1H-indol-3-yl}acetic acid;
methyl 2-{5-[({[2-(azepan-1-yl)phenyl](phenyl)methyl}carbamoyl)methyl]-1H-indol-3-yl}acetate;
2-{5-[({[2-(azepan-1-yl)phenyl](phenyl)methyl}carbamoyl)methyl]-1H-indol-3-yl}acetic acid;
tert-butyl 3-{5-[({[4-methyl-2-(piperidin-1-yl)phenyl](phenyl)methyl}carbamoyl)methyl]-1H-indol-3-yl}propanoate;
3-{5-[({[4-methyl-2-(piperidin-1-yl)phenyl](phenyl)methyl}carbamoyl)methyl]-1H-indol-3-yl}propanoic acid;
tert-butyl 3-{5-[({phenyl[2-(pyrrolidin-1-yl)phenyl]methyl}carbamoyl)methyl]-1H-indol-3-yl}propanoate;
3-{5-[({phenyl[2-(pyrrolidin-1-yl)phenyl]methyl}carbamoyl)methyl]-1H-indol-3-yl}propanoic acid;

tert-butyl 3-{5-[({[4-methyl-2-(morpholin-4-yl)phenyl](phenyl)methyl}carbamoyl)methyl]-1H-indol-3-yl}propanoate;
3-{5-[({[4-methyl-2-(morpholin-4-yl)phenyl](phenyl)methyl}carbamoyl)methyl]-1H-indol-3-yl}propanoic acid;
tert-butyl 3-{5-({[(4-methoxy-2-methylphenyl)(phenyl)methyl]carbamoyl}methyl)-1H-indol-3-yl]propanoate;
3-[5-({[(4-methoxy-2-methylphenyl)(phenyl)methyl]carbamoyl}methyl)-1H-indol-3-yl]propanoic acid;
methyl 2-{5-[({[4-chloro-2-(pyrrolidin-1-yl)phenyl](phenyl)methyl}carbamoyl)methyl]-1H-indol-3-yl}acetate;
2-{5-[({[4-chloro-2-(pyrrolidin-1-yl)phenyl](phenyl)methyl}carbamoyl)methyl]-1H-indol-3-yl}acetic acid;
methyl 2-{5-[({[4-methyl-2-(piperidin-1-yl)phenyl](phenyl)methyl}carbamoyl)methyl]-1H-indol-3-yl}acetate;
2-{5-[({[4-methyl-2-(piperidin-1-yl)phenyl](phenyl)methyl}carbamoyl)methyl]-1H-indol-3-yl}acetic acid;
methyl 2-{5-[({phenyl[2-(pyrrolidin-1-yl)-4-(trifluoromethyl)phenyl]methyl}carbamoyl)methyl]-1H-indol-3-yl}acetate;
2-{5-[({phenyl[2-(pyrrolidin-1-yl)-4-(trifluoromethyl)phenyl]methyl}carbamoyl)methyl]-1H-indol-3-yl}acetic acid;
tert-butyl 3-{5-[({[4-chloro-2-(pyrrolidin-1-yl)phenyl](phenyl)methyl}carbamoyl)methyl]-1H-indol-3-yl}propanoate;
3-{5-[({[4-chloro-2-(pyrrolidin-1-yl)phenyl](phenyl)methyl}carbamoyl)methyl]-1H-indol-3-yl}propanoic acid;
tert-butyl 3-{5-[({[4-fluoro-2-(pyrrolidin-1-yl)phenyl](phenyl)methyl}carbamoyl)methyl]-1H-indol-3-yl}propanoate;
3-{5-[({[4-fluoro-2-(pyrrolidin-1-yl)phenyl](phenyl)methyl}carbamoyl)methyl]-1H-indol-3-yl}propanoic acid;
tert-butyl 3-{5-[({phenyl[2-(piperidin-1-yl)phenyl]methyl}carbamoyl)amino]-1H-pyrrolo[2,3-b]pyridin-3-yl}propanoate;
3-{5-[({phenyl[2-(piperidin-1-yl)phenyl]methyl}carbamoyl)amino]-1H-pyrrolo[2,3-b]pyridin-3-yl}propanoic acid;
methyl 2-{5-[({[4-methyl-2-(morpholin-4-yl)phenyl](phenyl)methyl}carbamoyl)methyl]-1H-indol-3-yl}acetate;
2-{5-[({[4-methyl-2-(morpholin-4-yl)phenyl](phenyl)methyl}carbamoyl)methyl]-1H-indol-3-yl}acetic acid;
tert-butyl 3-[5-({[(2-methoxy-4-methylphenyl)(phenyl)methyl]carbamoyl}methyl)-1H-indol-3-yl]propanoate;
3-[5-({[(2-methoxy-4-methylphenyl)(phenyl)methyl]carbamoyl}methyl)-1H-indol-3-yl]propanoic acid;
tert-butyl 3-[5-({[(2,4-dimethylphenyl)(5-methylthiophen-2-yl)methyl]carbamoyl}methyl)-1H-indol-3-yl]propanoate;
3-[5-({[(2,4-dimethylphenyl)(5-methylthiophen-2-yl)methyl]carbamoyl}methyl)-1H-indol-3-yl]propanoic acid;
tert-butyl 3-{5-[({[4-methyl-2-(4-methylpiperazin-1-yl)phenyl](phenyl)methyl}carbamoyl)methyl]-1H-indol-3-yl}propanoate;
3-{5-[({[4-methyl-2-(4-methylpiperazin-1-yl)phenyl](phenyl)methyl}carbamoyl)methyl]-1H-indol-3-yl}propanoic acid;
tert-butyl 3-[5-({[3-methyl-1-(naphthalen-1-yl)butyl]carbamoyl}methyl)-1H-indol-3-yl]propanoate;
3-[5-({[3-methyl-1-(naphthalen-1-yl)butyl]carbamoyl}methyl)-1H-indol-3-yl]propanoic acid;
tert-butyl 3-{5-[({phenyl[2-(1H-pyrrol-1-yl)phenyl]methyl}carbamoyl)methyl]-1H-indol-3-yl}propanoate;
3-{5-[({phenyl[2-(1H-pyrrol-1-yl)phenyl]methyl}carbamoyl)methyl]-1H-indol-3-yl}propanoic acid;
tert-butyl 3-{5-[({[4-methoxy-2-(pyrrolidin-1-yl)phenyl](phenyl)methyl}carbamoyl)methyl]-1H-indol-3-yl}propanoate;
3-{5-[({[4-methoxy-2-(pyrrolidin-1-yl)phenyl](phenyl)methyl}carbamoyl)methyl]-1H-indol-3-yl}propanoic acid;
tert-butyl 3-{5-[({[4-methoxy-2-(piperidin-1-yl)phenyl](phenyl)methyl}carbamoyl)methyl]-1H-indol-3-yl}propanoate;
3-{5-[({[4-methoxy-2-(piperidin-1-yl)phenyl](phenyl)methyl}carbamoyl)methyl]-1H-indol-3-yl}propanoic acid;
N,N-dimethyl-2-{5-[({[4-methyl-2-(morpholin-4-yl)phenyl](phenyl)methyl}carbamoyl)methyl]-1H-indol-3-yl}acetamide;
tert-butyl 3-{5-[({[5-methyl-2-(piperidin-1-yl)phenyl](phenyl)methyl}carbamoyl)methyl]-1H-indol-3-yl}propanoate;
3-{5-[({[5-methyl-2-(piperidin-1-yl)phenyl](phenyl)methyl}carbamoyl)methyl]-1H-indol-3-yl}propanoic acid;
N-methyl-3-{5-[({phenyl[2-(piperidin-1-yl)phenyl]methyl}carbamoyl)methyl]-1H-indol-3-yl}propanamide;
tert-butyl 3-{5-[({[5-bromo-2-(pyrrolidin-1-yl)phenyl](phenyl)methyl}carbamoyl)methyl]-1H-indol-3-yl}propanoate;
3-{5-[({[5-bromo-2-(pyrrolidin-1-yl)phenyl](phenyl)methyl}carbamoyl)methyl]-1H-indol-3-yl}propanoic acid;
3-{5-[({phenyl[2-(piperidin-1-yl)phenyl]methyl}carbamoyl)methyl]-1H-indol-3-yl}-N-(propan-2-yl)propanamide;
tert-butyl 3-{5-[({[2-(ethylamino)-4-methylphenyl](phenyl)methyl}carbamoyl)methyl]-1H-indol-3-yl}propanoate;
3-{5-[({[2-(ethylamino)-4-methylphenyl](phenyl)methyl}carbamoyl)methyl]-1H-indol-3-yl}propanoic acid;
tert-butyl 3-(5-{[({2-[(dimethylamino)methyl]phenyl}(phenyl)methyl)carbamoyl]methyl}-1H-indol-3-yl)propanoate;
3-(5-{[({2-[(dimethylamino)methyl]phenyl}(phenyl)methyl)carbamoyl]methyl}-1H-indol-3-yl)propanoic acid;
tert-butyl 3-{5-[({[2-(3-hydroxypiperidin-1-yl)phenyl](phenyl)methyl}carbamoyl)methyl]-1H-indol-3-yl}propanoate;
3-{5-[({[2-(3-hydroxypiperidin-1-yl)phenyl](phenyl)methyl}carbamoyl)methyl]-1H-indol-3-yl}propanoic acid;
tert-butyl 3-{5-[({4-methyl-2-[(propan-2-yl)amino]phenyl}(phenyl)methyl)carbamoyl]methyl}-1H-indol-3-yl)propanoate;
3-(5-{[({4-methyl-2-[(propan-2-yl)amino]phenyl}(phenyl)methyl)carbamoyl]methyl}-1H-indol-3-yl)propanoic acid;
tert-butyl 3-{5-[({phenyl[2-(1,2,3,6-tetrahydropyridin-1-yl)phenyl]methyl}carbamoyl)methyl]-1H-indol-3-yl}propanoate;

3-{5-[({phenyl[2-(1,2,3,6-tetrahydropyridin-1-yl)phenyl]methyl}carbamoyl)methyl]-1H-indol-3-yl}propanoic acid;

tert-butyl 3-{5-[({1-[2-(pyrrolidin-1-yl)phenyl]cyclopentyl}carbamoyl)methyl]-1H-indol-3-yl}propanoate;

3-{5-[({1-[2-(pyrrolidin-1-yl)phenyl]cyclopentyl}carbamoyl)methyl]-1H-indol-3-yl}propanoic acid;

tert-butyl 3-{5-[({[4-methyl-2-(piperidin-1-yl)phenyl](pyrimidin-2-yl)methyl}carbamoyl)methyl]-1H-indol-3-yl}propanoate;

3-{5-[({[4-methyl-2-(piperidin-1-yl)phenyl](pyrimidin-2-yl)methyl}carbamoyl)methyl]-1H-indol-3-yl}propanoic acid;

tert-butyl 3-{5-[({1-[2-(dimethylamino)-4-methylphenyl]-3-methylbutyl}carbamoyl)methyl]-1H-indol-3-yl}propanoate;

3-{5-[({1-[2-(dimethylamino)-4-methylphenyl]-3-methylbutyl}carbamoyl)methyl]-1H-indol-3-yl}propanoic acid;

tert-butyl 3-{5-[({[5-methoxy-2-(piperidin-1-yl)phenyl](phenyl)methyl}carbamoyl)methyl]-1H-indol-3-yl}propanoate;

3-{5-[({[5-methoxy-2-(piperidin-1-yl)phenyl](phenyl)methyl}carbamoyl)methyl]-1H-indol-3-yl}propanoic acid;

tert-butyl 3-{5-[({[4-methyl-2-(piperidin-1-yl)phenyl](5-methylthiophen-2-yl)methyl}carbamoyl)methyl]-1H-indol-3-yl}propanoate;

3-{5-[({[4-methyl-2-(piperidin-1-yl)phenyl](5-methylthiophen-2-yl)methyl}carbamoyl)methyl]-1H-indol-3-yl}propanoic acid;

tert-butyl 3-{5-[({[4-methyl-2-(piperidin-1-yl)phenyl](1,3-thiazol-2-yl)methyl}carbamoyl)methyl]-1H-indol-3-yl}propanoate;

3-{5-[({[4-methyl-2-(piperidin-1-yl)phenyl](1,3-thiazol-2-yl)methyl}carbamoyl)methyl]-1H-indol-3-yl}propanoic acid;

tert-butyl 3-{5-[({[2-(azepan-1-yl)-4-methoxyphenyl](phenyl)methyl}carbamoyl)methyl]-1H-indol-3-yl}propanoate;

3-{5-[({[2-(azepan-1-yl)-4-methoxyphenyl](phenyl)methyl}carbamoyl)methyl]-1H-indol-3-yl}propanoic acid;

tert-butyl 3-{5-[({1-[2-(piperidin-1-yl)phenyl]cyclohexyl}carbamoyl)methyl]-1H-indol-3-yl}propanoate;

3-{5-[({1-[2-(piperidin-1-yl)phenyl]cyclohexyl}carbamoyl)methyl]-1H-indol-3-yl}propanoic acid;

tert-butyl 3-{5-[({[4-methyl-2-(propan-2-yloxy)phenyl](phenyl)methyl}carbamoyl)methyl]-1H-indol-3-yl}propanoate;

3-{5-[({[4-methyl-2-(propan-2-yloxy)phenyl](phenyl)methyl}carbamoyl)methyl]-1H-indol-3-yl}propanoic acid;

tert-butyl 3-[5-({[(5-methylfuran-2-yl)[2-(piperidin-1-yl)phenyl]methyl]carbamoyl}methyl)-1H-indol-3-yl]propanoate;

3-[5-({[(5-methylfuran-2-yl)[2-(piperidin-1-yl)phenyl]methyl]carbamoyl}methyl)-1H-indol-3-yl]propanoic acid;

tert-butyl 3-{5-[({[4-ethoxy-2-(piperidin-1-yl)phenyl](phenyl)methyl}carbamoyl)methyl]-1H-indol-3-yl}propanoate;

3-{5-[({[4-ethoxy-2-(piperidin-1-yl)phenyl](phenyl)methyl}carbamoyl)methyl]-1H-indol-3-yl}propanoic acid;

tert-butyl 3-{5-[({phenyl[2-(piperidin-1-yl)-4-(propan-2-yloxy)phenyl]methyl}carbamoyl)methyl]-1H-indol-3-yl}propanoate;

3-{5-[({phenyl[2-(piperidin-1-yl)-4-(propan-2-yloxy)phenyl]methyl}carbamoyl)methyl]-1H-indol-3-yl}propanoic acid;

tert-butyl 3-[5-({[(5-methyl-1,3-thiazol-2-yl)[2-(piperidin-1-yl)phenyl]methyl]carbamoyl}methyl)-1H-indol-3-yl]propanoate;

3-[5-({[(5-methyl-1,3-thiazol-2-yl)[2-(piperidin-1-yl)phenyl]methyl]carbamoyl}methyl)-1H-indol-3-yl]propanoic acid;

tert-butyl 3-[5-({[(2-methyl-1,3-thiazol-5-yl)[2-(piperidin-1-yl)phenyl]methyl]carbamoyl}methyl)-1H-indol-3-yl]propanoate;

3-[5-({[(2-methyl-1,3-thiazol-5-yl)[2-(piperidin-1-yl)phenyl]methyl]carbamoyl}methyl)-1H-indol-3-yl]propanoic acid;

tert-butyl 3-[5-({[(3-methylphenyl)[2-(piperidin-1-yl)phenyl]methyl]carbamoyl}methyl)-1H-indol-3-yl]propanoate;

3-[5-({[(3-methylphenyl)[2-(piperidin-1-yl)phenyl]methyl]carbamoyl}methyl)-1H-indol-3-yl]propanoic acid;

ethyl 3-{5-[({[4-methyl-2-(propan-2-yloxy)phenyl](phenyl)methyl}carbamoyl)methyl]-1H-indazol-3-yl}propanoate;

3-{5-[({[4-methyl-2-(propan-2-yloxy)phenyl](phenyl)methyl}carbamoyl)methyl]-1H-indazol-3-yl}propanoic acid;

tert-butyl 3-{5-[({2-cyclohexyl-1-[2-(piperidin-1-yl)phenyl]ethyl}carbamoyl)methyl]-1H-indol-3-yl}propanoate;

3-{5-[({2-cyclohexyl-1-[2-(piperidin-1-yl)phenyl]ethyl}carbamoyl)methyl]-1H-indol-3-yl}propanoic acid;

tert-butyl 3-[5-({[cyclopropyl(4-methylnaphthalen-1-yl)methyl]carbamoyl}methyl)-1H-indol-3-yl]propanoate;

3-[5-({[cyclopropyl(4-methylnaphthalen-1-yl)methyl]carbamoyl}methyl)-1H-indol-3-yl]propanoic acid;

methyl 2-{5-[({[5-chloro-2-(piperidin-1-yl)phenyl](phenyl)methyl}carbamoyl)methyl]-1H-indol-3-yl}acetate;

2-{5-[({[5-chloro-2-(piperidin-1-yl)phenyl](phenyl)methyl}carbamoyl)methyl]-1H-indol-3-yl}acetic acid;

tert-butyl 3-[5-({[1H-indol-7-yl(phenyl)methyl]carbamoyl}methyl)-1H-indol-3-yl]propanoate;

3-[5-({[1H-indol-7-yl(phenyl)methyl]carbamoyl}methyl)-1H-indol-3-yl]propanoic acid;

tert-butyl 3-[5-({[(1-methyl-1H-indol-7-yl)(phenyl)methyl]carbamoyl}methyl)-1H-indol-3-yl]propanoate;

3-[5-({[(1-methyl-1H-indol-7-yl)(phenyl)methyl]carbamoyl}methyl)-1H-indol-3-yl]propanoic acid;

tert-butyl 3-{5-[({1-[2-(piperidin-1-yl)phenyl]pentyl}carbamoyl)methyl]-1H-indol-3-yl}propanoate;

3-{5-[({1-[2-(piperidin-1-yl)phenyl]pentyl}carbamoyl)methyl]-1H-indol-3-yl}propanoic acid;

tert-butyl 3-{5-[({1-[2-(diethylamino)phenyl]-3-methylbutyl}carbamoyl)methyl]-1H-indol-3-yl}propanoate;

3-{5-[({1-[2-(diethylamino)phenyl]-3-methylbutyl}carbamoyl)methyl]-1H-indol-3-yl}propanoic acid;

tert-butyl 3-[5-({[2-(3-methylphenyl)-1-[2-(piperidin-1-yl)phenyl]ethyl]carbamoyl}methyl)-1H-indol-3-yl]propanoate;

3-[5-({[2-(3-methylphenyl)-1-[2-(piperidin-1-yl)phenyl]ethyl]carbamoyl}methyl)-1H-indol-3-yl]propanoic acid;

tert-butyl 3-{5-[({3-methyl-1-[2-(piperidin-1-yl)phenyl]butyl}carbamoyl)amino]-1H-pyrrolo[2,3-b]pyridin-3-yl}propanoate;

3-{5-[({3-methyl-1-[2-(piperidin-1-yl)phenyl]butyl}carbamoyl)amino]-1H-pyrrolo[2,3-b]pyridin-3-yl}propanoic acid;

tert-butyl 3-{5-[({[2-(4,4-difluoropiperidin-1-yl)phenyl](phenyl)methyl}carbamoyl)methyl]-1H-indol-3-yl}propanoate;

3-{5-[({[2-(4,4-difluoropiperidin-1-yl)phenyl](phenyl)methyl}carbamoyl)methyl]-1H-indol-3-yl}propanoic acid;

tert-butyl 3-{5-[({1-[4-bromo-2-(pyrrolidin-1-yl)phenyl]-3-methylbutyl}carbamoyl)methyl]-1H-indol-3-yl}propanoate;

3-{5-[({1-[4-bromo-2-(pyrrolidin-1-yl)phenyl]-3-methylbutyl}carbamoyl)methyl]-1H-indol-3-yl}propanoic acid;

tert-butyl 3-[5-({[(2-amino-4-methylphenyl)(phenyl)methyl]carbamoyl}methyl)-1H-indol-3-yl]propanoate;

3-[5-({[(2-amino-4-methylphenyl)(phenyl)methyl]carbamoyl}methyl)-1H-indol-3-yl]propanoic acid;

tert-butyl 3-{5-[({3,3-dimethyl-1-[2-(piperidin-1-yl)phenyl]butyl}carbamoyl)methyl]-1H-indol-3-yl}propanoate;

3-{5-[({3,3-dimethyl-1-[2-(piperidin-1-yl)phenyl]butyl}carbamoyl)methyl]-1H-indol-3-yl}propanoic acid;

tert-butyl 3-[5-({[(4-methylphenyl)[2-(piperidin-1-yl)phenyl]methyl]carbamoyl}methyl)-1H-indol-3-yl]propanoate;

3-[5-({[(4-methylphenyl)[2-(piperidin-1-yl)phenyl]methyl]carbamoyl}methyl)-1H-indol-3-yl]propanoic acid;

tert-butyl 3-[5-({[2-(oxan-4-yl)-1-[2-(piperidin-1-yl)phenyl]ethyl]carbamoyl}methyl)-1H-indol-3-yl]propanoate;

3-[5-({[2-(oxan-4-yl)-1-[2-(piperidin-1-yl)phenyl]ethyl]carbamoyl}methyl)-1H-indol-3-yl]propanoic acid;

tert-butyl 3-{5-[({[2-(dimethylamino)-4-methylphenyl](phenyl)methyl}carbamoyl)methyl]-1H-indol-3-yl}propanoate;

3-{5-[({[2-(dimethylamino)-4-methylphenyl](phenyl)methyl}carbamoyl)methyl]-1H-indol-3-yl}propanoic acid;

methyl 2-{5-[({3-methyl-1-[2-(piperidin-1-yl)phenyl]butyl}carbamoyl)methyl]-1H-indol-3-yl}acetate;

2-{5-[({3-methyl-1-[2-(piperidin-1-yl)phenyl]butyl}carbamoyl)methyl]-1H-indol-3-yl}acetic acid;

tert-butyl 3-{5-[({[2-(morpholin-4-yl)phenyl](phenyl)methyl}carbamoyl)methyl]-1H-indol-3-yl}propanoate;

3-{5-[({[2-(morpholin-4-yl)phenyl](phenyl)methyl}carbamoyl)methyl]-1H-indol-3-yl}propanoic acid;

tert-butyl 3-{5-[({1-[2-(azepan-1-yl)phenyl]-3-methylbutyl}carbamoyl)methyl]-1H-indol-3-yl}propanoate;

3-{5-[({1-[2-(azepan-1-yl)phenyl]-3-methylbutyl}carbamoyl)methyl]-1H-indol-3-yl}propanoic acid;

tert-butyl 3-{5-[({[2-(2,5-dihydro-1H-pyrrol-1-yl)-4-methylphenyl](phenyl)methyl}carbamoyl)methyl]-1H-indol-3-yl}propanoate;

3-{5-[({[2-(2,5-dihydro-1H-pyrrol-1-yl)-4-methylphenyl](phenyl)methyl}carbamoyl)methyl]-1H-indol-3-yl}propanoic acid;

tert-butyl 3-{5-[({[3-methyl-2-(piperidin-1-yl)phenyl](phenyl)methyl}carbamoyl)methyl]-1H-indol-3-yl}propanoate;

3-{5-[({[3-methyl-2-(piperidin-1-yl)phenyl](phenyl)methyl}carbamoyl)methyl]-1H-indol-3-yl}propanoic acid;

tert-butyl 3-{5-[({[4-methyl-2-(methylamino)phenyl](phenyl)methyl}carbamoyl)methyl]-1H-indol-3-yl}propanoate;

3-{5-[({[4-methyl-2-(methylamino)phenyl](phenyl)methyl}carbamoyl)methyl]-1H-indol-3-yl}propanoic acid;

methyl 5-[({phenyl[2-(piperidin-1-yl)phenyl]methyl}carbamoyl)methyl]-1H-indole-3-carboxylate;

1-(2-{2-[3-carboxy-1H-indol-5-yl)acetamido](phenyl)methyl}phenyl)piperidin-1-ium chloride;

5-({[(2-bromo-4-methylphenyl)(phenyl)methyl]carbamoyl}methyl)-1H-indole-3-carboxylic acid;

tert-butyl 3-[5-({2-[4-methyl-2-(piperidin-1-yl)phenyl]-2-phenylacetamido}methyl)-1H-indol-3-yl]propanoate;

3-[5-({2-[4-methyl-2-(piperidin-1-yl)phenyl]-2-phenylacetamido}methyl)-1H-indol-3-yl]propanoic acid;

ethyl 4-oxo-4-{5-[({phenyl[2-(piperidin-1-yl)phenyl]methyl}carbamoyl)methyl]-1H-indol-3-yl}butanoate;

ethyl 4-{5-[({phenyl[2-(piperidin-1-yl)phenyl]methyl}carbamoyl)methyl]-1H-indol-3-yl}butanoate;

4-{5-[({phenyl[2-(piperidin-1-yl)phenyl]methyl}carbamoyl)methyl]-1H-indol-3-yl}butanoic acid;

4-oxo-4-{5-[({phenyl[2-(piperidin-1-yl)phenyl]methyl}carbamoyl)methyl]-1H-indol-3-yl}butanoic acid;

ethyl 5-oxo-5-{5-[({phenyl[2-(piperidin-1-yl)phenyl]methyl}carbamoyl)methyl]-1H-indol-3-yl}pentanoate;

5-oxo-5-{5-[({phenyl[2-(piperidin-1-yl)phenyl]methyl}carbamoyl)methyl]-1H-indol-3-yl}pentanoic acid;

ethyl 5-{5-[({phenyl[2-(piperidin-1-yl)phenyl]methyl}carbamoyl)methyl]-1H-indol-3-yl}pentanoate;

5-{5-[({phenyl[2-(piperidin-1-yl)phenyl]methyl}carbamoyl)methyl]-1H-indol-3-yl}pentanoic acid;

tert-butyl 3-{5-[({1-[2-(diethylamino)phenyl]pentyl}carbamoyl)methyl]-1H-indol-3-yl}propanoate;

3-{5-[({1-[2-(diethylamino)phenyl]pentyl}carbamoyl)methyl]-1H-indol-3-yl}propanoic acid;

methyl 2-[5-({[(2-bromo-4-methylphenyl)(phenyl)methyl]carbamoyl}methyl)-1H-indol-3-yl]acetate;

2-[5-({[(2-bromo-4-methylphenyl)(phenyl)methyl]carbamoyl}methyl)-1H-indol-3-yl]acetic acid;

methyl 2-[5-({[(2,4-dimethylphenyl)(5-methylthiophen-2-yl)methyl]carbamoyl}methyl)-1H-indol-3-yl]acetate;

2-[5-({[(2,4-dimethylphenyl)(5-methylthiophen-2-yl)methyl]carbamoyl}methyl)-1H-indol-3-yl]acetic acid;

methyl 2-{5-[({[2-(morpholin-4-yl)phenyl](phenyl)methyl}carbamoyl)methyl]-1H-indol-3-yl}acetate;

2-{5-[({[2-(morpholin-4-yl)phenyl](phenyl)methyl}carbamoyl)methyl]-1H-indol-3-yl}acetic acid;

tert-butyl 3-[5-({[(2-bromo-4-methylphenyl)(pyrimidin-2-yl)methyl]carbamoyl}methyl)-1H-indol-3-yl]propanoate;

3-[5-({[(2-bromo-4-methylphenyl)(pyrimidin-2-yl)methyl]carbamoyl}methyl)-1H-indol-3-yl]propanoic acid;

tert-butyl 3-[5-({[(4-methyl-1H-indol-7-yl)(phenyl)methyl]carbamoyl}methyl)-1H-indol-3-yl]propanoate;

3-[5-({[(4-methyl-1H-indol-7-yl)(phenyl)methyl]carbamoyl}methyl)-1H-indol-3-yl]propanoic acid;

tert-butyl 3-{5-[({1-[4-methyl-2-(piperidin-1-yl)phenyl]pentyl}carbamoyl)methyl]-1H-indol-3-yl}propanoate;

3-{5-[({1-[4-methyl-2-(piperidin-1-yl)phenyl]pentyl}carbamoyl)methyl]-1H-indol-3-yl}propanoic acid;

tert-butyl 3-{5-[({[2-(3,3-difluoropiperidin-1-yl)phenyl](phenyl)methyl}carbamoyl)methyl]-1H-indol-3-yl}propanoate;

3-{5-[({[2-(3,3-difluoropiperidin-1-yl)phenyl](phenyl)methyl}carbamoyl)methyl]-1H-indol-3-yl}propanoic acid;

tert-butyl N-[(3-{5-[({phenyl[2-(piperidin-1-yl)phenyl]methyl}carbamoyl)methyl]-1H-indol-3-yl}propanamido)methanimidoyl]carbamate;

1-{2-[(2-{3-[2-(carbamimidoylcarbamoyl)ethyl]-1H-indol-5-yl}acetamido)(phenyl)methyl]phenyl}piperidin-1-ium chloride;

ethyl 3-{5-[({phenyl[2-(piperidin-1-yl)phenyl]methyl}carbamoyl)methyl]-1H-indazol-3-yl}propanoate;

3-{5-[({phenyl[2-(piperidin-1-yl)phenyl]methyl}carbamoyl)methyl]-1H-indazol-3-yl}propanoic acid;

methyl 2-{5-[({phenyl[3-(piperidin-1-yl)phenyl]methyl}carbamoyl)methyl]-1H-indol-3-yl}acetate;

2-{5-[({phenyl[3-(piperidin-1-yl)phenyl]methyl}carbamoyl)methyl]-1H-indol-3-yl}acetic acid;

tert-butyl 3-{5-[({3-methyl-1-[2-(propan-2-yloxy)phenyl]butyl}carbamoyl)methyl]-1H-indol-3-yl}propanoate;

3-{5-[({3-methyl-1-[2-(propan-2-yloxy)phenyl]butyl}carbamoyl)methyl]-1H-indol-3-yl}propanoic acid;

tert-butyl 3-[5-({[1-(2-ethoxyphenyl)-3-methylbutyl]carbamoyl}methyl)-1H-indol-3-yl]propanoate;

3-[5-({[1-(2-ethoxyphenyl)-3-methylbutyl]carbamoyl}methyl)-1H-indol-3-yl]propanoic acid;

tert-butyl 3-{5-[({4-methyl-1-[2-(piperidin-1-yl)phenyl]pentyl}carbamoyl)methyl]-1H-indol-3-yl}propanoate;

3-{5-[({4-methyl-1-[2-(piperidin-1-yl)phenyl]pentyl}carbamoyl)methyl]-1H-indol-3-yl}propanoic acid;

tert-butyl 3-[5-({[(2,4-diethoxyphenyl)(phenyl)methyl]carbamoyl}methyl)-1H-indol-3-yl]propanoate;

3-[5-({[(2,4-diethoxyphenyl)(phenyl)methyl]carbamoyl}methyl)-1H-indol-3-yl]propanoic acid;

tert-butyl 3-{5-[({3-methyl-1-[4-methyl-2-(propan-2-yloxy)phenyl]butyl}carbamoyl)methyl]-1H-indol-3-yl}propanoate;

3-{5-[({3-methyl-1-[4-methyl-2-(propan-2-yloxy)phenyl]butyl}carbamoyl)methyl]-1H-indol-3-yl}propanoic acid;

tert-butyl 3-{5-[({[2-(azepan-1-yl)-4-methylphenyl](phenyl)methyl}carbamoyl)methyl]-1H-indol-3-yl}propanoate;

3-{5-[({[2-(azepan-1-yl)-4-methylphenyl](phenyl)methyl}carbamoyl)methyl]-1H-indol-3-yl}propanoic acid;

tert-butyl 3-[5-({[(4,5-dimethylfuran-2-yl)[2-(piperidin-1-yl)phenyl]methyl]carbamoyl}methyl)-1H-indol-3-yl]propanoate;

3-[5-({[(4,5-dimethylfuran-2-yl) [2-(piperidin-1-yl)phenyl]methyl]carbamoyl}methyl)-1H-indol-3-yl]propanoic acid;

tert-butyl 3-[5-({[(5-methylfuran-2-yl)[2-(propan-2-yloxy)phenyl]methyl]carbamoyl}methyl)-1H-indol-3-yl]propanoate;

3-[5-({[(5-methylfuran-2-yl)[2-(propan-2-yloxy)phenyl]methyl]carbamoyl}methyl)-1H-indol-3-yl]propanoic acid;

methyl 2-[5-({[(2-bromo-4-methylphenyl)(pyrimidin-2-yl)methyl]carbamoyl}methyl)-1H-indol-3-yl]acetate;

2-[5-({[(2-bromo-4-methylphenyl)(pyrimidin-2-yl)methyl]carbamoyl}methyl)-1H-indol-3-yl]acetic acid;

N-methoxy-N-methyl-2-{5-[({phenyl[2-(piperidin-1-yl)phenyl]methyl}carbamoyl)methyl]-1H-indol-3-yl}acetamide;

tert-butyl 3-{5-[({[4-hydroxy-2-(piperidin-1-yl)phenyl](phenyl)methyl}carbamoyl)methyl]-1H-indol-3-yl}propanoate;

tert-butyl 3-{5-[({1-[2-(piperidin-1-yl)phenyl]but-3-yn-1-yl}carbamoyl)methyl]-1H-indol-3-yl}propanoate;

3-{5-[)({1-[2-(piperidin-1-yl)phenyl]but-3-yn-1-yl}carbamoyl)methyl]-1H-indol-3-yl}propanoic acid;

tert-butyl 3-{5-[({3-methyl-1-[2-(piperidin-1-yl)phenyl]butyl}carbamoyl)amino]-1H-indol-3-yl}propanoate;

tert-butyl 3-{5-[({[2-(4-benzylpiperazin-1-yl)-4-methylphenyl](phenyl)methyl}carbamoyl)methyl]-1H-indol-3-yl}propanoate;

tert-butyl 3-{5-[({[4-hydroxy-2-(piperidin-1 yl)phenyl](phenyl)methyl}carbamoyl)methyl]-1H-indol-3-yl}propanoate;

3-{5-[({[4-hydroxy-2-(piperidin-1-yl)phenyl](phenyl)methyl}carbamoyl)methyl]-1H-indol-3-yl}propanoic acid;

3-(hexadecanoyloxy)-2-[(3-{5-[({phenyl[2-(piperidin-1-yl)phenyl]methyl}carbamoyl)methyl]-1H-indol-3-yl}propanoyl)oxy]propyl hexadecanoate;

tert-butyl 3-{5-[({[4-methyl-2-(piperidin-1-yl)phenyl](5-methylfuran-2-yl)methyl}carbamoyl)methyl]-1H-indol-3-yl}propanoate; and 3-{5-[({[4-methyl-2-(piperidin-1-yl)phenyl](5-methylfuran-2-yl)methyl}carbamoyl)methyl]-1H-indol-3-yl}propanoic acid.

10. A pharmaceutical composition comprising a compound according to claim 1, and a pharmaceutically acceptable carrier.

11. The pharmaceutical composition according to claim 10, wherein said composition is formulated as an injectable suspension, a gel, an oil, a pill, a suppository, a powder, a capsule, an aerosol, an ointment, a cream, a patch, or means of galenic forms for a prolonged and/or slow release.

12. A method for the treatment of an autoimmune disease, and autoimmune-related disease, and inflammatory disease, a fibrotic disease or a cholestatic disease, comprising administering to a subject in need there of a therapeutically effective amount of the compound according to claim 1.

13. The method according to claim 12, wherein said disease is selected from arthritis, asthma, severe, glucocorticoid-nonresponsive asthma, asthma exacerbations due to ongoing and/or past pulmonary infection, Addison's disease, allergy, agammaglobulinemia, alopecia areata, ankylosing spondylitis, atherosclerosis, atopic allergy, atopic dermatitis, autoimmune cardiomyopathy, autoimmune enteropathy, autoimmune hemolytic anemia, autoimmune hepatitis, autoimmune lymphoproliferative syndrome, autoimmune pancreatitis, autoimmune peripheral neuropathy, Crohn's disease, Celiac disease, colitis, chronic inflammatory demyelinating polyneuropathy, chronic obstructive pulmonary disease (COPD), dermatomyositis, diabetes mellitus type 1, diffuse cutaneous systemic sclerosis, eczema, gastrointestinal disorder, Goodpasture's syndrome, Graves' disease, Guillain-Barre syndrome, Hashimoto's encephalopathy, Hashimoto's thyroiditis, idiopathic thrombocytopenic purpura, inflammatory bowel disease (IBD), irritable bowel syndrome, lupus, lupus erythematosus, lupus nephritis, mixed connective tissue disease, Kawasaki disease, multiple sclerosis, neuromyelitis optica, myasthenia gravis, narcolepsy, optic neuritis, osteorathritis, pemphigus vulgaris, pernicious anaemia, polymyositis, psoriasis, psoriatic arthritis, reactive arthritis, relapsing polychondritis, respiratory disorder, rheumatoid arthritis, rheumatic fever, Sjorgen's syndrome, systemic lupus erythematosus, transverse myelitis, undifferentiated connective tissue disease, ulcerative colitis, uveitis, vasculitis, Wegener's granulomatosis, systemic inflammatory response syndrome (SIRS), sepsis, Behcets disease, allergic contact dermatitis, cutaneous lupus erythematosus, dry eye and glomerulonephritis, myocarditis, acute liver failure (ALF), including acute-on-chronic liver failure (ACLF), pulmonary fibrosis (idiopathic pulmonary, interstitial lung, cystic and progressive massive fibrosis), liver fibrosis and cirrhosis of diverse etiologies (congenital, of autoimmune origin, induced by cardiometabolic diseases, alcohol consumption, cholestasis, drugs, infectious agents, trauma, radiation), metabolic syndrome, NonAlcoholic SteatoHepatitis (NASH) and Alcoholic SteatoHepatitis (ASH), cardiac fibrosis and heart myocardial and endomyocardial fibrosis, arterial fibrosis, atherosclerosis/restenosis, mediastinal fibrosis (soft tissue of the mediastinum), macular degeneration, retinal and vitreal retinopathy, ocular scarring, cataract, Alzheimer's disease, cancer, local, disseminated or metastatic cancer, scleroderma, glioblastoma, myelofibrosis (bone marrow), retroperitoneal fibrosis (soft tissue of the retroperitoneum), nephrogenic systemic fibrosis (skin, joints, eyes, and internal organs), keloid (skin), intestinal fibrosis (occurs for example in Crohn's disease and collagenous colitis), kidney fibrosis, scleroderma and systemic sclerosis (skin, lungs, kidneys, heart, and gastrointestinal tract), arthrofibrosis (knee, shoulder, other joints), Peyronie's disease (penis), Dupuytren's contracture (hands and fingers), some forms of adhesive capsulitis (shoulder), obesity, Primary Biliary Cirrhosis (PBC), Primary Sclerosing Cholangitis (PSC), Intarhepatic Cholestasis of Pregnancy (ICP), Progressive Familial Intrahepatic Cholestasis (PFIC), Biliary atresia, Cholelithiasis, Infectious cholangitis, Cholangitis associated with Langerhans cell histiocytosis, Alagille syndrome, Nonsyndromic ductal paucity, Hepatitis (hepatitis A, hepatitis B, hepatitis C), Alpha1-antitrypsin deficiency, Inborn errors of bile acid synthesis, Drug-induced cholestasis, and Total parenteral nutrition (TPN)-associated cholestasis.

14. The compound according to claim 2, wherein:
   A is a C-R1b group or a nitrogen atom;
   R1a is a halogen atom, a nitrile group, a nitro group (NO$_2$), an alkyl group, an alkyloxy group, an alkylthio group, an amino group, an alkylamino group, a dialkylamino group or a heterocyclic group;
   R1b is a hydrogen atom or a heterocyclic group;

wherein R1a and R1b can optionally form, together with the carbon atoms to which they are attached, an aryl group or a heterocyclic group;
R1c is a hydrogen atom, a halogen atom, an alkyl group, an alkyloxy group, an alkylthio or a heterocyclic group;
R1d is a hydrogen atom, a halogen atom or an alkyl group;
R2 and R'2 are independently a hydrogen atom, an alkyl group, a cycloalkyl group, an aryl group, or a heterocyclic group, with the proviso that R2 and R'2 are not simultaneously a hydrogen atom,
or R2 and R2' can form, together with the carbon atom to which they are attached, a cycloalkyl group or a heterocycloalkyl group;
L is a NR7-CO—CH$_2$, NR7-CO—NH, NR7-CO—C(CH$_3$)$_2$, NR7-CS—CH$_2$, NR7-CS—NH, NR7-CS—C(CH$_3$)$_2$, NR7-SO$_2$—CH$_2$, NR7-SO$_2$—C(CH$_3$)$_2$, CO—NH—CH$_2$ or CO—NH—C(CH$_3$)$_2$ group;
HET is a heterocyclic group selected from:

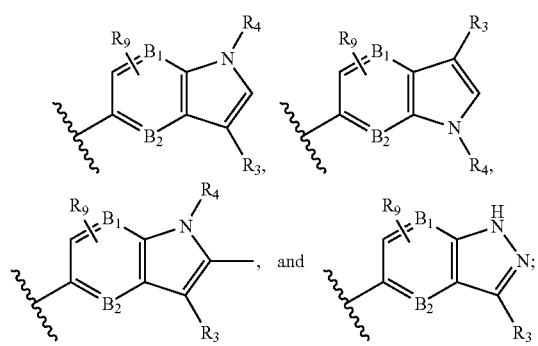

B1 and B2 are independently a nitrogen atom or a carbon atom;
R3 is a COR5 group or an alkyl group substituted by a COR5 group;
R4 is a hydrogen atom or a hydroxyl group;
R5 is a hydroxyl group, an alkyloxy group, a NR8R8'group or a —O—CH—(CH$_2$—O—CO—R6)$_2$ group;
R6 is a long chain alkyl group;
R7 is a hydrogen atom or an alkyl group;
R8 and R8' are independently a hydrogen atom or an alkyl group; and
R9 is a hydrogen atom, an alkyl group or a halogen atom.

15. The compound according to claim 2, wherein:
A is a C-R1b group;
R1a is a halogen atom, a nitrile group, a nitro group (NO$_2$), an alkyl group, an alkyloxy group, an alkylthio group, an alkylamino group, a dialkylamino group, a 1-pyrrolidinyl group, a 1-azepanyl group, a 4-morpholinyl group, a 1-piperidinyl group, a 1-piperazinyl group, wherein said piperidinyl or piperazinyl group can be optionally substituted by one or more alkyl groups;
R1b is hydrogen, a 1-pyrrolidinyl group, a 1-azepanyl group, a 4-morpholinyl group, a 1-piperidinyl group or a 1-piperazinyl group;
R1c is hydrogen, a halogen atom, an alkyl group or an alkyloxy group;
R2 is an alkyl group, a cycloalkyl group, an aryl group or a heteroaryl group, and
R'2 is a hydrogen atom.

16. The compound according to claim 3, wherein:

A is a C-R1b group;

R1a is a halogen atom, a nitrile group, a nitro group (NO$_2$), an alkyl group, an alkyloxy group, an alkylthio group, an alkylamino group, a dialkylamino group, a 1-pyrrolidinyl group, a 1-azepanyl group, a 4-morpholinyl group, a 1-piperidinyl group, a 1-piperazinyl group, wherein said piperidinyl or piperazinyl group can be optionally substituted by one or more alkyl groups;

R1b is hydrogen, a 1-pyrrolidinyl group, a 1-azepanyl group, a 4-morpholinyl group, a 1-piperidinyl group or a 1-piperazinyl group;

R1c is hydrogen, a halogen atom, an alkyl group or an alkyloxy group;

R2 is an alkyl group, a cycloalkyl group, an aryl group or a heteroaryl group, and R'2 is a hydrogen atom.

17. The compound according to claim 4, wherein B1 and B2 are carbon atoms.

18. The compound according to claim 2, wherein L is NH—CO—CH$_2$, NH—CO—NH, NH—SO$_2$—CH$_2$, CO—NH—CH$_2$, N(CH$_3$)—CO—CH$_2$ or NH—CO—C(CH$_3$)$_2$.

19. The compound according to claim 3, wherein L is NH—CO—CH$_2$, NH—CO—NH, NH—SO$_2$—CH$_2$, CO—NH—CH$_2$, N(CH$_3$)—CO—CH$_2$ or NH—CO—C(CH$_3$)$_2$.

* * * * *